(12) United States Patent
Moon et al.

(10) Patent No.: US 11,495,750 B2
(45) Date of Patent: *Nov. 8, 2022

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Doo-Hyeon Moon, Gyeonggi-do (KR); Bitnari Kim, Gyeonggi-do (KR); Sang-Hee Cho, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 574 days.

This patent is subject to a terminal disclaimer.

(21) Appl. No.: 16/461,055

(22) PCT Filed: Oct. 26, 2017

(86) PCT No.: PCT/KR2017/011876
§ 371 (c)(1),
(2) Date: May 15, 2019

(87) PCT Pub. No.: WO2018/105888
PCT Pub. Date: Jun. 14, 2018

(65) Prior Publication Data
US 2019/0288222 A1    Sep. 19, 2019

(30) Foreign Application Priority Data

Dec. 9, 2016  (KR) .......................... 10-2016-0167780
Feb. 2, 2017  (KR) .......................... 10-2017-0015097
Oct. 2, 2017  (KR) .......................... 10-2017-0128489

(51) Int. Cl.
| | | |
|---|---|---|
| *H01L 51/00* | (2006.01) | |
| *C07D 403/10* | (2006.01) | |
| *C09K 11/06* | (2006.01) | |
| *C07D 409/14* | (2006.01) | |
| *C07D 251/24* | (2006.01) | |
| *C07D 401/10* | (2006.01) | |
| *C07D 405/14* | (2006.01) | |
| *H01L 51/50* | (2006.01) | |
| *C07D 401/14* | (2006.01) | |
| *C07D 209/56* | (2006.01) | |

(52) U.S. Cl.
CPC ........ *H01L 51/0072* (2013.01); *C07D 209/56* (2013.01); *C07D 251/24* (2013.01); *C07D 401/10* (2013.01); *C07D 401/14* (2013.01); *C07D 403/10* (2013.01); *C07D 405/14* (2013.01); *C07D 409/14* (2013.01); *C09K 11/06* (2013.01); *H01L 51/00* (2013.01); *H01L 51/0052* (2013.01); *H01L 51/0058* (2013.01); *H01L 51/0067* (2013.01); *H01L 51/50* (2013.01); *C09K 2211/1018* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
CPC . H01L 51/0072; H01L 51/00; H01L 51/0052; H01L 51/0058; H01L 51/0067; H01L 51/50; H01L 51/5012; H01L 51/5016; H01L 51/5056; H01L 51/5072; H01L 51/5088; H01L 51/5092; H01L 51/5096; H01L 2227/32; C07D 209/56; C07D 251/24; C07D 401/10; C07D 401/14; C07D 403/10; C07D 405/14; C07D 409/14; C09K 11/06; C09K 2211/1018; C09K 2211/1029
USPC .......................................................... 428/690
See application file for complete search history.

(56) References Cited

U.S. PATENT DOCUMENTS

| | | | |
|---|---|---|---|
| 9,172,046 B1 | 10/2015 | Kim et al. | |
| 11,107,997 B2 * | 8/2021 | Cho | .................... H01L 51/0073 |
| 2016/0013427 A1 | 1/2016 | Kim et al. | |
| 2016/0133844 A1 | 5/2016 | Kim et al. | |
| 2017/0047527 A1 * | 2/2017 | Lee | ...................... H01L 51/0065 |
| 2017/0077415 A1 * | 3/2017 | Kim | ..................... C07D 403/10 |
| 2019/0131542 A1 | 5/2019 | Kim | ..................... H01L 51/0052 |
| 2019/0157569 A1 * | 5/2019 | Lee | ..................... H01L 51/0053 |
| 2020/0013964 A1 * | 1/2020 | Lee | ..................... H01L 51/0067 |

(Continued)

FOREIGN PATENT DOCUMENTS

| | | |
|---|---|---|
| KR | 2016-0034804 A | 3/2016 |
| KR | 20160079548 A | 7/2016 |
| KR | 2017-0092128 A | 8/2017 |

(Continued)

OTHER PUBLICATIONS

International Search Report for PCT/KR2017/011876, dated Dec. 22, 2017. (Year: 2017).*

(Continued)

*Primary Examiner* — Douglas J McGinty
(74) *Attorney, Agent, or Firm* — G. Creston Campbell

(57) ABSTRACT

The present disclosure relates to an organic electroluminescent compound and an organic electroluminescent device comprising the same. By comprising the organic electroluminescent compound of the present disclosure, an organic electroluminescent device having low driving voltage, high luminous efficiency, and/or excellent lifespan characteristics can be provided.

9 Claims, No Drawings

(56) References Cited

U.S. PATENT DOCUMENTS

2020/0165234 A1* 5/2020 Kim .................... C07D 251/24
2021/0328154 A1* 10/2021 Kim .................... H01L 51/0073

FOREIGN PATENT DOCUMENTS

| KR | 2017-0092129 A | 8/2017 |
| KR | 2017-0113334 A | 10/2017 |
| WO | 2017183859 A1 | 10/2017 |
| WO | 2018056645 A1 | 3/2018 |

OTHER PUBLICATIONS

Cited Reference for Japanese Patent Application No. 2019-527436; Application Date: Oct. 26, 2017.
Supplementary European Search Report for U.S. Appl. No. 17/877,640; dated Oct. 26, 2017.

* cited by examiner

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer [Appl. Phys. Lett. 51, 913, 1987].

The most important factor in determining luminous efficiency in an organic electroluminescent device is light-emitting materials. Until now, fluorescent materials have been widely used as a light-emitting material. However, in view of electroluminescent mechanisms, since phosphorescent light-emitting materials theoretically enhance luminous efficiency by four (4) times compared to fluorescent light-emitting materials, development of phosphorescent light-emitting materials are widely being researched. To date, iridium(III) complexes have been widely known as phosphorescent light-emitting materials, including bis(2-(2'-benzothienyl)-pyridinato-N,C3')iridium(acetylacetonate) ((acac)Ir(btp)$_2$), tris(2-phenylpyridine)iridium (Ir(ppy)$_3$) and bis (4,6-difluorophenylpyridinato-N,C2)picolinate iridium (Firpic) as red, green, and blue materials, respectively.

At present, 4,4'-N,N'-dicarbazol-biphenyl (CBP) is the most widely known phosphorescent host material. Recently, Pioneer (Japan) et al. developed a high performance organic electroluminescent device using bathocuproine (BCP) and aluminum(III)bis(2-methyl-8-quinolinate)(4-phenylphenolate) (BAlq) etc., which were used as hole blocking layer materials, as host materials.

Although these materials provide good light-emitting characteristics, they have the following disadvantages: (1) Due to their low glass transition temperature and poor thermal stability, their degradation may occur during a high-temperature deposition process in a vacuum, and the lifespan of the device decreases. (2) The power efficiency of an organic electroluminescent device is given by [($\pi$/voltage)×current efficiency], and the power efficiency is inversely proportional to the voltage. Although an organic electroluminescent device comprising phosphorescent host materials provides higher current efficiency (cd/A) than one comprising fluorescent materials, a significantly high driving voltage is necessary. Thus, there is no merit in terms of power efficiency (lm/W). (3) Further, when these materials are used in an organic electroluminescent device, the operational lifespan of an organic electroluminescent device is short and luminous efficiency is still required to be improved.

In addition, an electron transport material actively transports electrons from a cathode to a light-emitting layer and inhibits transport of holes which are not recombined in the light-emitting layer to increase recombination opportunity of holes and electrons in the light-emitting layer. Thus, electron-affinitive materials are used as an electron transport material. Organic metal complexes having light-emitting function such as Alq$_3$ are excellent in transporting electrons, and thus have been conventionally used as an electron transport material. However, Alq$_3$ has problems in that it moves to other layers and shows a reduction of color purity when used in blue light-emitting devices. Therefore, new electron transport materials have been required, which do not have the above problems, are highly electron-affinitive, and quickly transport electrons in organic EL devices to provide organic EL devices having high luminous efficiency.

In order to enhance luminous efficiency, driving voltage and/or lifespan, various materials or concepts for an organic layer of an organic electroluminescent device have been proposed. However, they were not satisfactory to use practically.

Korean Patent Appln. Laying-Open No. KR 2016-0034804 A discloses a compound wherein a substituted triazinyl or pyrimidinyl group is bonded to a benzocarbazole via a linker of a biphenylene group at a nitrogen position. However, said reference does not specifically disclose a compound wherein a substituted triazinyl or pyrimidinyl group, etc., is bonded to a benzocarbazole via a linker of an arylene group having 10 carbon atoms at a nitrogen position. Further, it is not sufficiently satisfactory in terms of driving voltage, luminous efficiency, and/or lifespan characteristics.

DISCLOSURE OF THE INVENTION

Problems to be Solved

The objective of the present disclosure is to provide an organic electroluminescent compound which can efficiently produce an organic electroluminescent device having low driving voltage, high luminous efficiency, and/or excellent lifespan characteristics.

Solution to Problems

As a result of intensive studies to solve the technical problem above, the present inventors found that the above objective can be achieved by an organic electroluminescent compound represented by the following formula 1:

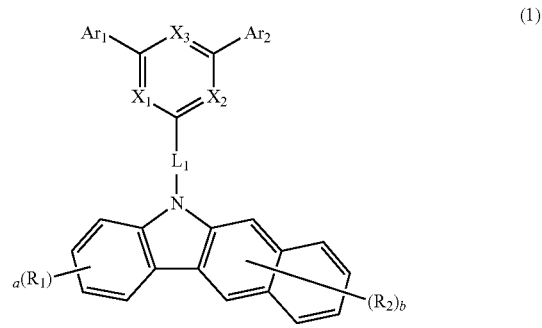

wherein
$X_1$ to $X_3$ each independently represent N or $CR_3$, with a proviso that at least one of them are N;
$L_1$ represents a substituted or unsubstituted arylene having 10 carbon atoms;
$Ar_1$, $Ar_2$, and $R_1$ to $R_3$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)

cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30) arylamino, or a substituted or unsubstituted (C1-C30)alkyl (C6-C30)arylamino; or are linked to an adjacent substituent to form a substituted or unsubstituted, mono- or polycyclic, (C3-C30) alicyclic, aromatic ring, or a combination thereof, whose carbon atom(s) may be replaced with at least one heteroatom selected from nitrogen, oxygen, and sulfur;

the heteroaryl contains at least one heteroatom selected from B, N, O, S, Si, and P;

a is an integer of 1 to 4, and b is an integer of 1 to 6;

where a or b is an integer of 2 or more, each $R_1$ and each $R_2$ may be the same or different.

Effects of the Invention

By using the organic electroluminescent compound according to the present disclosure, an organic electroluminescent device having low driving voltage, high luminous efficiency, and/or excellent lifespan characteristic can be produced.

EMBODIMENTS OF THE INVENTION

Hereinafter, the present disclosure will be described in detail. However, the following description is intended to explain the disclosure, and it is not meant in any way to restrict the scope of the disclosure.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The organic electroluminescent material of the present disclosure may comprise at least one compound represented by formula 1. The compound represented by formula 1 may be comprised in a light-emitting layer and/or an electron transport layer, but is not limited thereto. When comprised in the light-emitting layer, the compound of formula 1 can be comprised as a host, and when comprised in the electron transport layer, the compound of formula 1 can be comprised as an electron transport material.

Hereinafter, the compound represented by formula 1 will be described in detail.

The compound of formula 1 may be represented by any one of the following formulas 2 to 8:

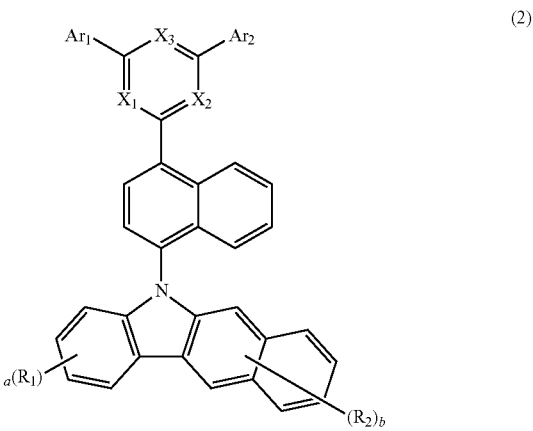

(2)

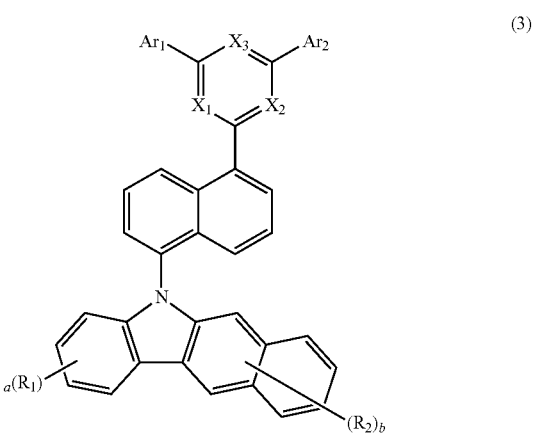

(3)

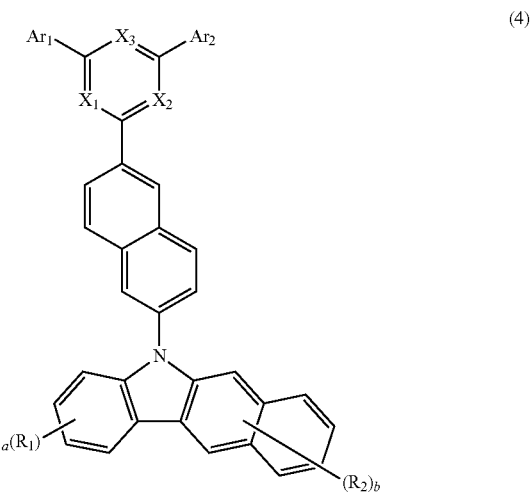

(4)

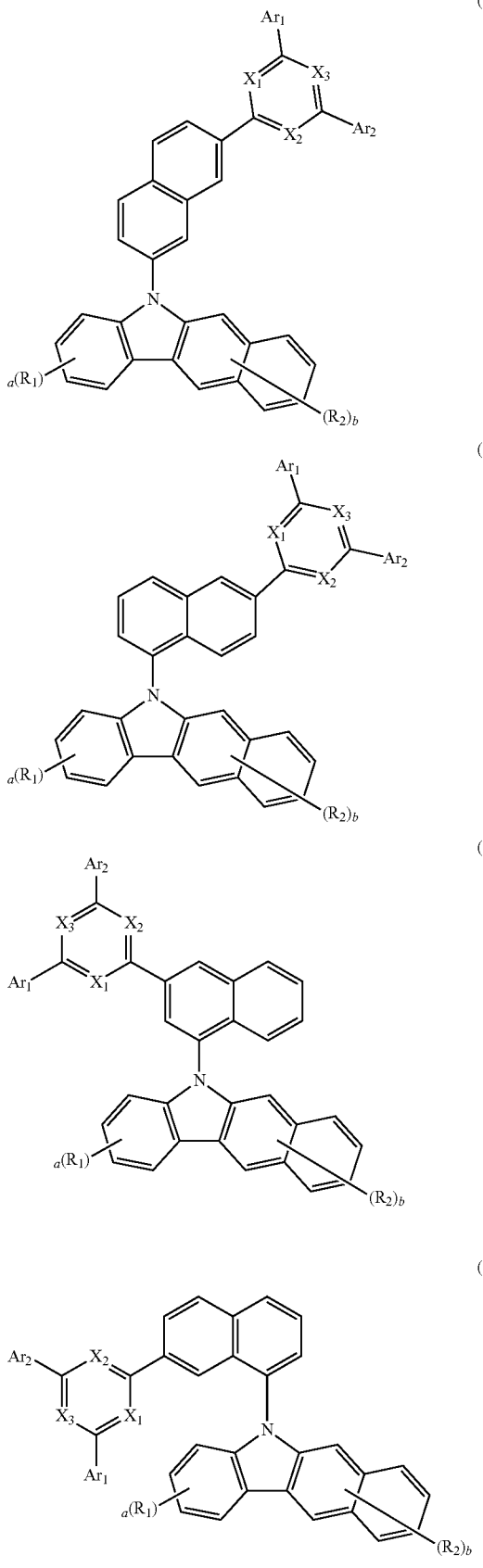

wherein

X₁ to X₃, Ar₁, Ar₂, and R₁ to R₃ are as defined in formula 1.

In formula 1 above, $X_1$ to $X_3$ each independently represent N or CR₃, with a proviso that at least one of them are N. Preferably, at least two of $X_1$ to $X_3$ are N.

L₁ represents a substituted or unsubstituted arylene having 10 carbon atoms, preferably represents a substituted or unsubstituted naphthylene, and more preferably represents an unsubstituted naphthylene.

Ar₁, Ar₂, and R₁ to R₃ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30) arylamino, or a substituted or unsubstituted (C1-C30)alkyl (C6-C30)arylamino; or are linked to an adjacent substituent to form a substituted or unsubstituted, mono- or polycyclic, (C3-C30) alicyclic, aromatic ring, or a combination thereof, whose carbon atom(s) may be replaced with at least one heteroatom selected from nitrogen, oxygen, and sulfur.

Further, Ar₁ and Ar₂ preferably each independently represent a substituted or unsubstituted (C6-C25)aryl, or a substituted or unsubstituted (5- to 20-membered)heteroaryl, and more preferably each independently represent a (C6-C25)aryl unsubstituted or substituted with a (C1-C30)alkyl, or an unsubstituted (5- to 20-membered)heteroaryl.

Further, R₁ to R₃ preferably each independently represent hydrogen, a substituted or unsubstituted (C6-C20)aryl, or a substituted or unsubstituted (5- to 20-membered)heteroaryl, and more preferably each independently represent hydrogen, an unsubstituted (C6-C20)aryl, or an unsubstituted (5- to 20-membered)heteroaryl.

According to one embodiment of the present disclosure, in formula 1 above, X₁ to X₃ each independently represent N or CR₃, with a proviso that at least two of them are N; L₁ represents a substituted or unsubstituted naphthylene; Ar₁ and Ar₂ each independently represent a substituted or unsubstituted (C6-C25)aryl, or a substituted or unsubstituted (5- to 20-membered)heteroaryl; and R₁ to R₃ each independently represent hydrogen, a substituted or unsubstituted (C6-C20) aryl, or a substituted or unsubstituted (5- to 20-membered) heteroaryl.

According to another embodiment of the present disclosure, in formula 1 above, X₁ to X₃ each independently represent N or CR₃, with a proviso that at least two of them are N; L₁ represents an unsubstituted naphthylene; Ar₁ and Ar₂ each independently represent a (C6-C25)aryl unsubstituted or substituted with a (C1-C30)alkyl, or an unsubstituted (5- to 20-membered)heteroaryl; and R₁ to R₃ each independently represent hydrogen, an unsubstituted (C6-C20)aryl, or an unsubstituted (5- to 20-membered)heteroaryl.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is meant to be a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is meant to be a cycloalkyl having at least one heteroatom selected from the group consisting of B, N, O, S, Si, and P, preferably selected from the group consisting of O, S, and N, and 3 to 7 ring backbone atoms, preferably 5 to 7 ring backbone atoms, and includes tetrahydrofuran, pyrrolidine, thiolan, tetrahydropyran, etc. "(C6-C30)aryl(ene)" is meant to be a monocyclic or fused ring radical derived from an aromatic hydrocarbon having 6 to 30 ring backbone carbon atoms and may be partially saturated, in which the number of ring backbone carbon atoms is preferably 6 to 25, more preferably 6 to 18, includes a spiro structure, and includes phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "(3- to 30-membered)heteroaryl(ene)" is meant to be an aryl group having at least one, preferably 1 to 4 heteroatoms selected from the group consisting of B, N, O, S, Si, and P, and 3 to 30 ring backbone atoms; is a monocyclic ring, or a fused ring condensed with at least one benzene ring; may be partially saturated; may be one formed by linking at least one heteroaryl or aryl group to a heteroaryl group via a single bond(s); includes a spiro structure; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, etc. "Halogen" includes F, Cl, Br, and I.

Herein, "substituted" in the expression "substituted or unsubstituted" means that a hydrogen atom in a certain functional group is replaced with another atom or functional group, i.e., a substituent. The substituents of the substituted arylene having 10 carbon atoms, the substituted (C1-C30) alkyl, the substituted (C6-C30)aryl(ene), the substituted (3- to 30-membered)heteroaryl, the substituted (C3-C30)cycloalkyl, the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-C30)arylamino, and the substituted mono- or polycyclic, (C3-C30) alicyclic, aromatic ring, or a combination thereof in $L_1$, $Ar_1$, $Ar_2$, and $R_1$ to $R_3$ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered)heteroaryl unsubstituted or substituted with a (C6-C30)aryl; a (C6-C30)aryl unsubstituted or substituted with a (5- to 30-membered) heteroaryl; a tri(C1-C30)alkylsilyl, a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl; a (C1-C30)alkyl(C6-C30) arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl (C6-C30)aryl; and preferably each independently are a (C1-C6)alkyl.

The compound represented by formula 1 includes the following compounds, but is not limited thereto:

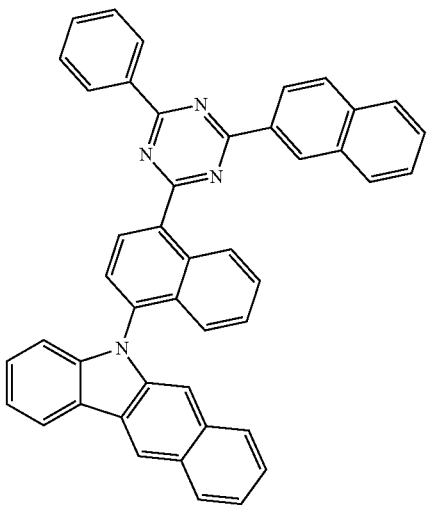

H-1

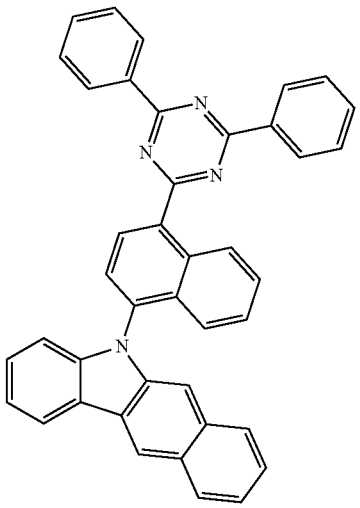

H-2

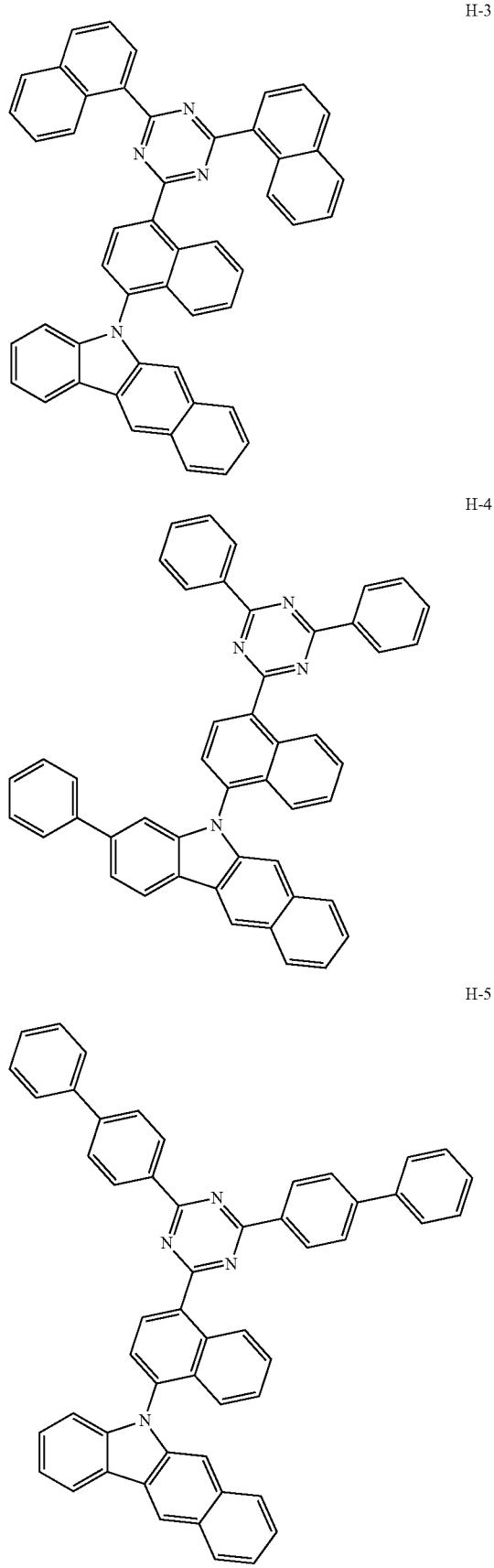
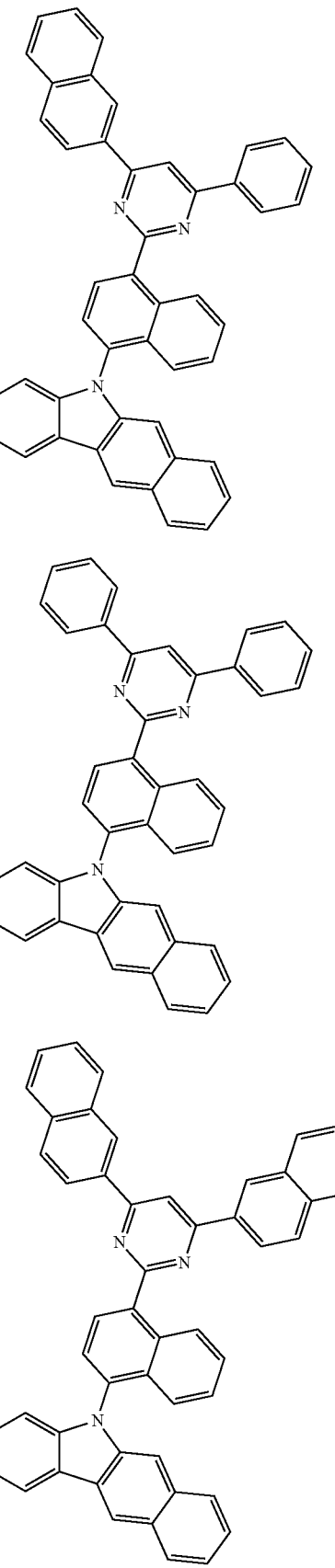

H-9
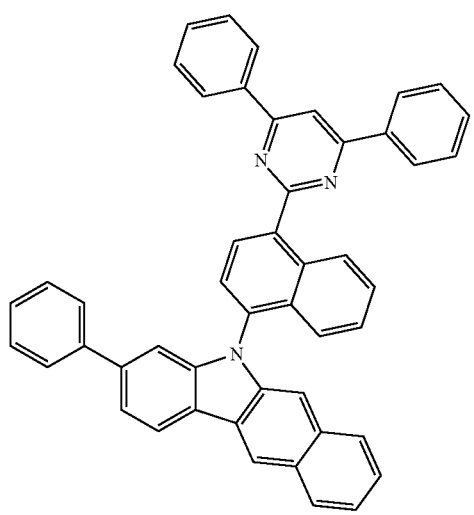
H-10
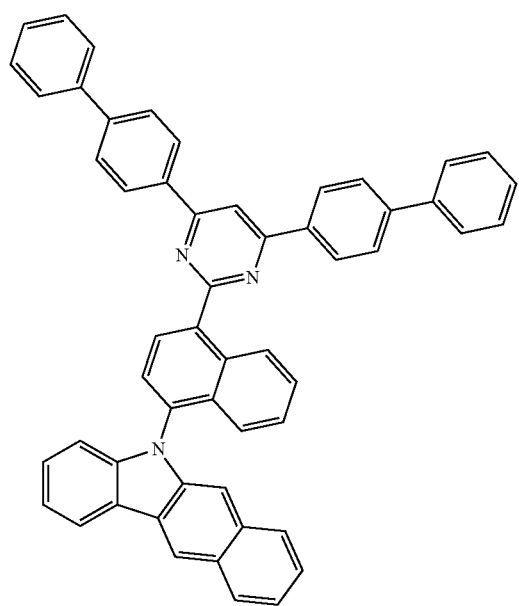
H-11
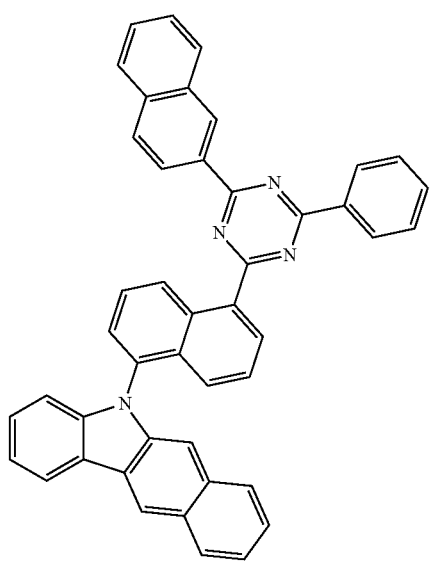
H-12
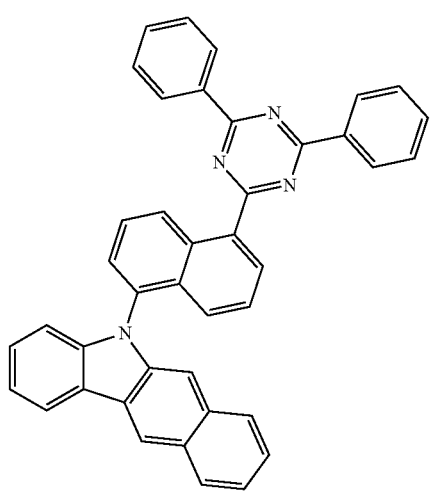
H-13
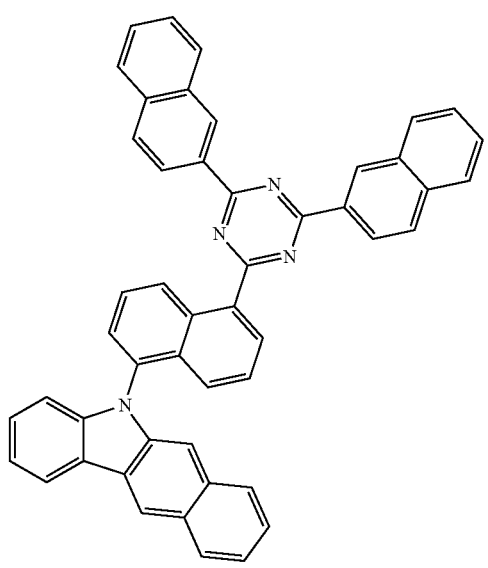

-continued
H-14
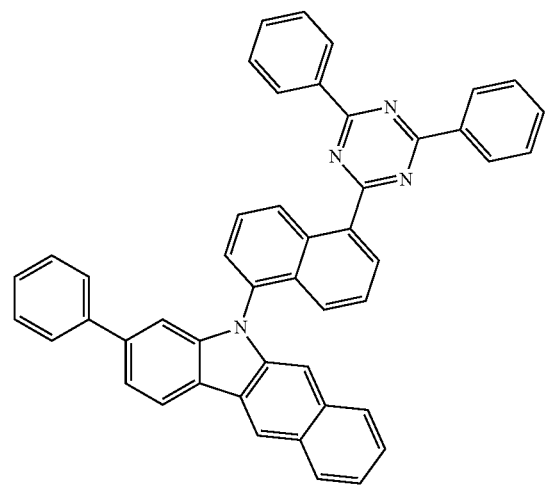
H-15
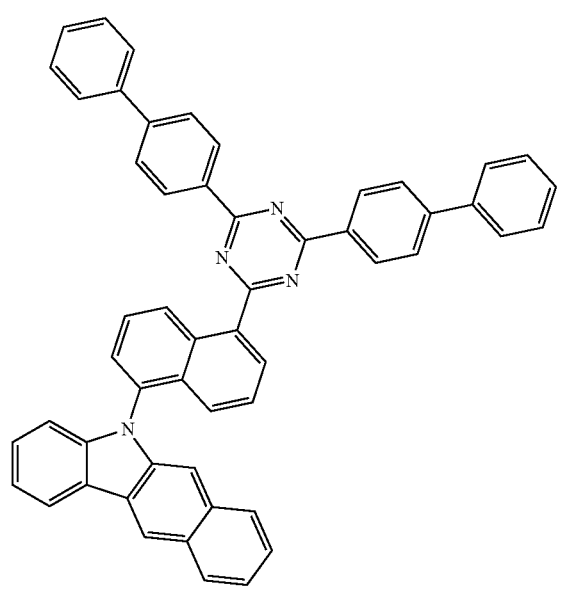
H-16
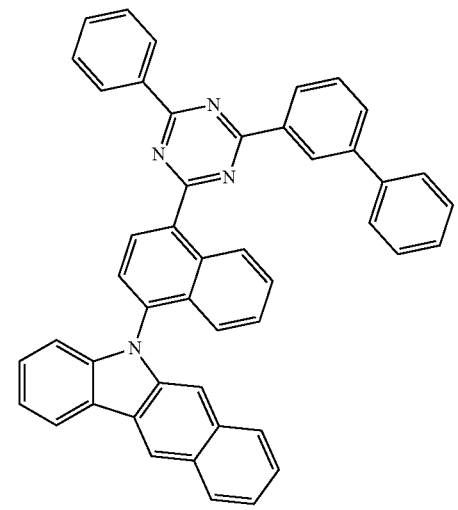
H-17
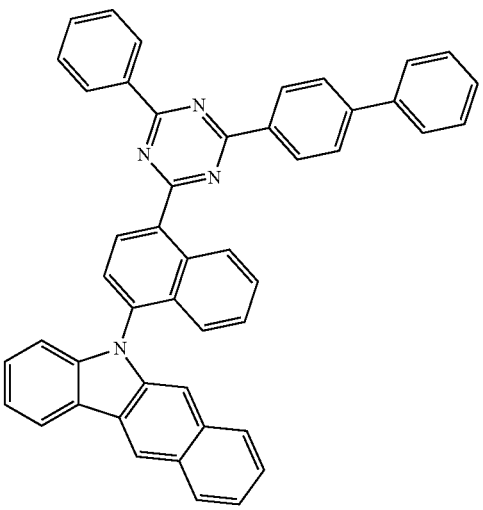
H-18
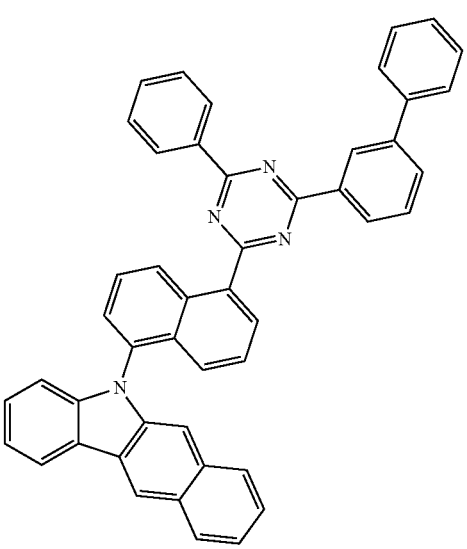
H-19
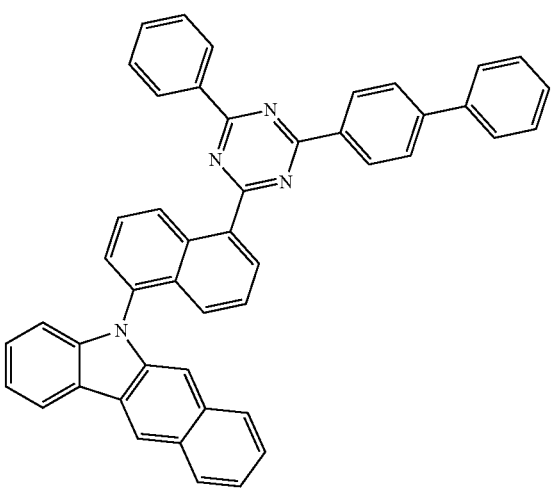

H-20
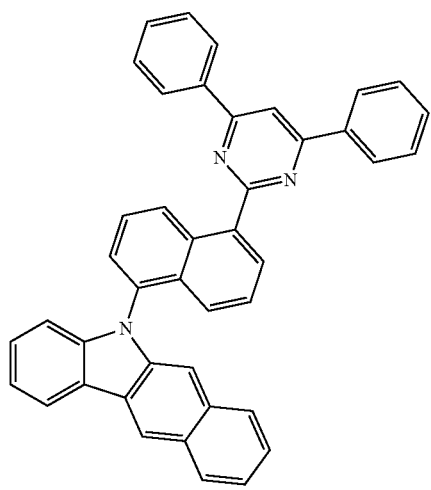
H-21
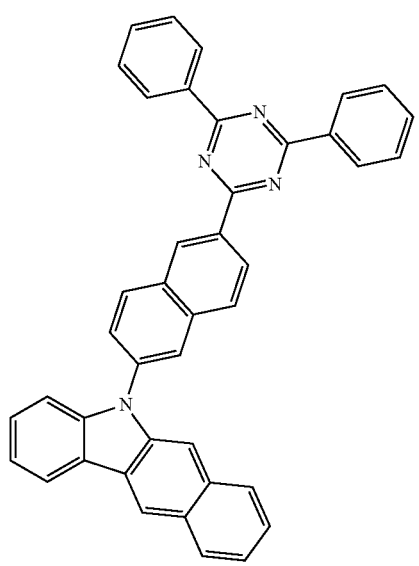
H-22
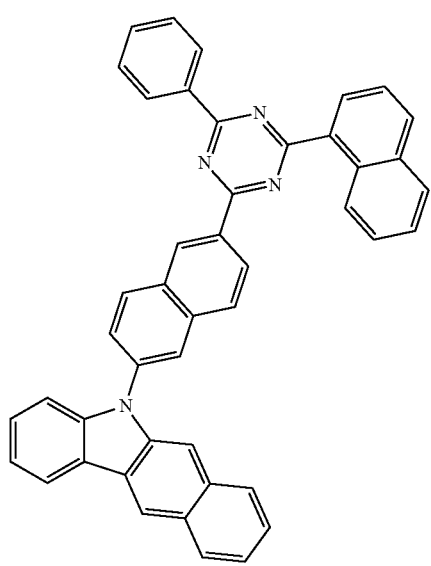
H-23
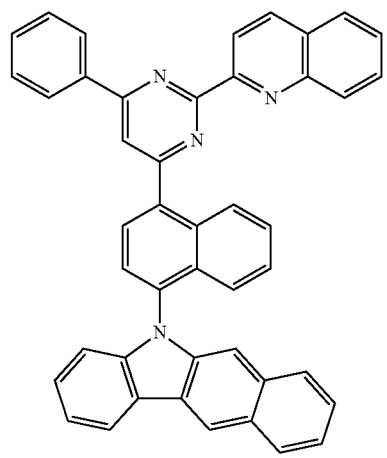
H-24
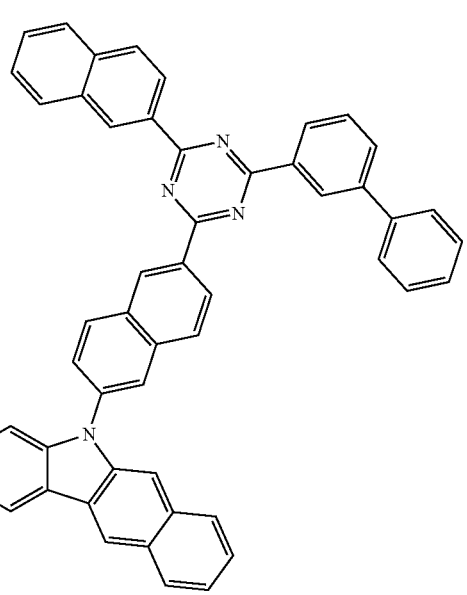
H-25
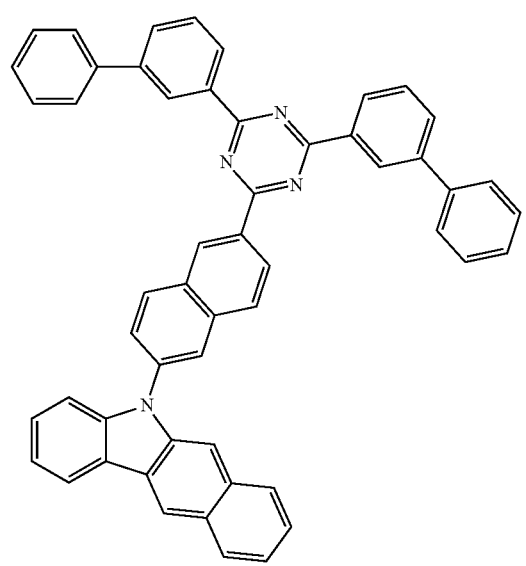

H-26
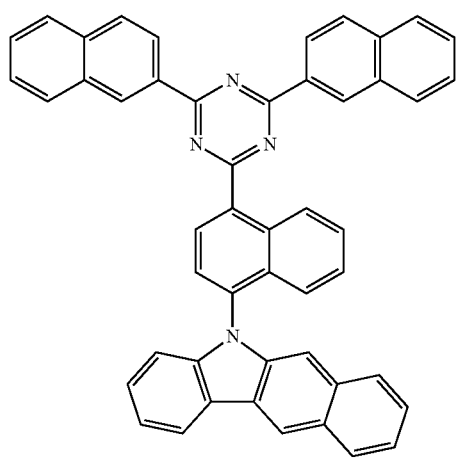
H-27
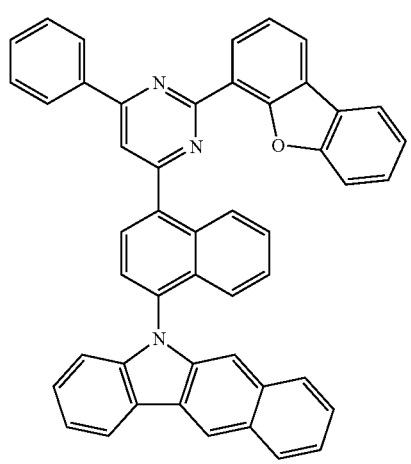
H-28
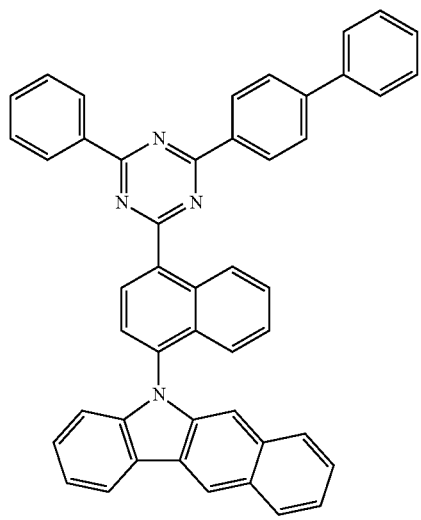
H-29
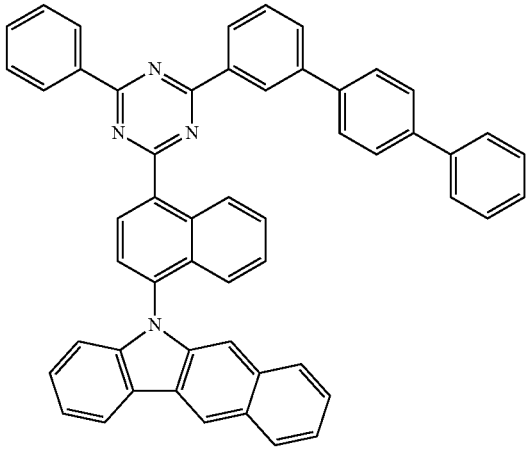
H-30
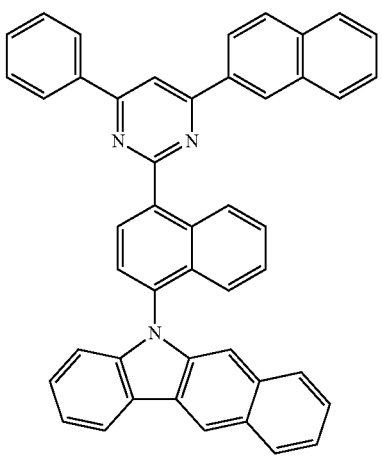
H-31
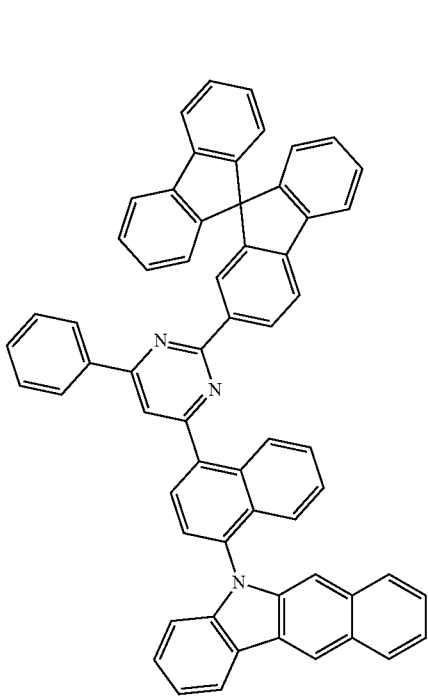

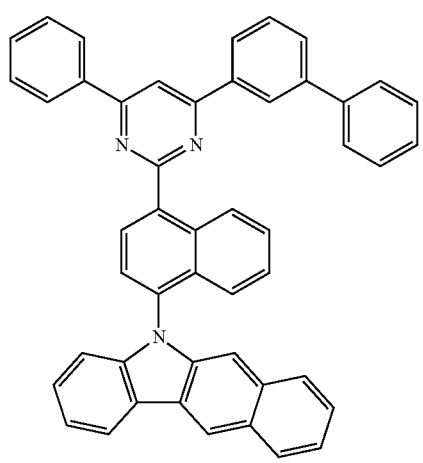
H-32
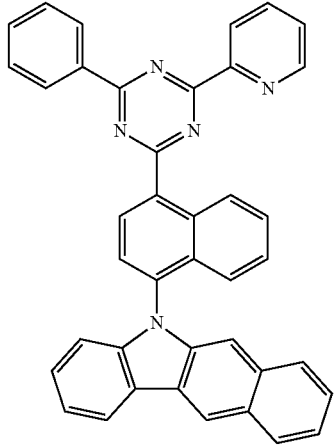
H-35
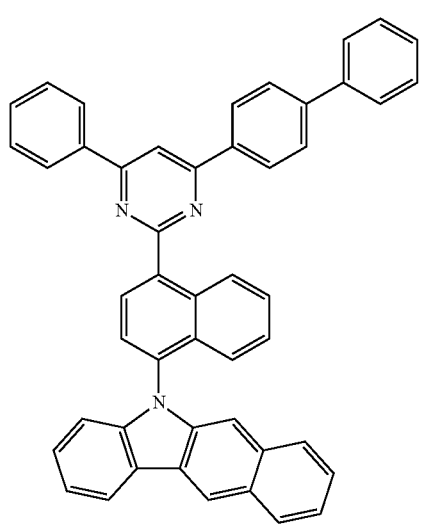
H-33
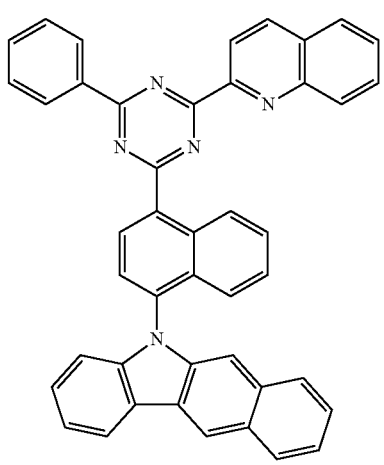
H-36
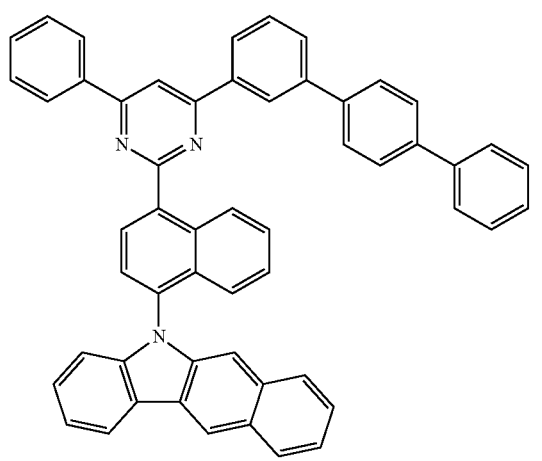
H-34
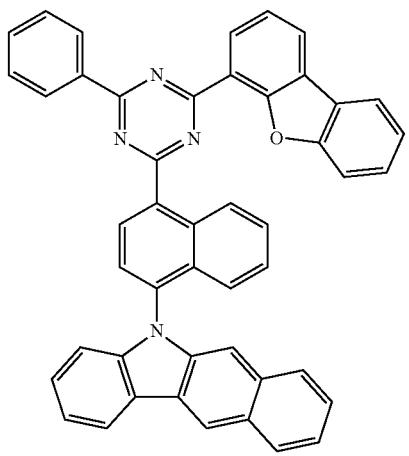
H-37

H-38
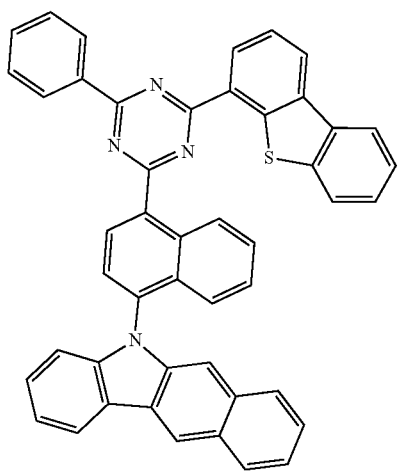
H-39
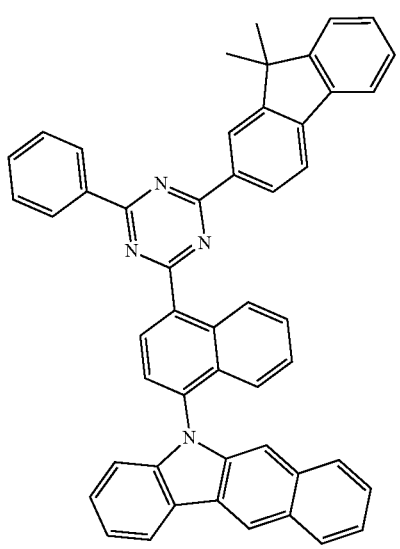
H-40
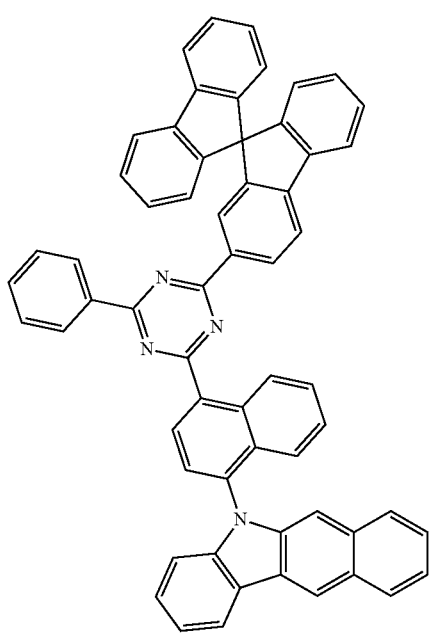
H-41
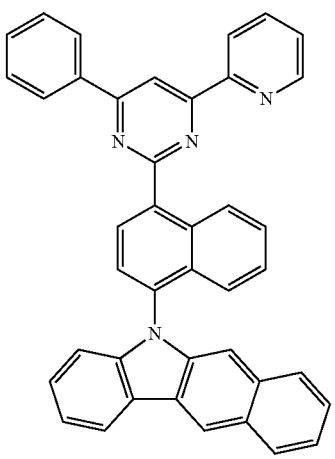
H-42
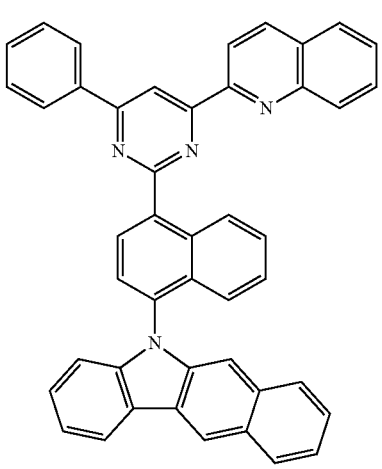
H-43
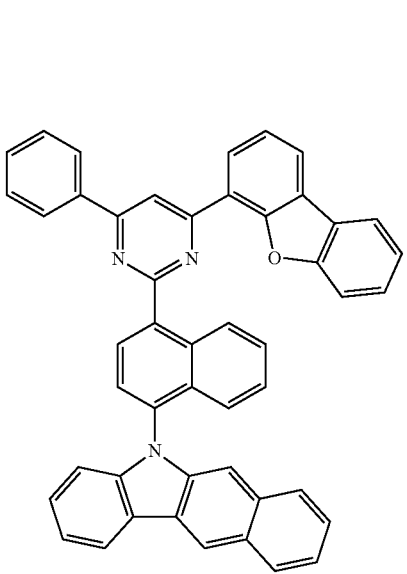

H-44
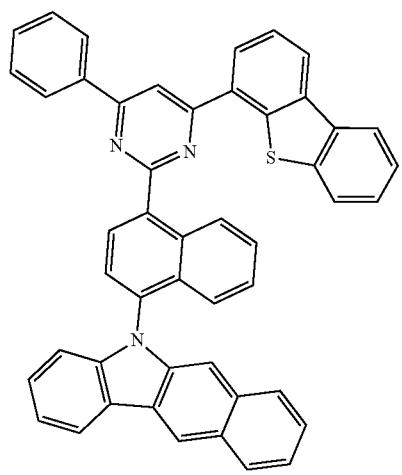
H-45
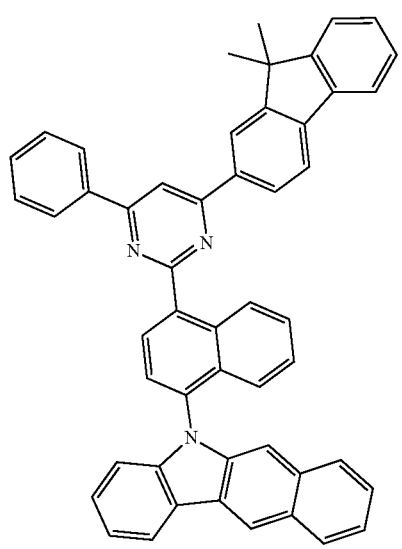
H-46
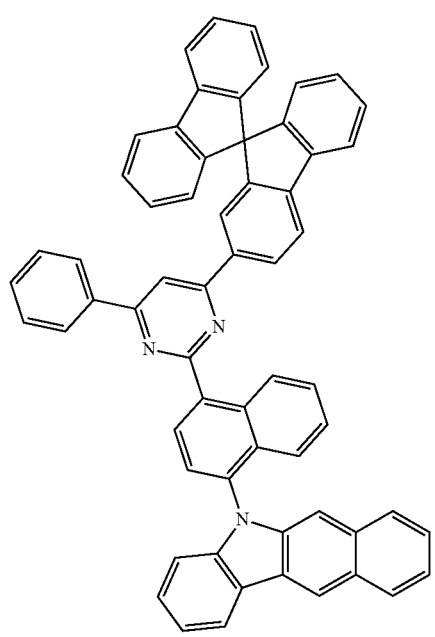
H-47
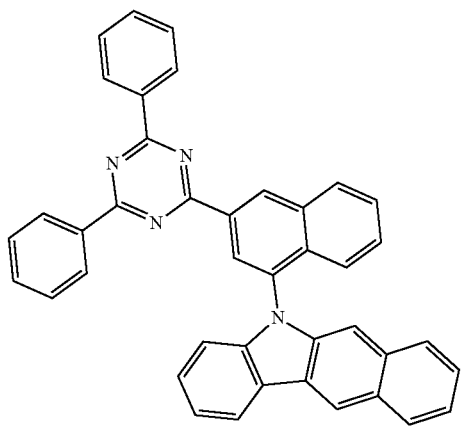
H-48
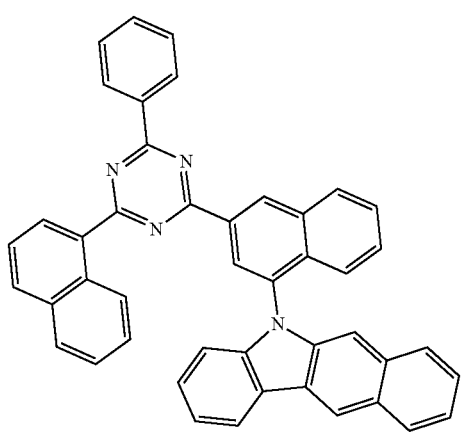
H-49
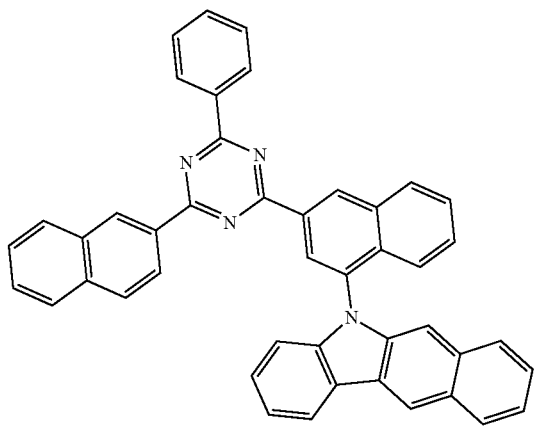

H-50
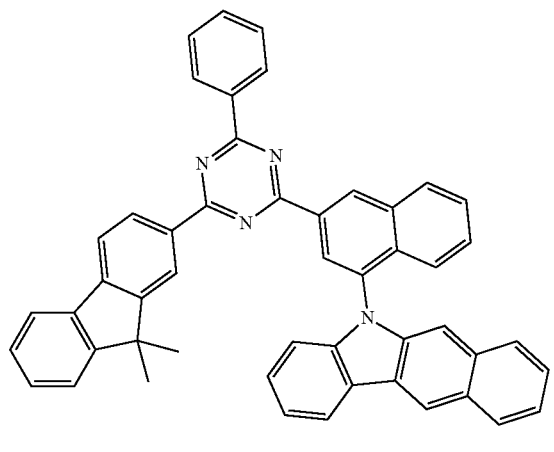
H-51
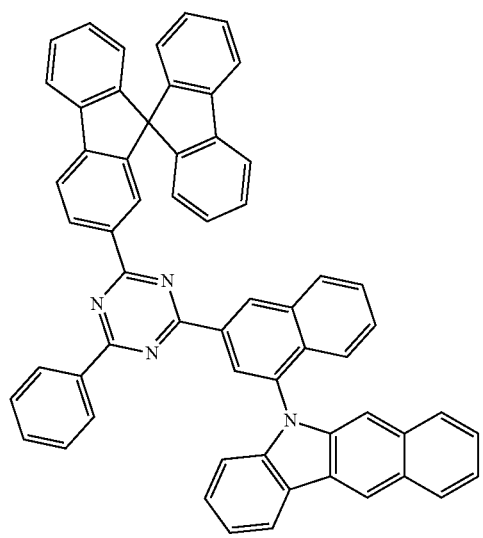
H-52
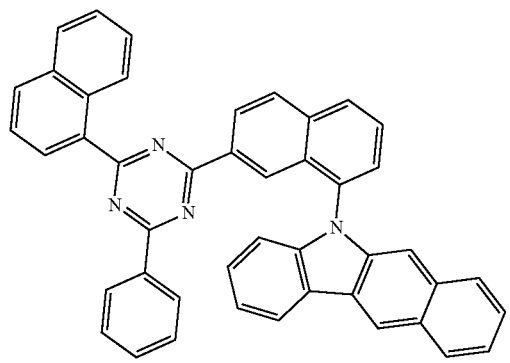
H-53
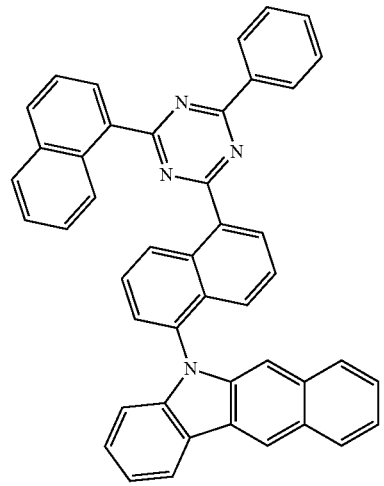
H-54
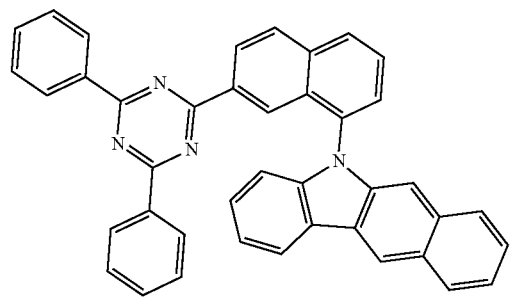
H-55
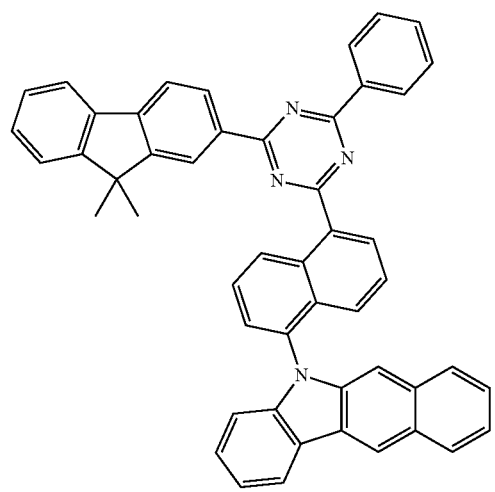

H-56
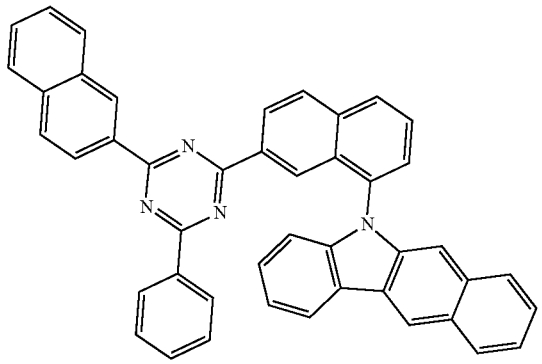
H-59
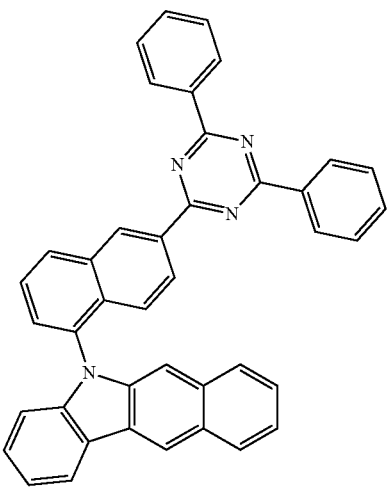
H-57
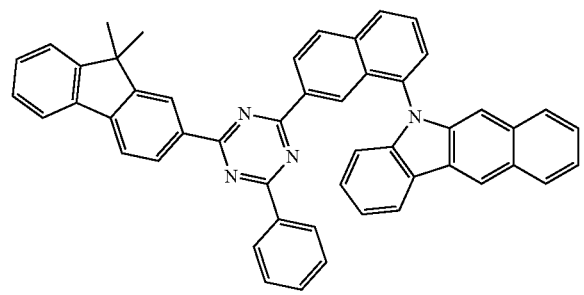
H-60
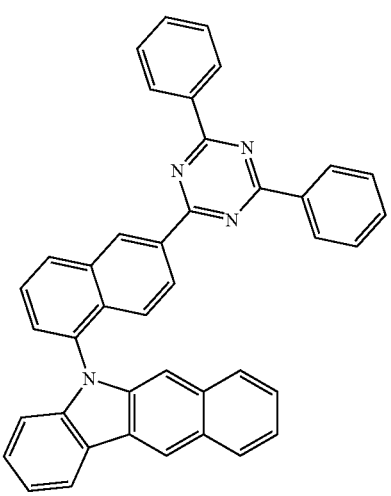
H-58
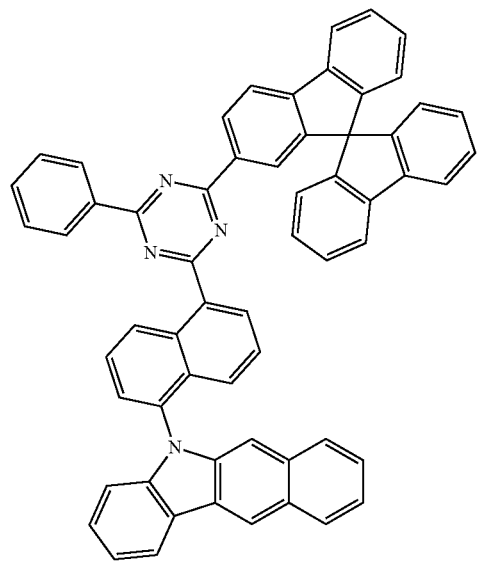
H-61
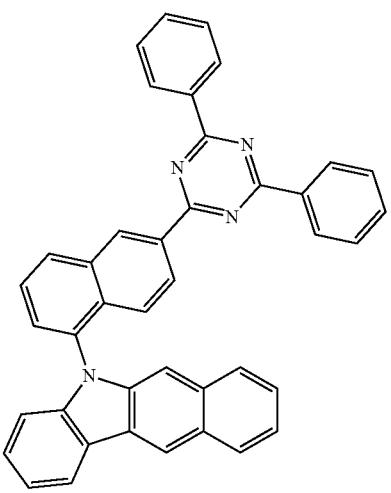

H-62
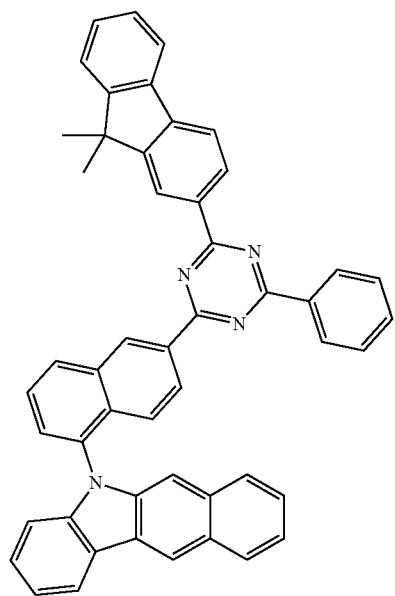
H-63
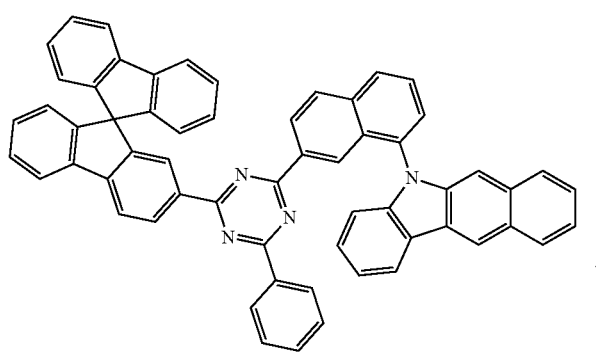
H-64
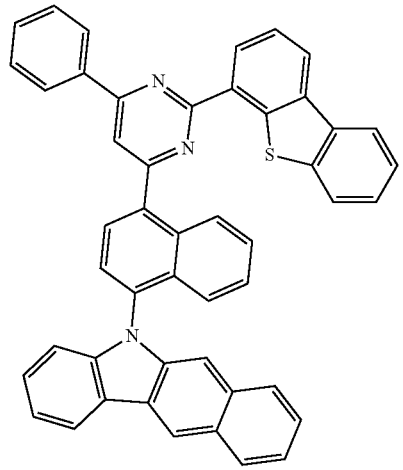
H-65
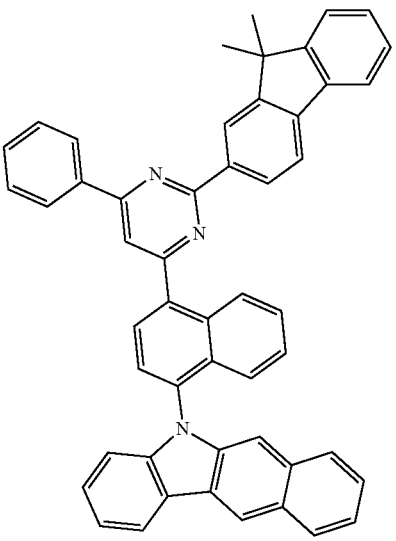
H-66
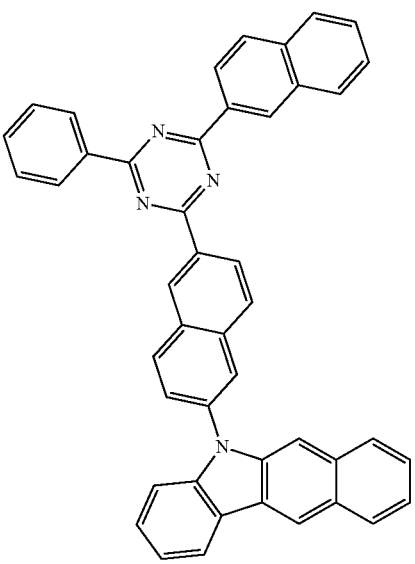
H-67
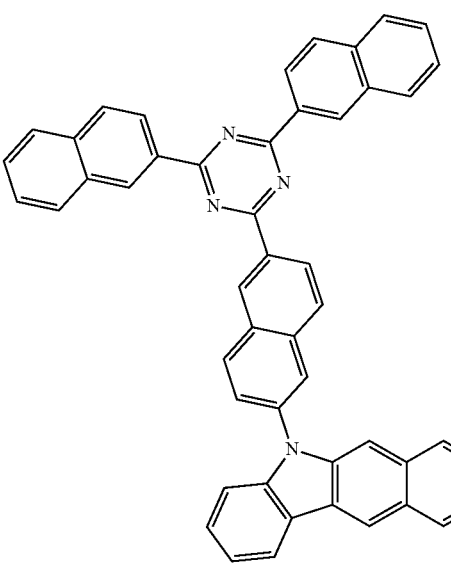

H-68
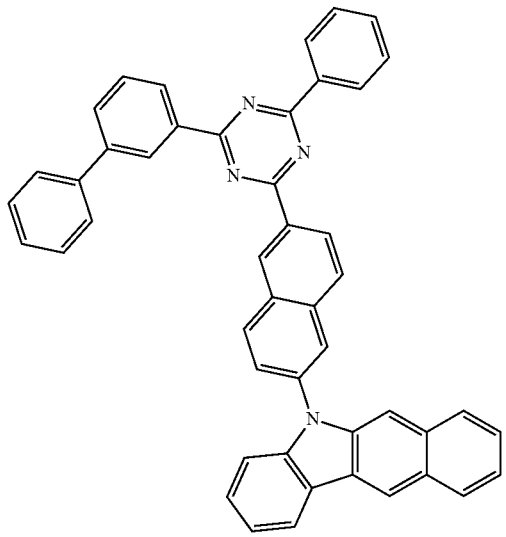
H-69
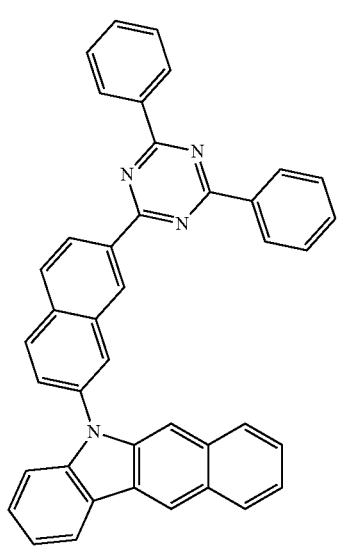
H-70
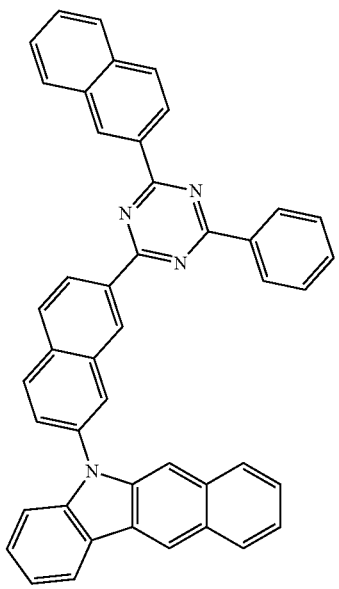
H-71
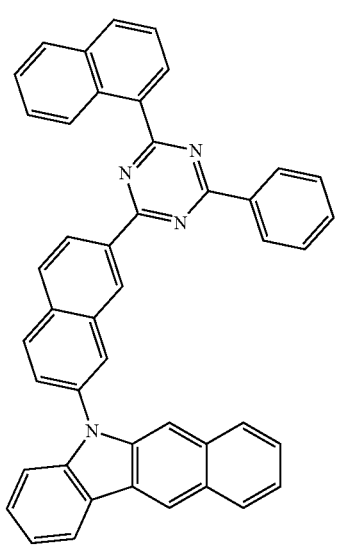

H-72
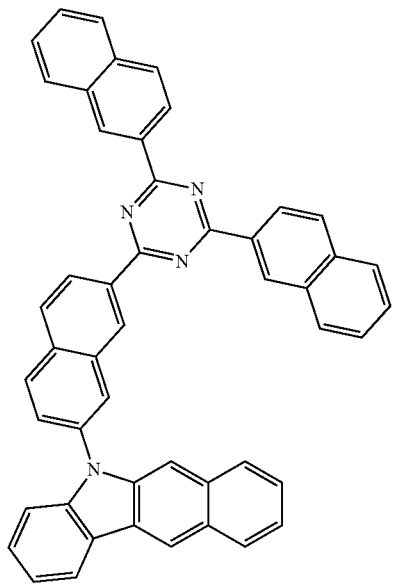
H-73
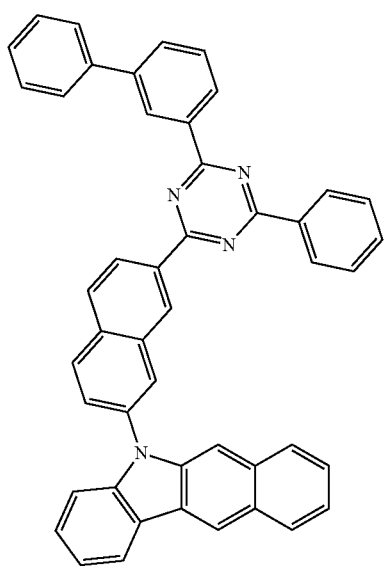
H-74
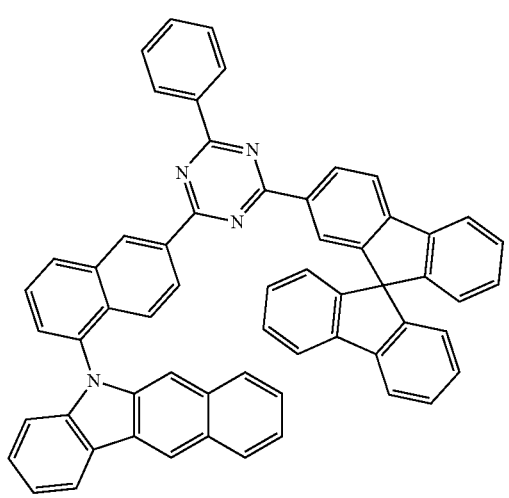
H-75
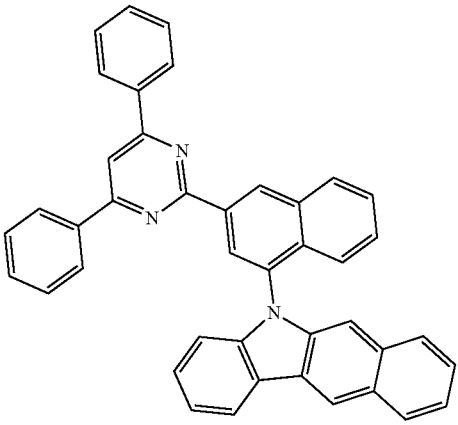
H-76
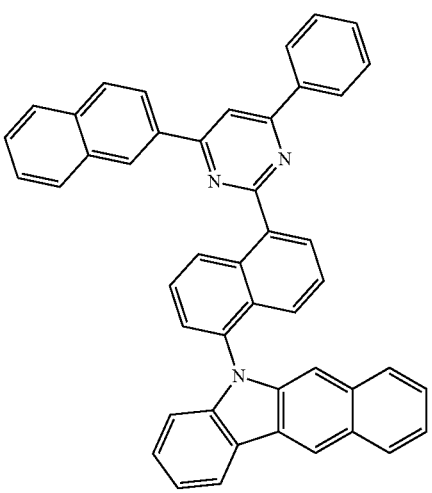
H-77
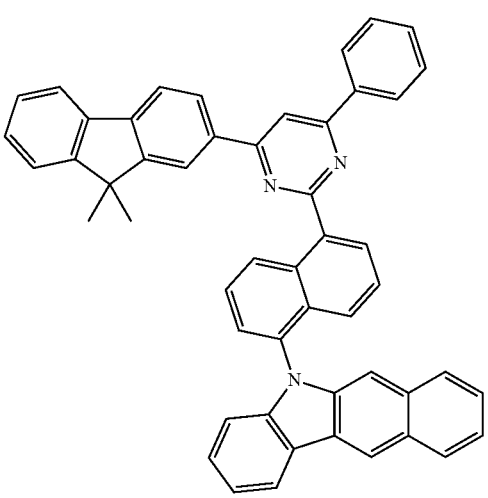

H-78
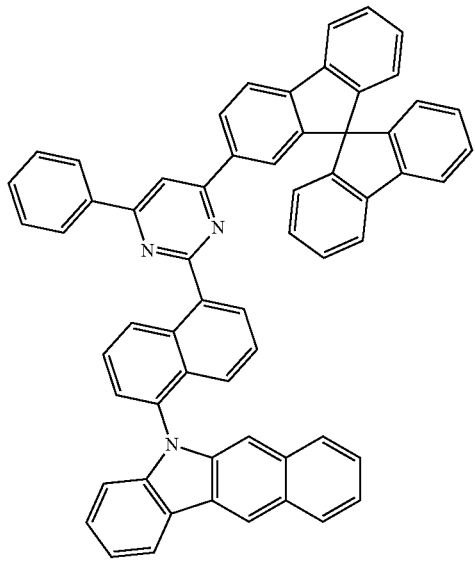
H-79
H-80
H-81
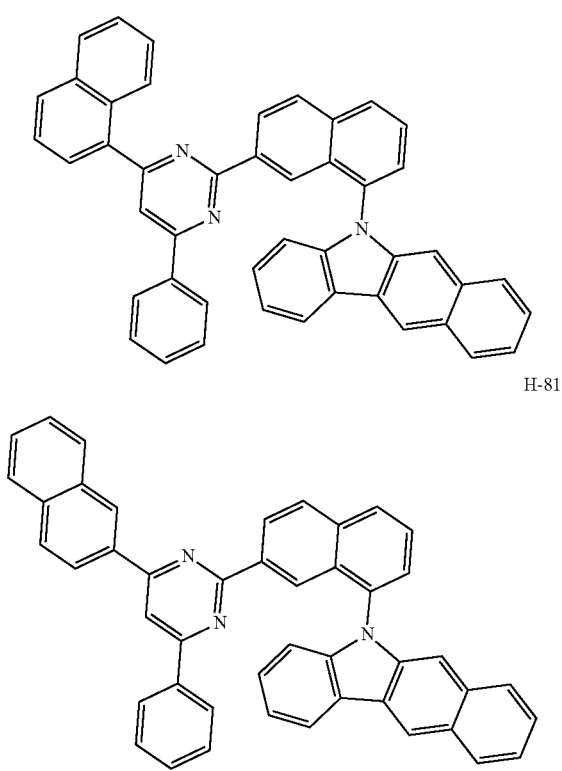
H-82
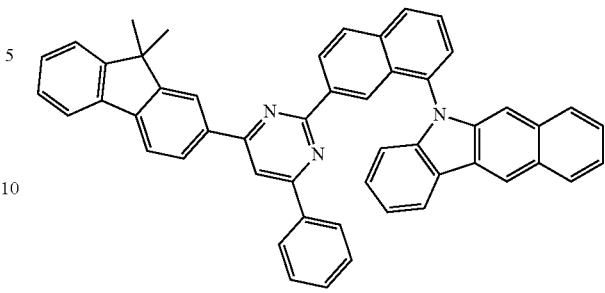
H-83
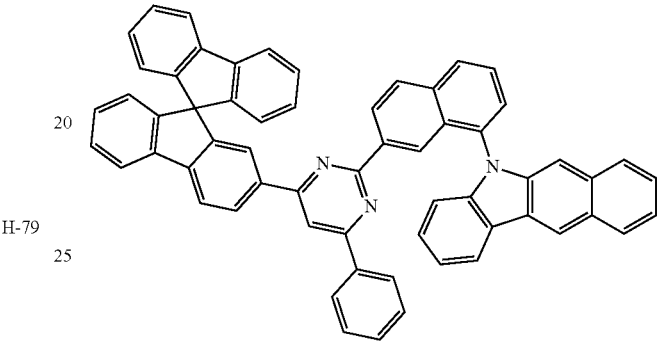
H-84
H-85
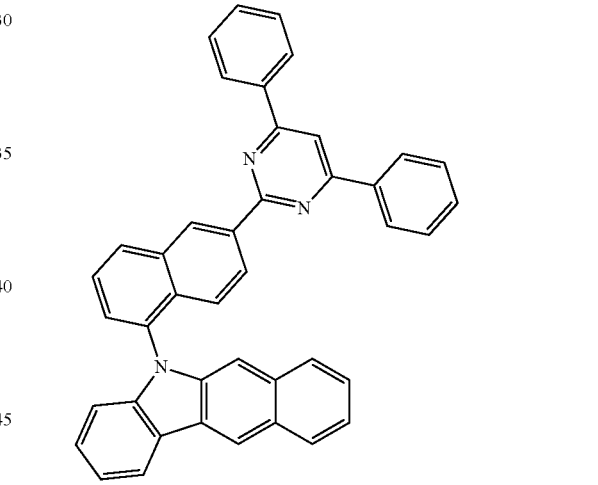

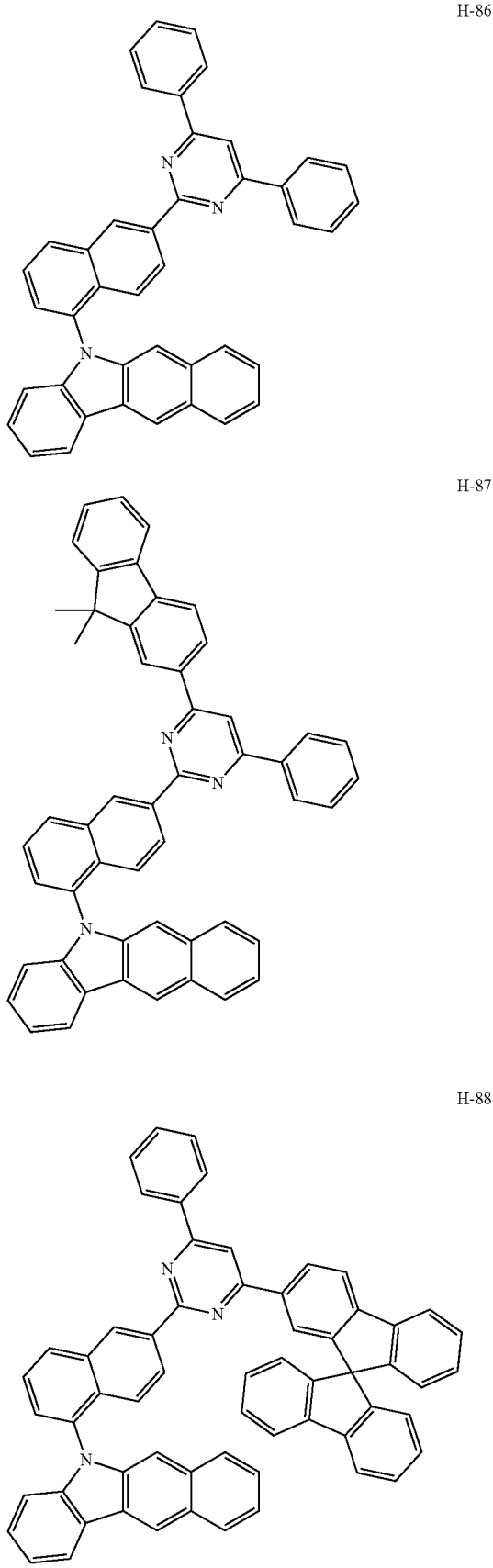
H-86
H-87
H-88
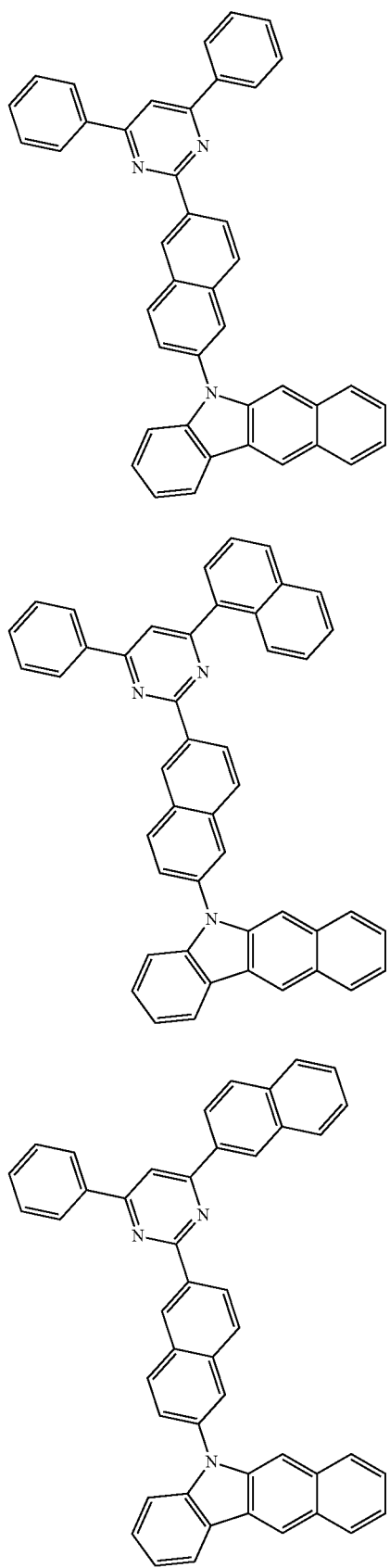
H-89
H-90
H-91

H-92
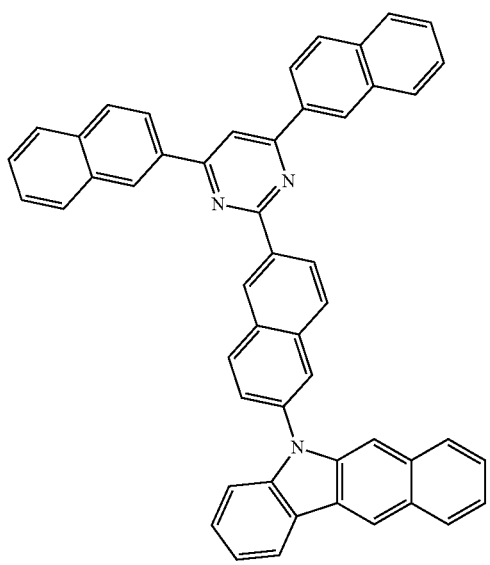
H-93
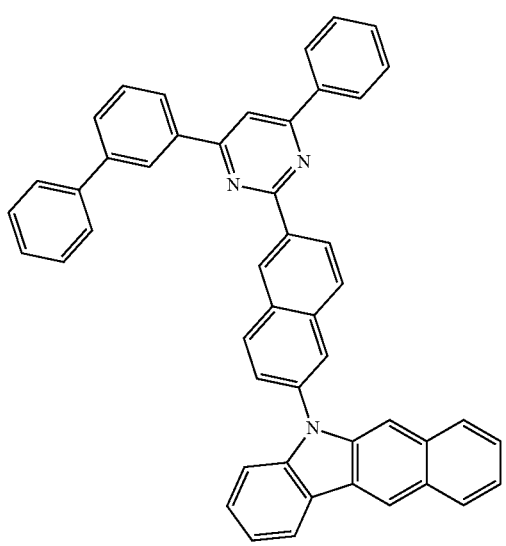
H-95
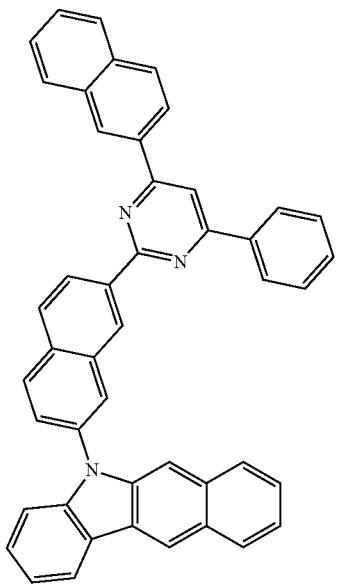
H-94
H-96
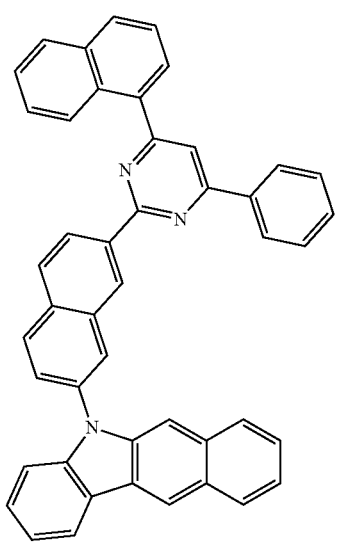

H-97
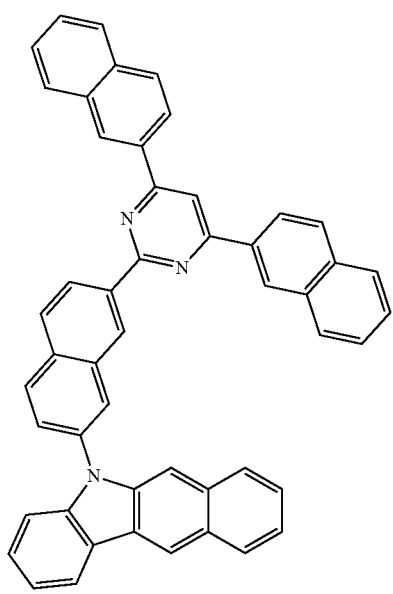
H-98
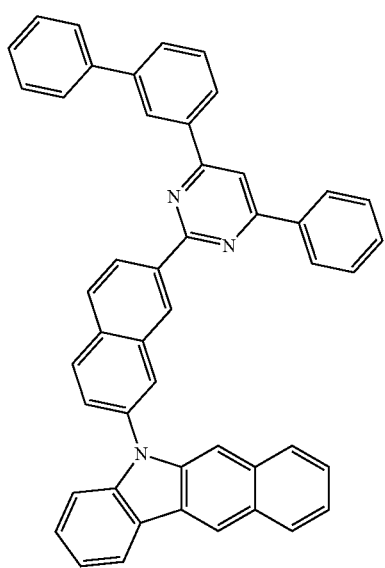
H-99
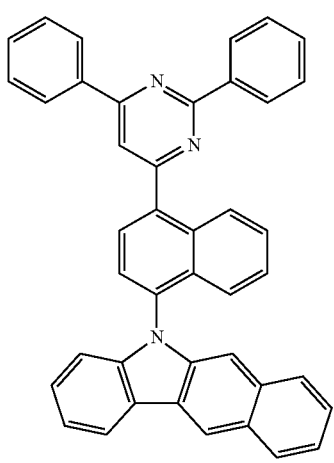
H-100
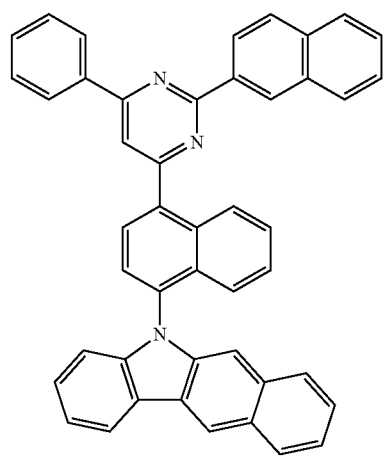
H-101
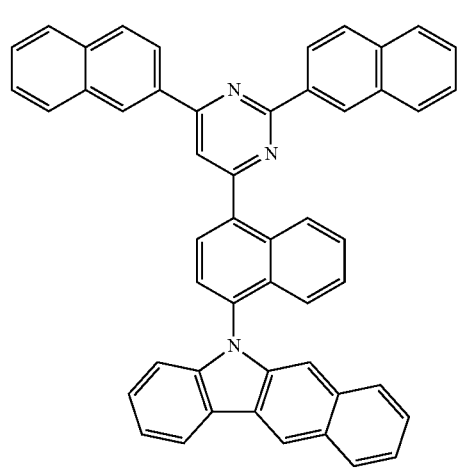
H-102
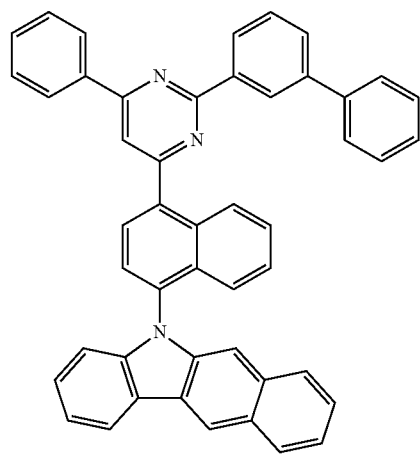

H-103
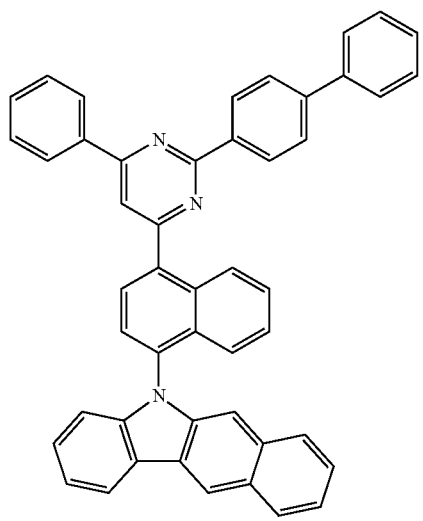
H-104
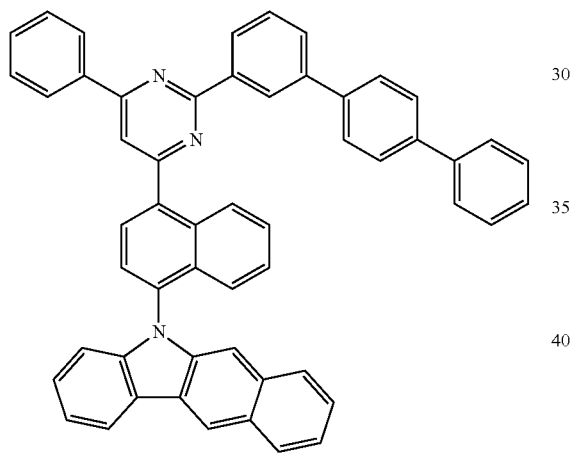
H-105
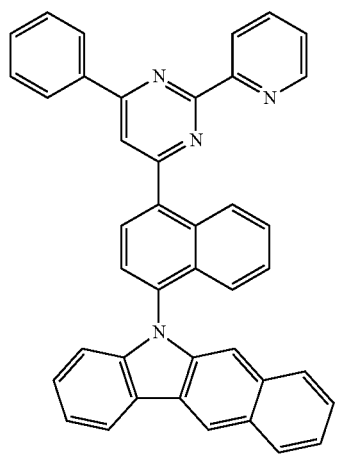
H-106
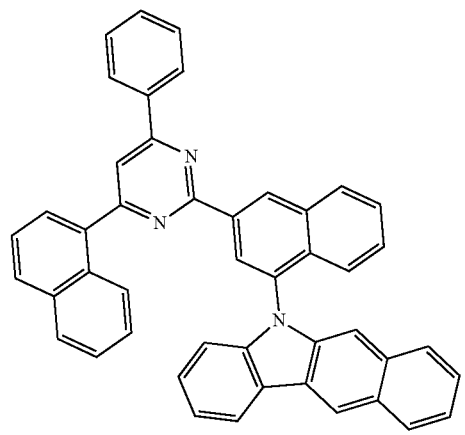
H-107
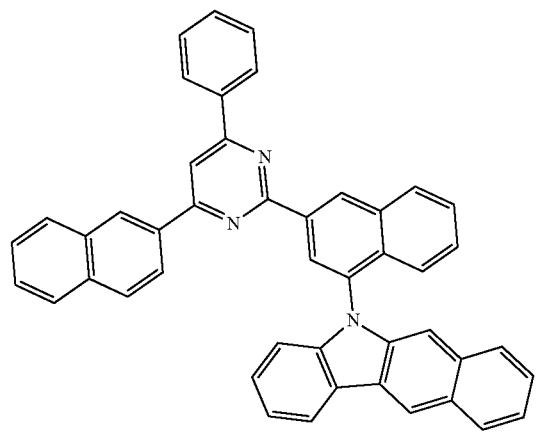
H-108
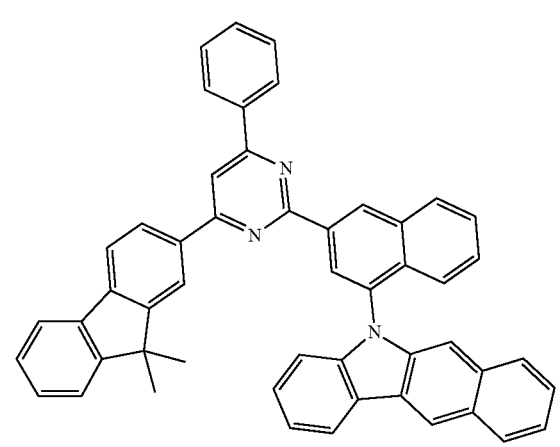

H-109

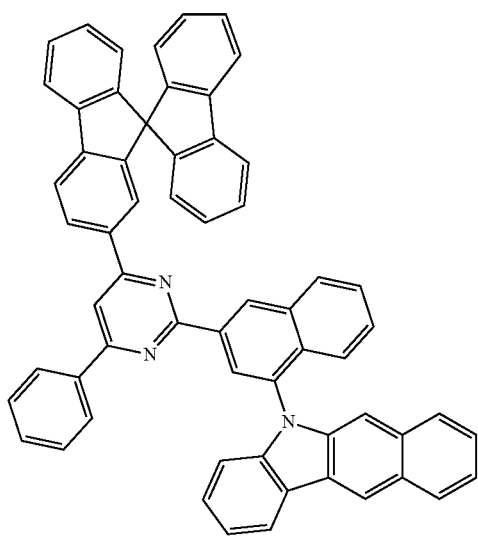

H-110

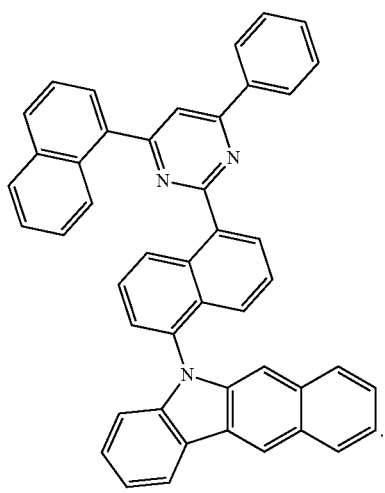

The compound of formula 1 according to the present disclosure can be prepared by a synthetic method known to a person skilled in the art. For example, it can be prepared according to the following reaction schemes.

[Reaction Scheme 1]

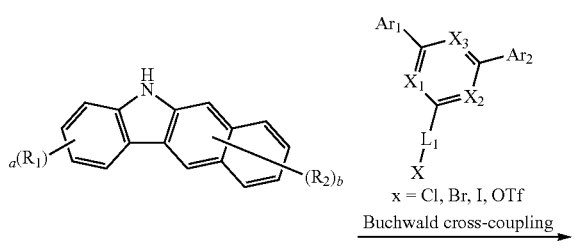

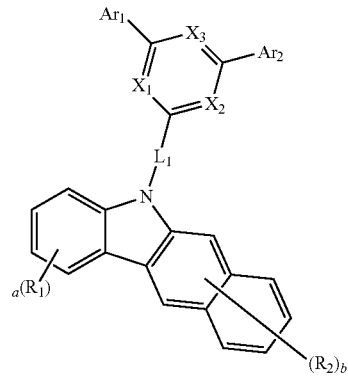

[Reaction Scheme 2]

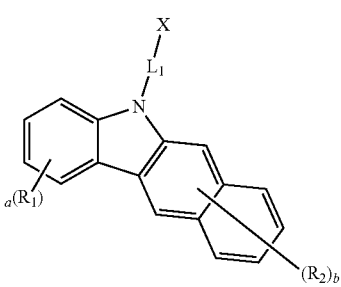

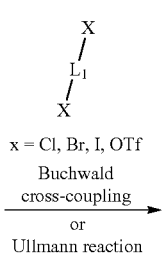

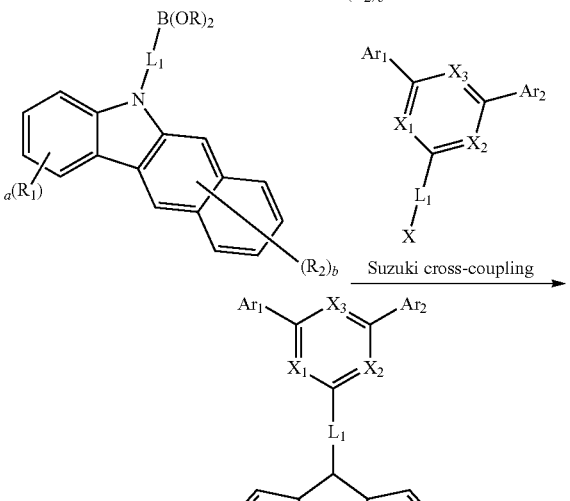

wherein $X_1$ to $X_3$, $L_1$, $Ar_1$, $Ar_2$, $R_1$, $R_2$, a, and b are as defined in formula 1, and OTf represents trifluoromethanesulfonate.

The present disclosure provides an organic electroluminescent material comprising the organic electroluminescent compound of formula 1, and an organic electroluminescent device comprising the material.

The above material can be comprised of the organic electroluminescent compound according to the present disclosure alone, or can further include conventional materials generally used in organic electroluminescent materials.

The organic electroluminescent device according to the present disclosure comprises a first electrode; a second electrode; and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The organic electroluminescent compound of formula 1 of the present disclosure may be comprised in one or more layers of the light-emitting layer, the hole injection layer, the hole transport layer, the hole auxiliary layer, the light-emitting auxiliary layer, the electron transport layer, the electron buffer layer, the electron injection layer, the interlayer, the hole blocking layer, and the electron blocking layer; and preferably in one or more layers of the light-emitting layer and the electron transport layer. Where used in the light-emitting layer, the organic electroluminescent compound of formula 1 of the present disclosure can be comprised as a host material. Preferably, the light-emitting layer can further comprise one or more dopants. If necessary, the organic electroluminescent compound of the present disclosure can be used as a co-host material. That is, the light-emitting layer can additionally comprise a compound other than the organic electroluminescent compound of formula 1 of the present disclosure (first host material) as a second host material. Herein, the weight ratio of the first host material to the second host material is in the range of 1:99 to 99:1.

The second host material can be any of the known hosts. The host selected from the group consisting of the compounds of formulas 11 to 17 below may be preferable.

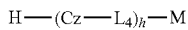
(11)

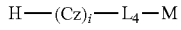
(12)

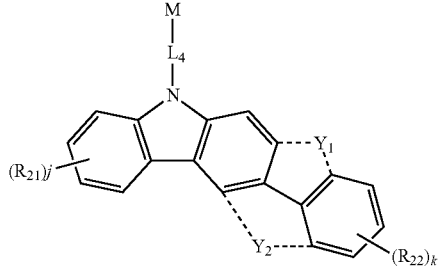
(13)

(14)

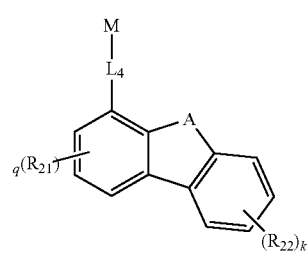
(15)

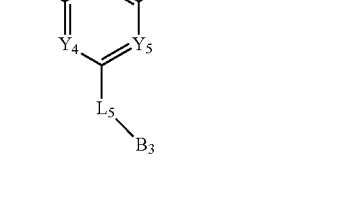
(16)

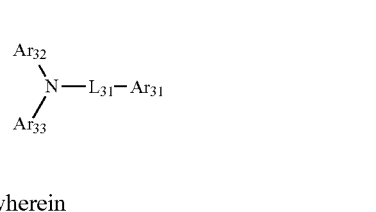
(17)

wherein
Cz represents the following structure:

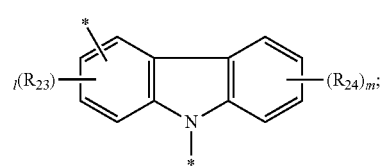

A represents —O— or —S—;

$R_{21}$ to $R_{24}$, each independently, represent hydrogen, deuterium, a halogen, a substituted or unsubstituted (C1-C30) alkyl, a substituted or unsubstituted (C6-C30)aryl, a substituted or unsubstituted (5- to 30-membered)heteroaryl, or —SiR$_{25}$R$_{26}$R$_{27}$; in which $R_{25}$ to $R_{27}$, each independently, represent a substituted or unsubstituted (C1-C30)alkyl, or a substituted or unsubstituted (C6-C30)aryl; $L_4$ represents a single bond, a substituted or unsubstituted (C6-C30)arylene, or a substituted or unsubstituted (5- to 30-membered)heteroarylene; M represents a substituted or unsubstituted (C6-C30)aryl, or a substituted or unsubstituted (5- to 30-membered)heteroaryl; $Y_1$ and $Y_2$, each independently, represent —O—, —S—, —N(R$_{31}$)— or —C(R$_{32}$)(R$_{33}$)—, with the proviso that $Y_1$ and $Y_2$ are not present simultaneously; $R_{31}$ to $R_{33}$, each independently, represent a substituted or unsubstituted (C1-C30)alkyl, a substituted or unsubstituted (C6-C30)aryl, or a substituted or unsubstituted (5- to 30-membered)heteroaryl; $R_{32}$ and $R_{33}$ may be the same or different; h and i, each independently, represent an integer of 1 to 3; j, k, l, and m, each independently, represent an integer of 1 to 4; q represents an integer of 1 to 3; if h, i, j, k, l, m, or q represents an integer of 2 or more, each (Cz-L$_4$), each (Cz), each $R_{21}$, each $R_{22}$, each $R_{23}$, or each $R_{24}$ may be the same or different;

$Y_3$ to $Y_5$, each independently, represent $CR_{34}$ or N;

$R_{34}$ represents hydrogen, a substituted or unsubstituted (C1-C30)alkyl, a substituted or unsubstituted (C6-C30)aryl, or a substituted or unsubstituted (5- to 30-membered)heteroaryl;

$B_1$ and $B_2$, each independently, represent hydrogen, a substituted or unsubstituted (C6-C30)aryl, or a substituted or unsubstituted (5- to 30-membered)heteroaryl; $B_3$ represents a substituted or unsubstituted (C6-C30)aryl, or a substituted or unsubstituted (5- to 30-membered)heteroaryl;

$L_5$ represents a single bond, a substituted or unsubstituted (C6-C30)arylene, or a substituted or unsubstituted (5- to 30-membered)heteroarylene;

$Ar_{31}$ to $Ar_{33}$, each independently, represent a substituted or unsubstituted (C6-C30)aryl, or a substituted or unsubstituted (3- to 30-membered)heteroaryl; or are linked to an adjacent substituent to form a substituted or unsubstituted, mono- or polycyclic, (3- to 30-membered) alicyclic, aromatic ring, or a combination thereof; and $L_{31}$ represents a single bond, a substituted or unsubstituted (C6-C30)arylene, or a substituted or unsubstituted (3- to 30-membered)heteroarylene.

In formula 17, $Ar_{31}$ to $Ar_{33}$, preferably each independently, represent a substituted or unsubstituted (C6-C25)aryl, or a substituted or unsubstituted (5- to 25-membered)heteroaryl. Specifically, $Ar_{31}$ to $Ar_{33}$, preferably each independently, may represent a substituted or unsubstituted phenyl, a substituted or unsubstituted naphthyl, a substituted or unsubstituted biphenyl, a substituted or unsubstituted fluorenyl, a substituted or unsubstituted benzofluorenyl, a substituted or unsubstituted dibenzofuranyl, a substituted or unsubstituted dibenzothiophenyl, a substituted or unsubstituted carbazolyl, a substituted or unsubstituted benzocarbazolyl, a substituted or unsubstituted dibenzocarbazolyl, a substituted or unsubstituted indolocarbazolyl, a substituted or unsubstituted indenocarbazolyl, a substituted or unsubstituted benzothienocarbazolyl, a substituted or unsubstituted benzofurocarbazolyl, a substituted or unsubstituted benzoindolocarbazolyl, a substituted or unsubstituted dibenzoindolocarbazolyl, a substituted or unsubstituted phenanthrooxazolyl, a substituted or unsubstituted phenanthrothiazolyl, etc., but not limited thereto.

$L_{31}$ preferably represents a single bond, a substituted or unsubstituted (C6-C25)arylene, or a substituted or unsubstituted (5- to 20-membered)heteroarylene, and more preferably represents a single bond, a substituted or unsubstituted (C6-C20)arylene, or an unsubstituted (5- to 15-membered)heteroarylene. Specifically, $L_{31}$ may represent a single bond, a substituted or unsubstituted phenylene, a substituted or unsubstituted naphthylene, a substituted or unsubstituted biphenylene, a substituted or unsubstituted fluorenylene, a substituted or unsubstituted benzofluorenylene, a substituted or unsubstituted terphenylene, a substituted or unsubstituted naphthylphenylene, a substituted or unsubstituted phenylnaphthylene, etc., but not limited thereto.

Specifically, the examples of the second host material are as follows, but are not limited thereto.

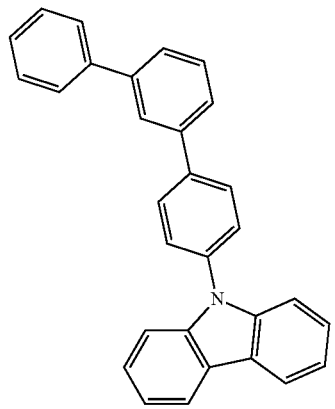

B-1

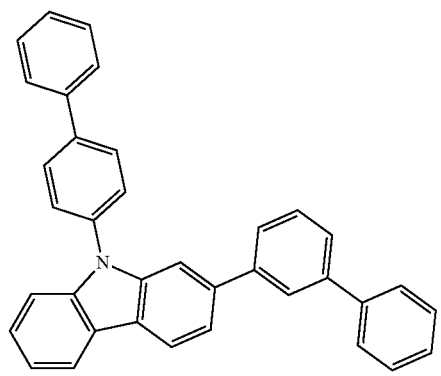

B-2

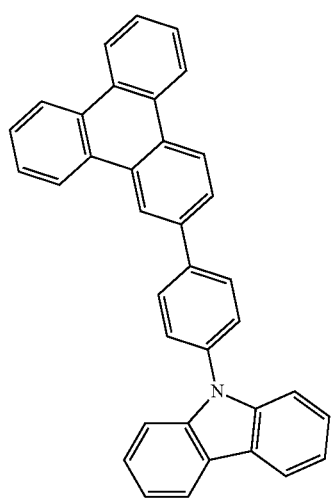

B-3

B-4
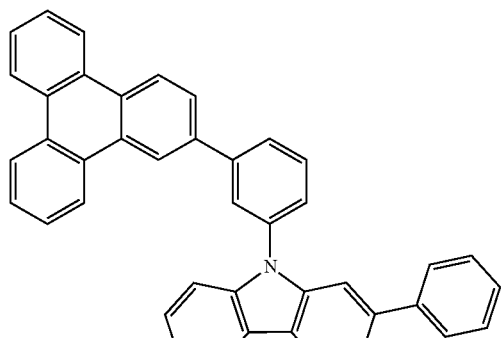
B-5
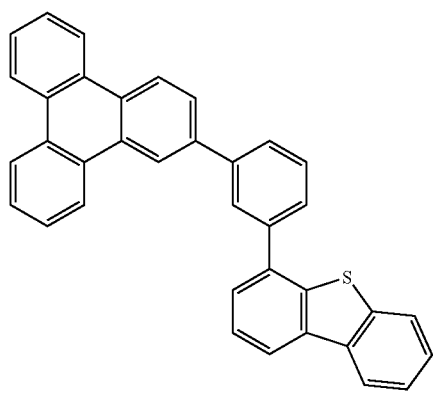
B-6
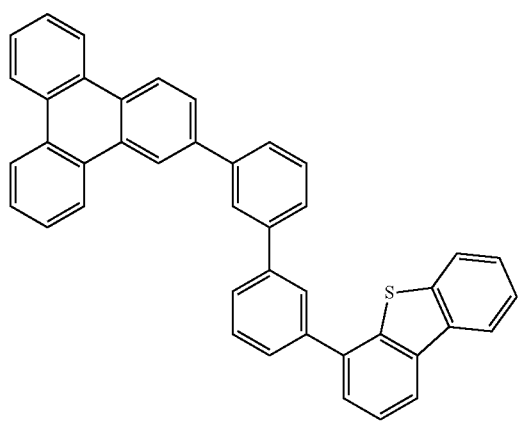
B-7
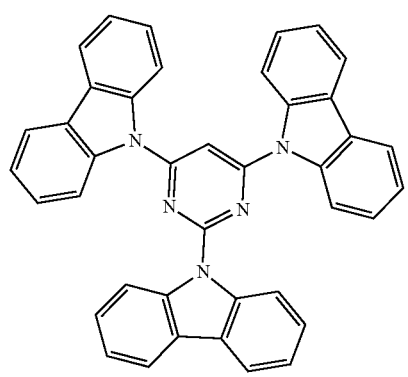
B-8
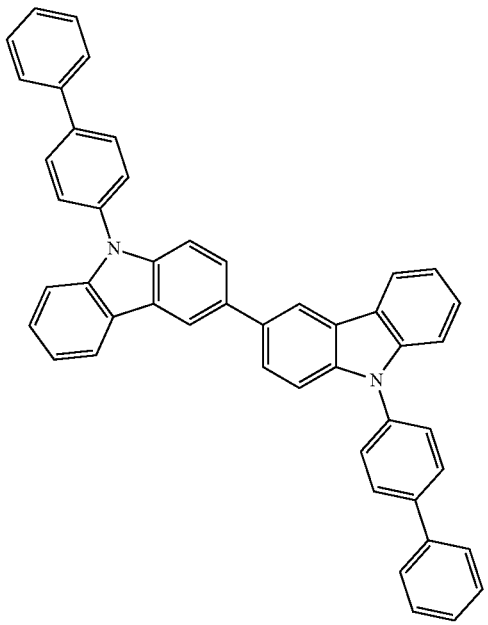
B-9
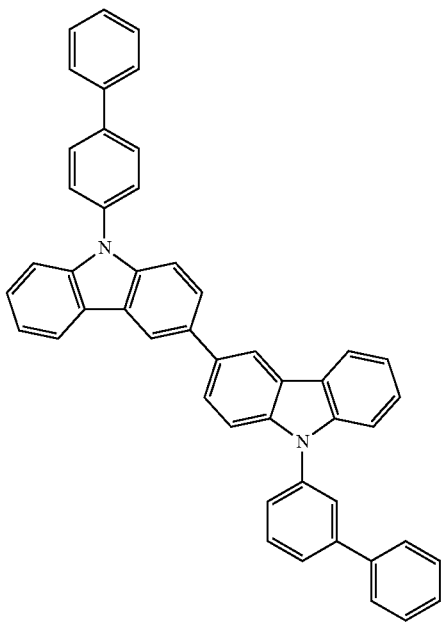

B-10
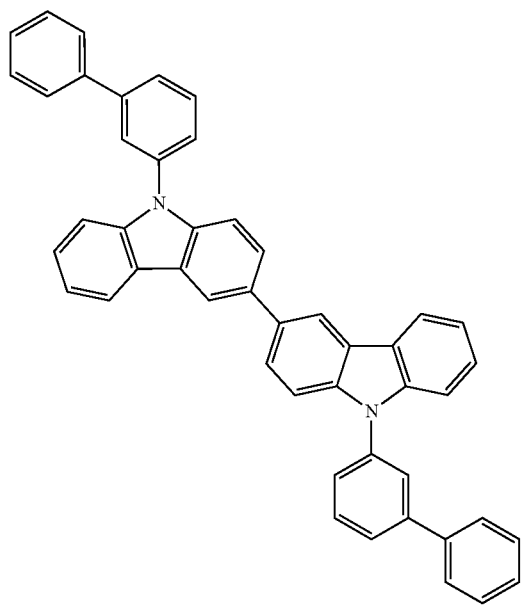
B-11
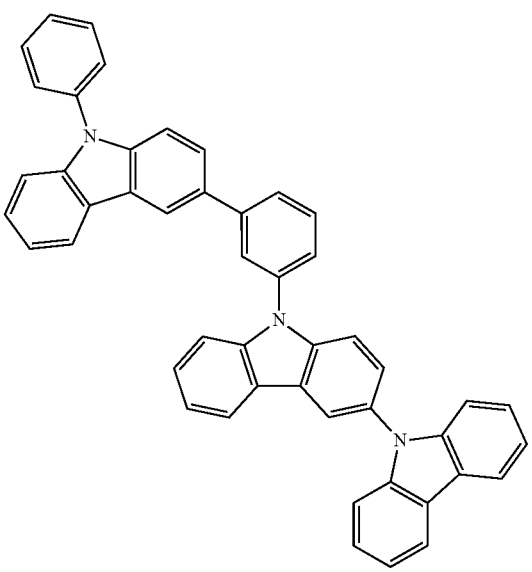
B-12
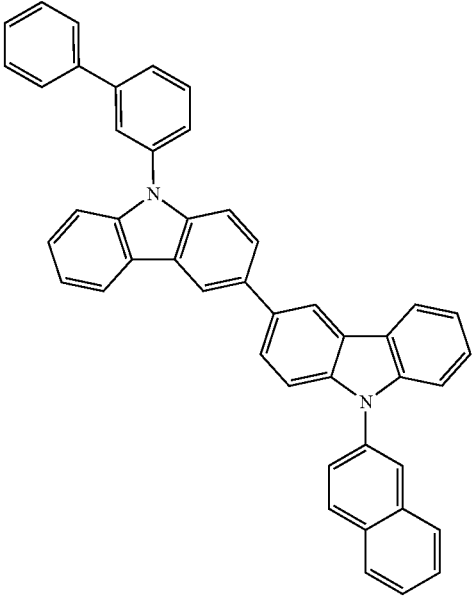
B-13
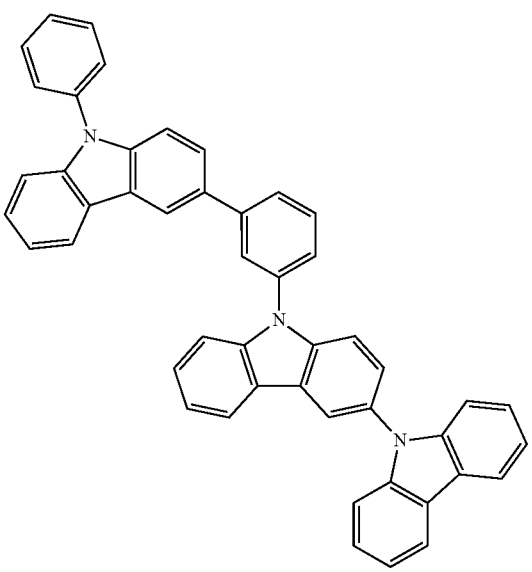
B-14
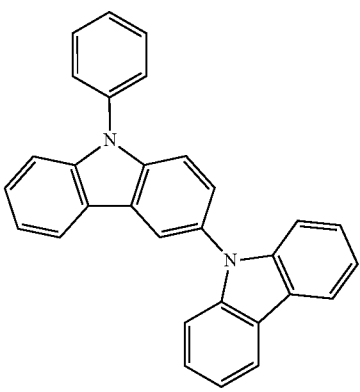

-continued
B-15
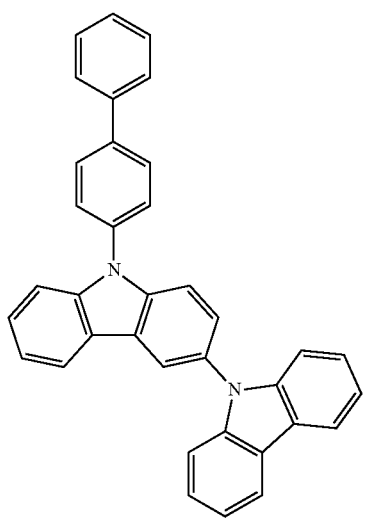
B-16
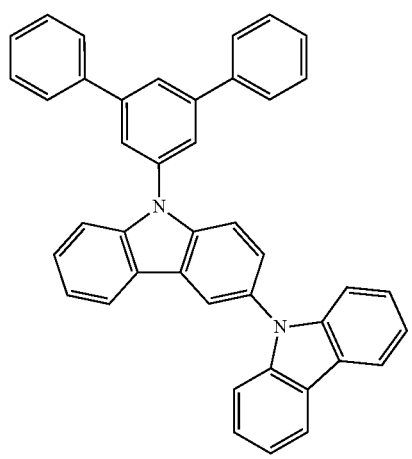
B-17
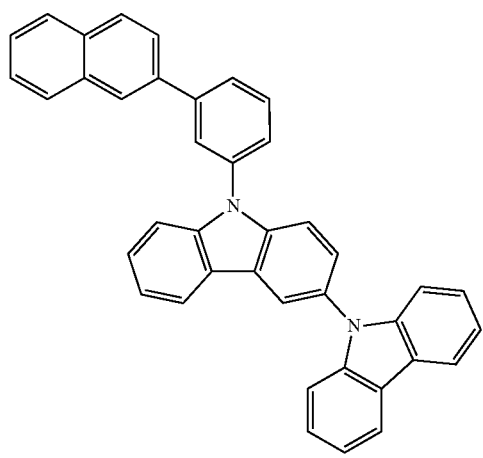
-continued
B-18
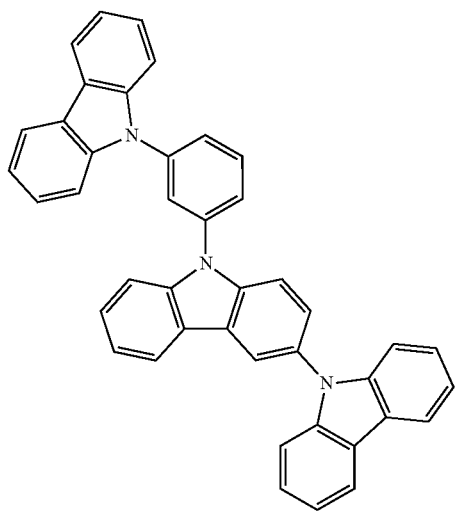
B-19
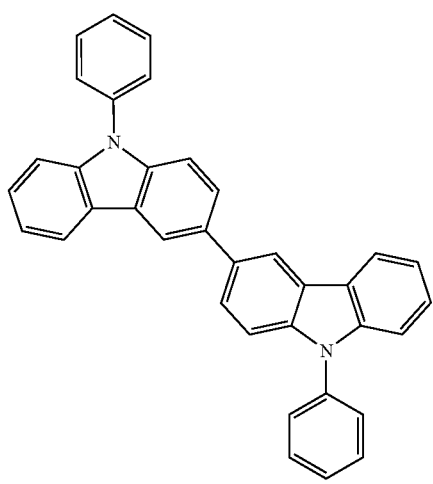
B-20
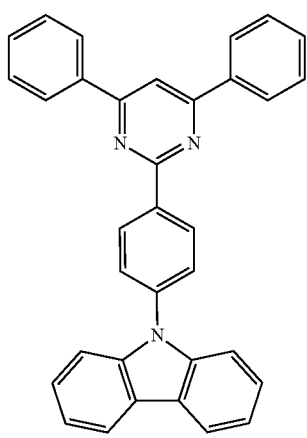

B-21
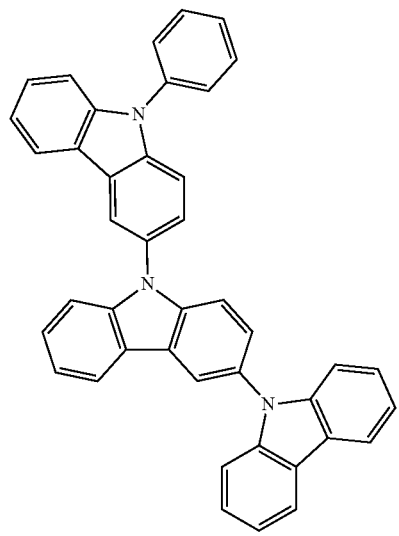
B-23
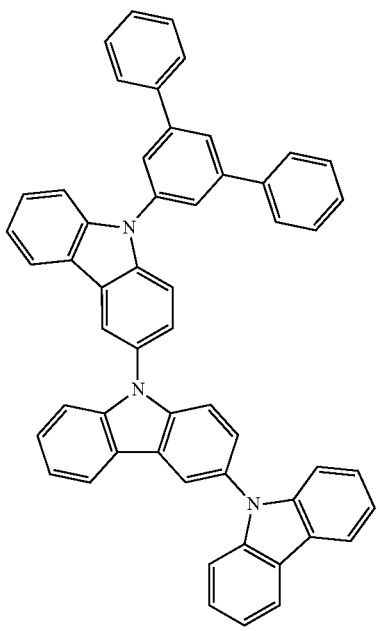
B-22
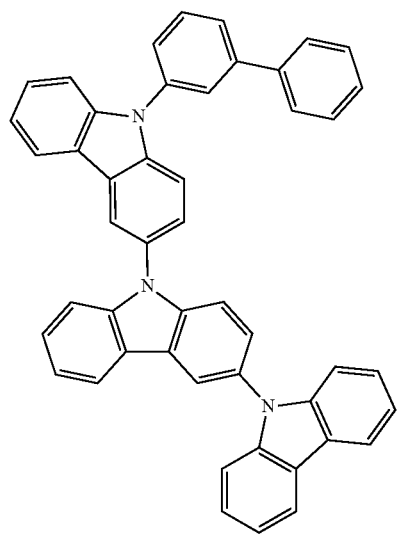
B-24
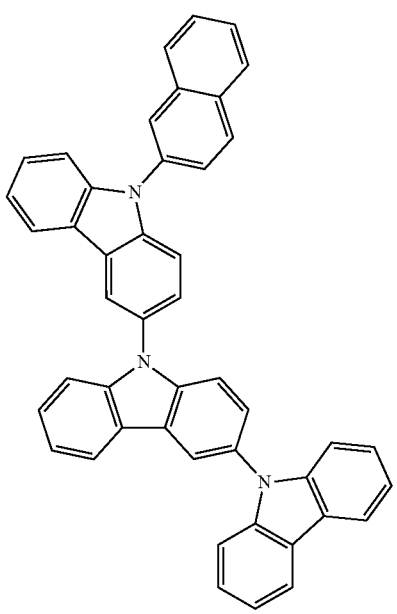

B-25
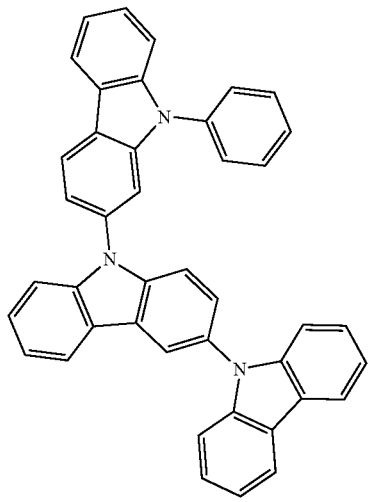
B-26
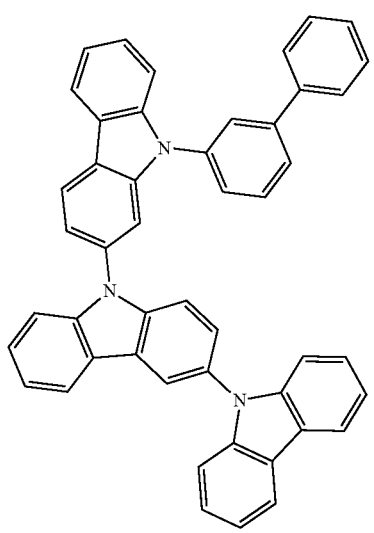
B-27
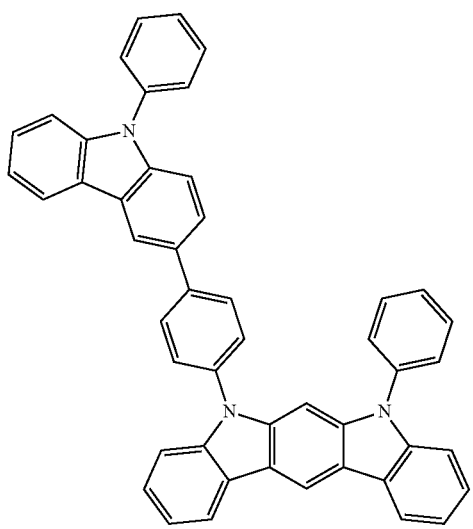
B-28
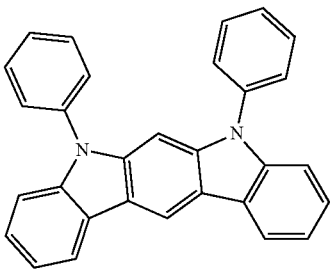
B-29
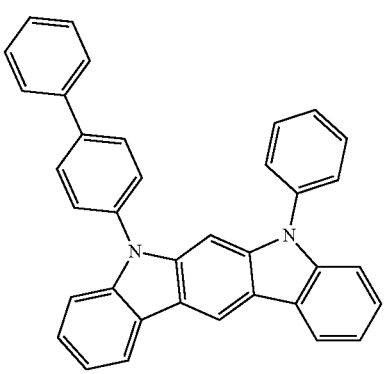
B-30
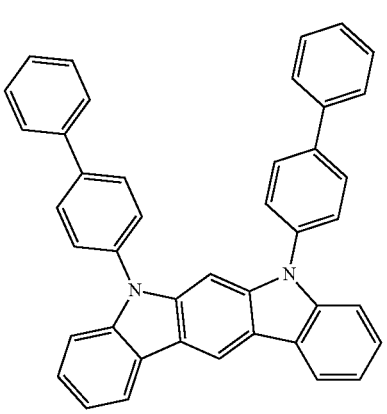
B-31
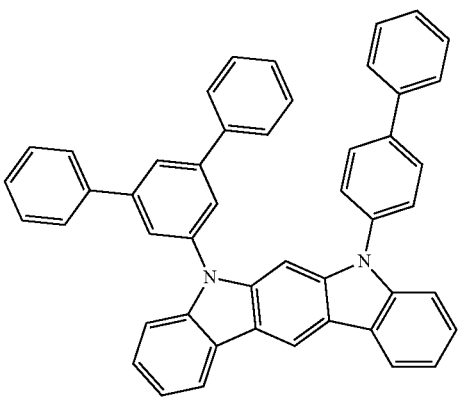

B-32
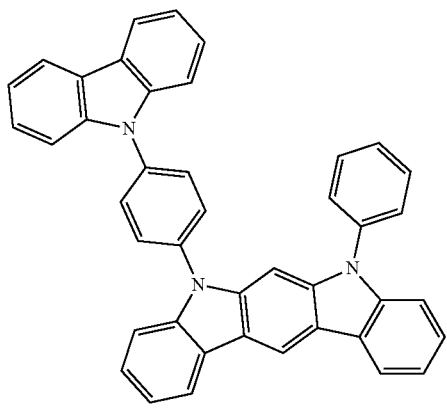
B-33
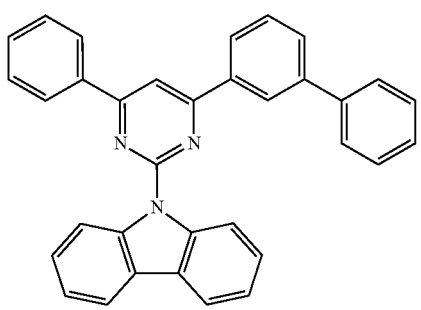
B-34
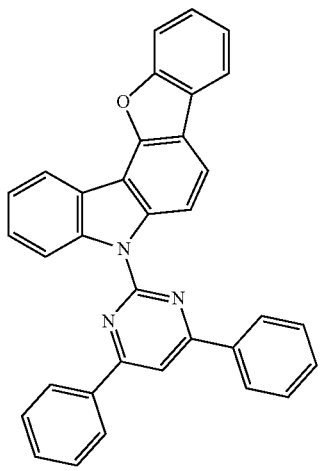
B-35
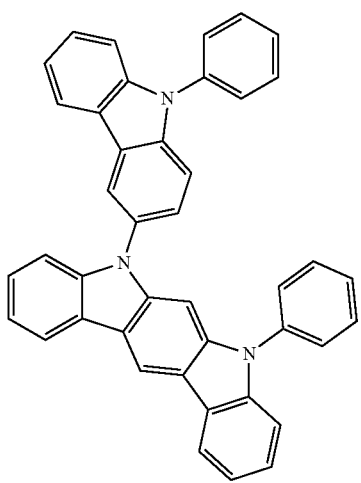
B-36
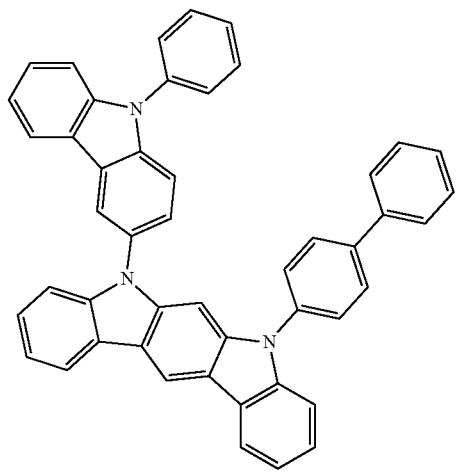
B-37
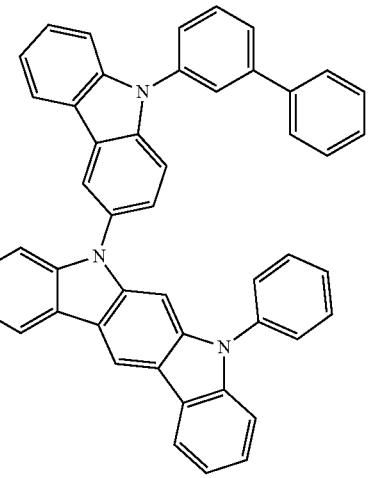
B-38
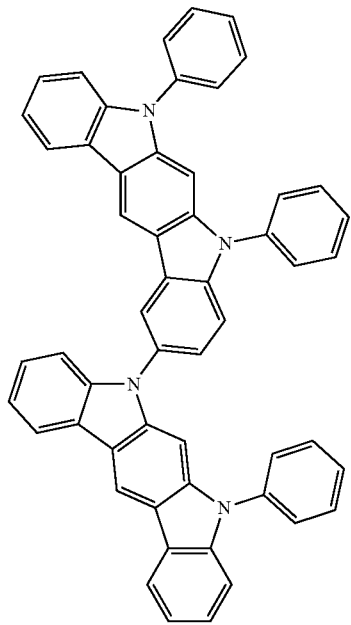

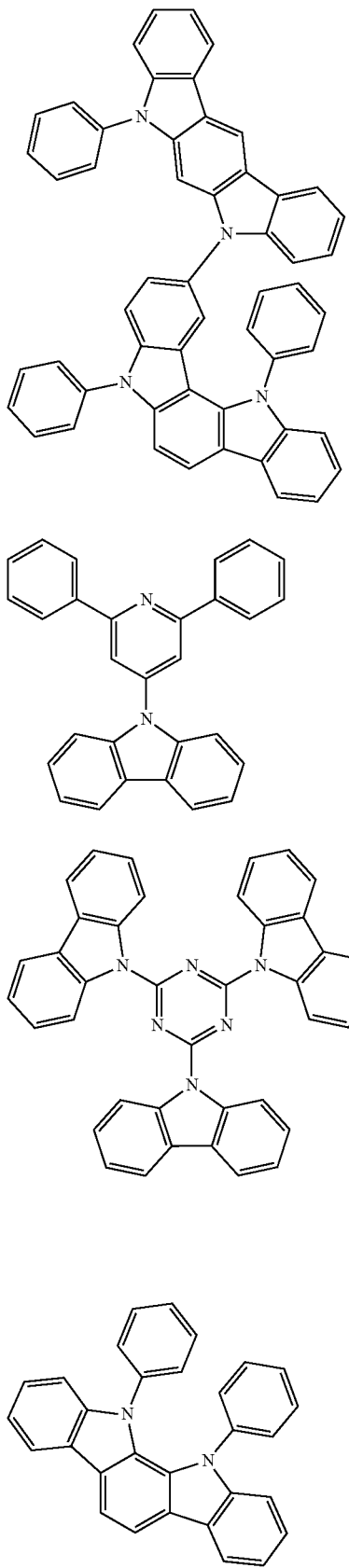
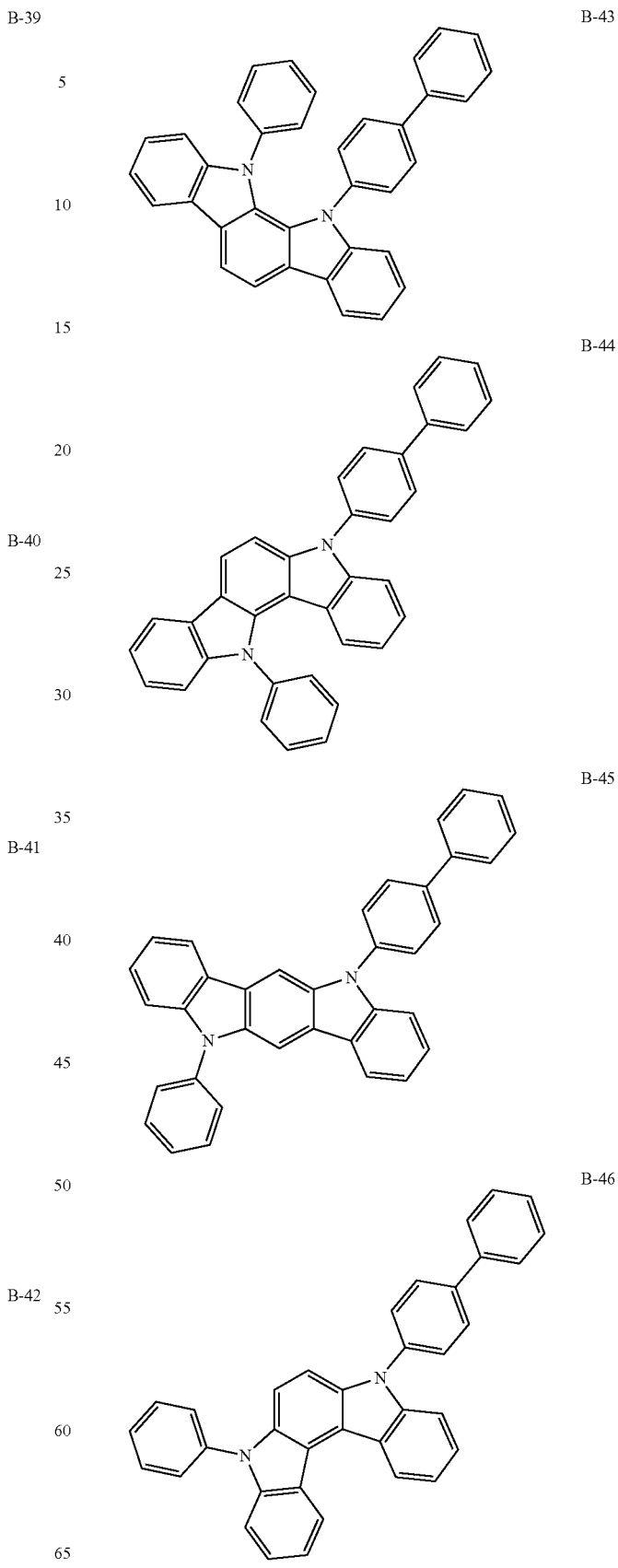

B-47
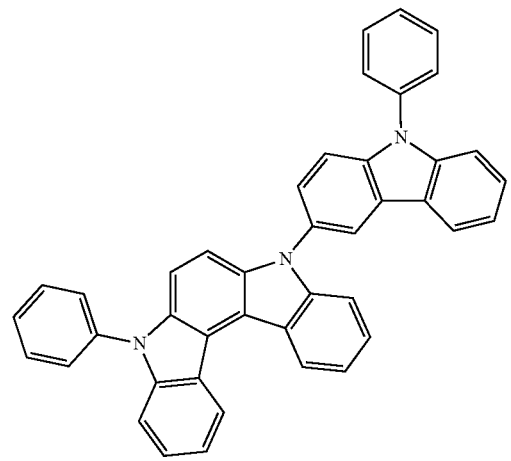
B-48
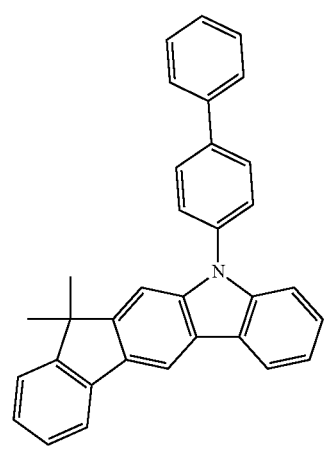
B-49
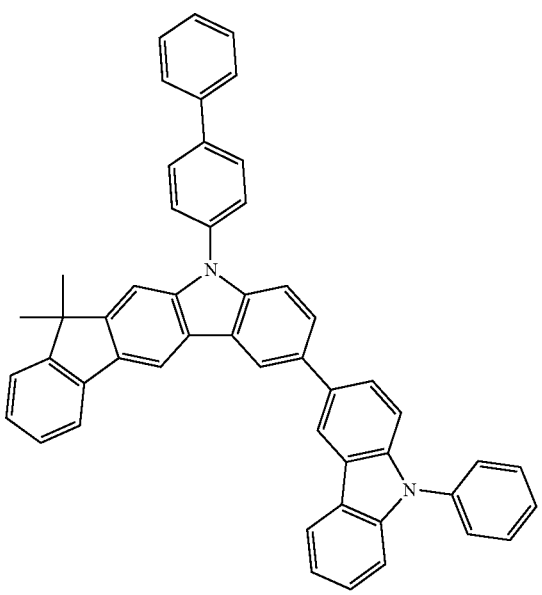
B-50
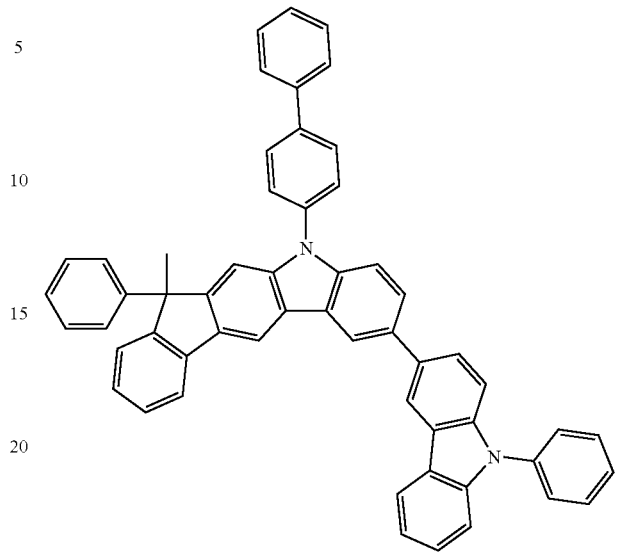
B-51
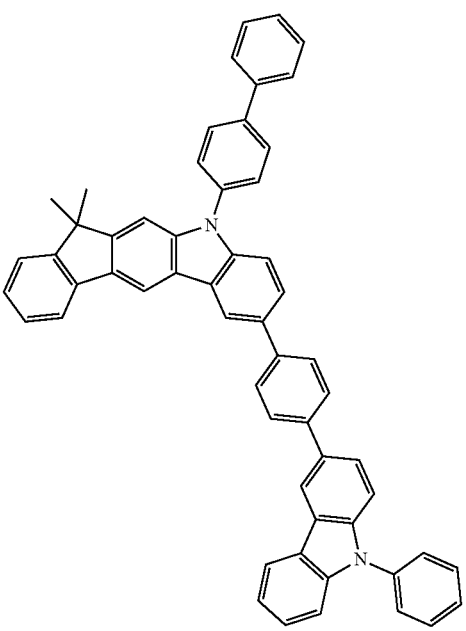

B-52
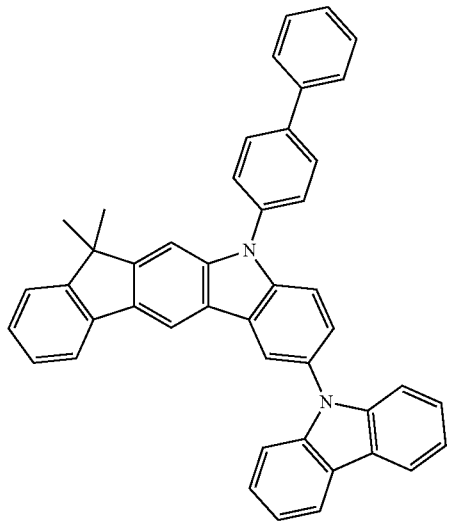
B-53
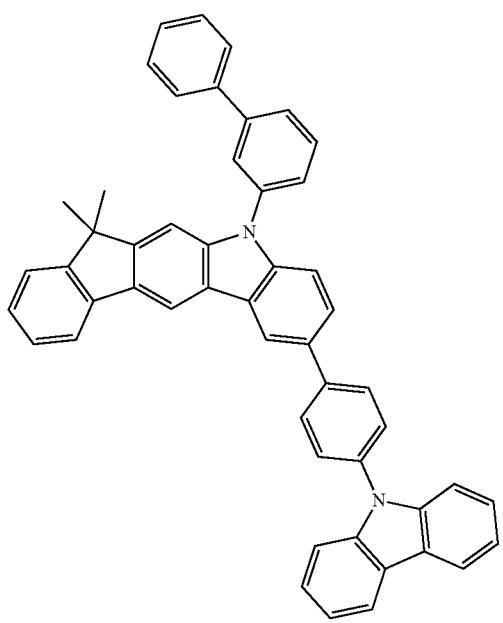
B-54
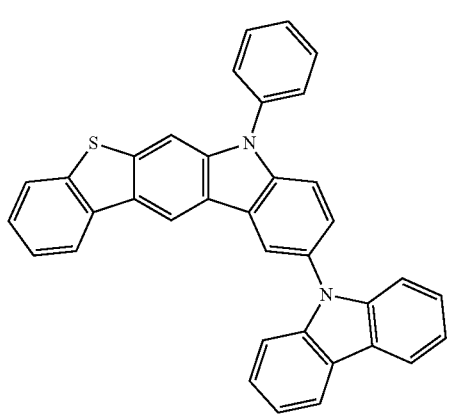
B-55
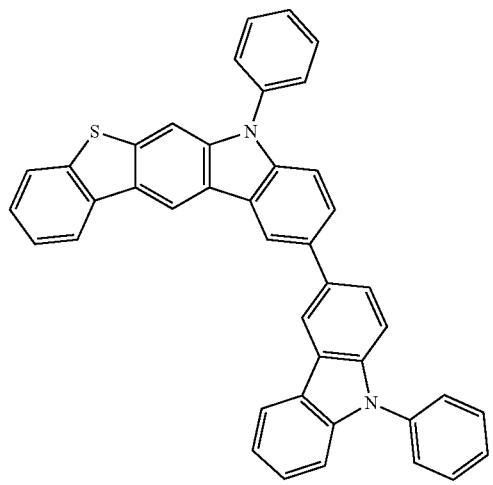
B-56
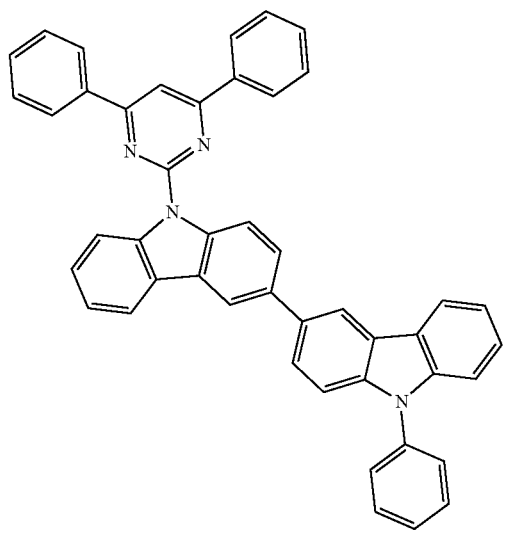

B-57
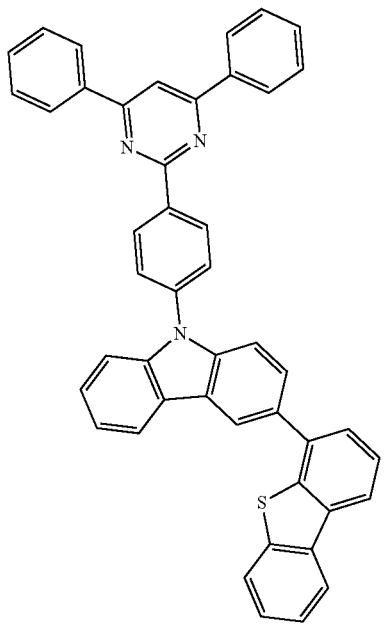
B-58
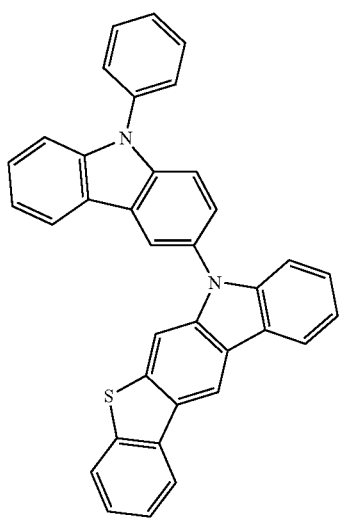
B-59
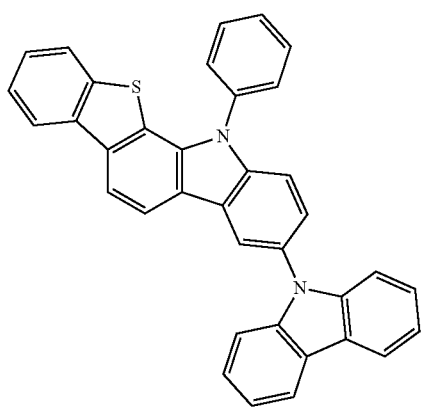
B-60
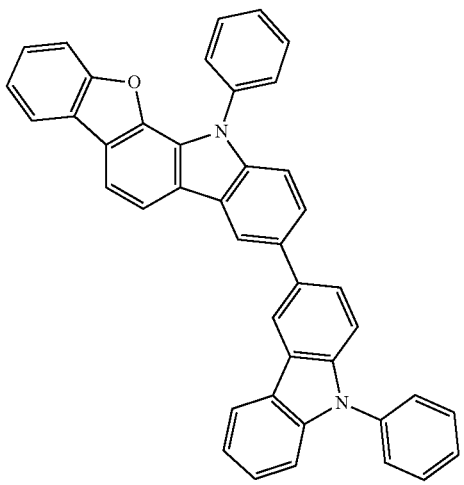
B-61
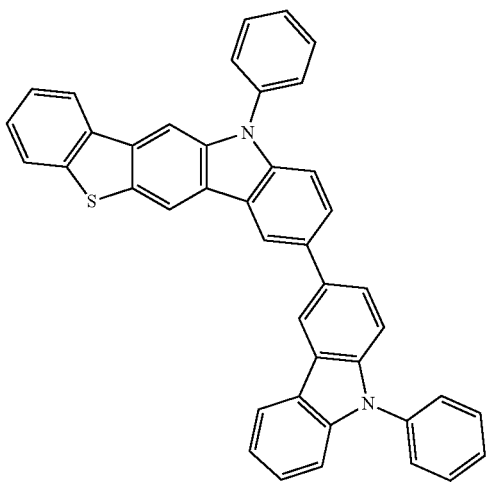
B-62
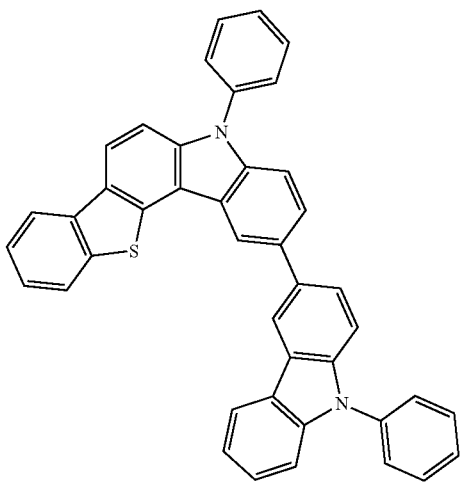

B-63
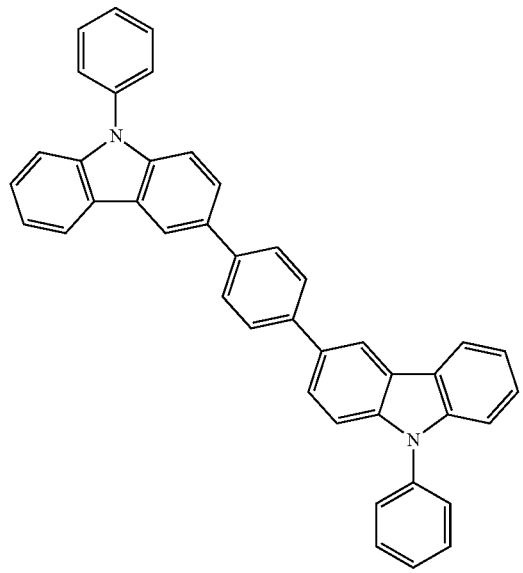
B-64
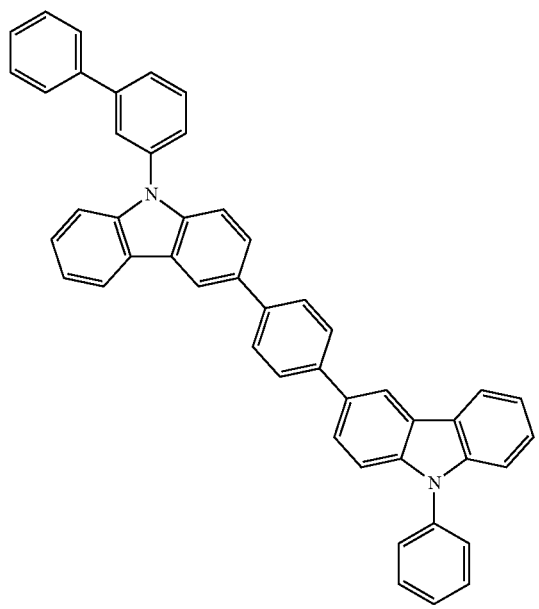
B-65
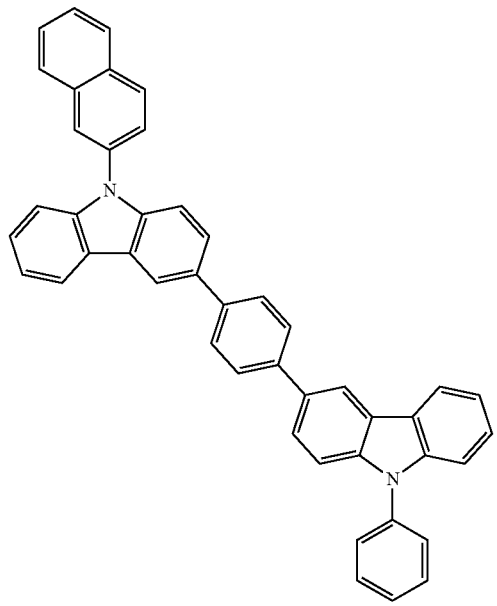
B-66
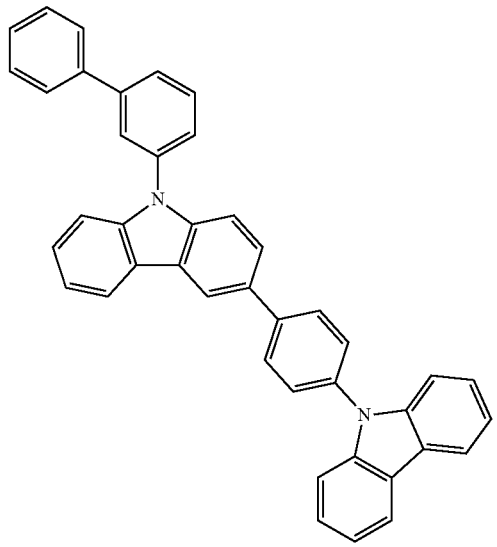

-continued
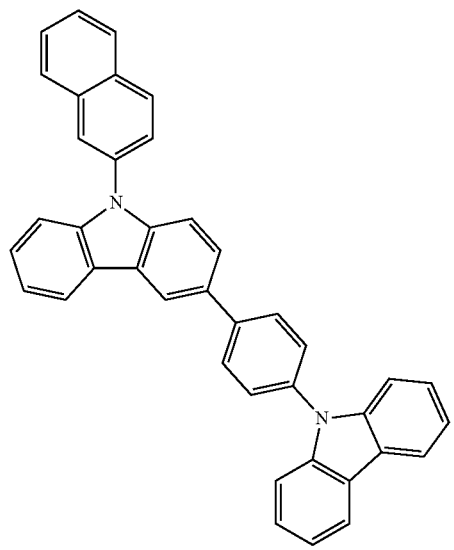
B-67
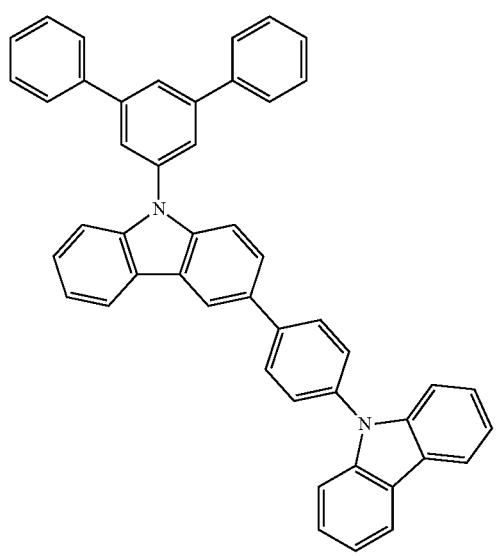
B-68
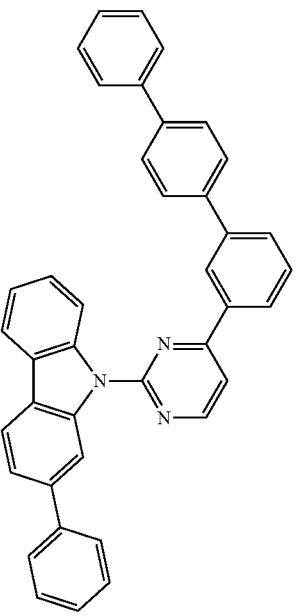
B-69
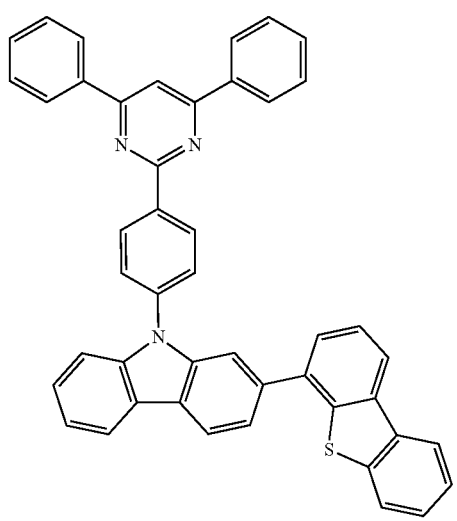
B-70
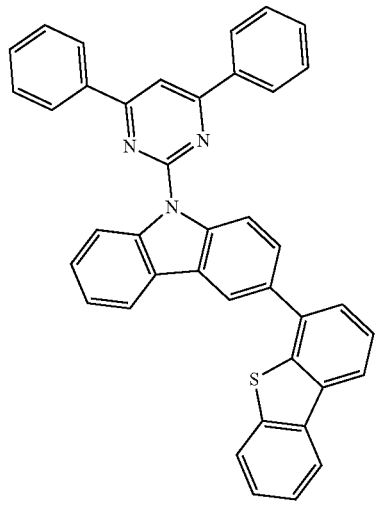
B-71

B-72
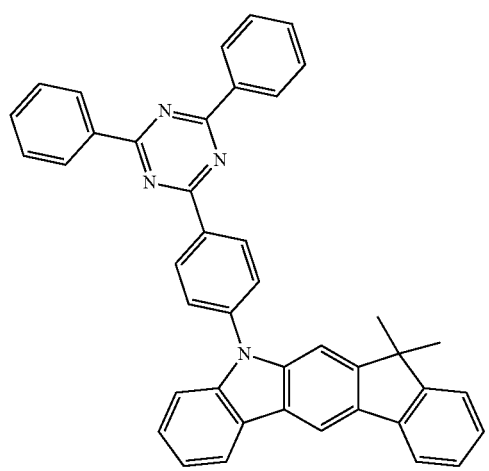
B-73
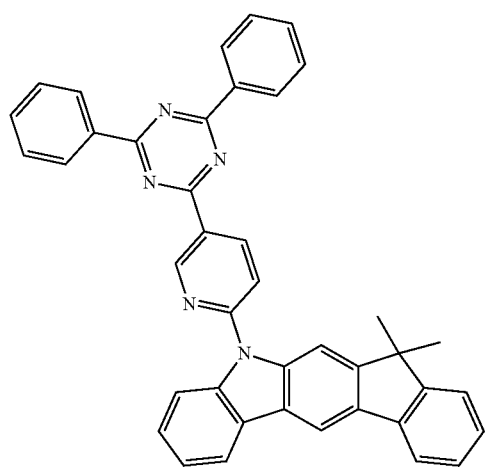
B-74
B-75
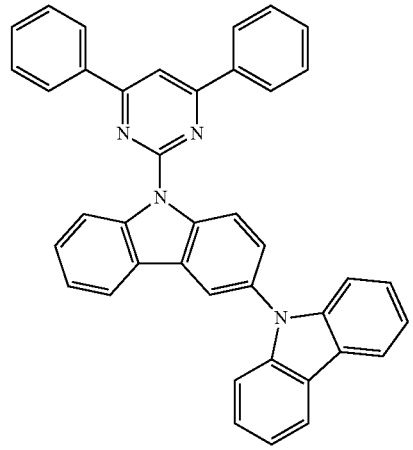
B-76
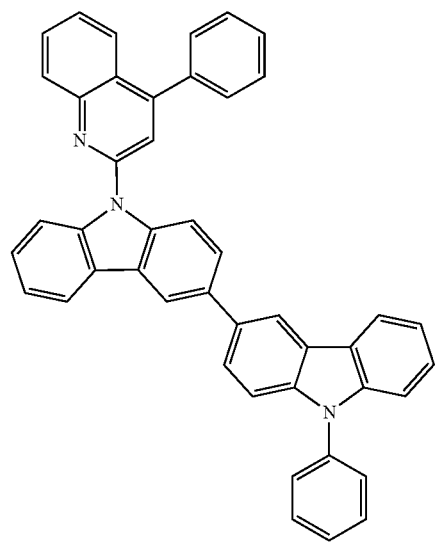
B-77
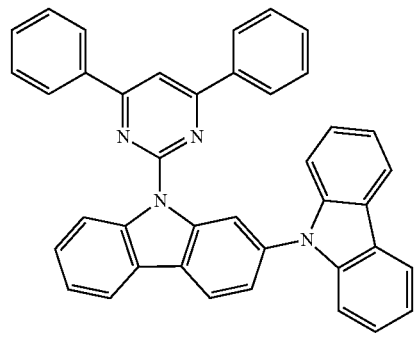

-continued
B-78
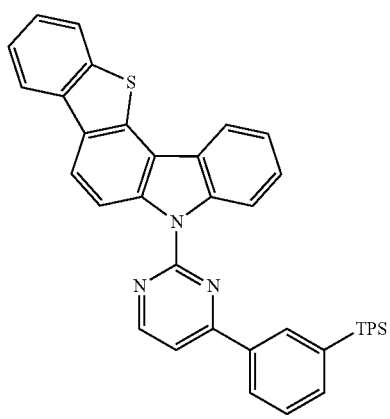
B-79
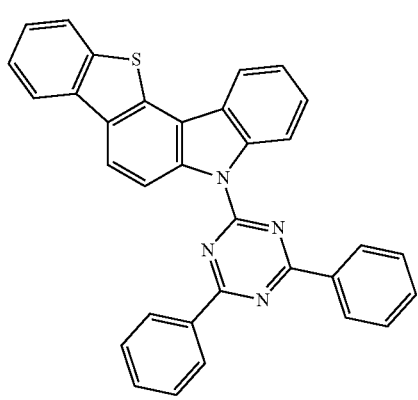
B-80
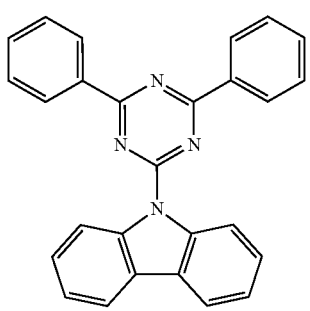
B-81
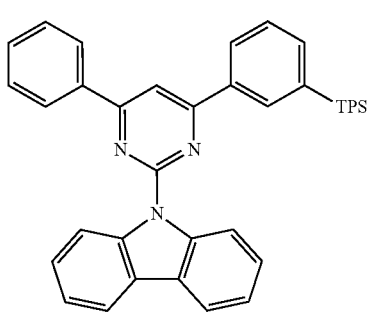
-continued
B-82
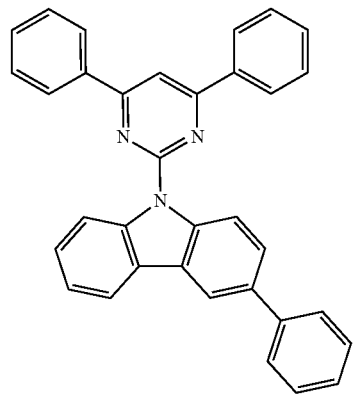
B-83
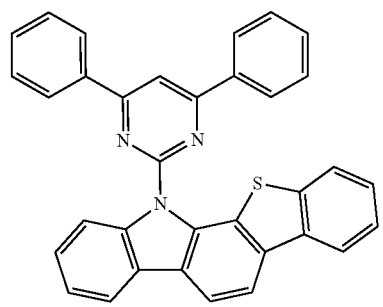
B-84
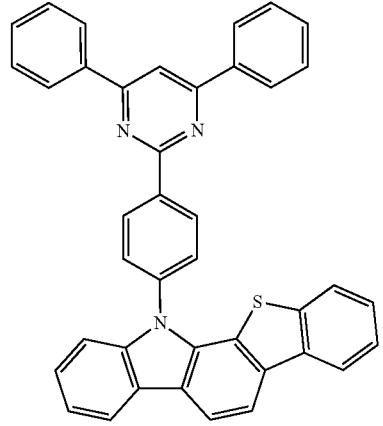
B-85
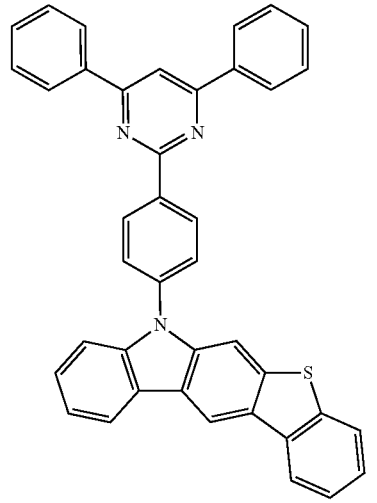

B-86
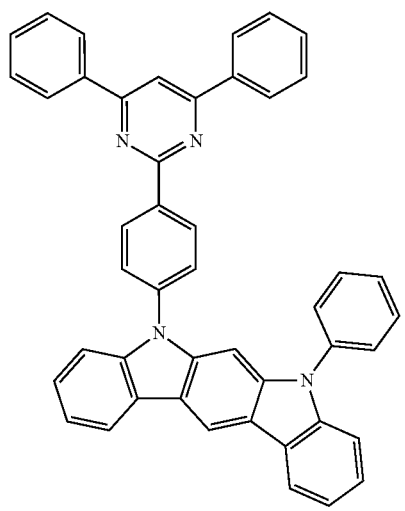
B-89
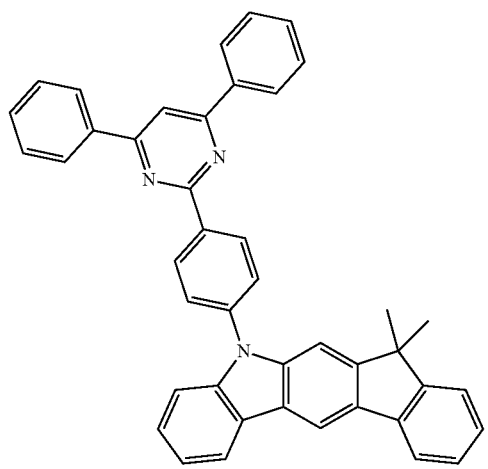
B-87
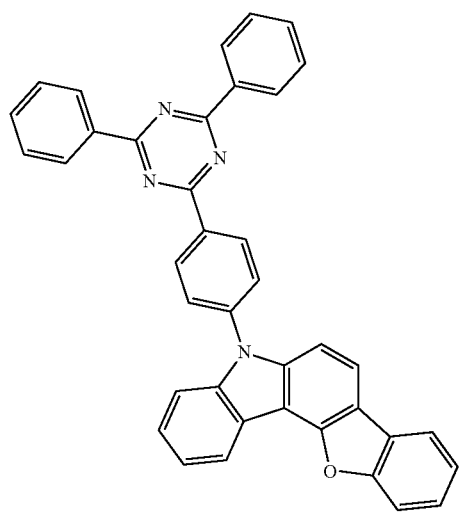
B-90
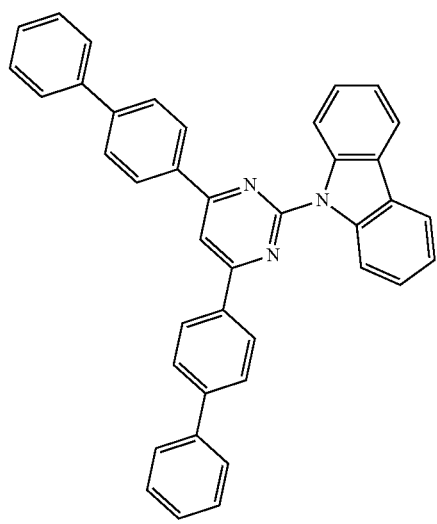
B-88
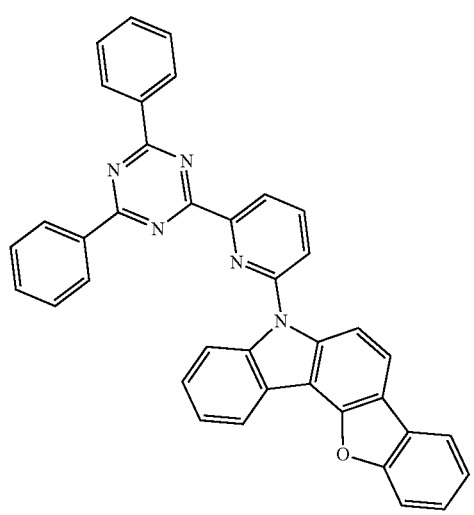
B-91
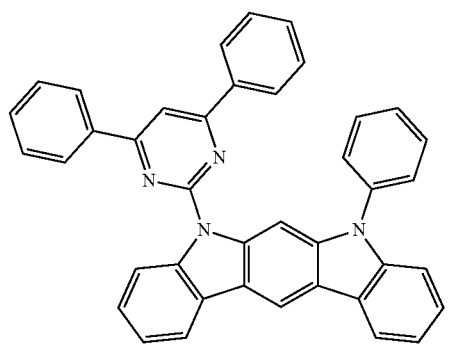

B-92
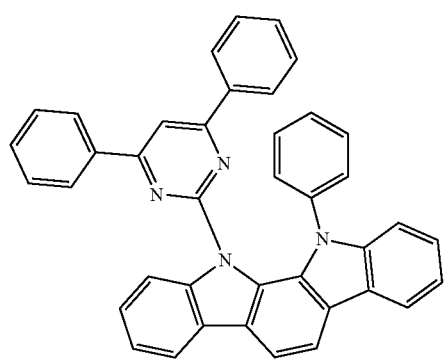
B-93
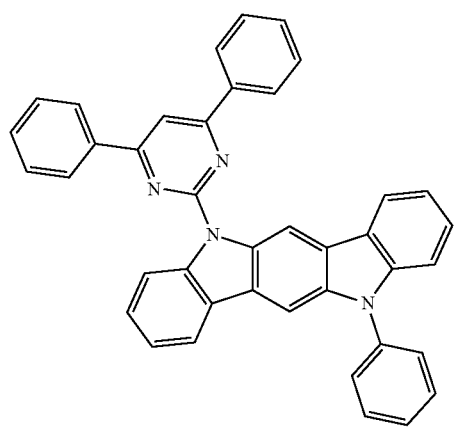
B-94
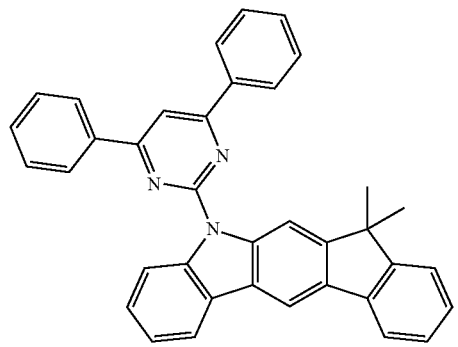
B-95
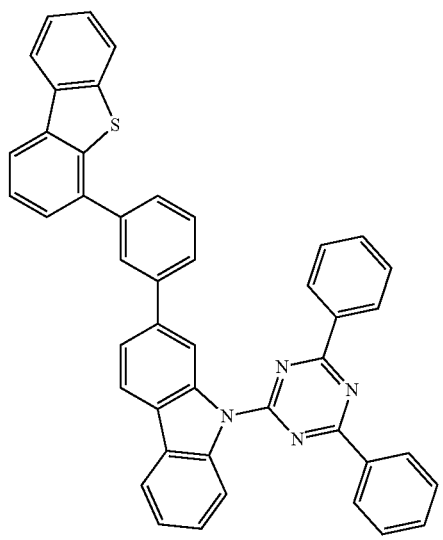
B-96
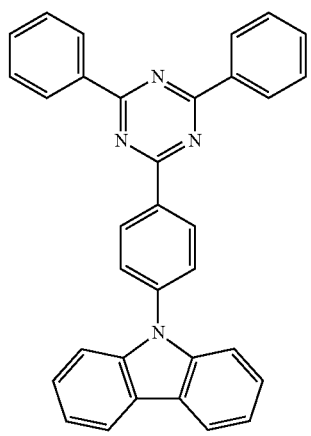
B-97
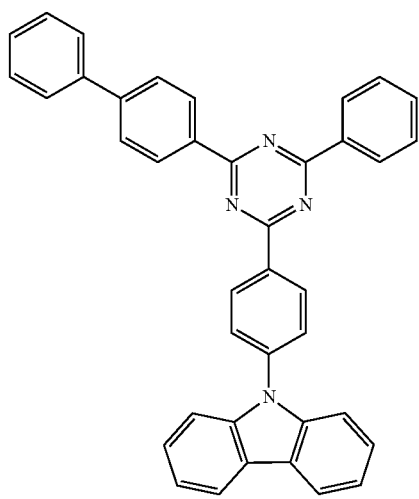

B-98
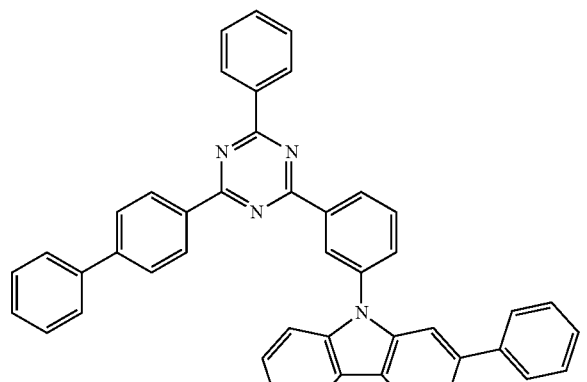
B-99
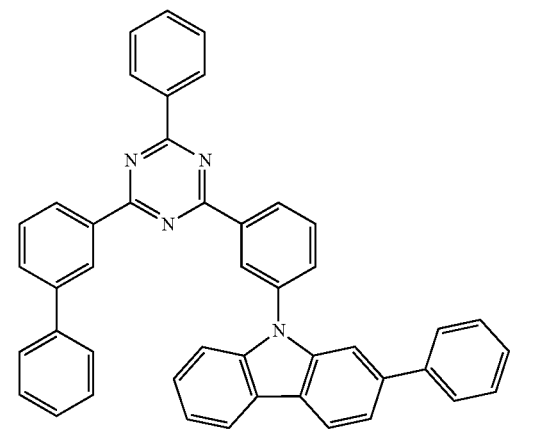
B-100
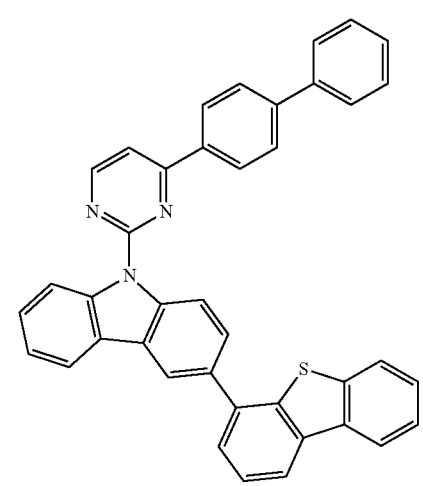
B-101
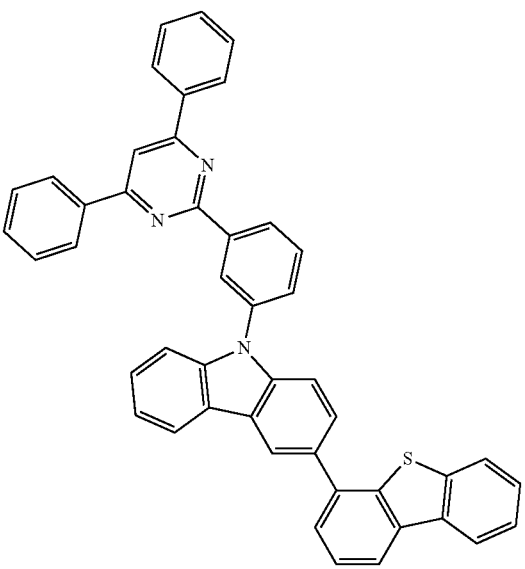
B-102
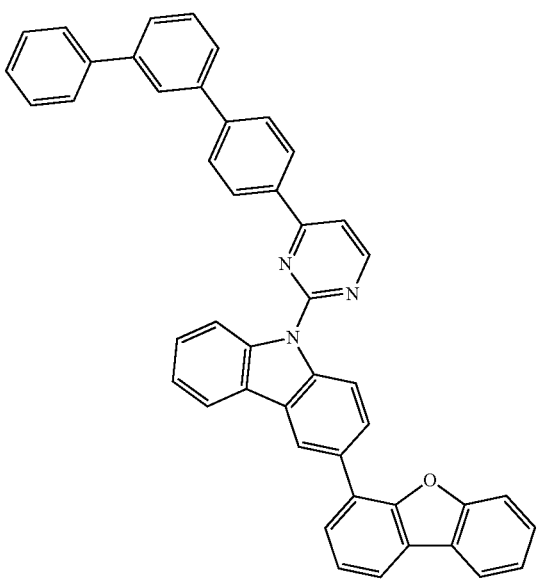

B-103
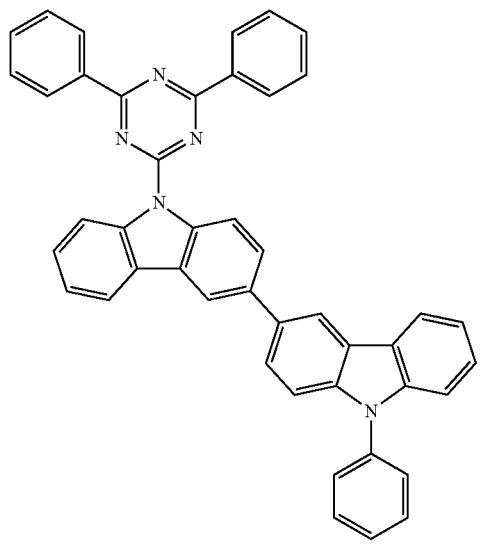
B-104
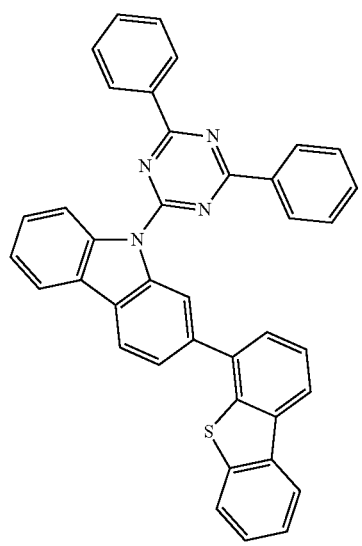
B-105
B-106
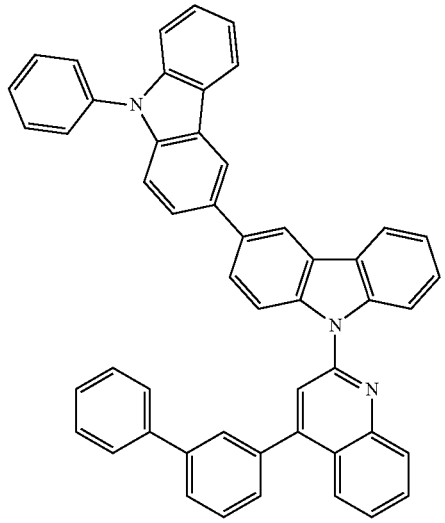
B-107
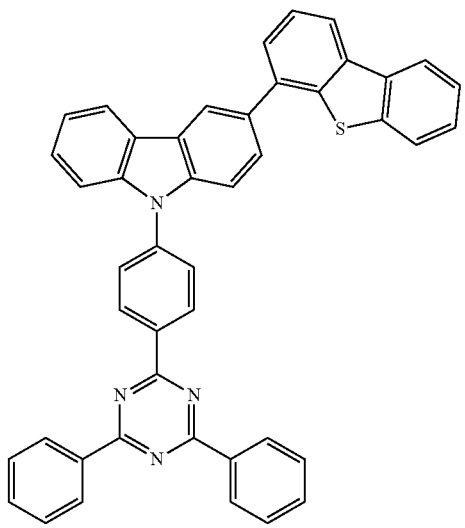
B-108
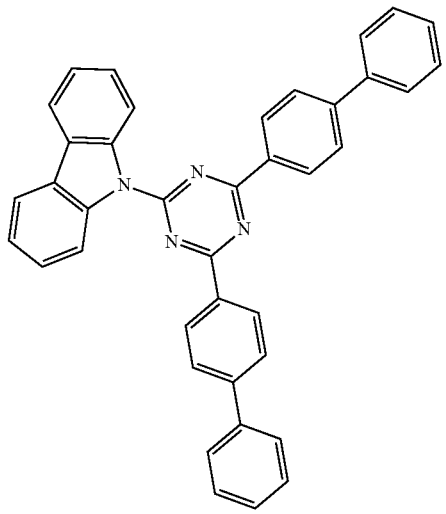

B-109
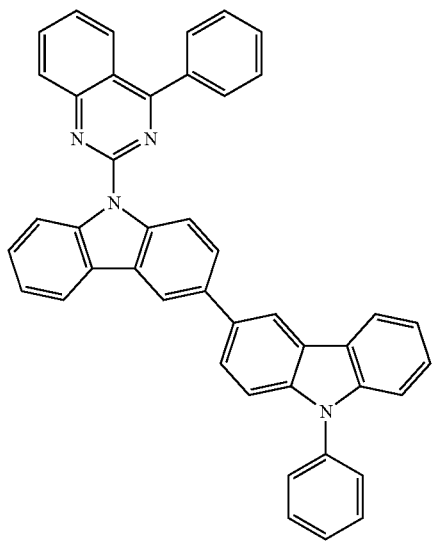
B-110
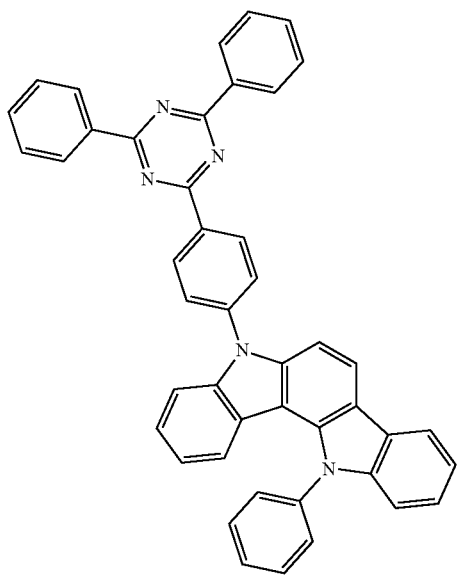
B-111
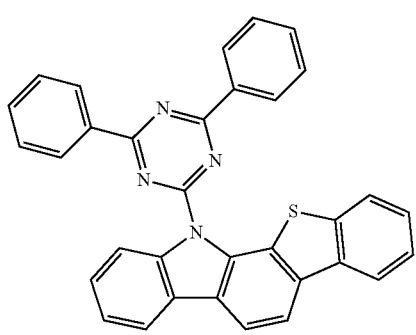
B-112
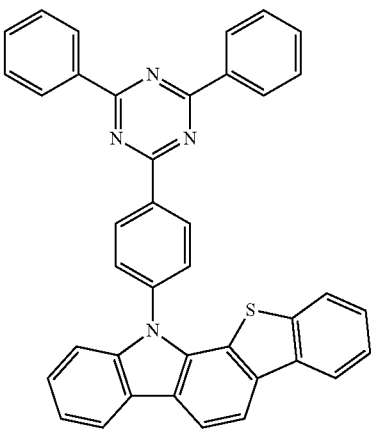
B-113
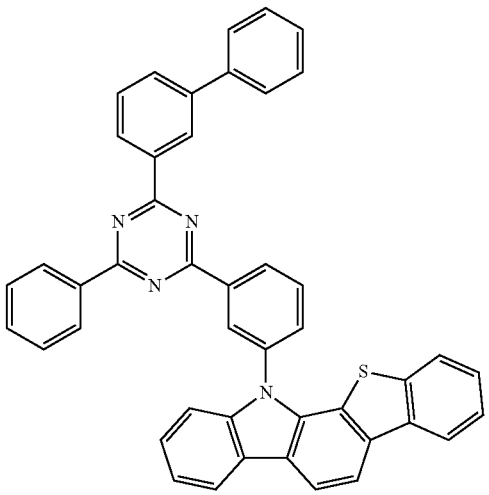
B-114
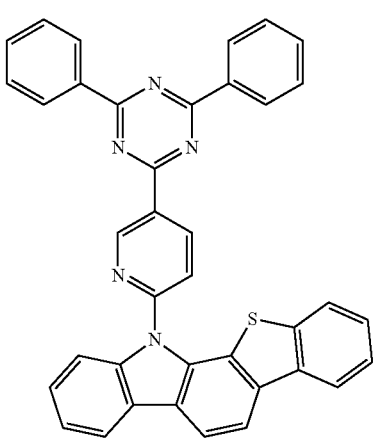

B-115
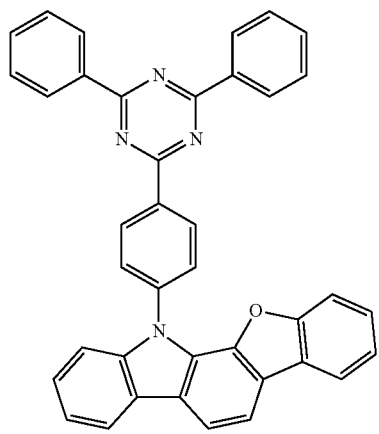
B-116
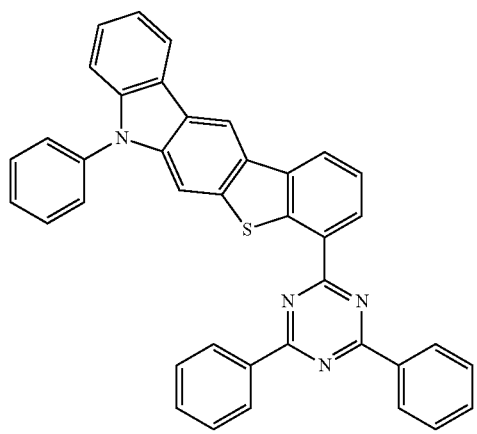
B-117
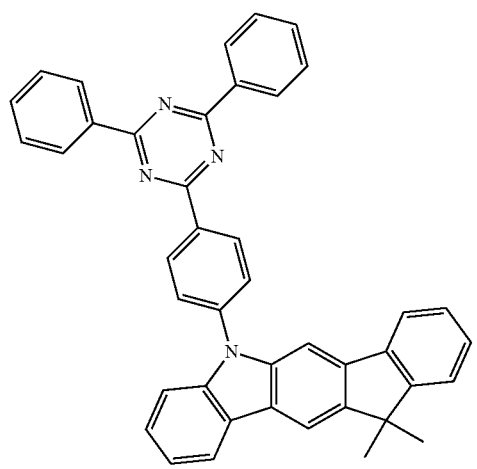
B-118
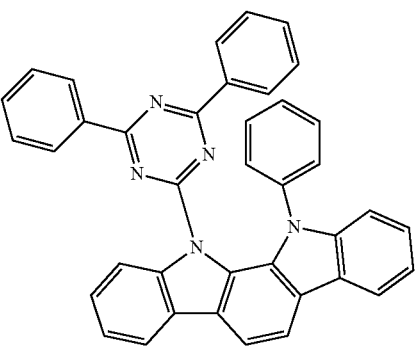
B-119
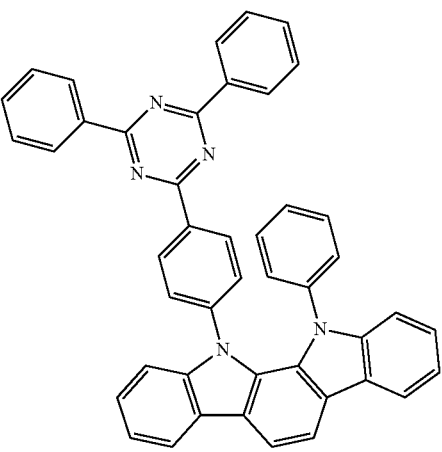
B-120
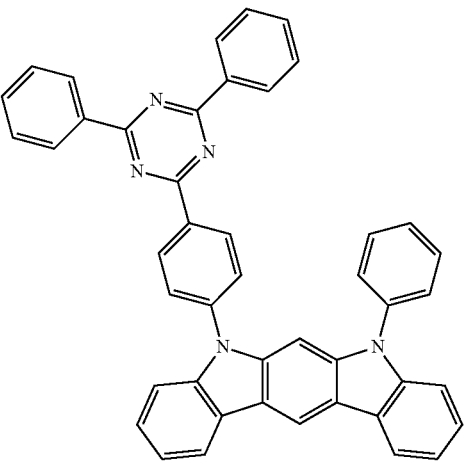

B-121
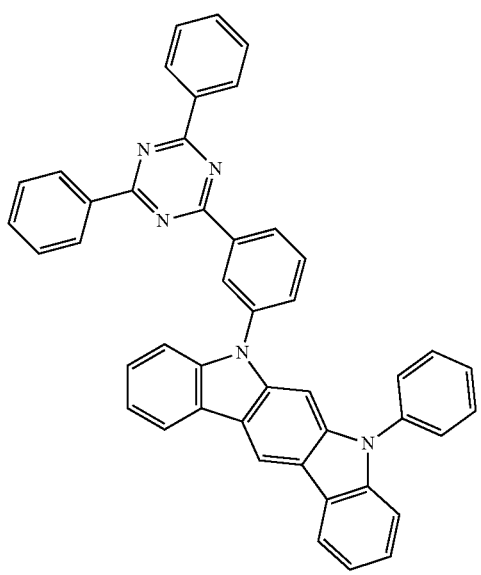
B-122
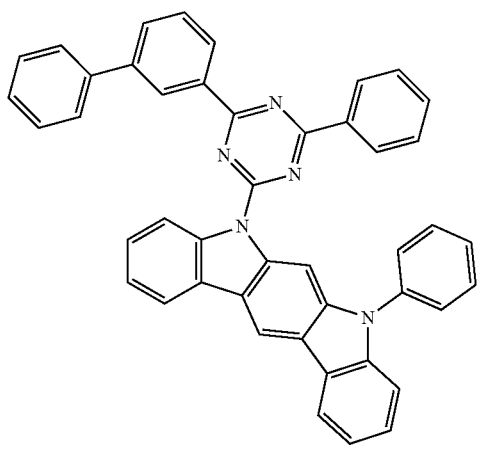
B-123
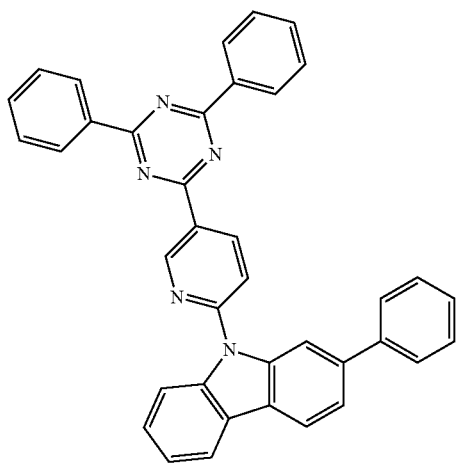
B-124
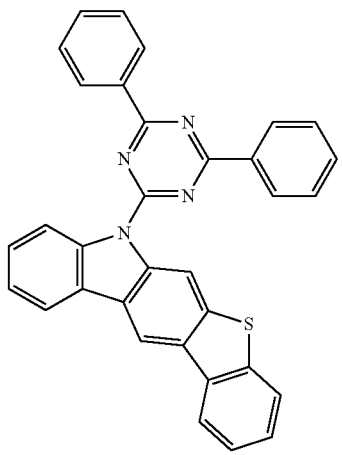
B-125
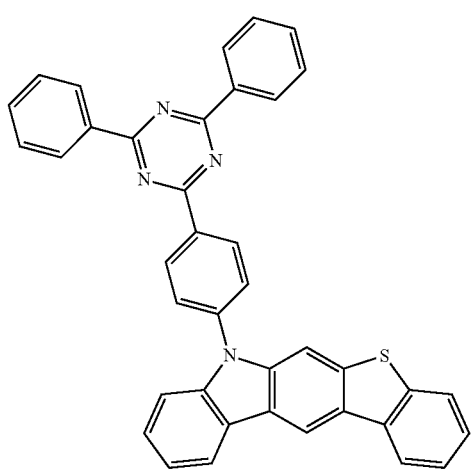
B-126
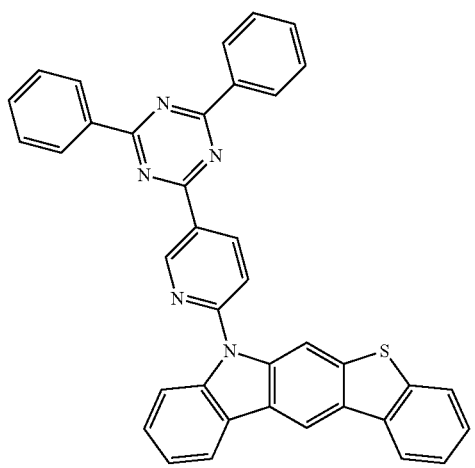

B-127
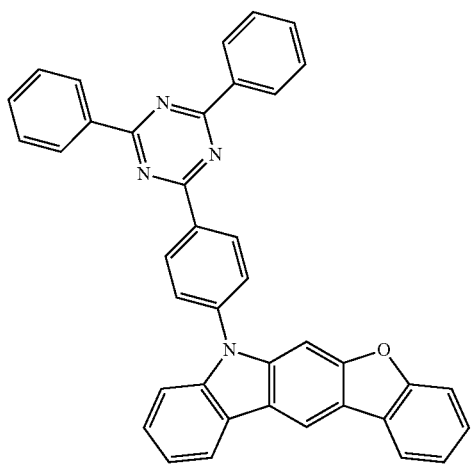
B-128
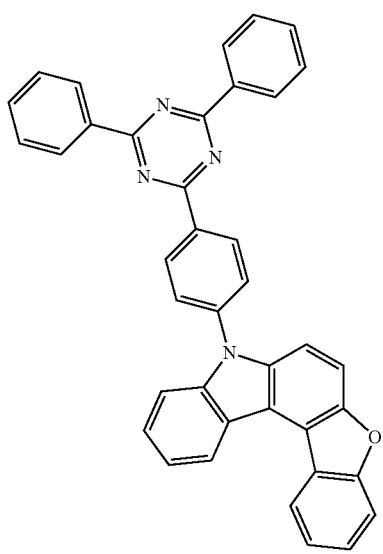
B-129
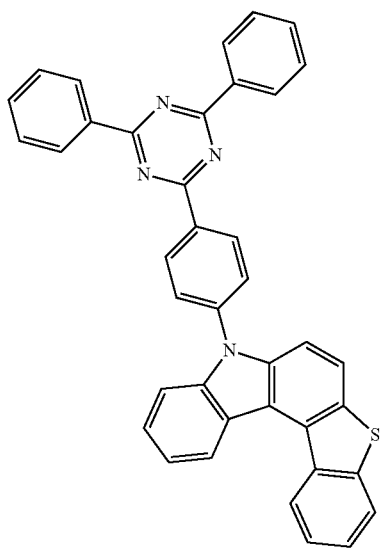
B-130
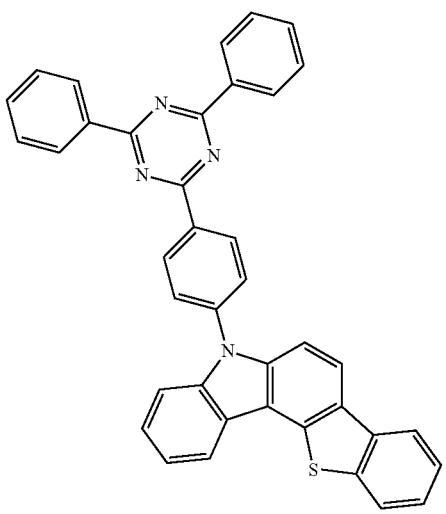
B-131
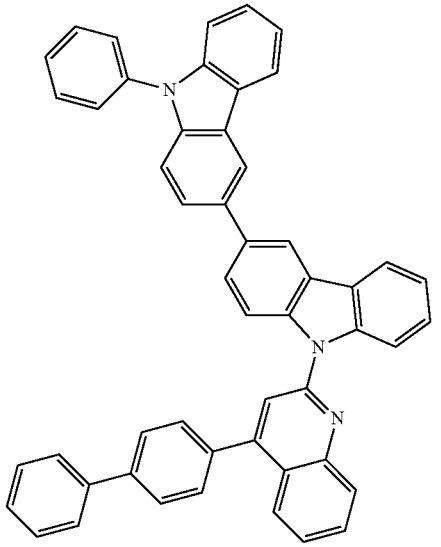
B-132
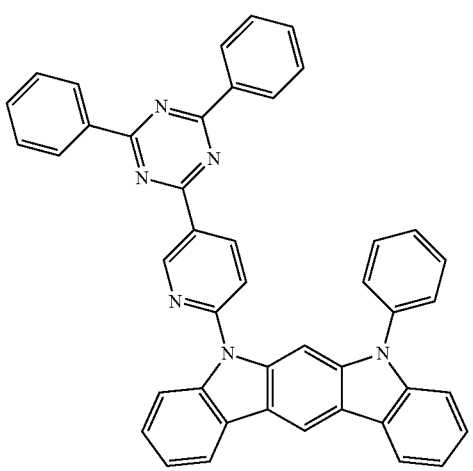

B-133
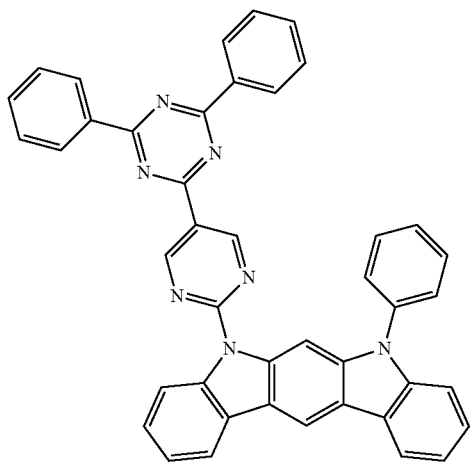
B-134
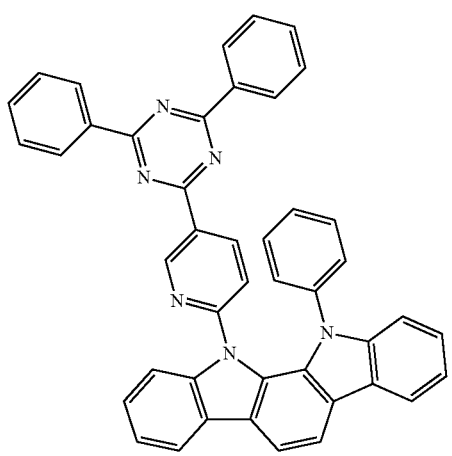
B-135
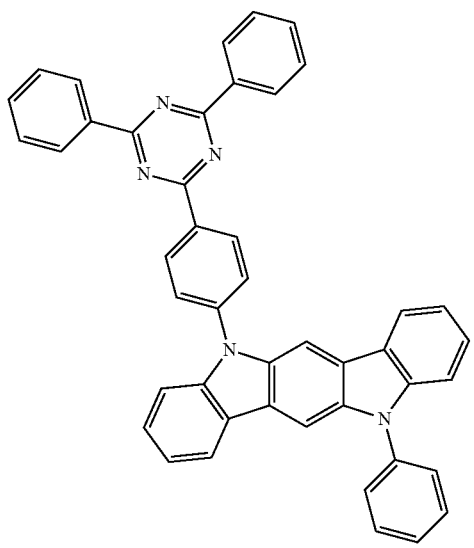
B-136
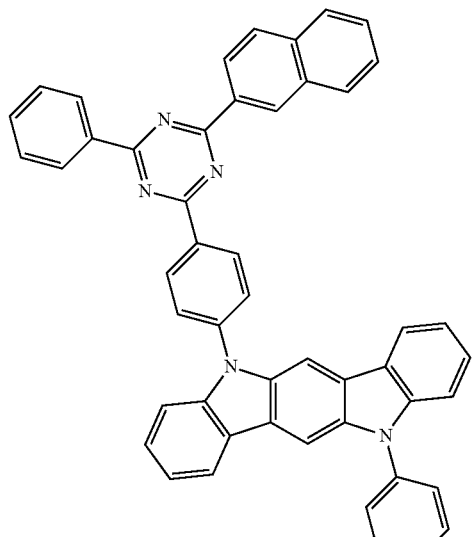
B-137
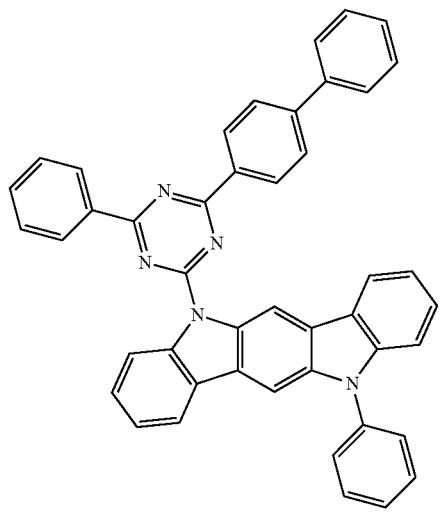
B-138
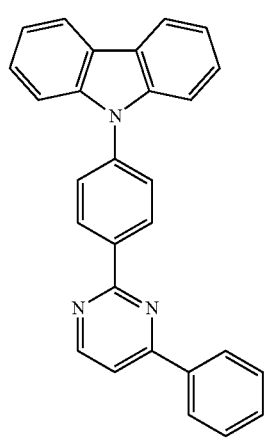

B-139
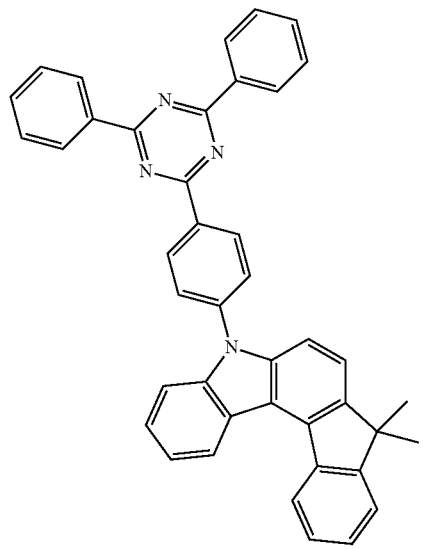
B-140
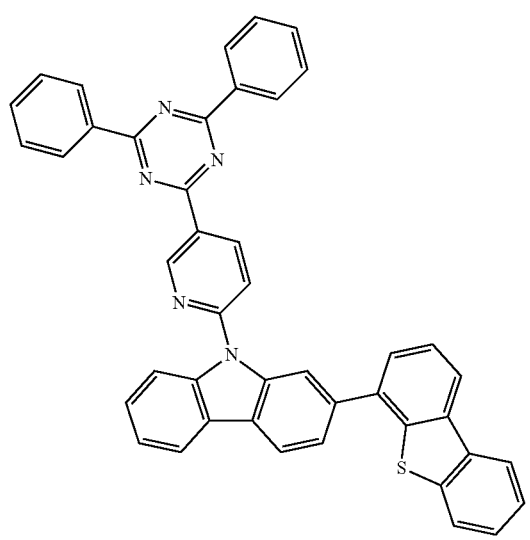
B-141
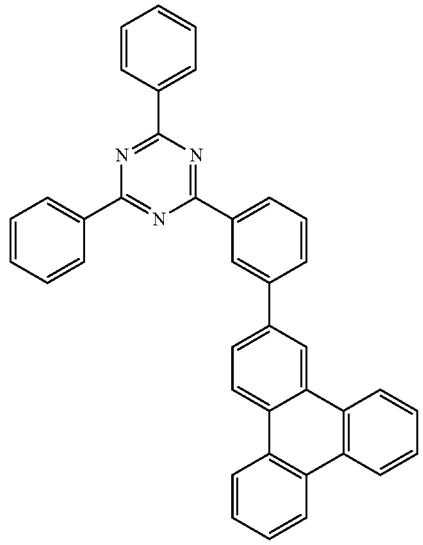
B-142
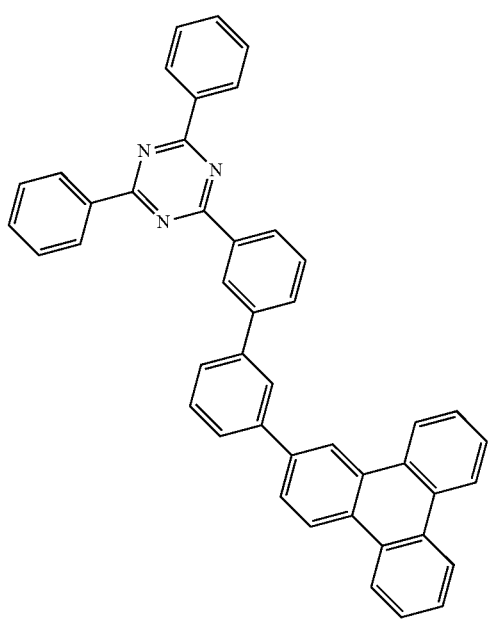
B-143
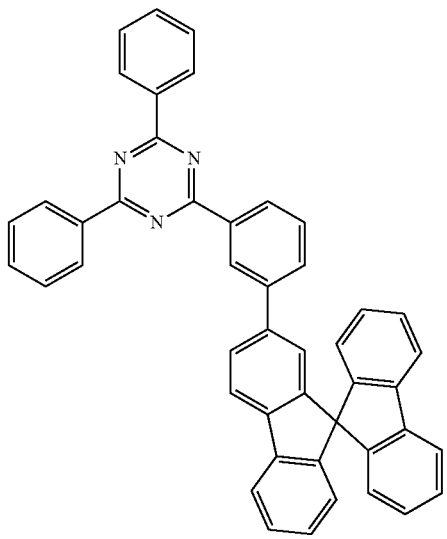

B-144
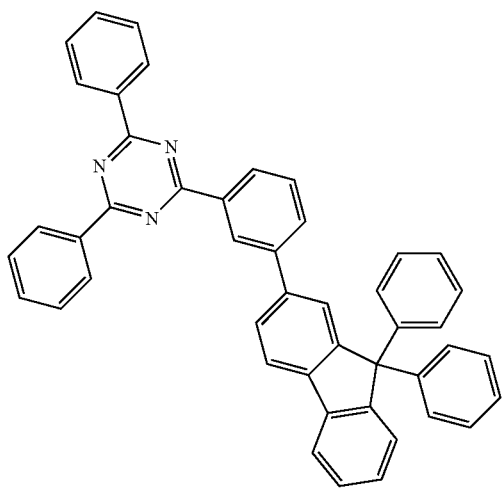
B-145
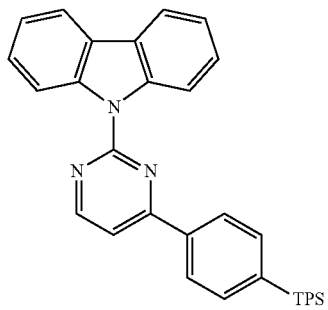
B-146
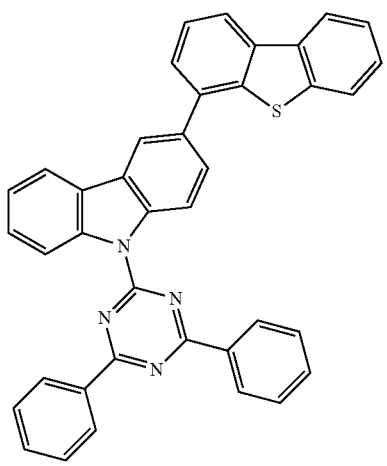
B-147
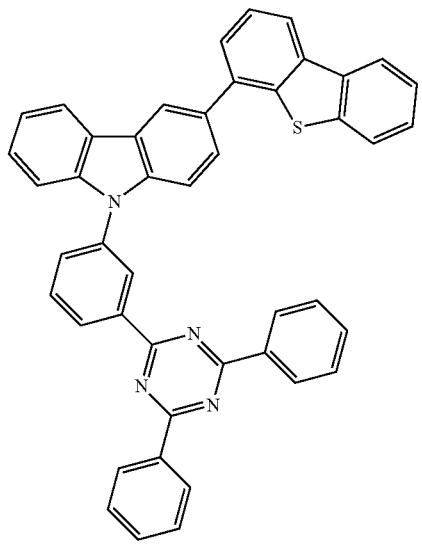
B-148
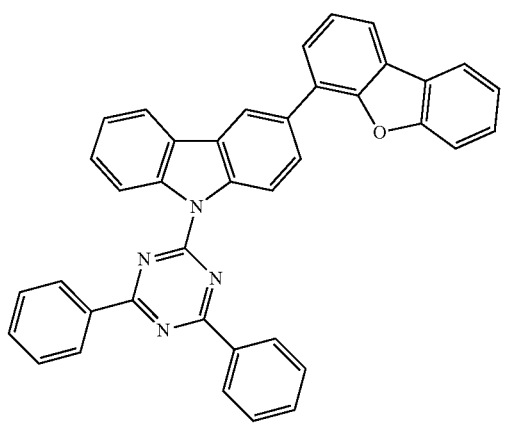
B-149
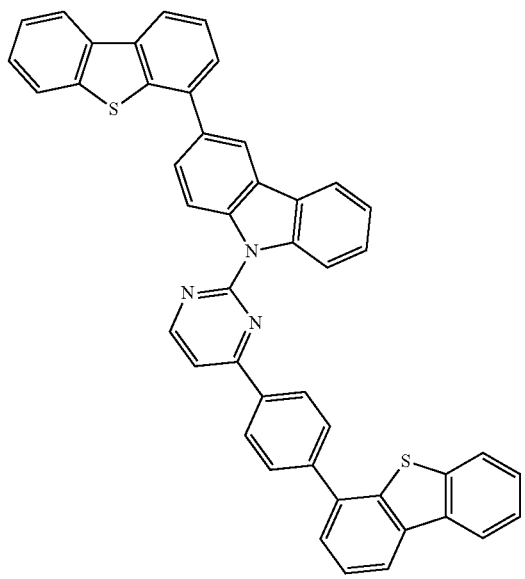

B-150
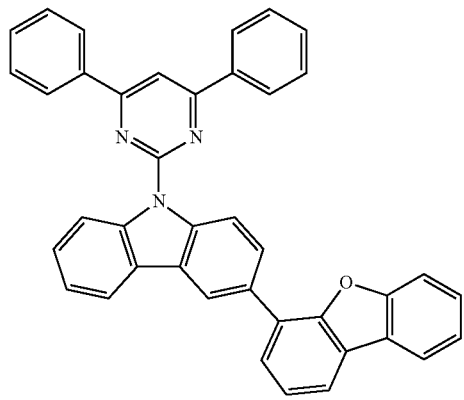
B-151
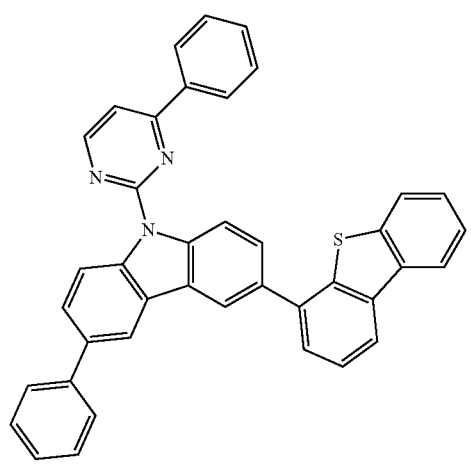
B-152
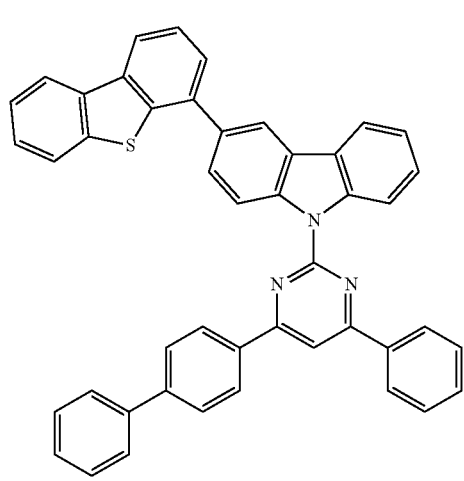
B-153
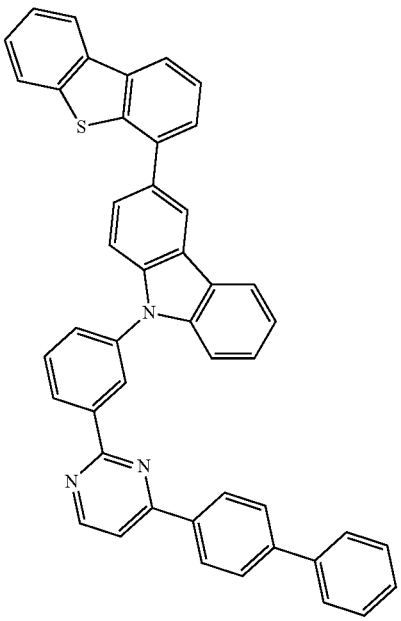
B-154
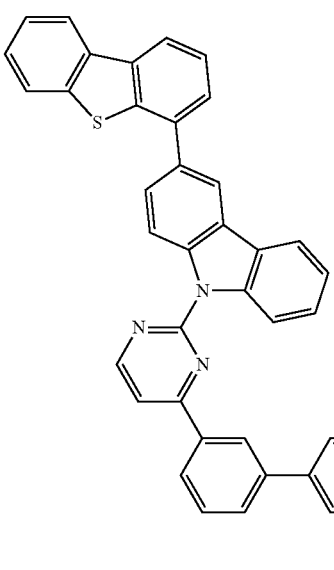

B-155
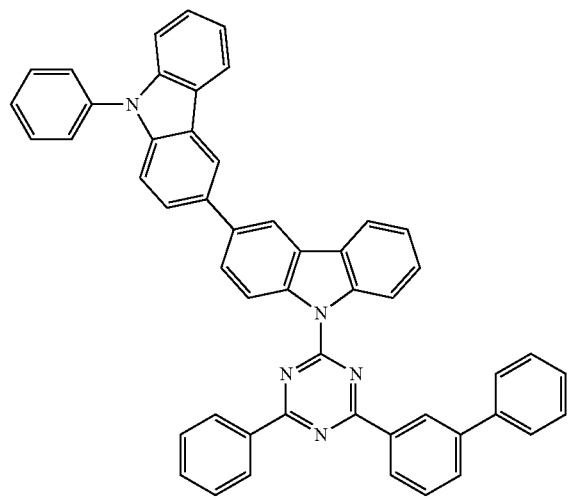
B-156
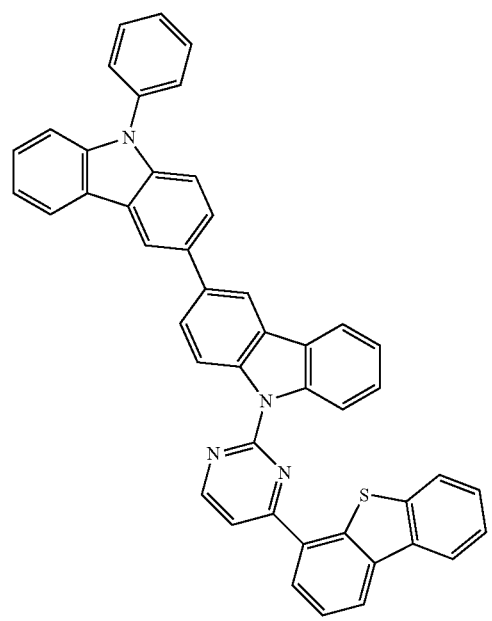
B-157
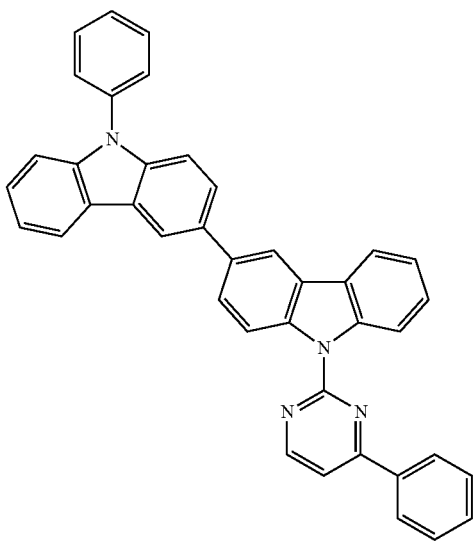
B-158
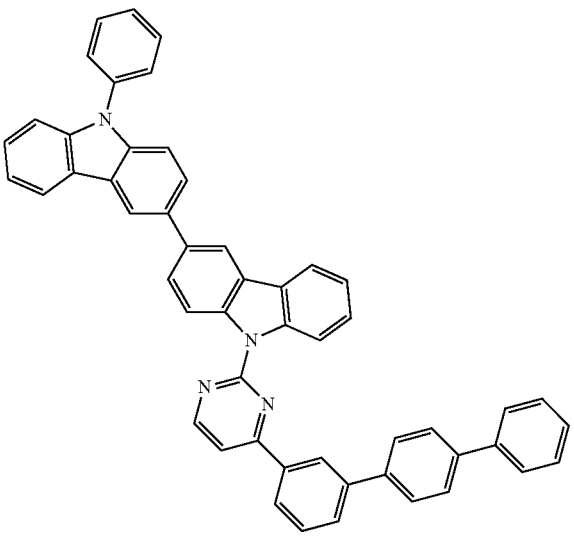

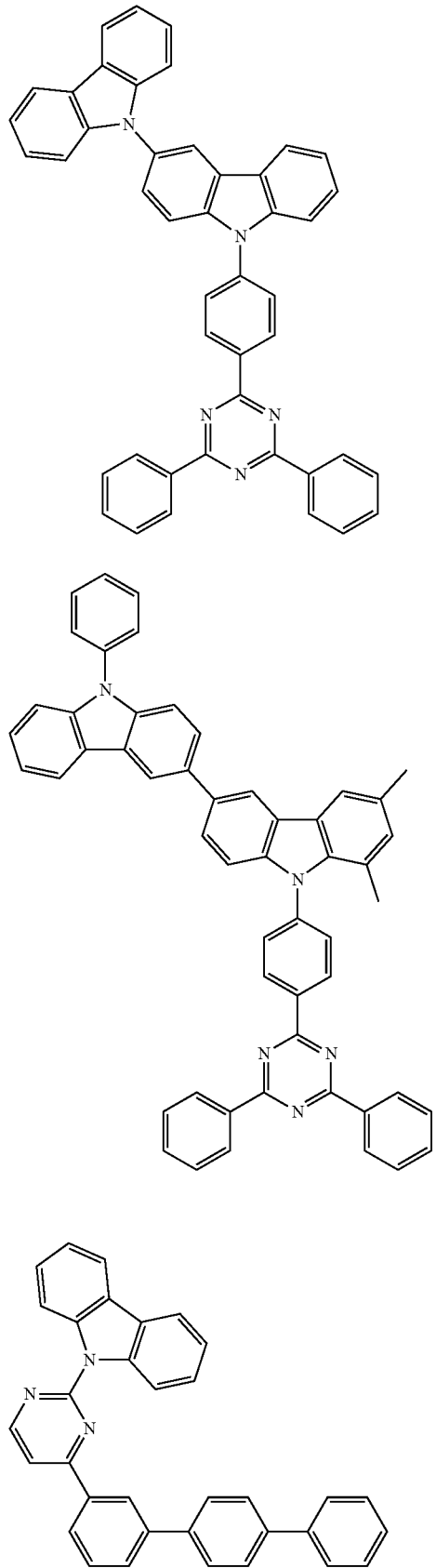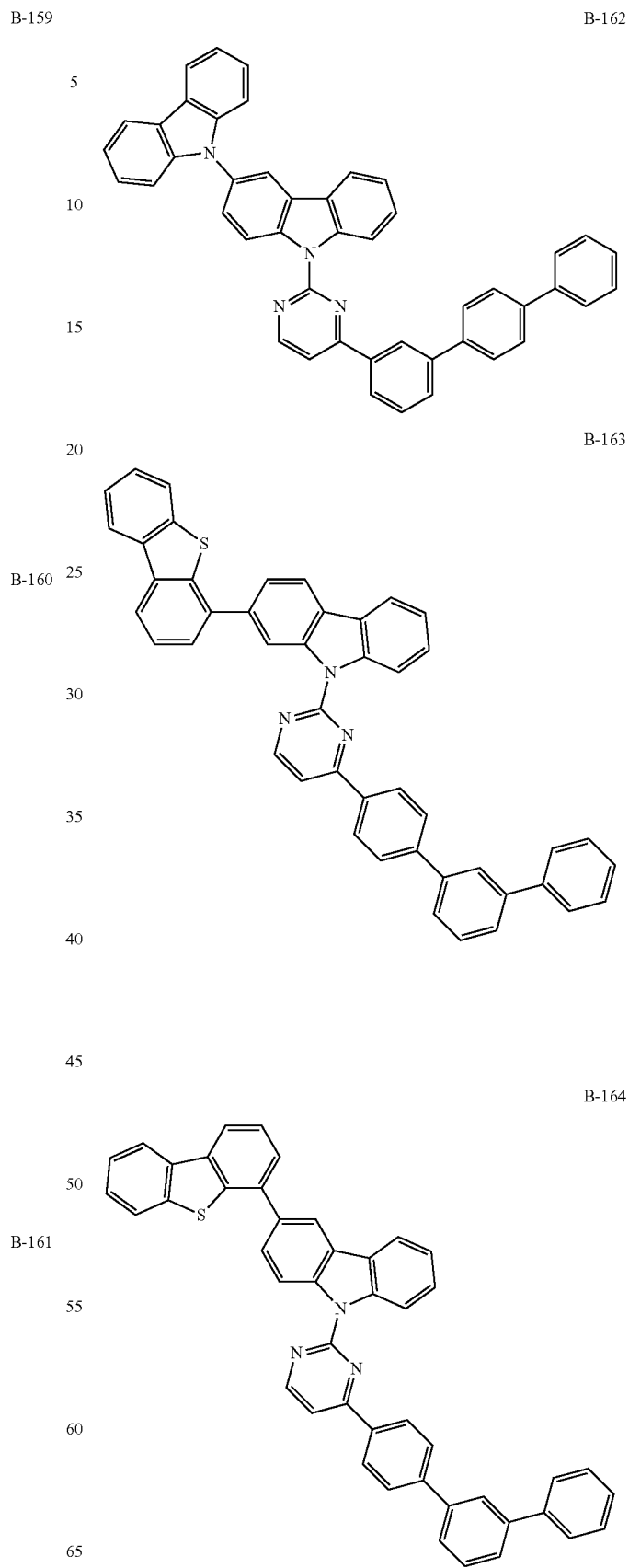

B-165
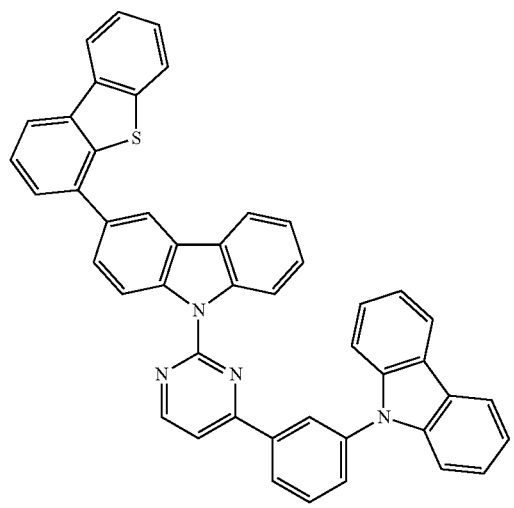
B-167
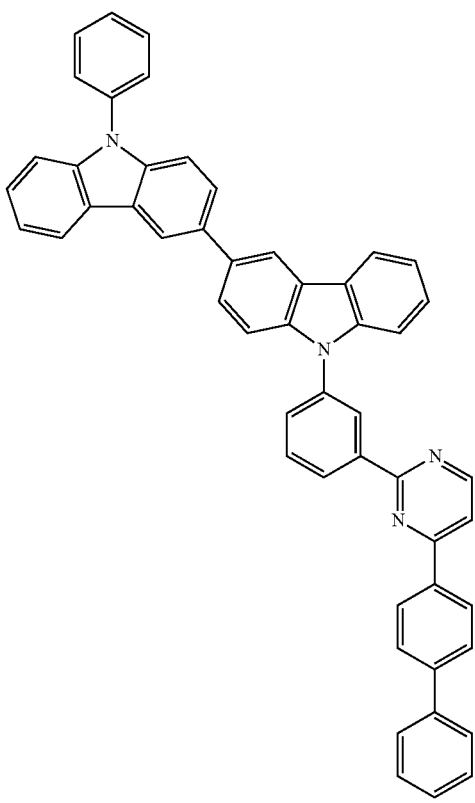
B-166
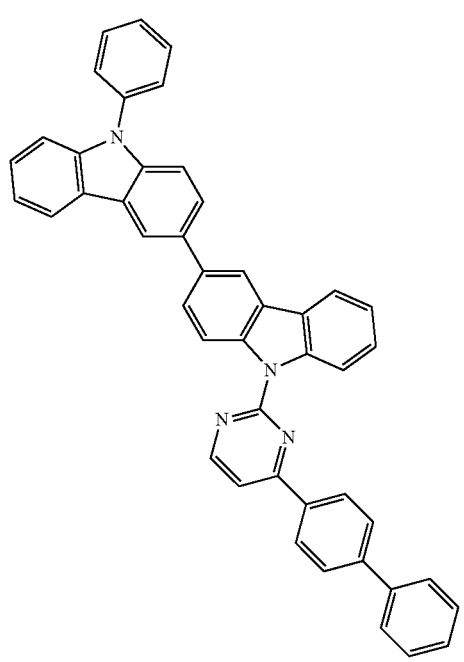
B-168
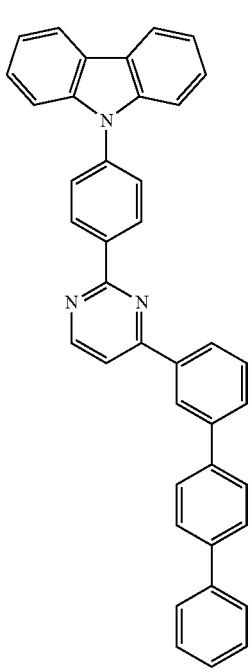

B-169
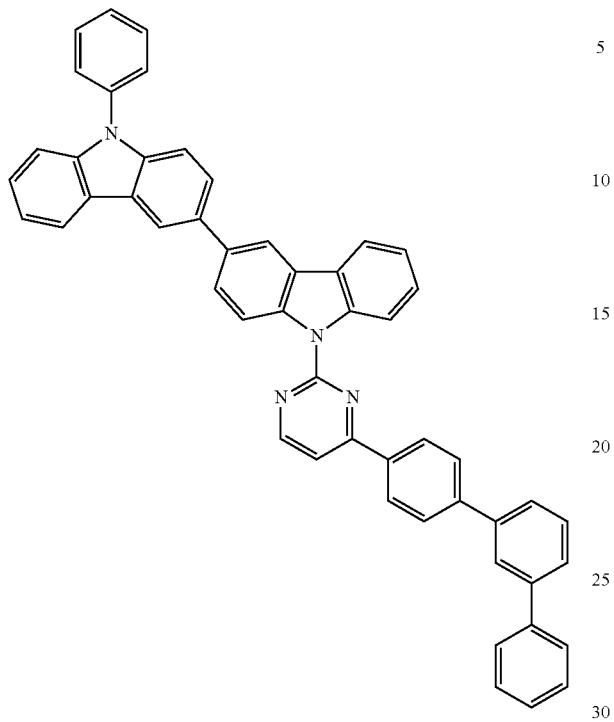
B-171
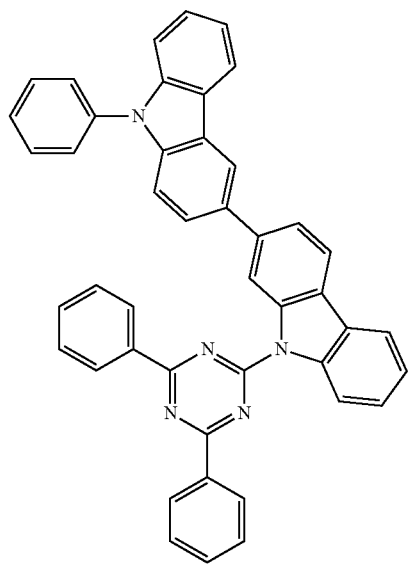
B-170
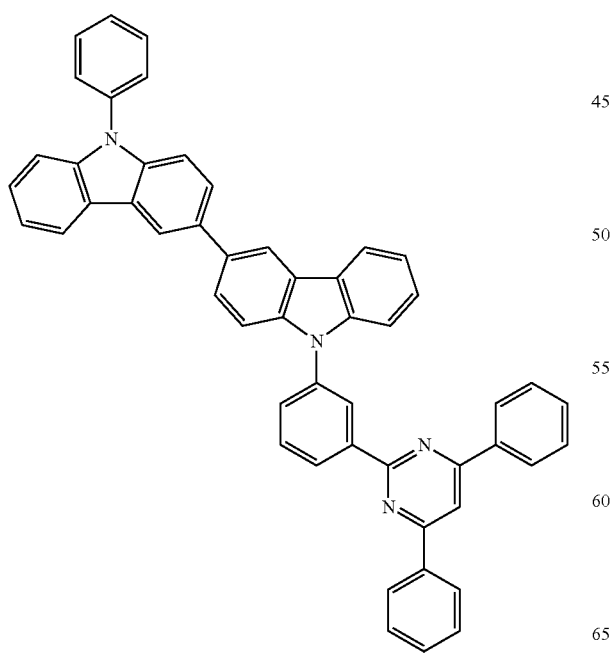
B-172
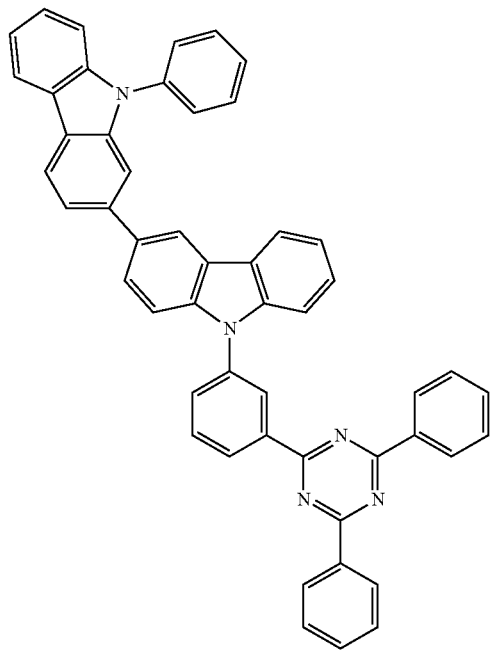

B-173
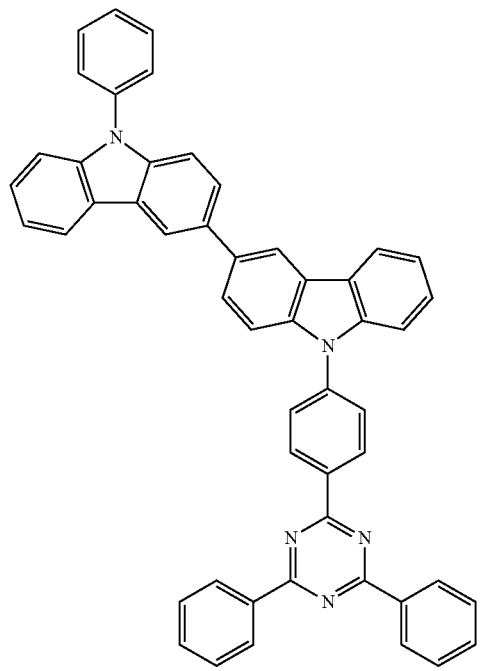
B-175
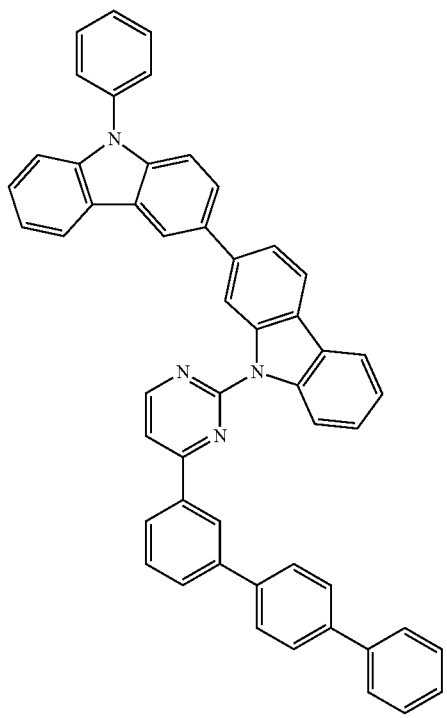
B-174
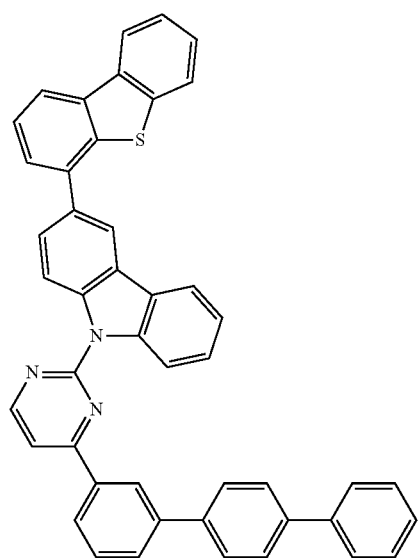
B-176
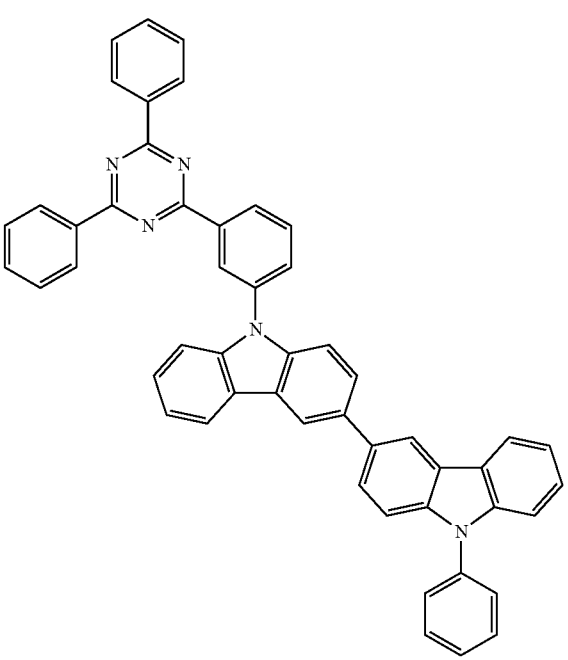

-continued
B-177
B-178
B-179
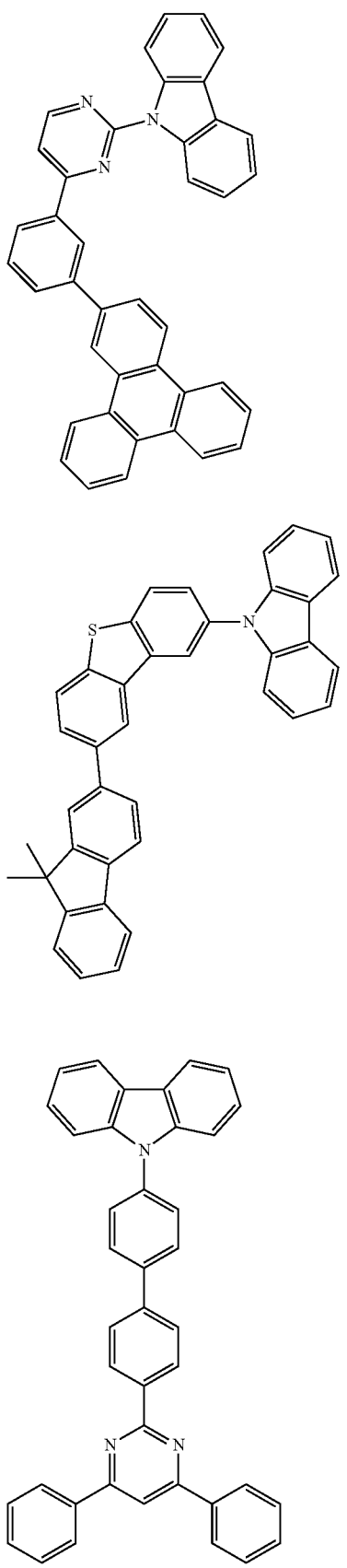
-continued
B-180
B-181
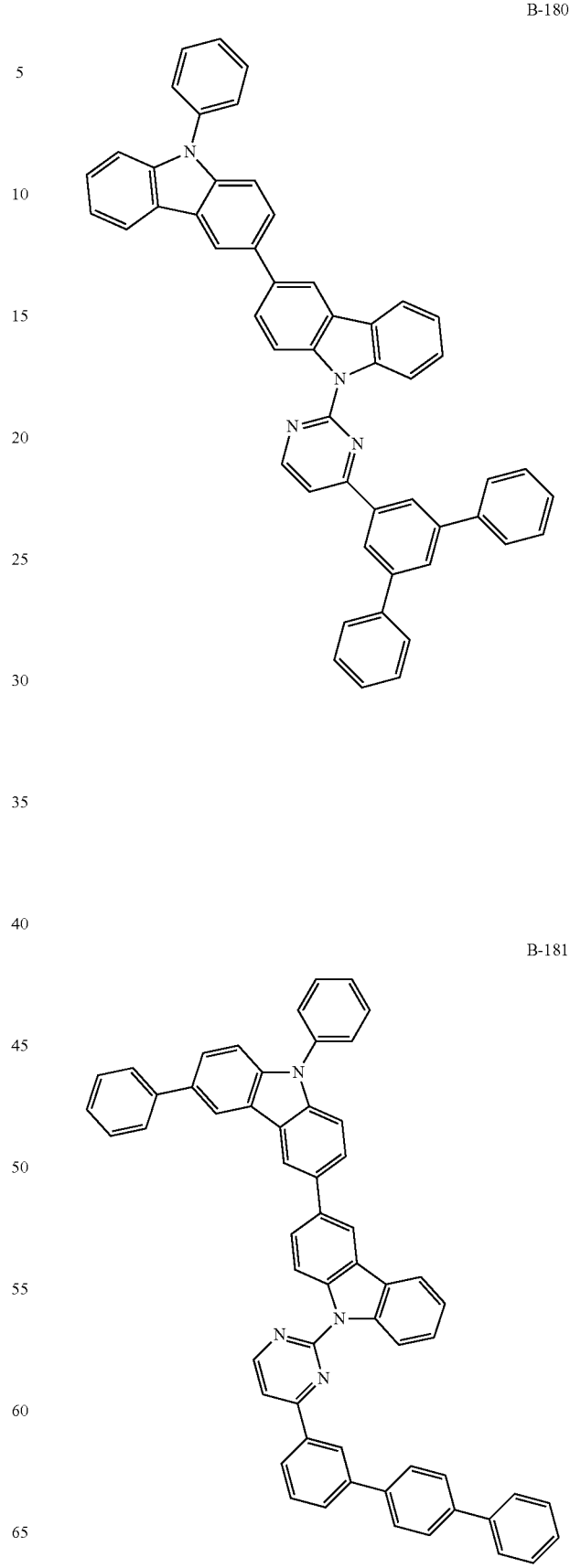

B-182
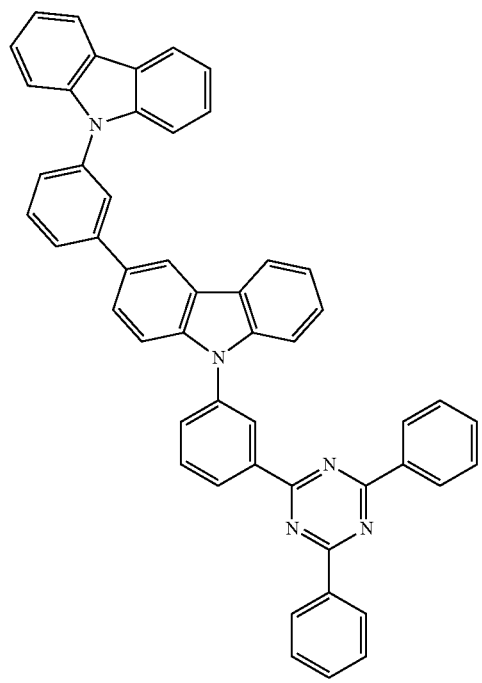
B-183
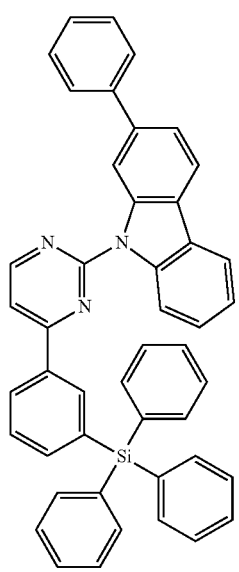
B-184
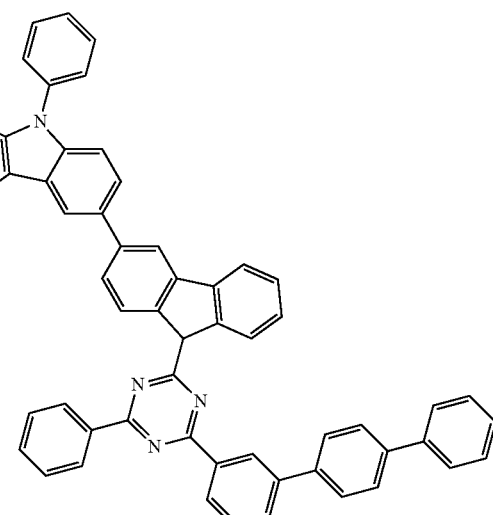
B-185
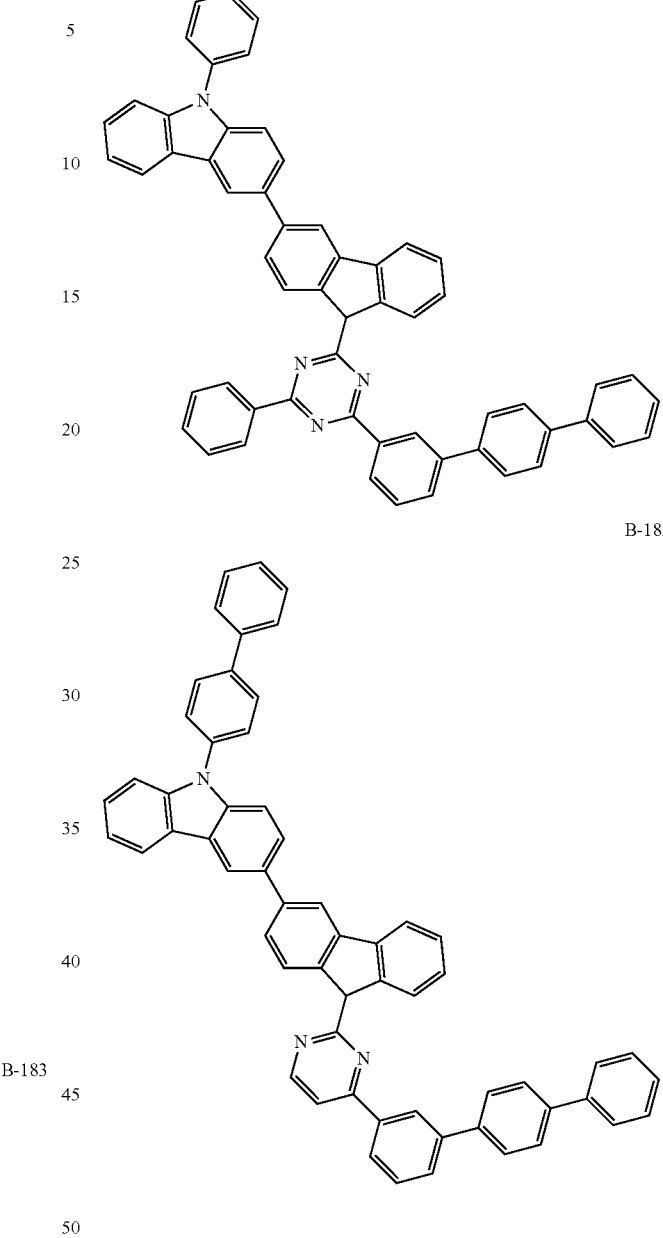
B-186
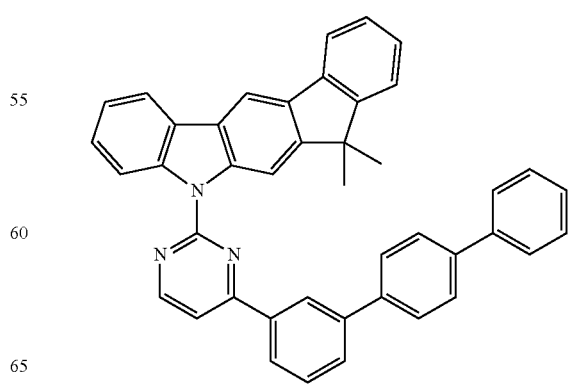

B-187
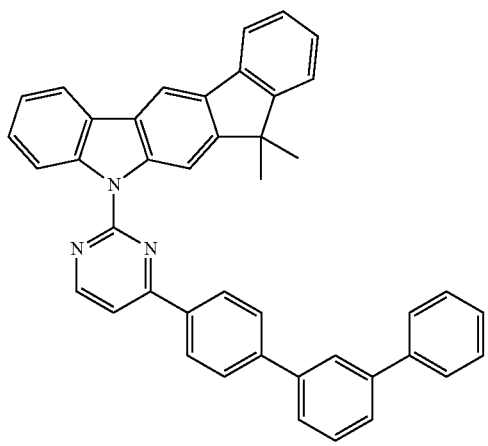
B-188
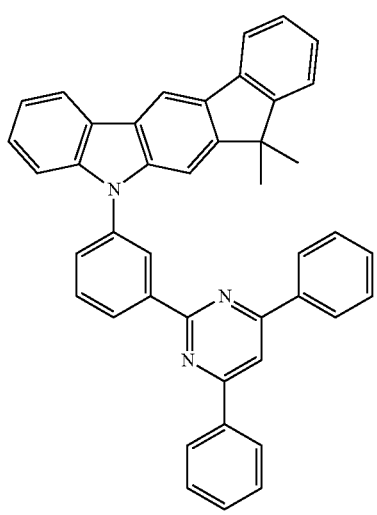
B-189
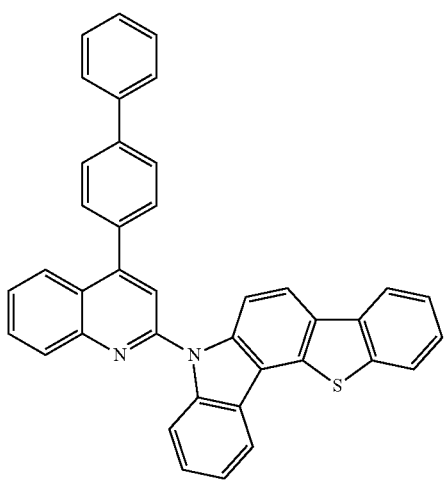
B-190
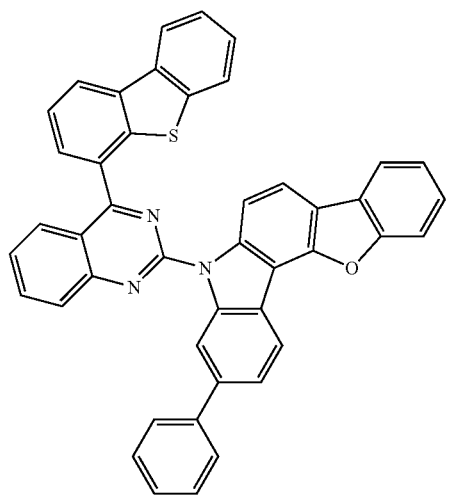
B-191
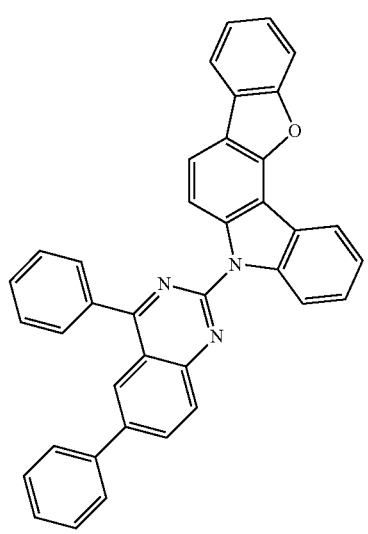
B-192
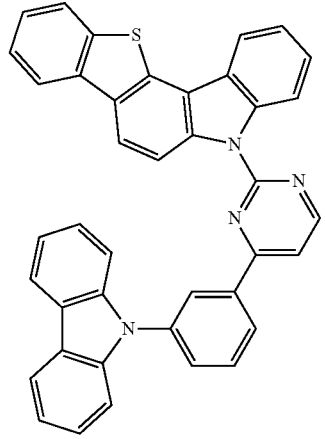

B-193
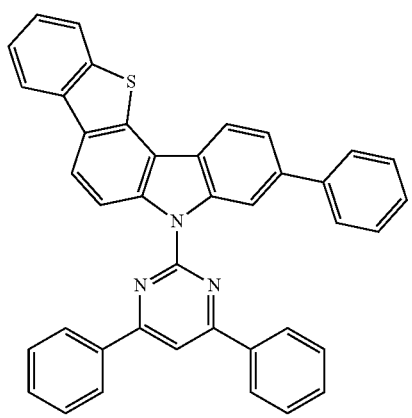
B-194
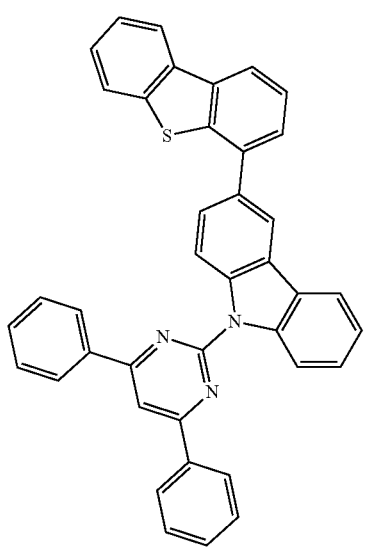
B-195
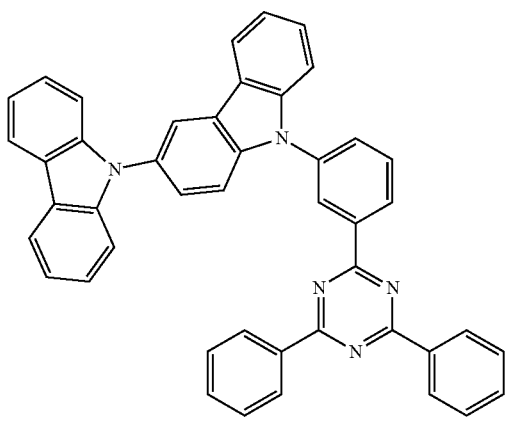
B-196
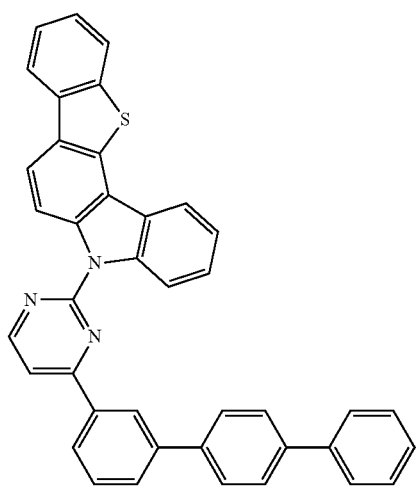
B-197
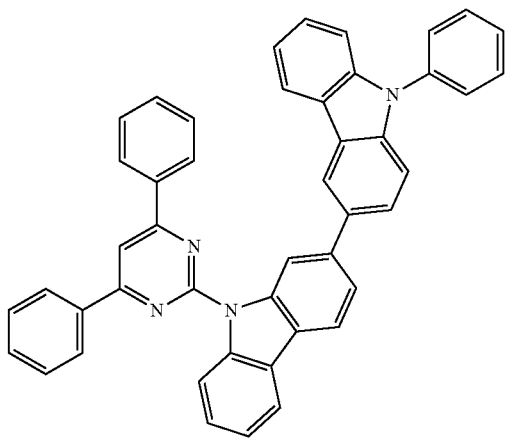
B-198
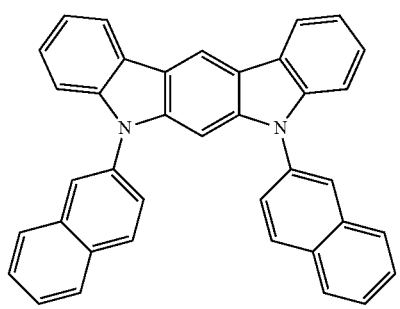
B-199
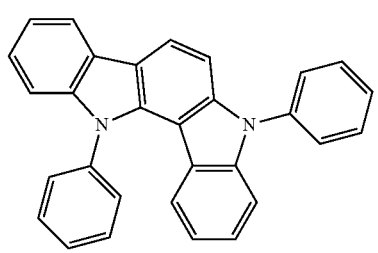

B-200
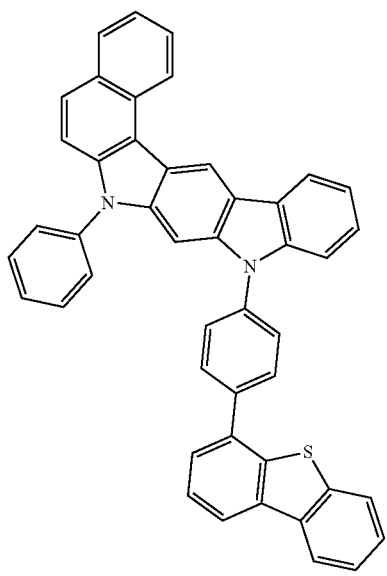
B-201
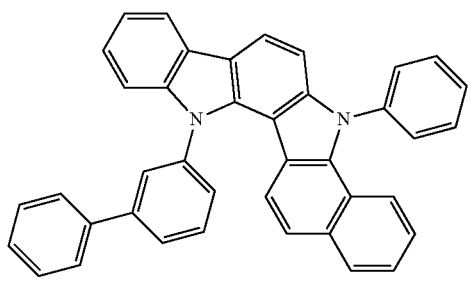
B-202
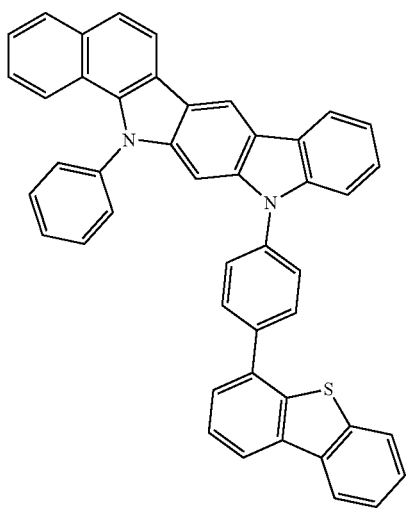
B-203
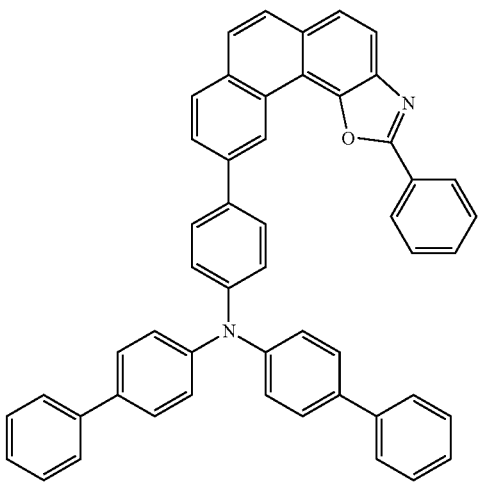
B-204
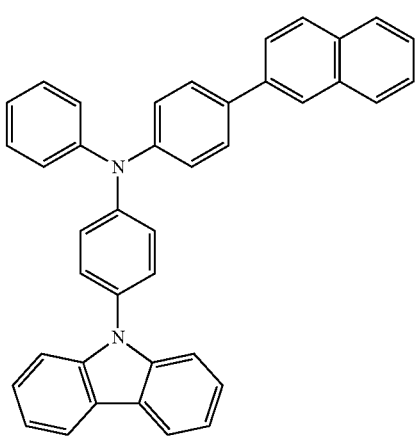
B-205
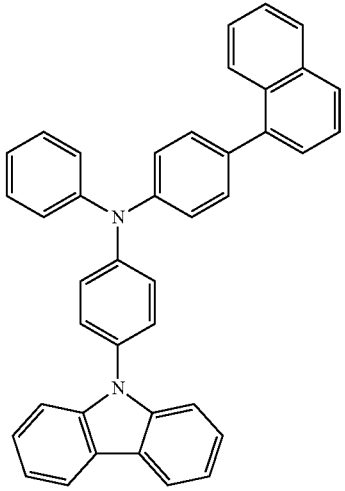

B-206
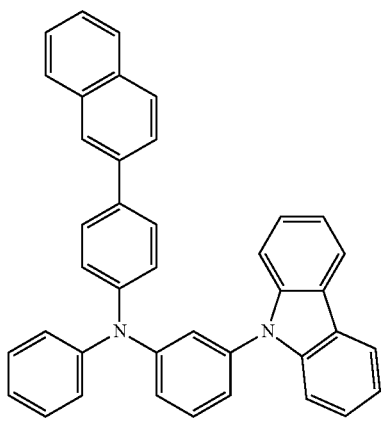
B-207
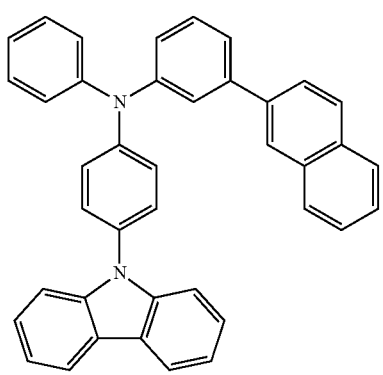
B-208
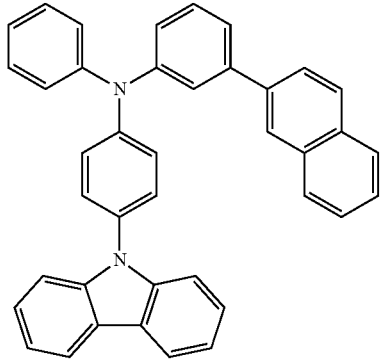
B-209
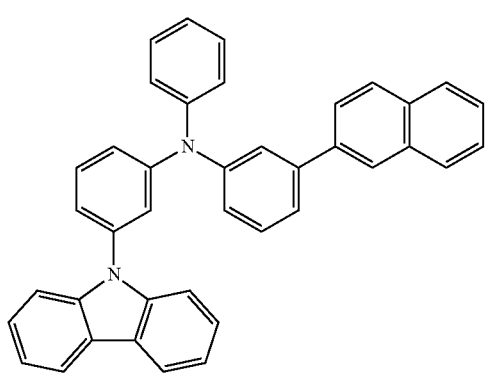
B-210
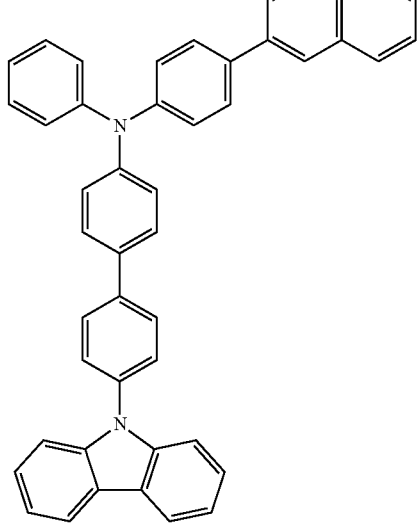
B-211
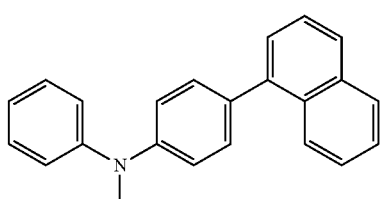
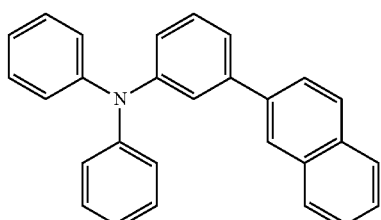
B-212
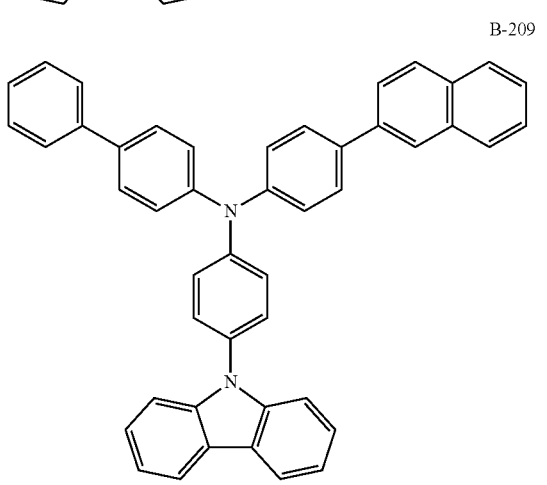

B-213
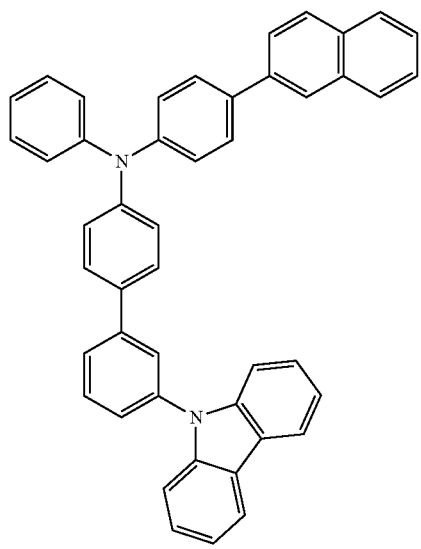
B-214
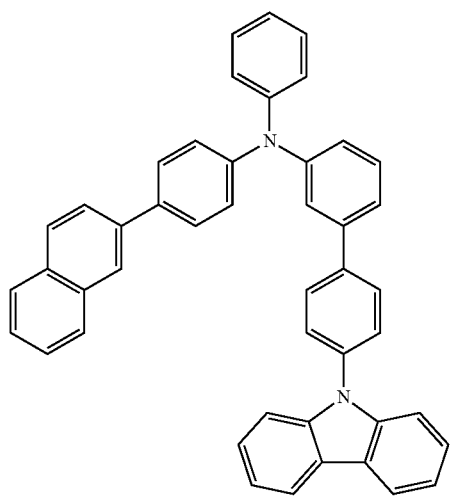
B-215
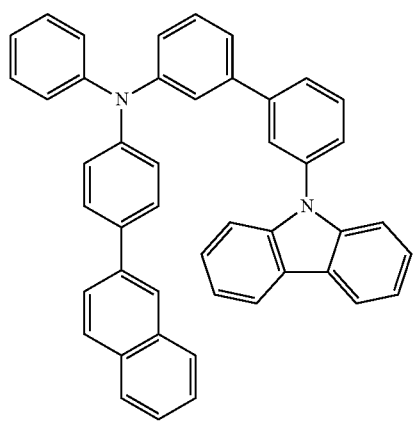
B-216
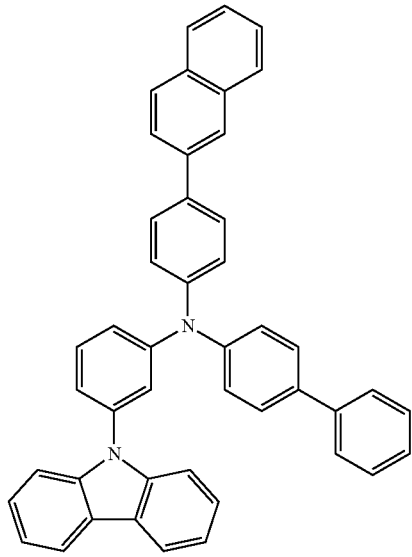
B-217
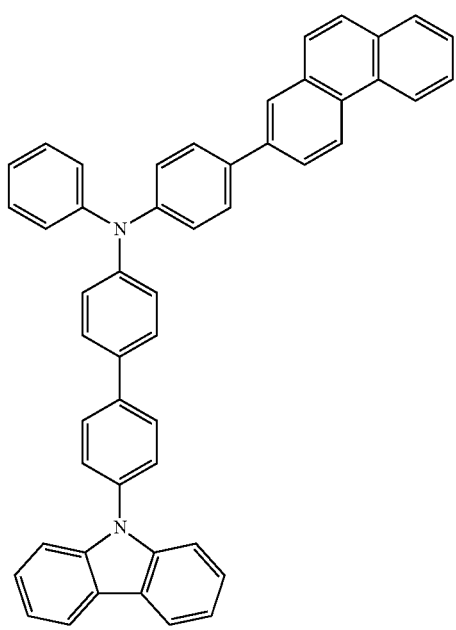

B-218
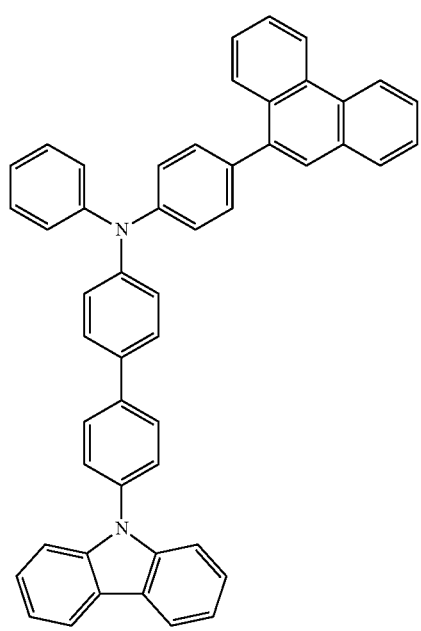
B-219
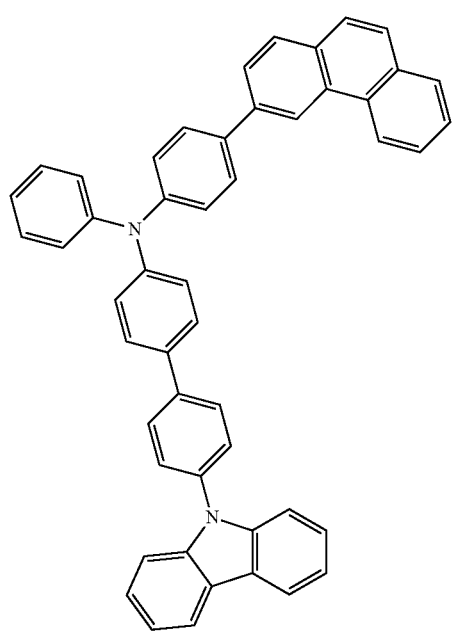
B-220
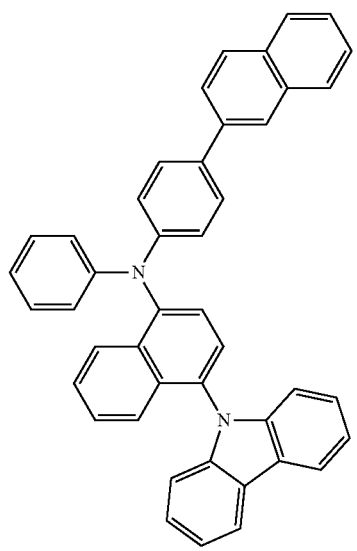
B-221
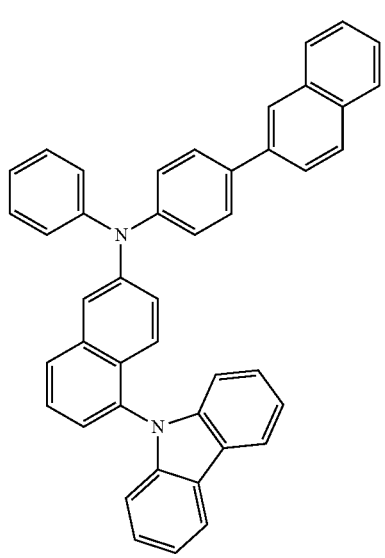
B-222
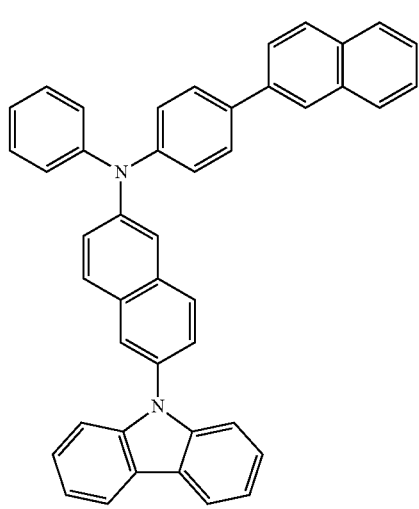

B-223
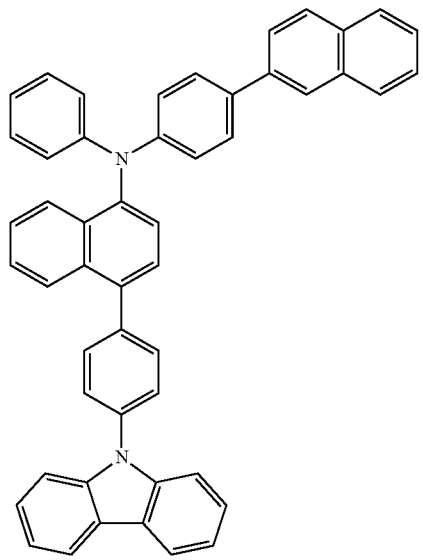
B-224
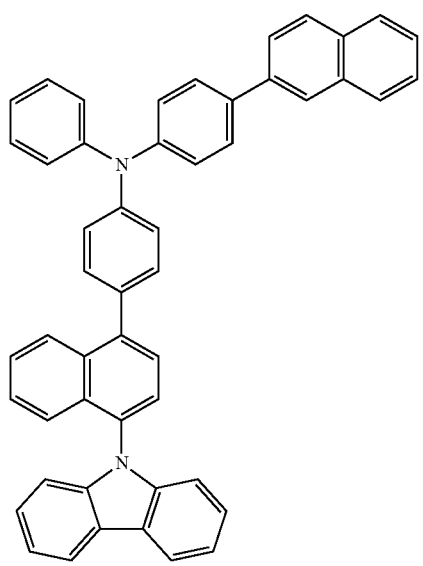
B-225
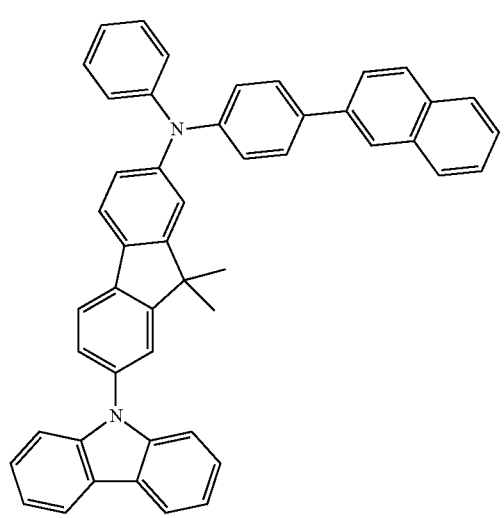
B-226
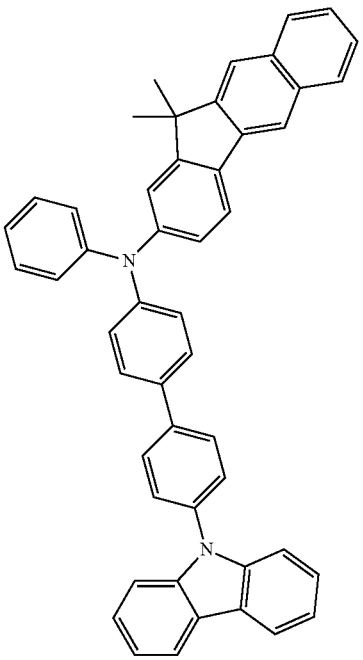
B-227
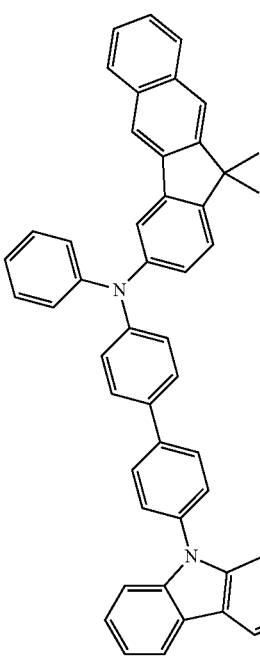

B-228
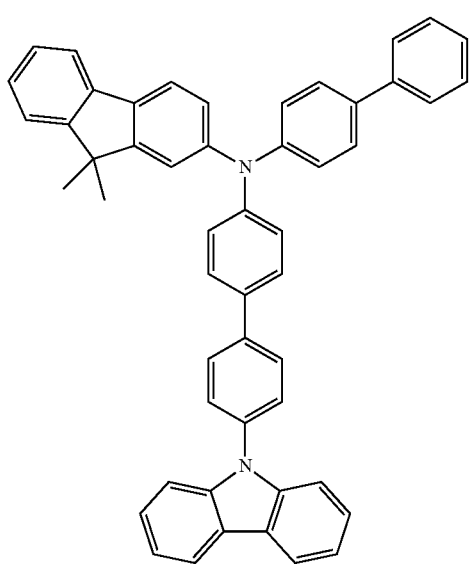
B-229
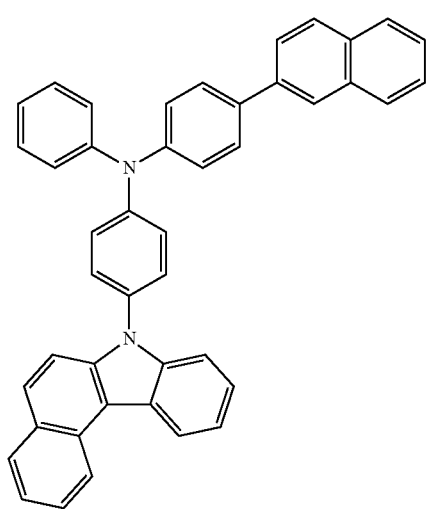
B-230
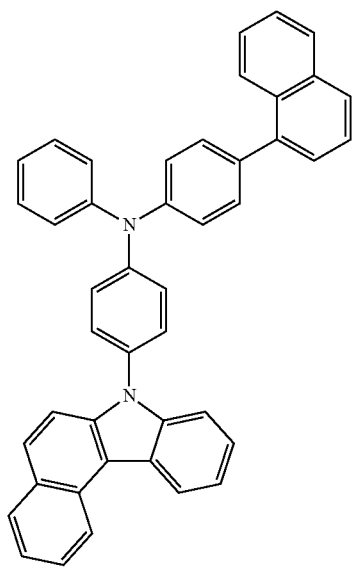
B-231
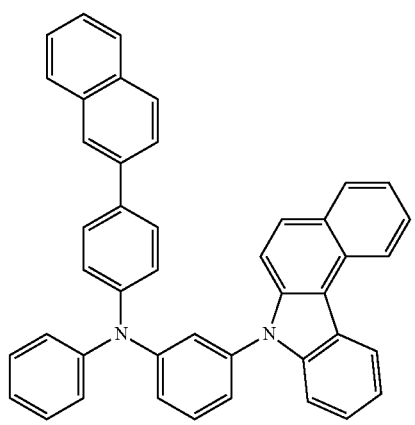
B-232
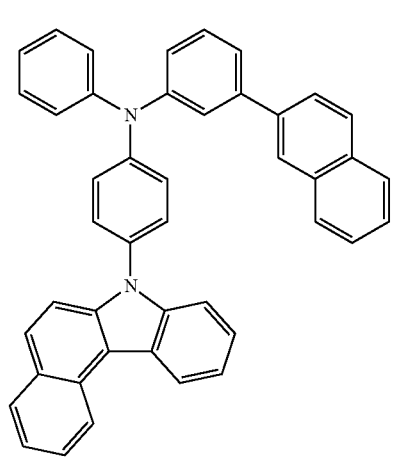
B-233
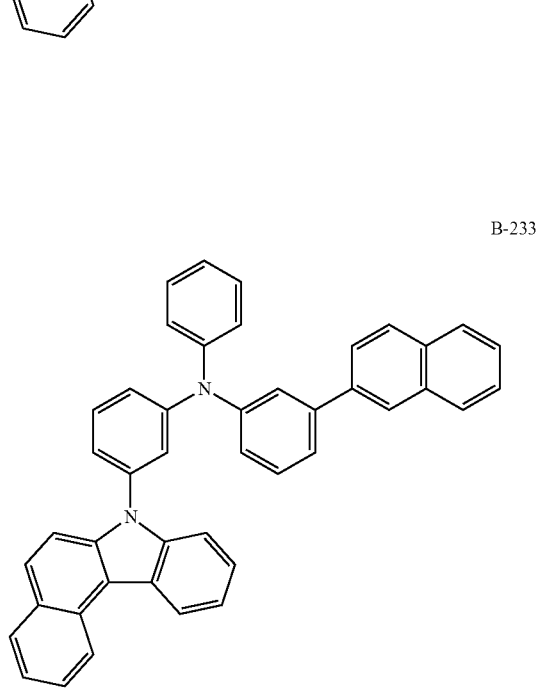

B-234
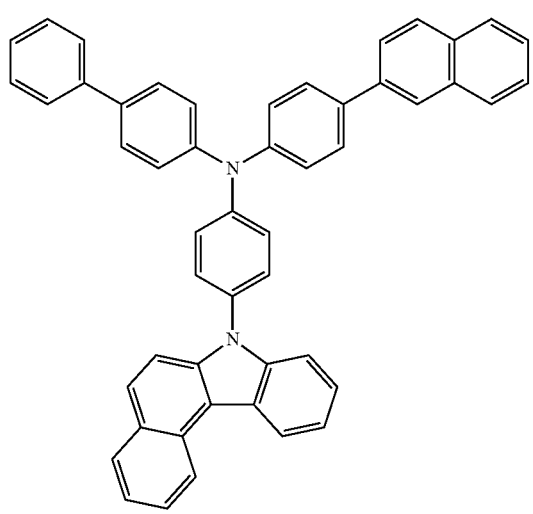
B-235
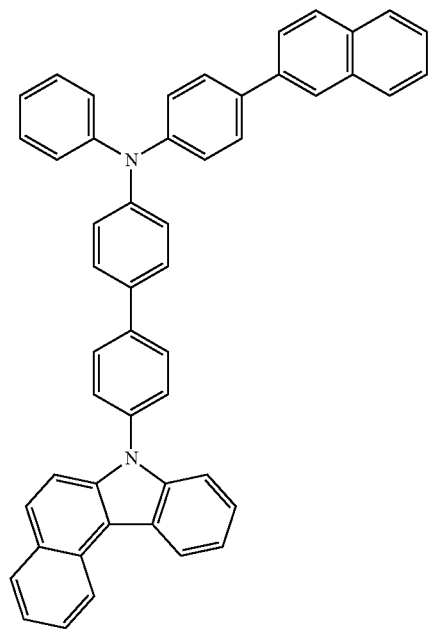
B-236
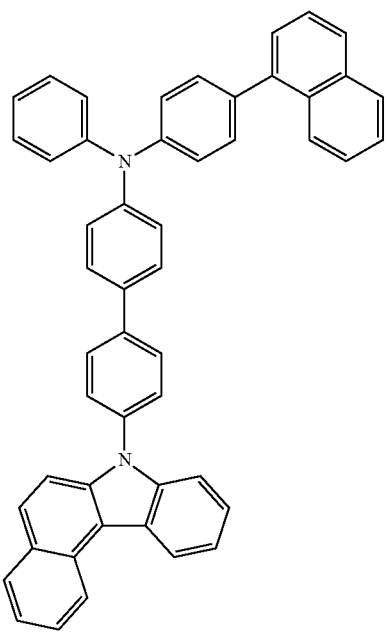
B-237
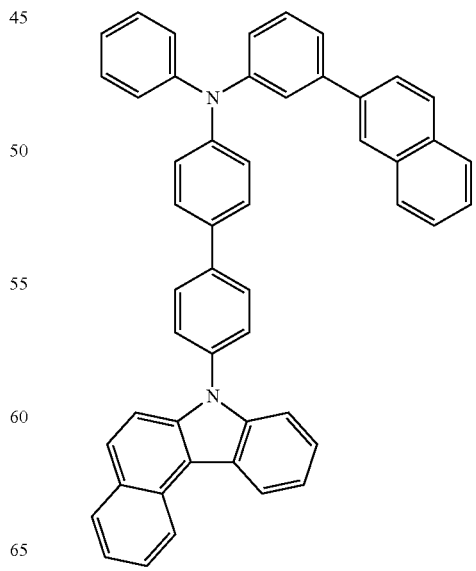

B-238
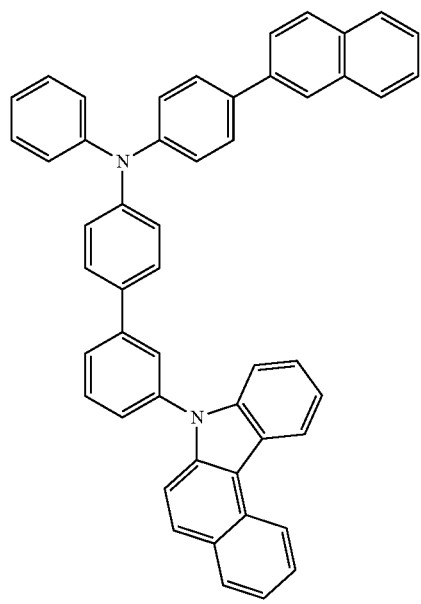
B-240
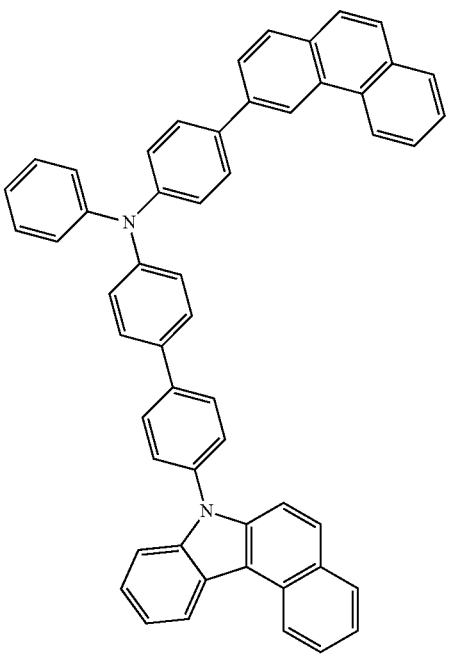
B-239
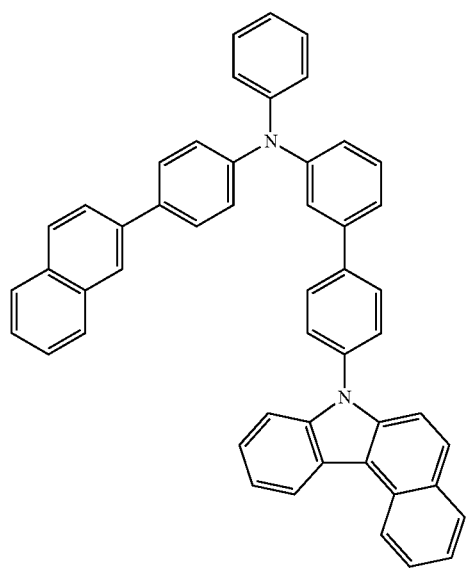
B-241
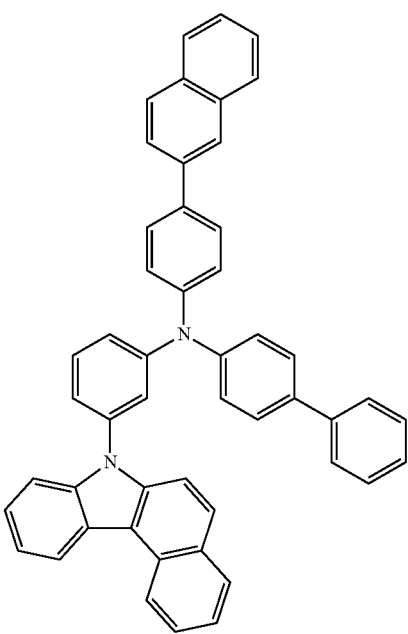

B-242
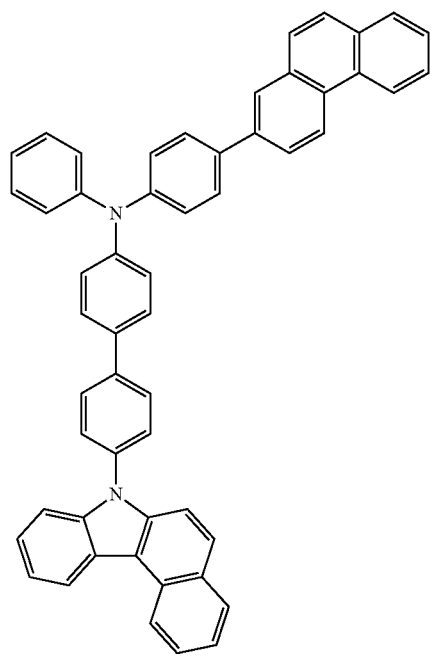
B-244
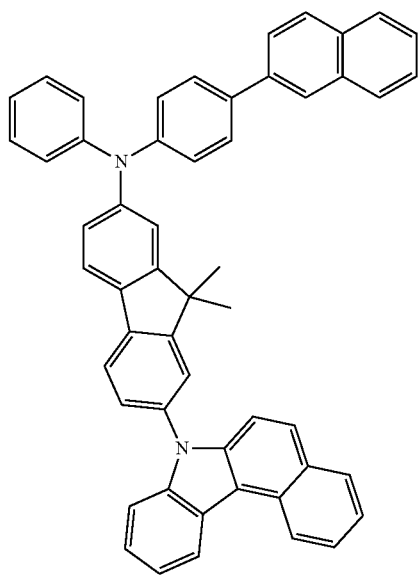
B-243
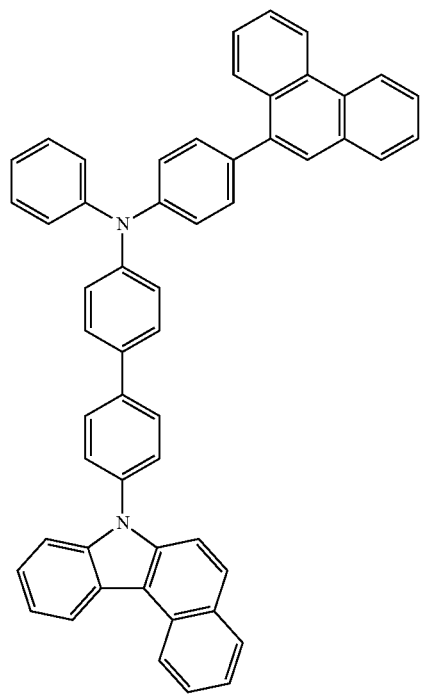
B-245

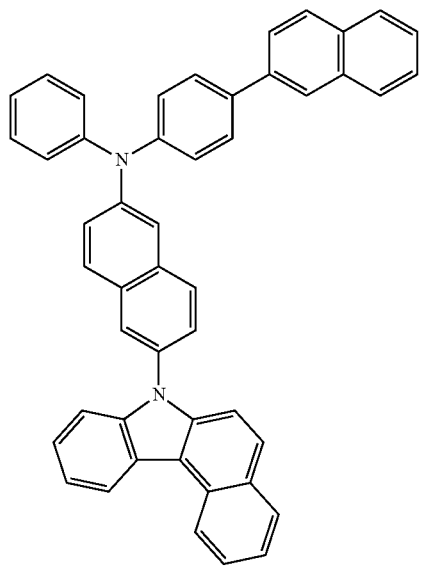
B-246
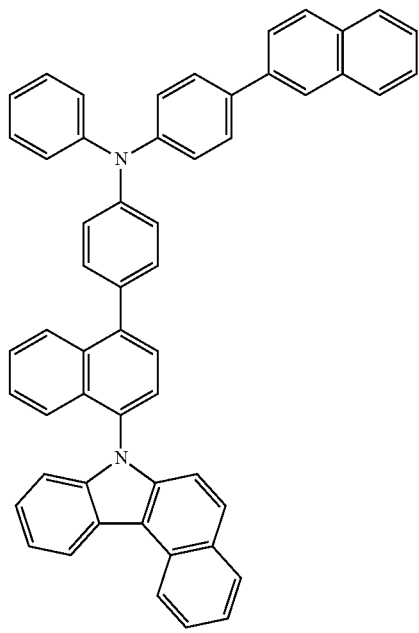
B-248
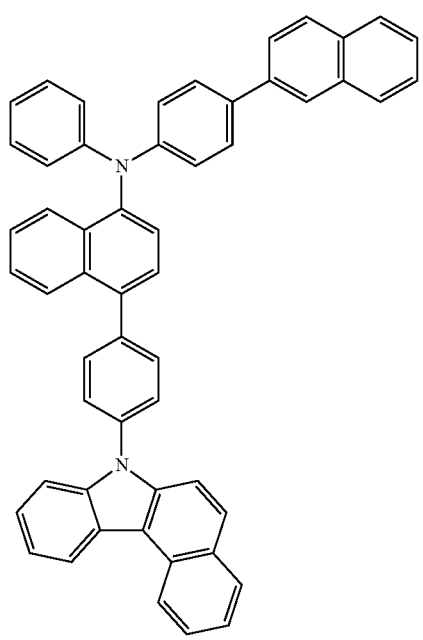
B-247
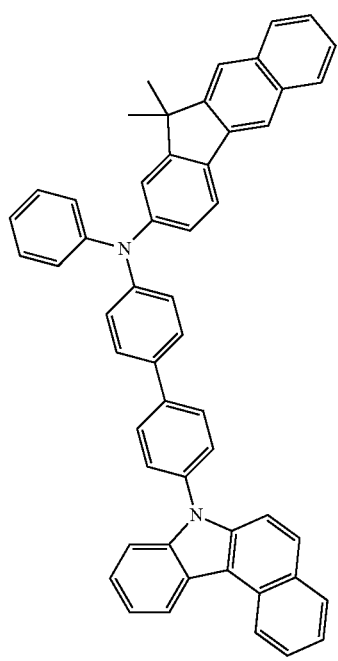
B-249

B-250
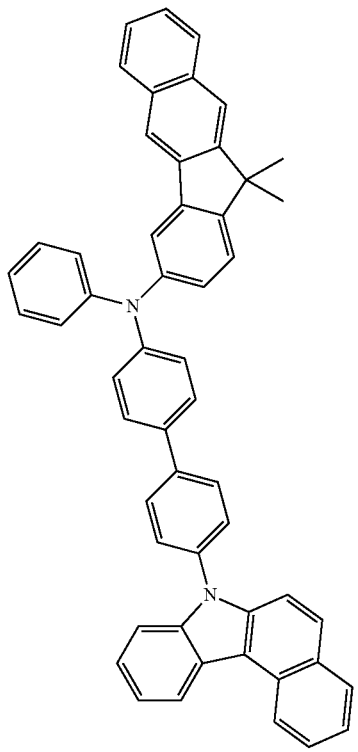
B-252
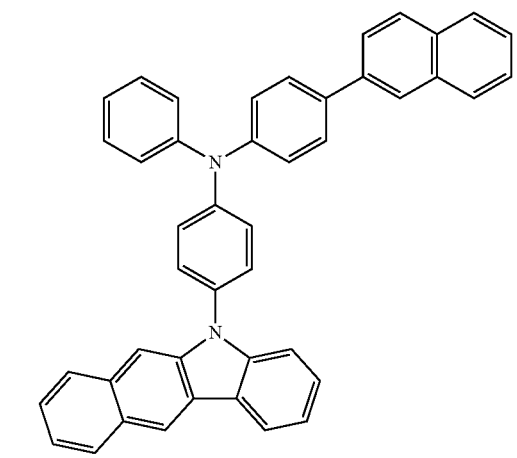
B-253
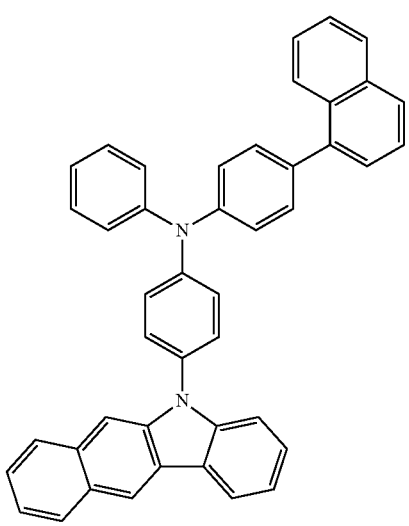
B-251
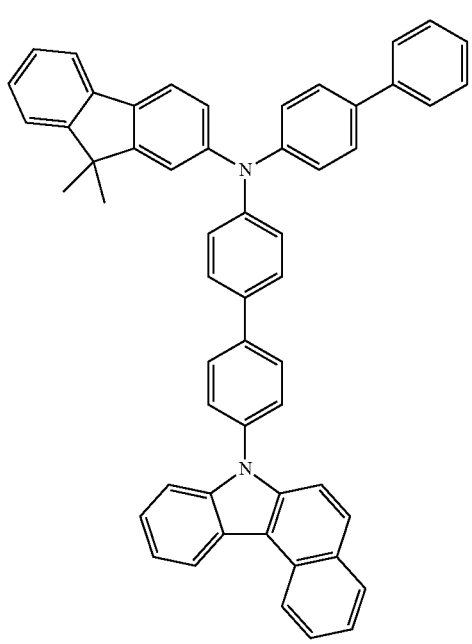
B-254
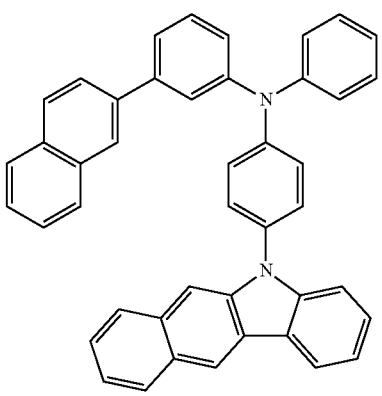

B-255
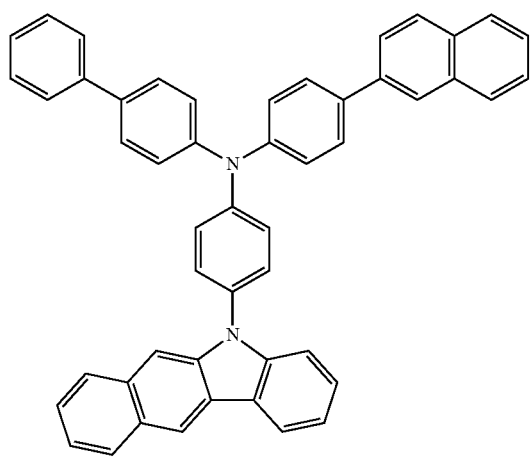
B-256
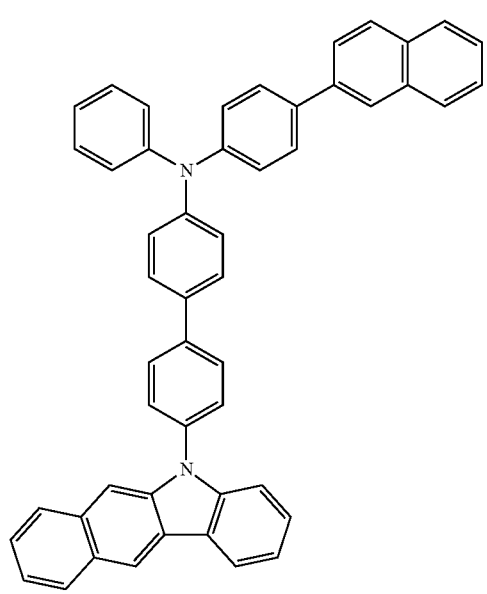
B-257
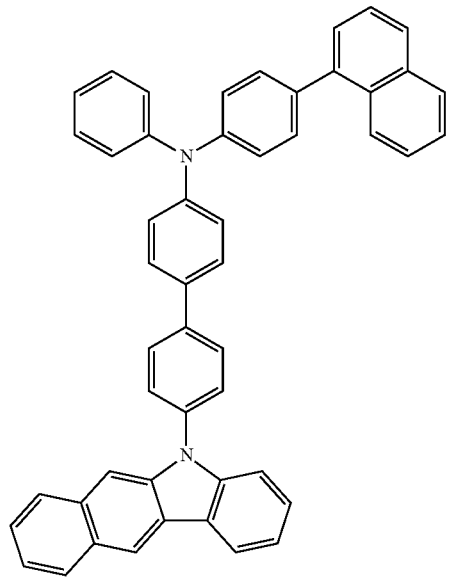
B-258
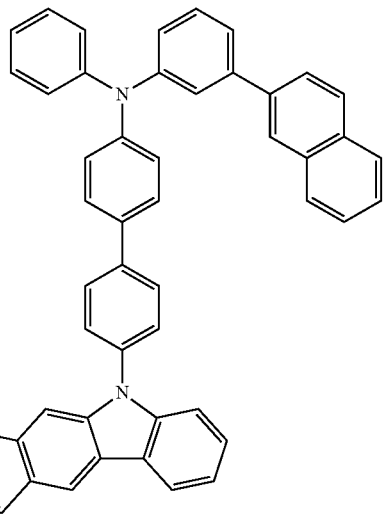
B-259
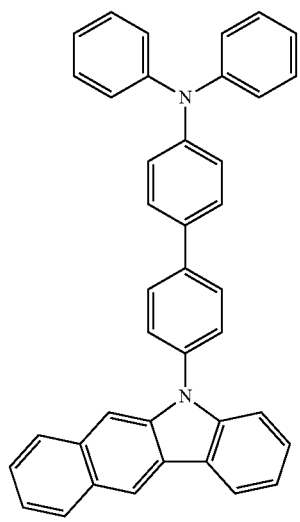
B-260
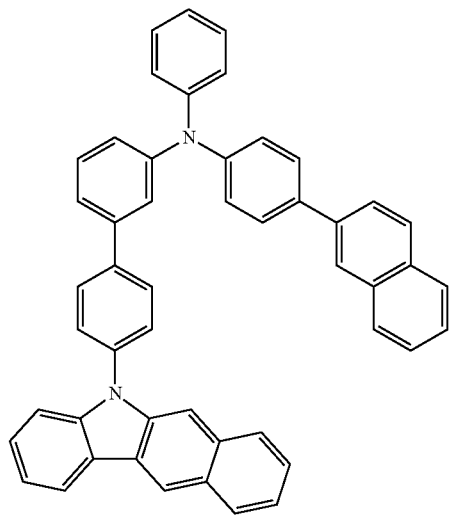

B-261
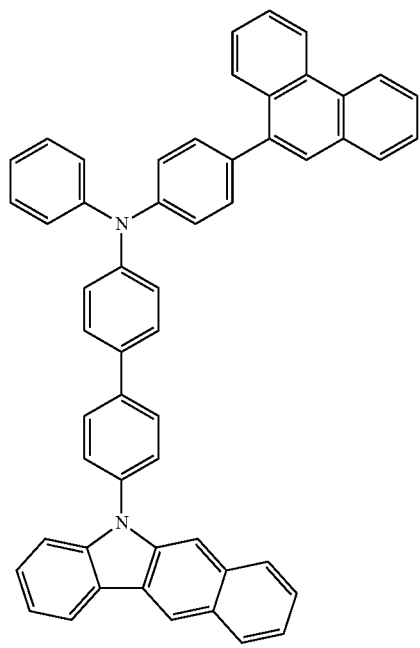
B-262
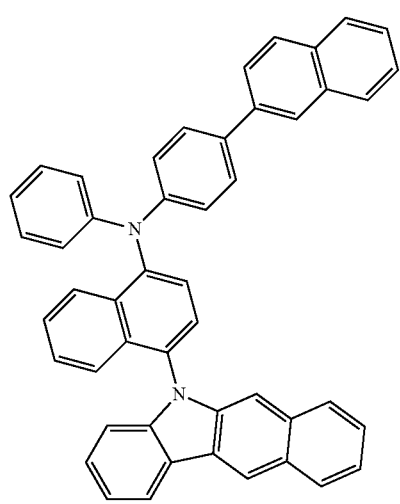
B-263
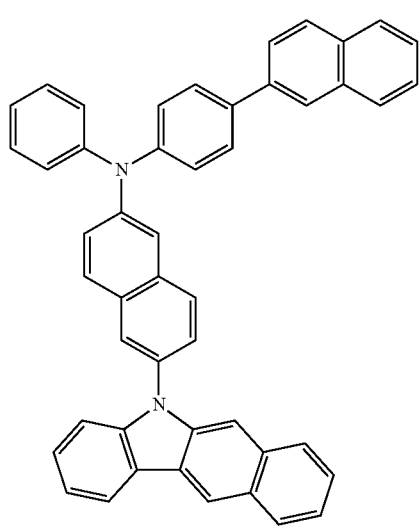
B-264
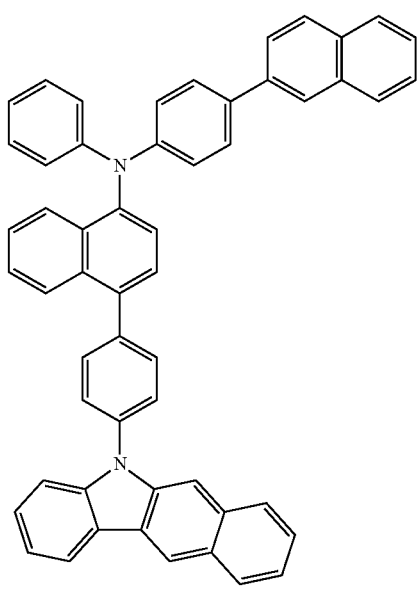
B-265
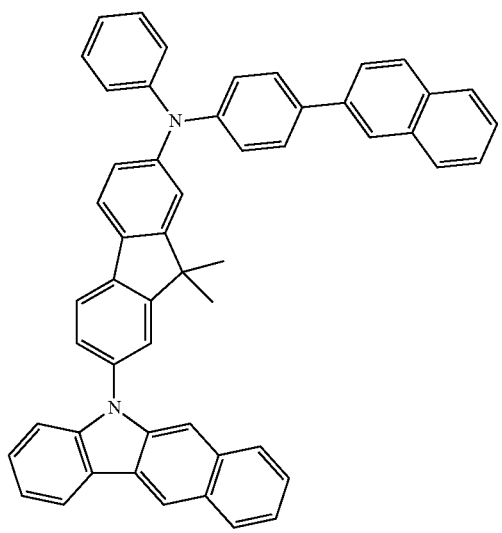

B-266
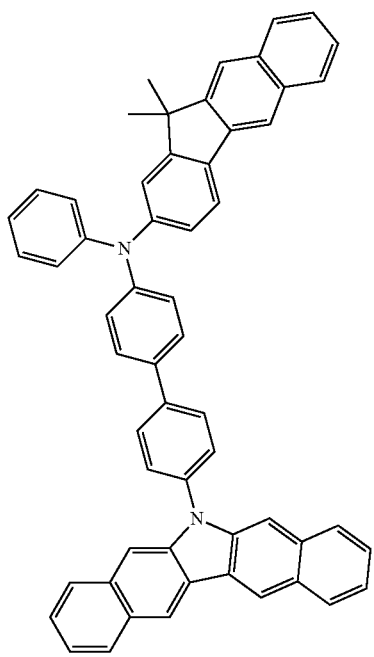
B-268
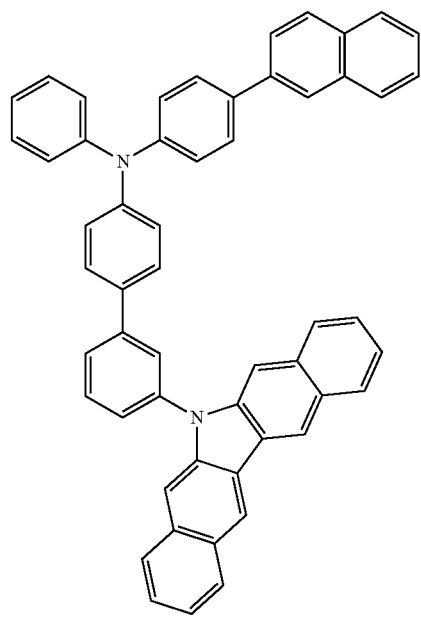
B-267
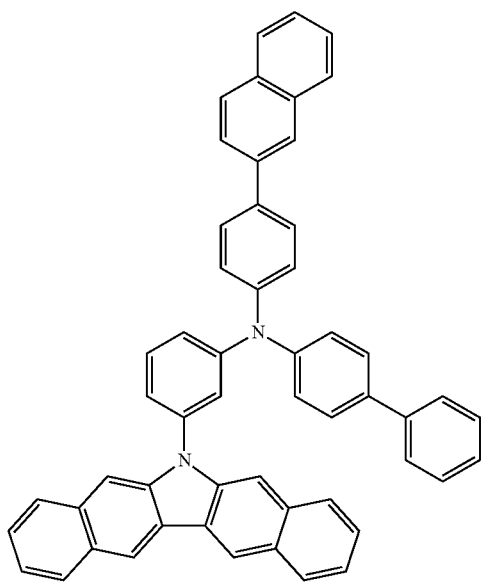
B-269
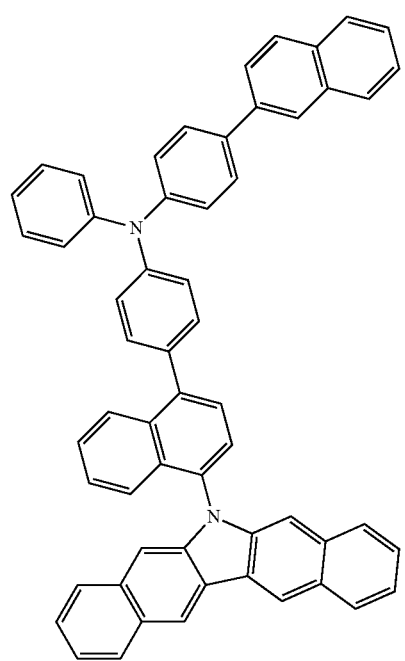

B-270
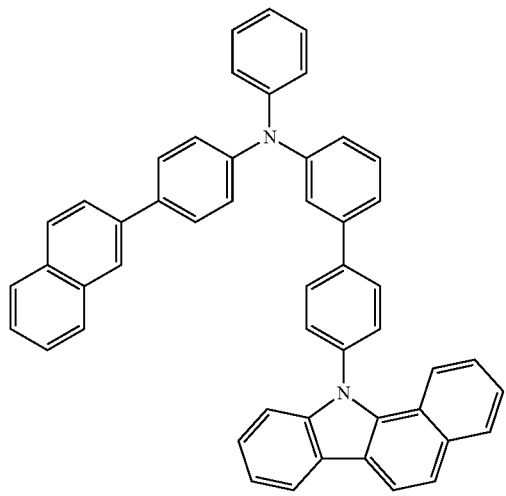
B-271
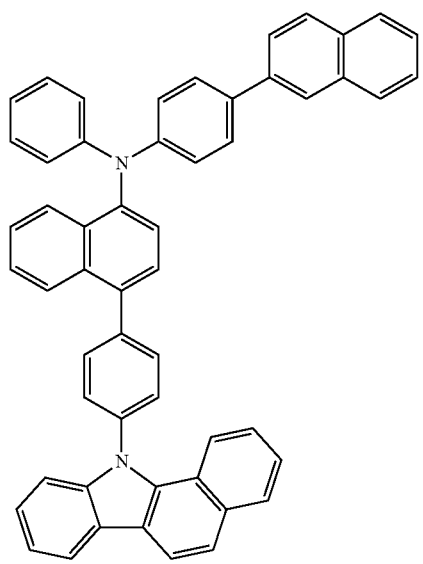
B-272
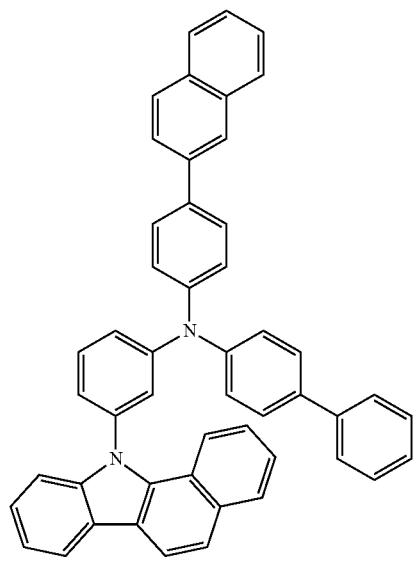
B-273
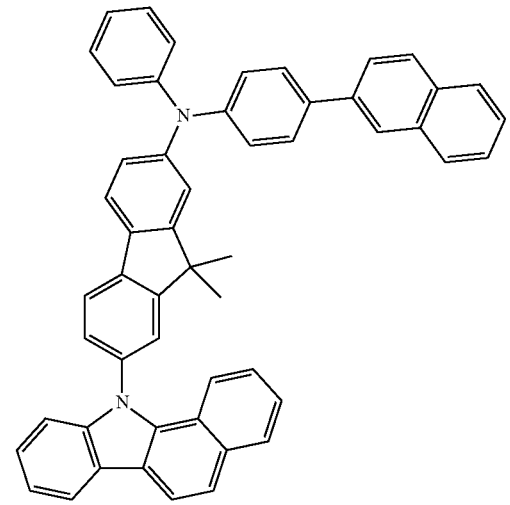
B-274
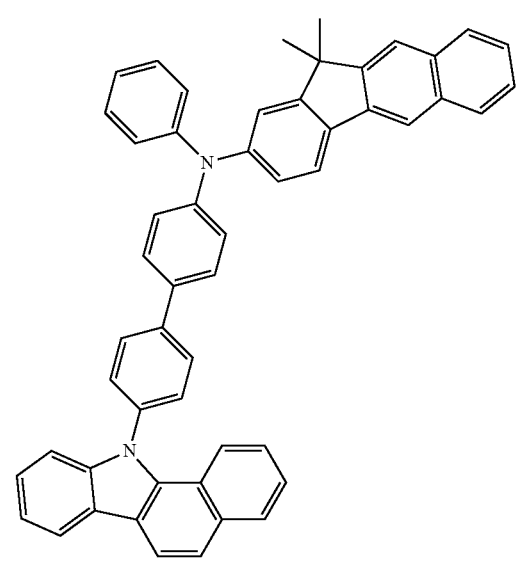
B-275
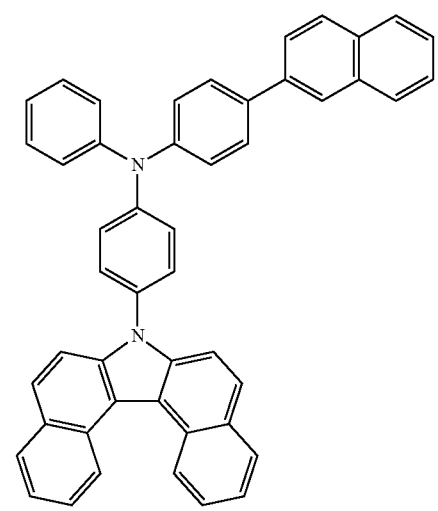

B-276
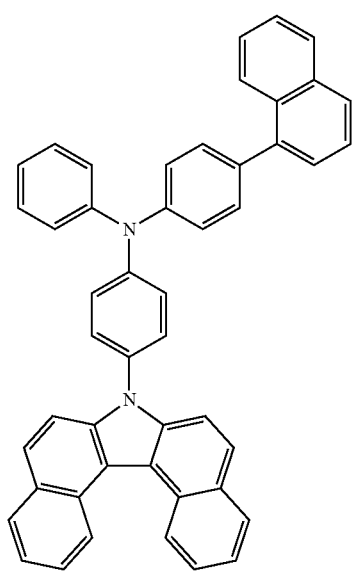
B-277
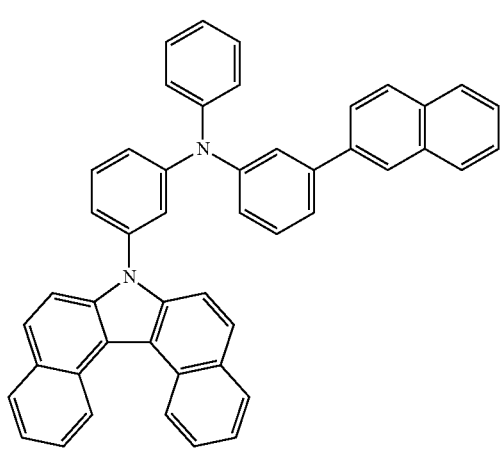
B-278
B-279
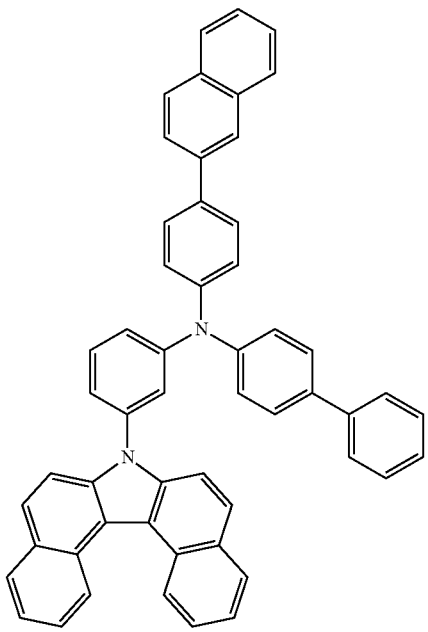
B-280
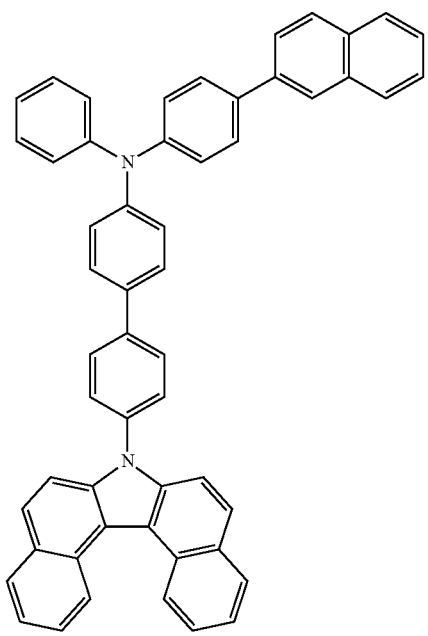

B-281
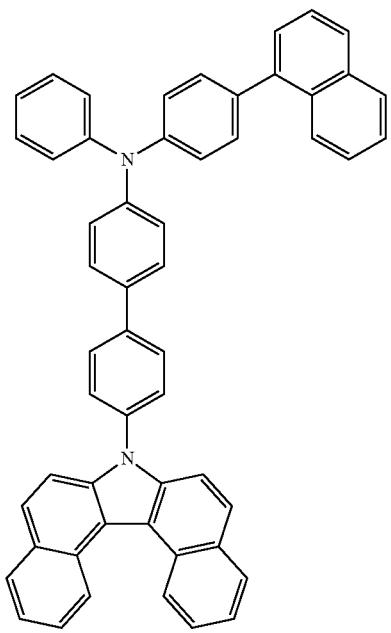
B-283
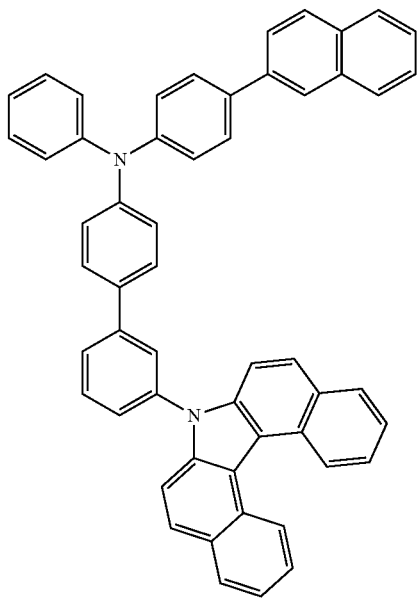
B-282
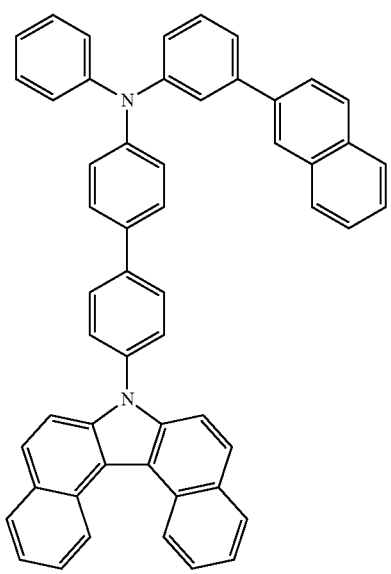
B-284
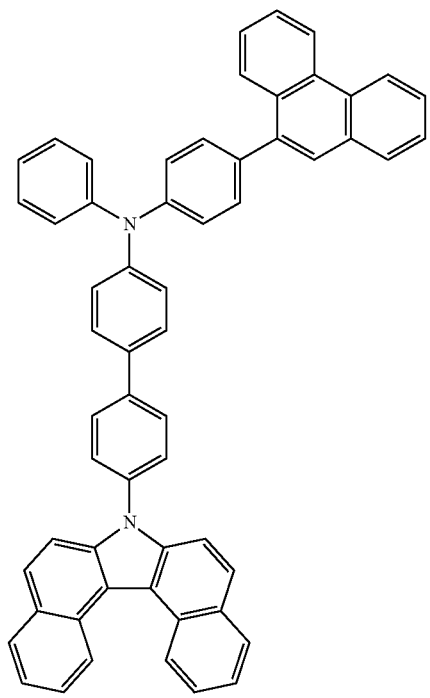

B-285
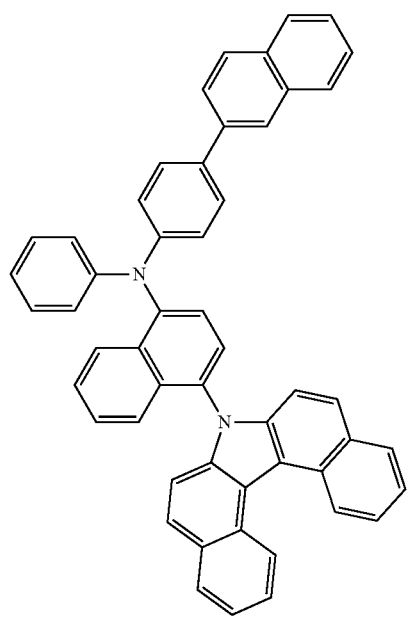
B-286
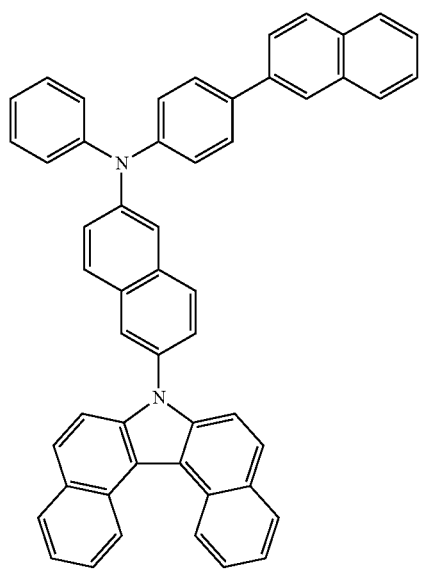
B-287
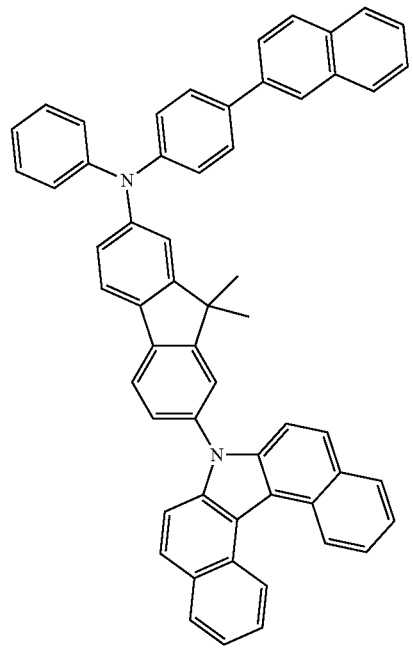
B-288
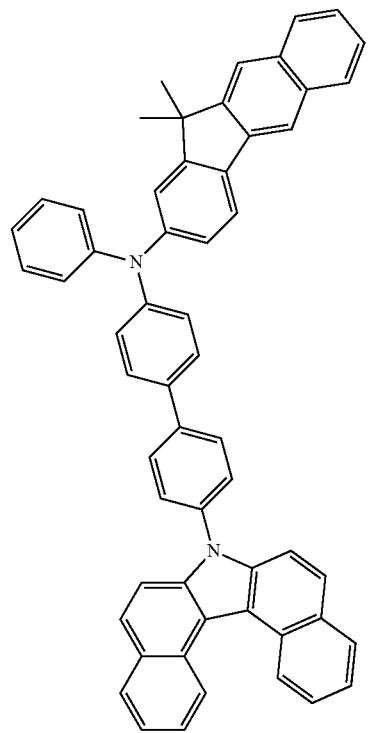

-continued
B-289
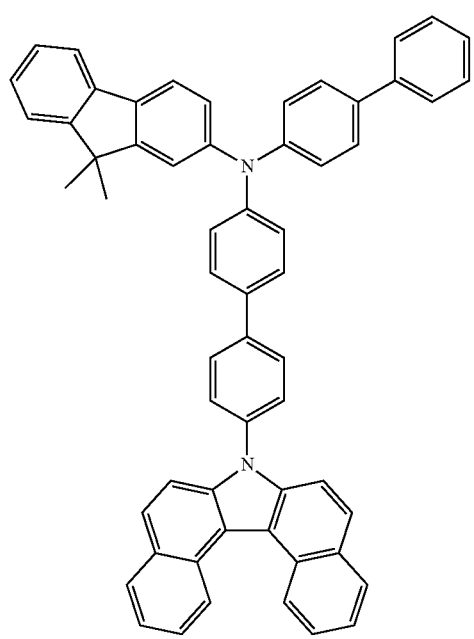
B-290
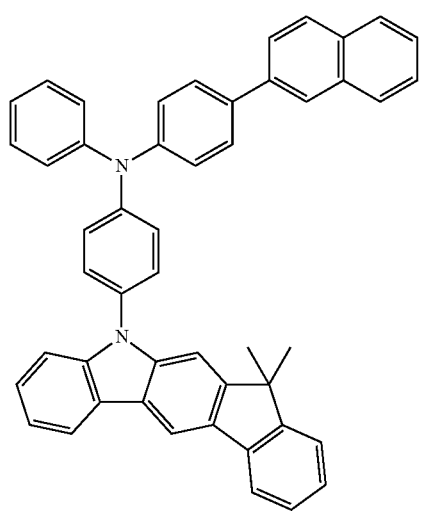
B-291
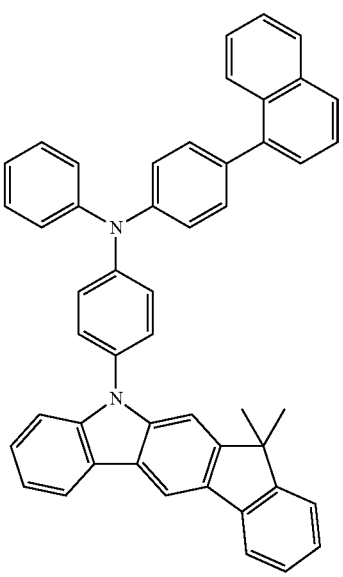
B-292
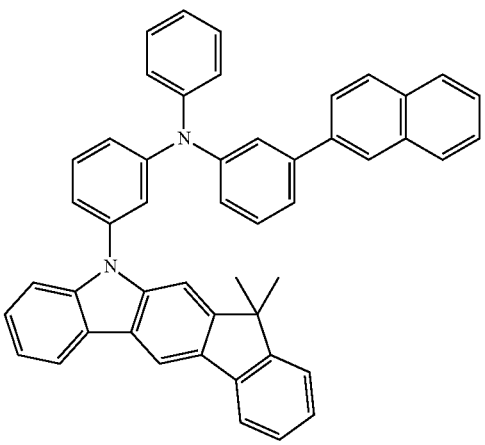
B-293

B-294
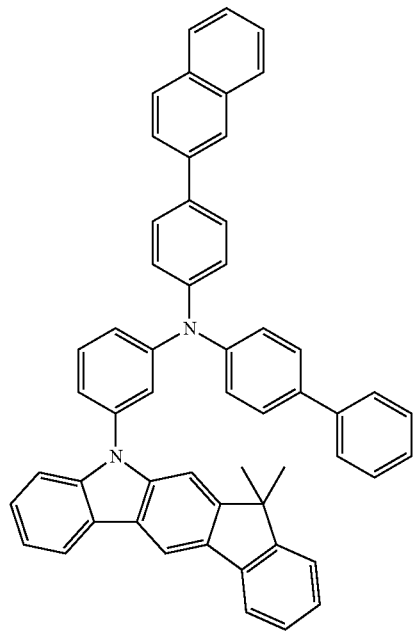
B-295
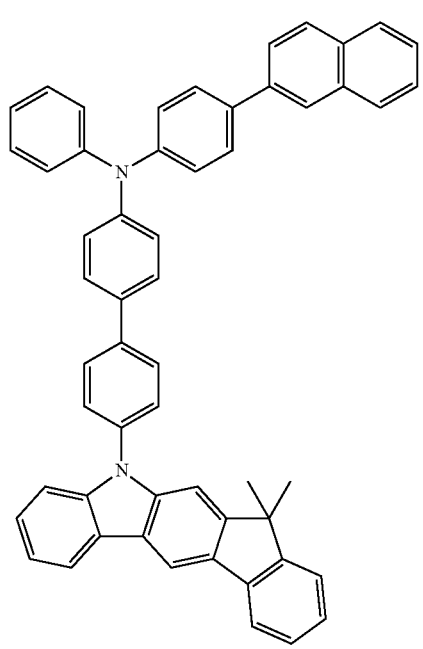
B-296
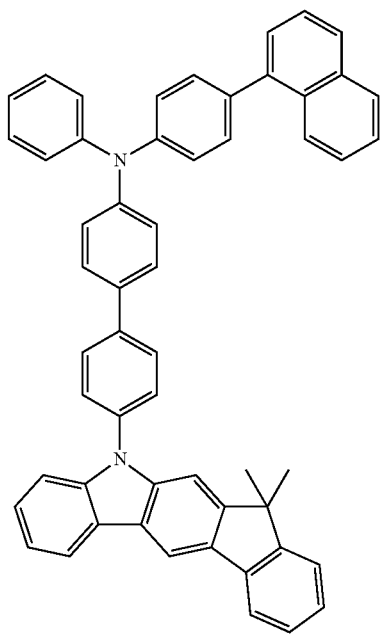
B-297
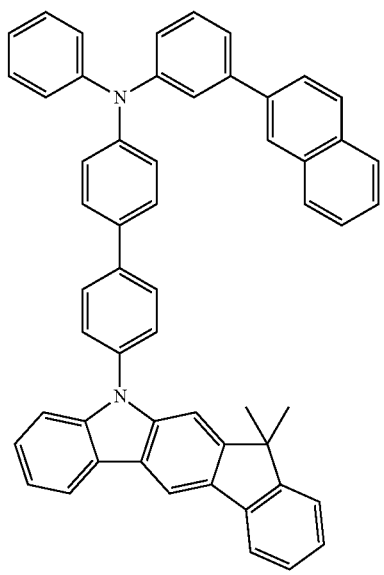

B-298
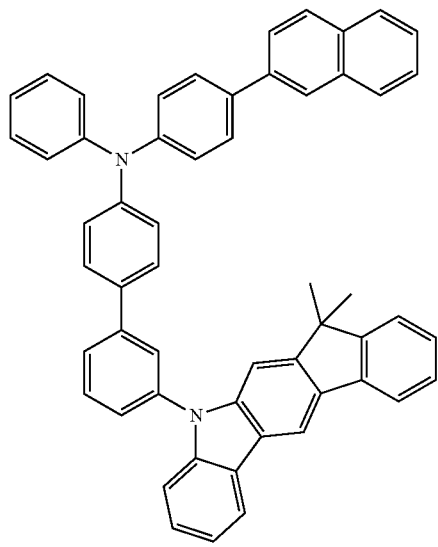
B-299
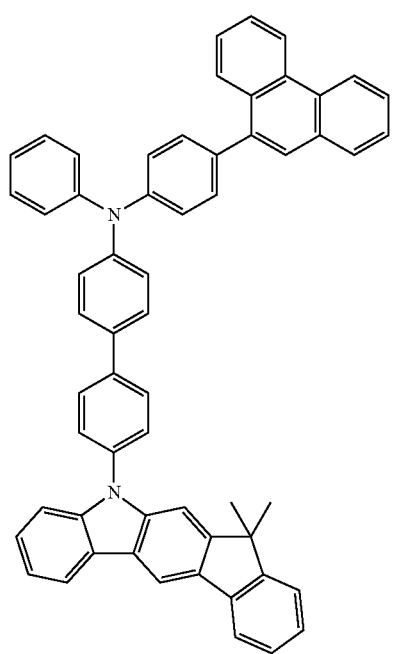
B-300
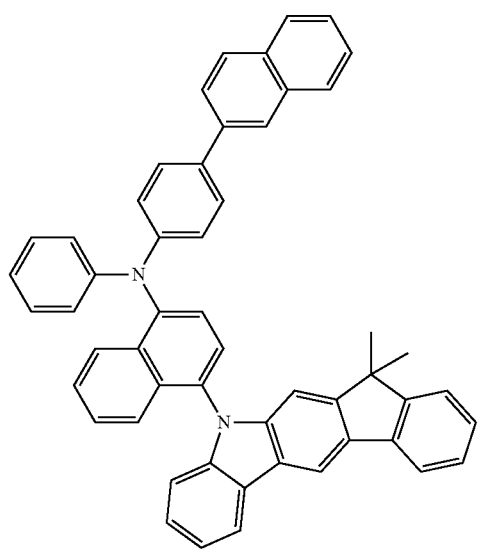
B-301
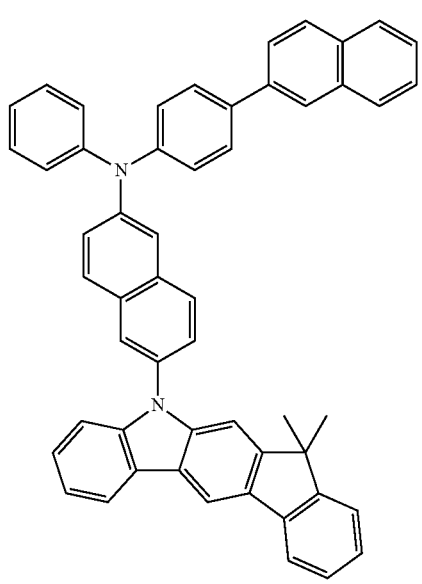

B-302
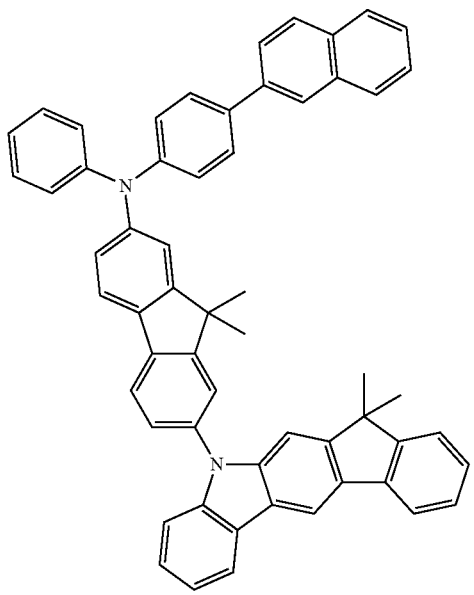
B-304
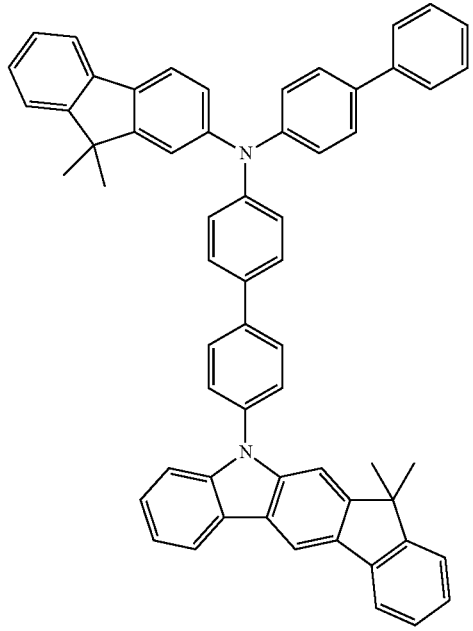
B-303
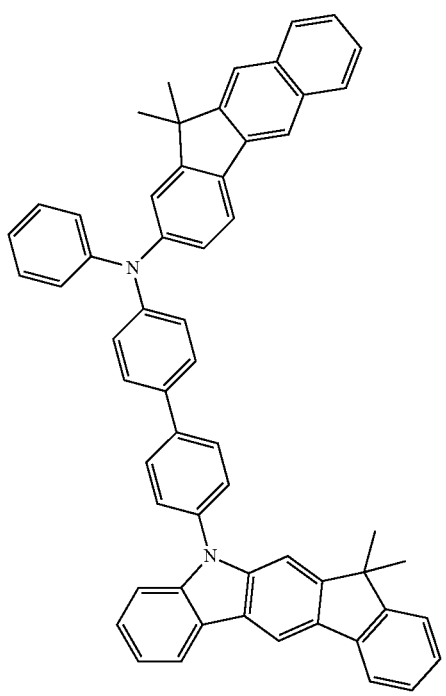
B-305
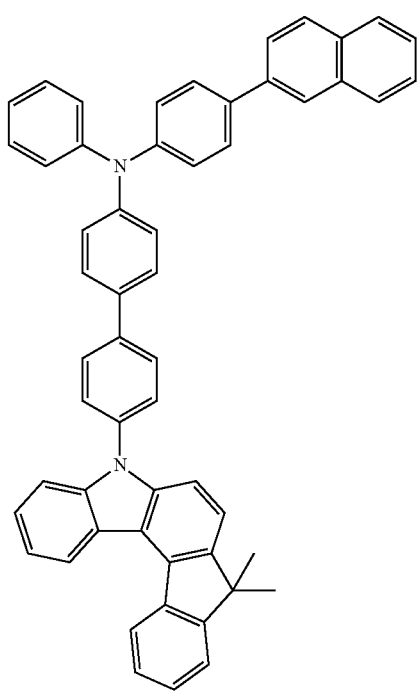

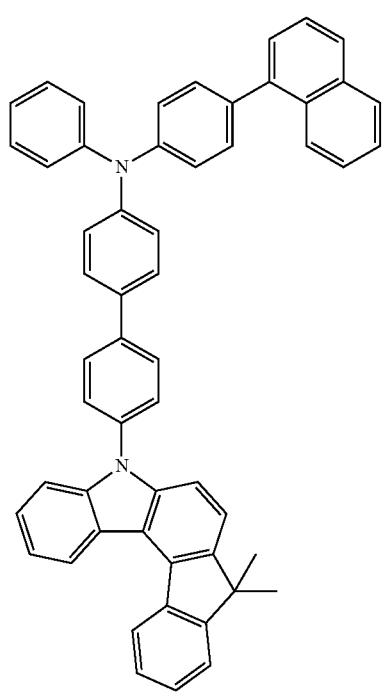
B-306
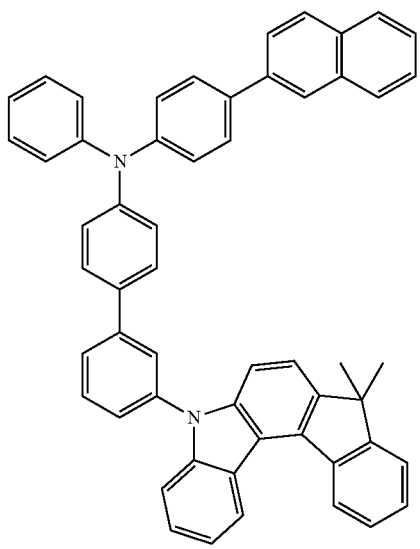
B-308
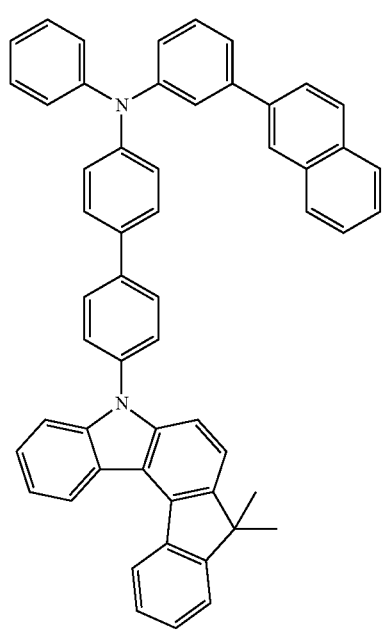
B-307
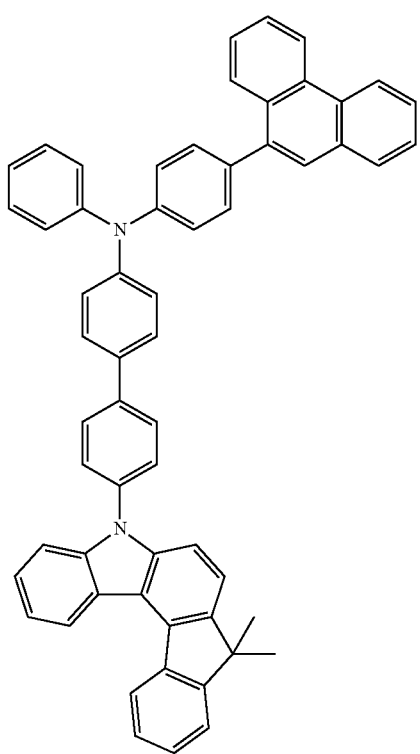
B-309

B-310
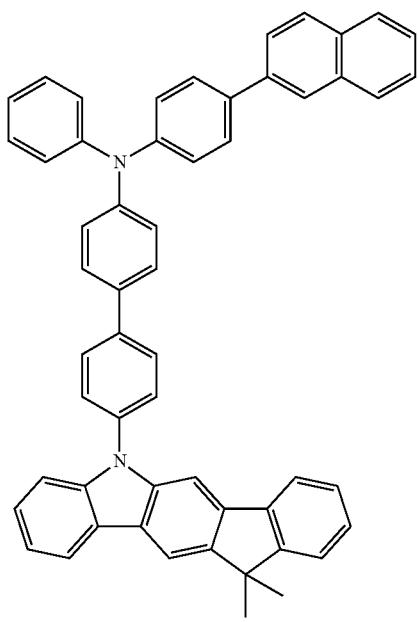
B-311
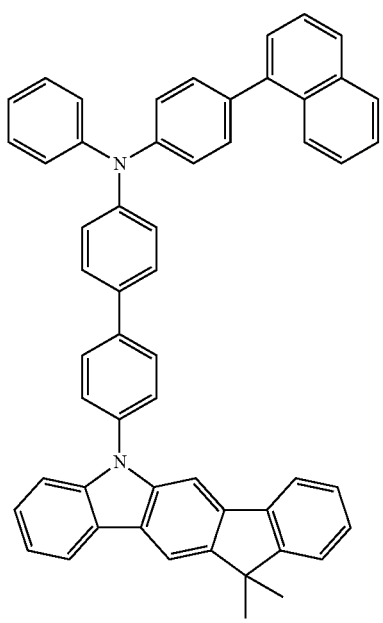
B-312
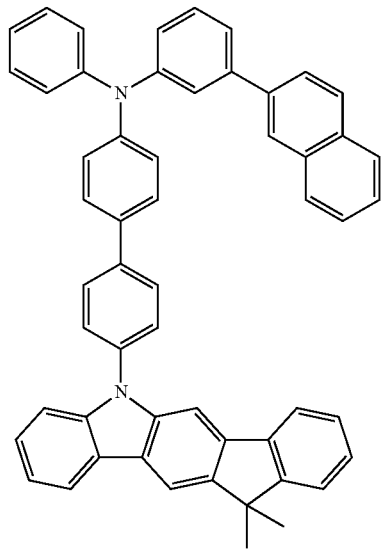
B-313
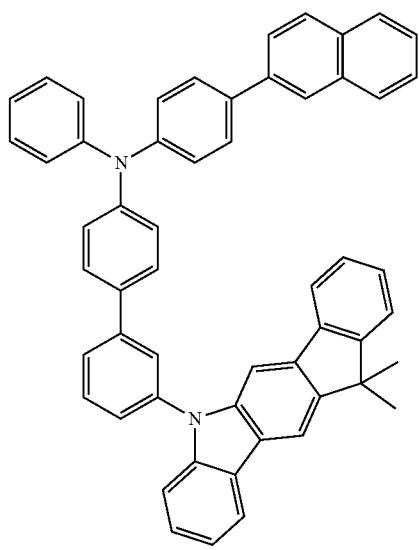

B-314
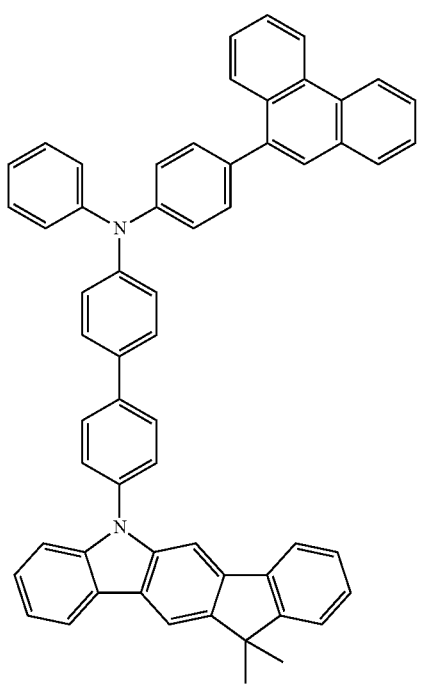
B-315
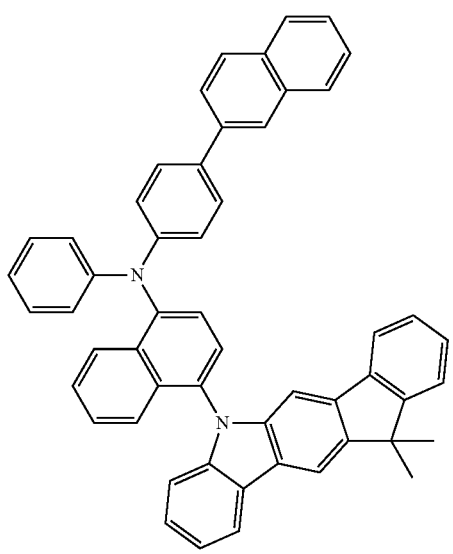
B-316
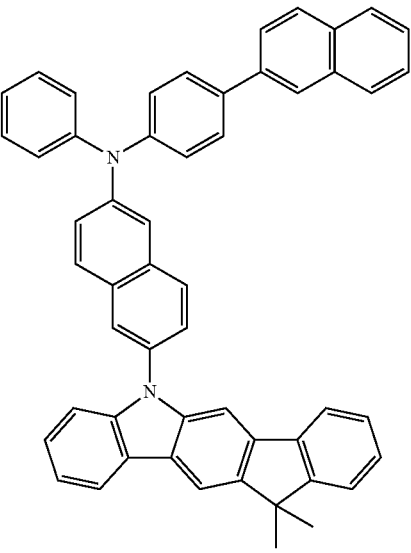
B-317
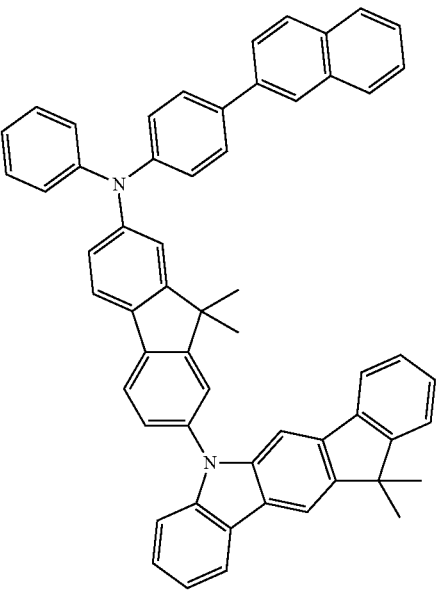

B-318
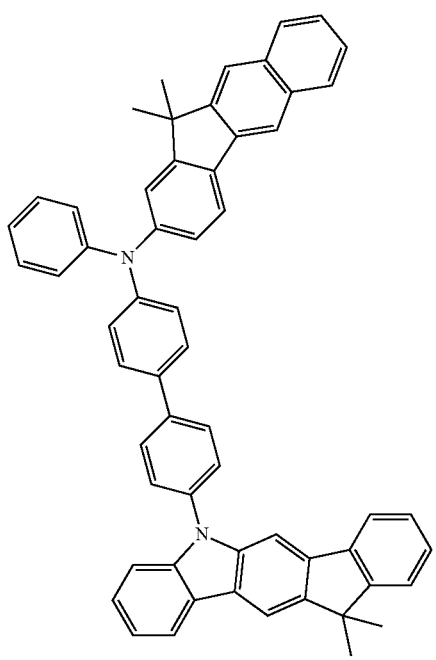
B-320
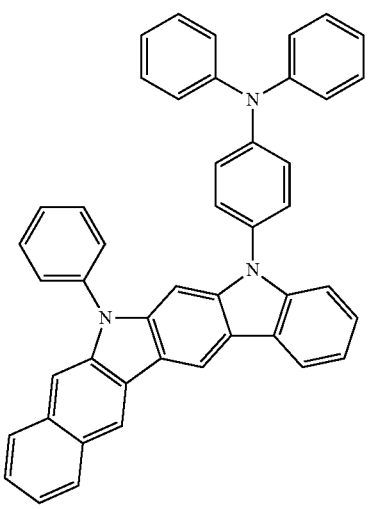
B-321
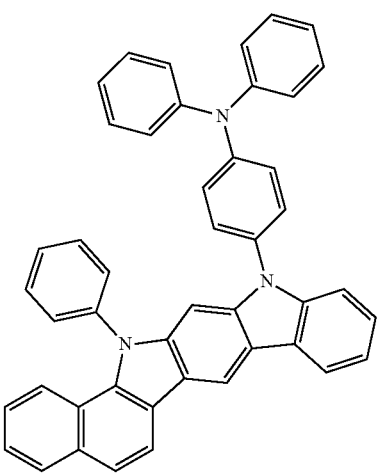
B-319
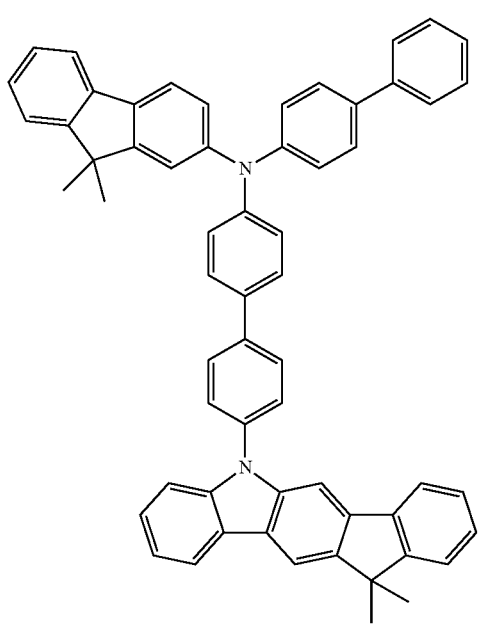
B-322
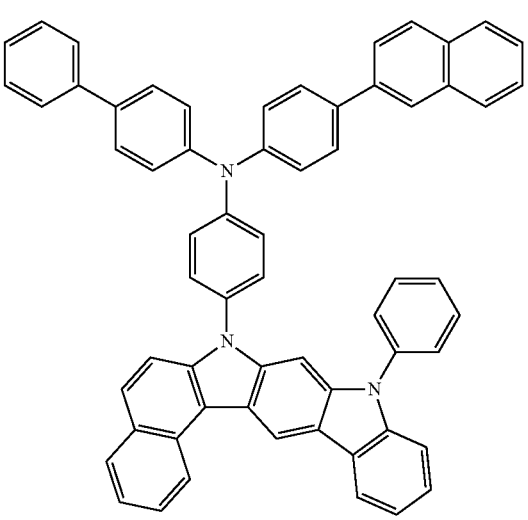

-continued
B-323
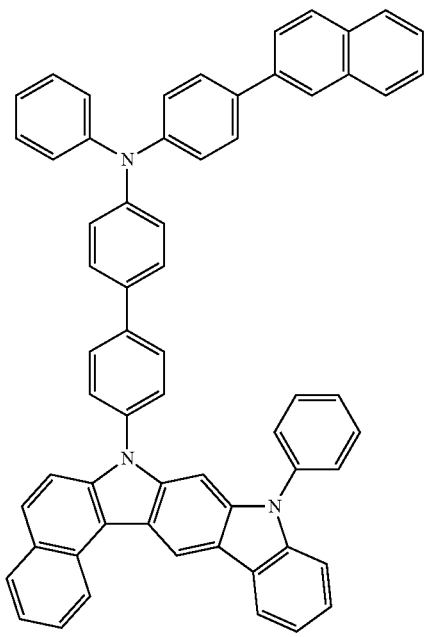
B-324
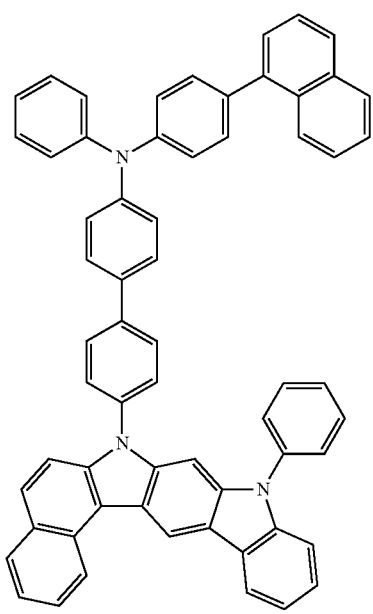
B-325
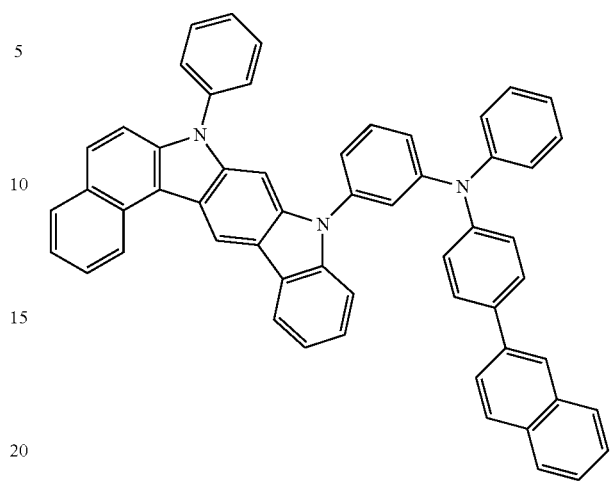
B-326
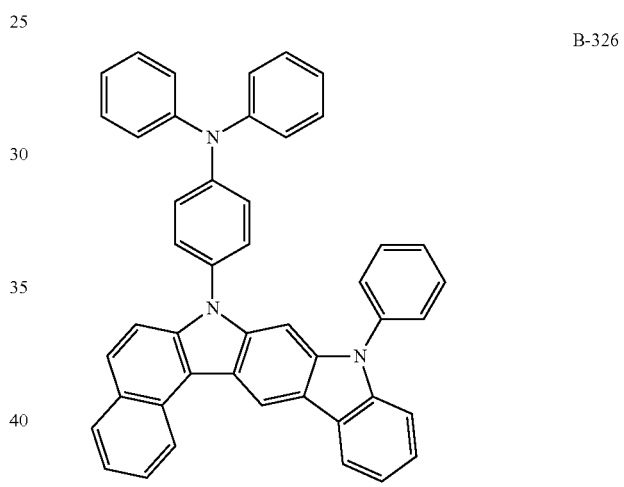
B-327
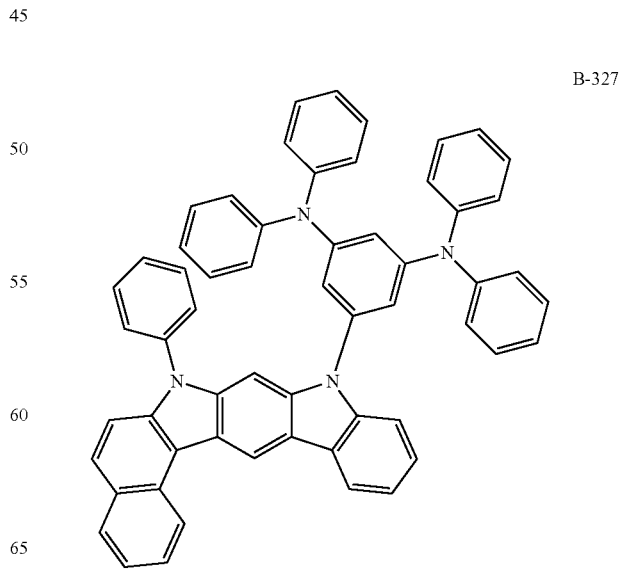

B-328
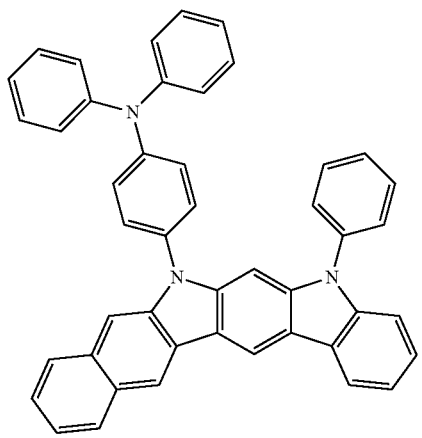
B-329
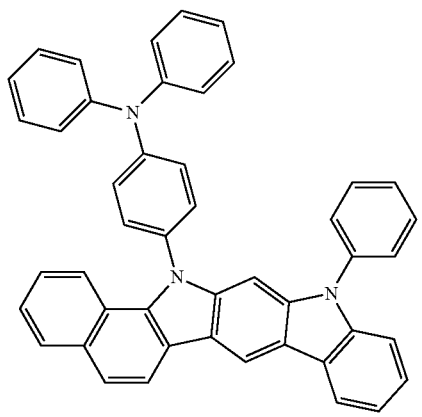
B-330
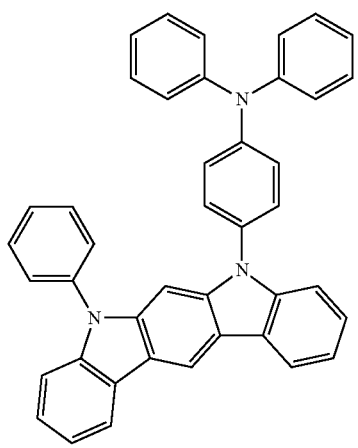
B-331
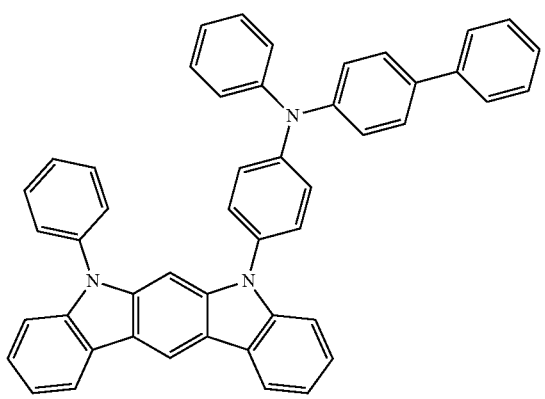
B-332
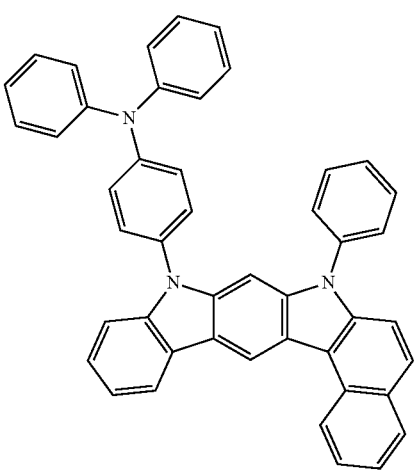
B-333
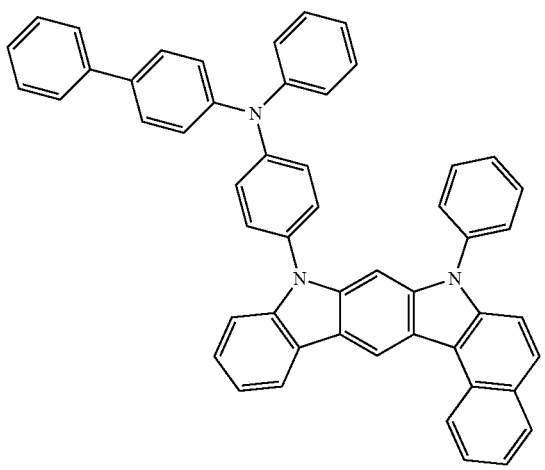

B-334
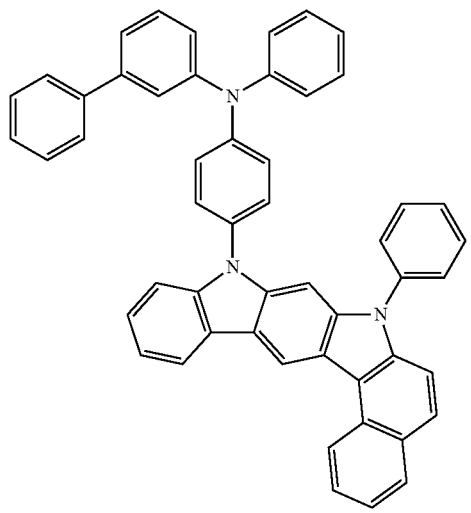
B-335
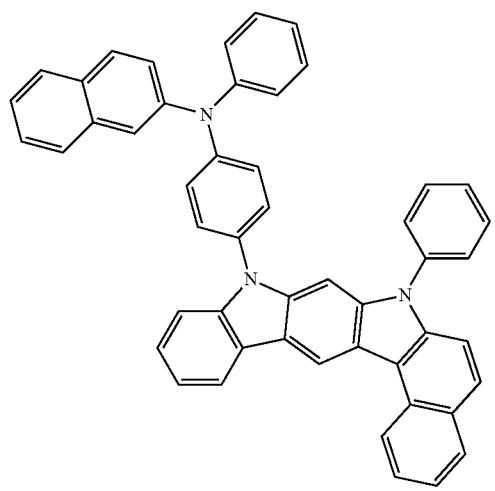
B-336
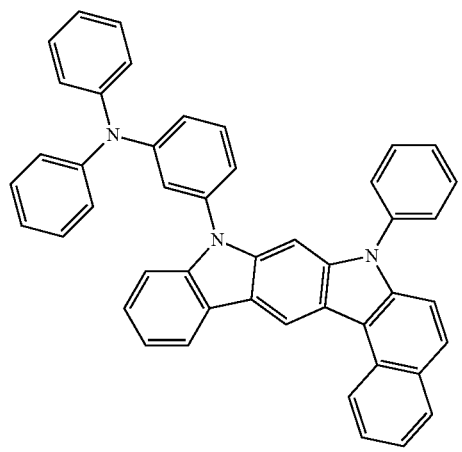
B-337
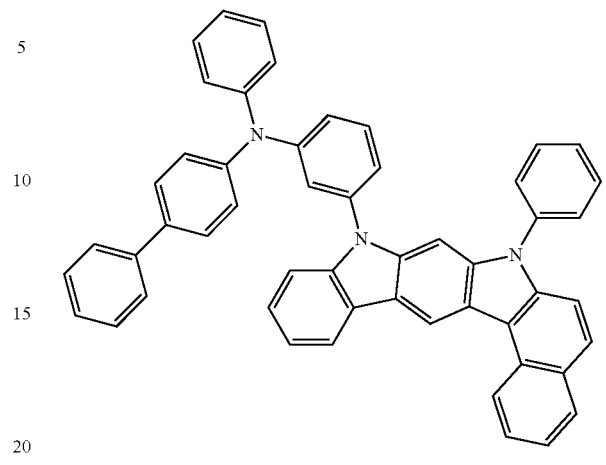
B-338
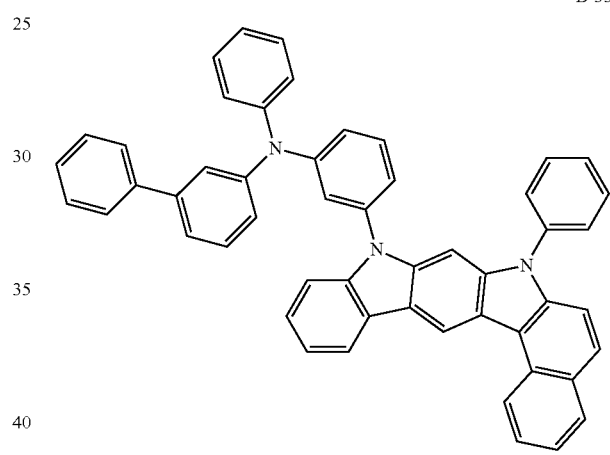
B-339
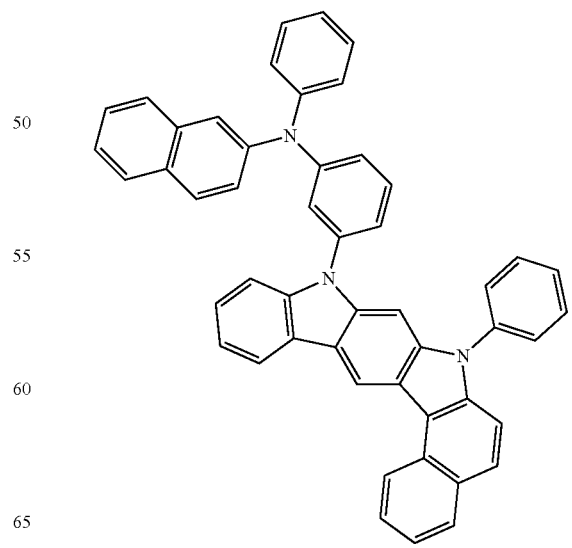

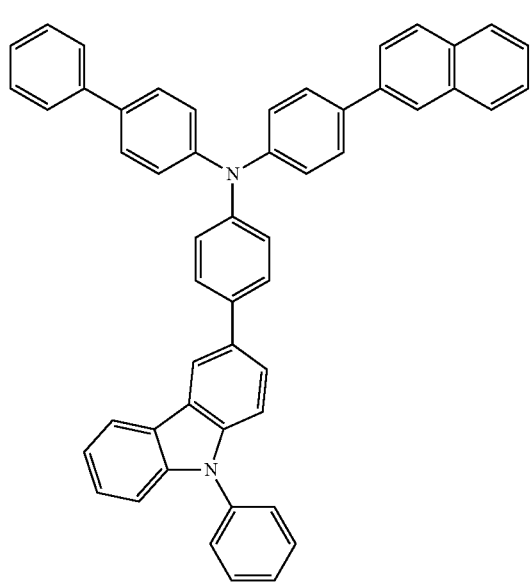
B-340
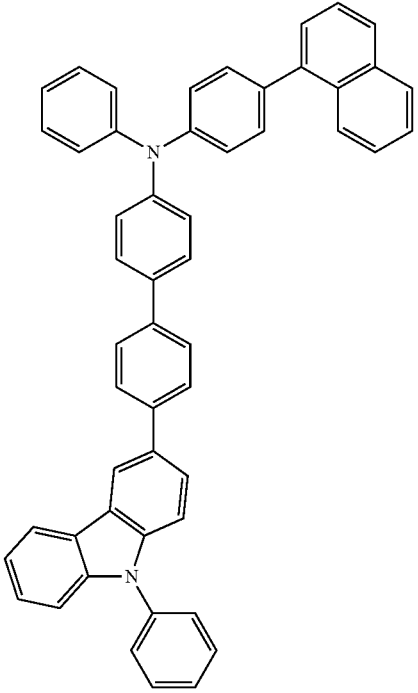
B-342
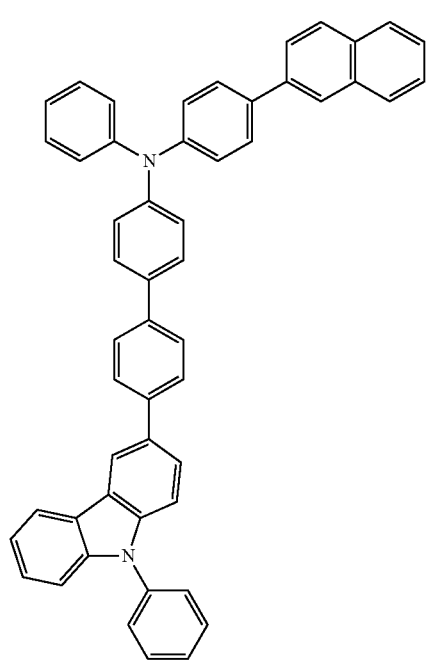
B-341
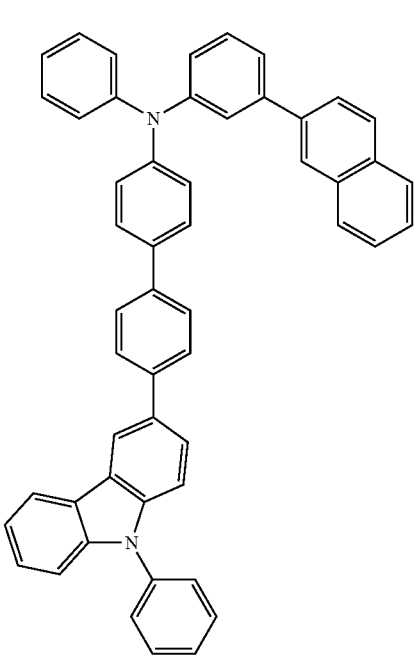
B-343

B-344
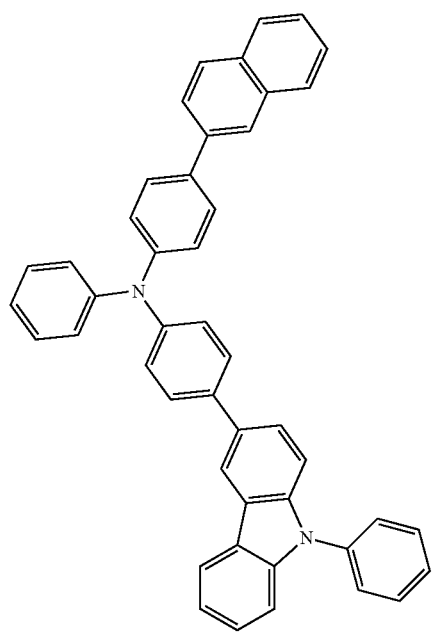
B-346
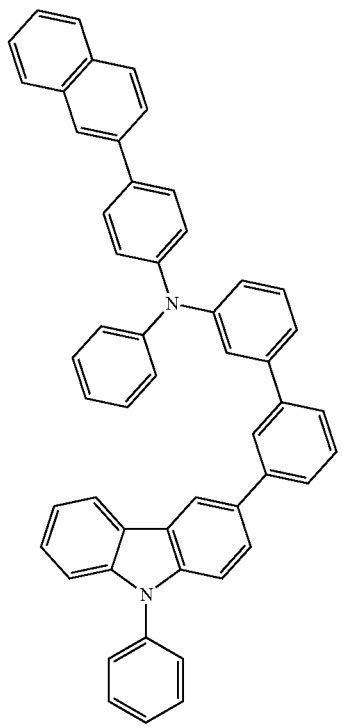
B-345
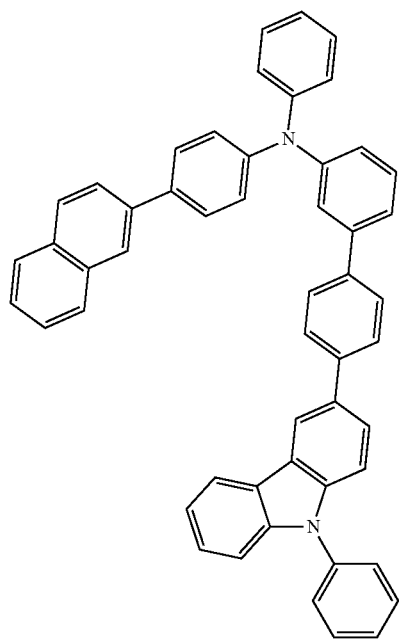
B-347
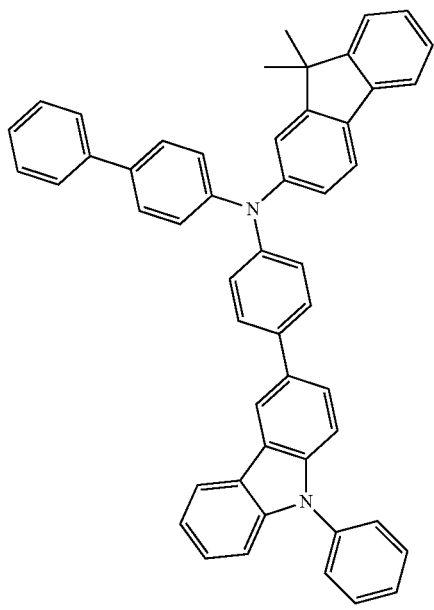

B-348
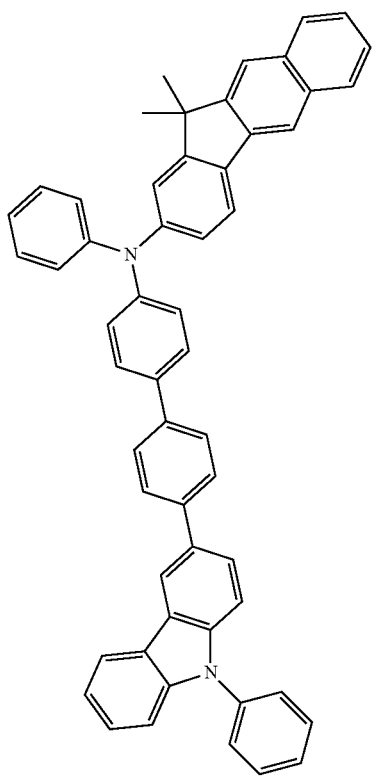
B-350
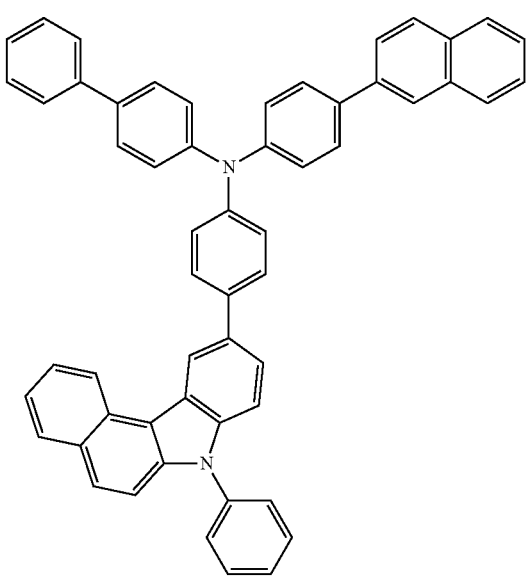
B-349
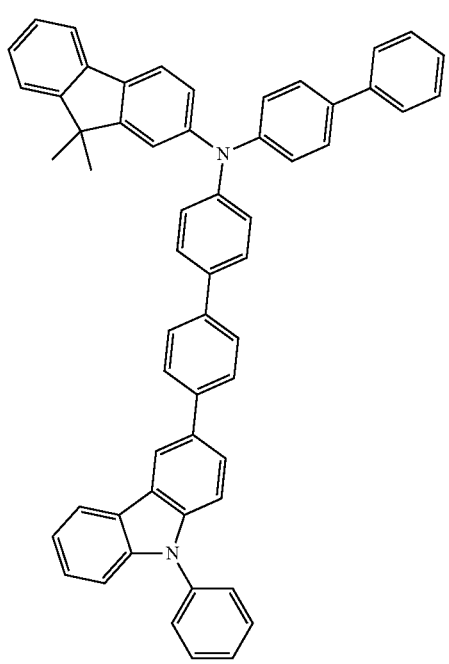
B-351
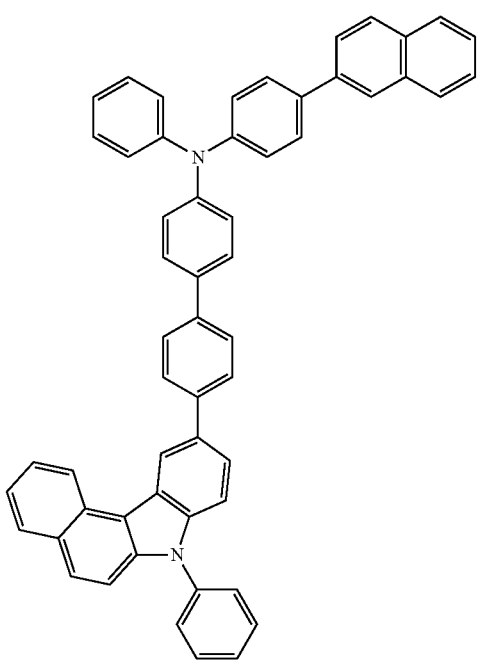

B-352

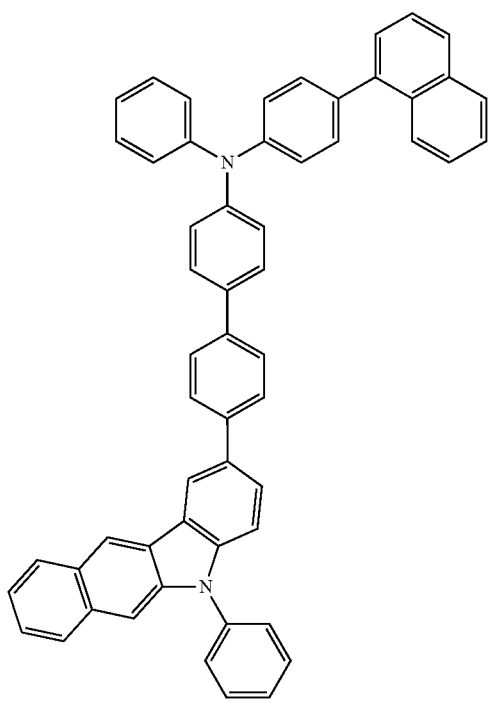

B-353

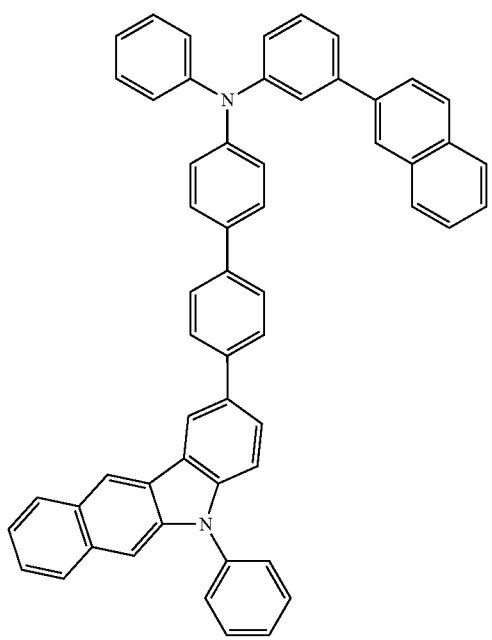

B-354

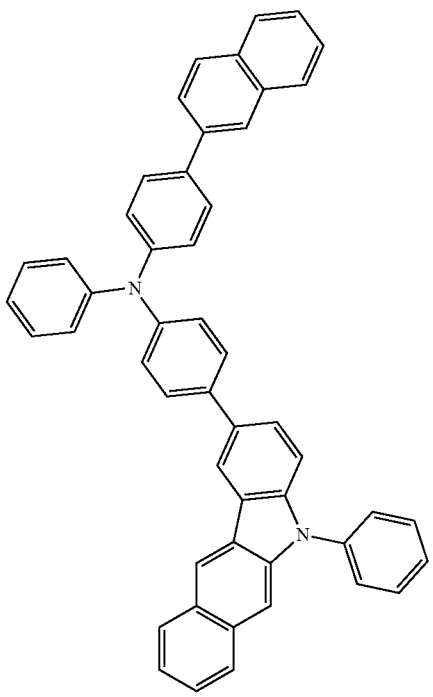

[wherein TPS represents a triphenylsilyl group]

The dopant comprised in the organic electroluminescent device according to the present disclosure may be preferably at least one phosphorescent dopant. The phosphorescent dopant materials applied to the organic electroluminescent device according to the present disclosure are not particularly limited, but may be selected from metallated complex compounds of iridium (Ir), osmium (Os), copper (Cu), and platinum (Pt), may be preferably selected from ortho-metallated complex compounds of iridium (Ir), osmium (Os), copper (Cu), and platinum (Pt), and may be more preferably an ortho-metallated iridium complex compound.

The dopant comprised in the organic electroluminescent device of the present disclosure may be selected from the group consisting of the compounds represented by formulas 101 to 104 below, but is not limited thereto.

(101)

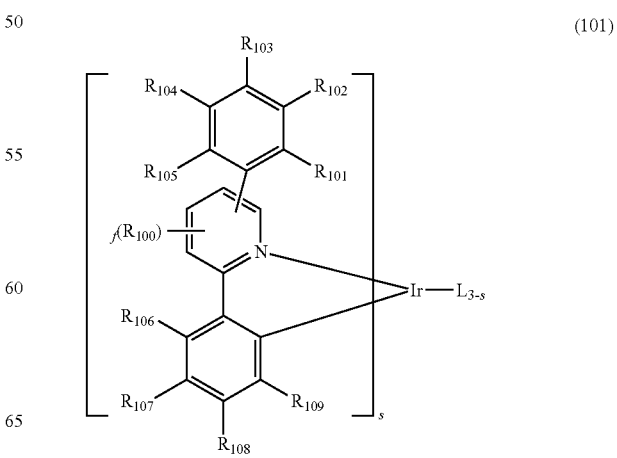

-continued (102)

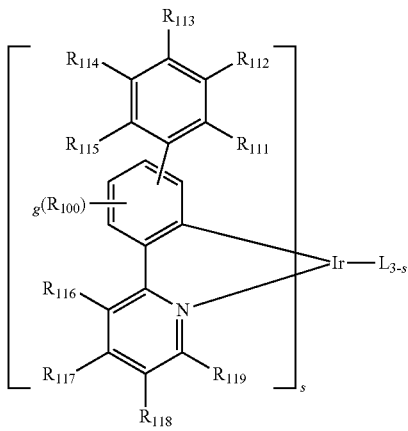

(103)

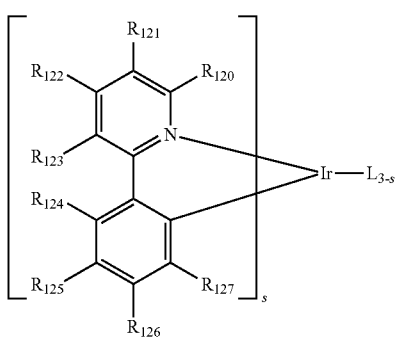

(104)

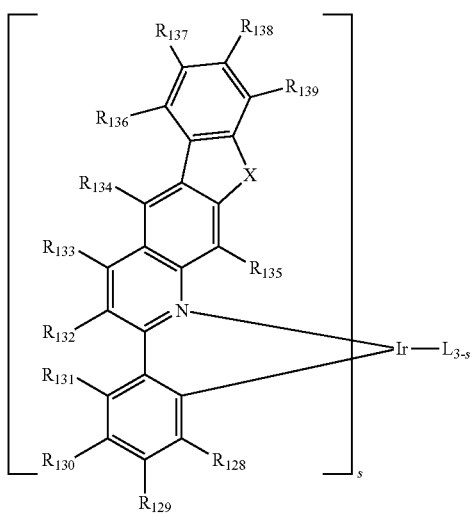

wherein L is selected from the following structures:

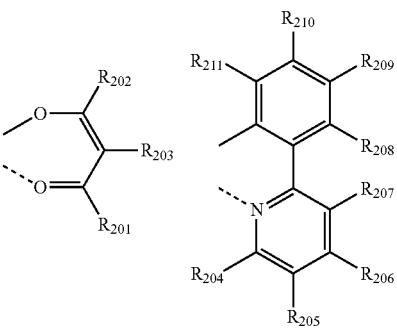

$R_{100}$, $R_{134}$, and $R_{135}$, each independently, represent hydrogen, deuterium, a substituted or unsubstituted (C1-C30)alkyl, or a substituted or unsubstituted (C3-C30)cycloalkyl;

$R_{101}$ to $R_{109}$ and $R_{111}$ to $R_{123}$, each independently, represent hydrogen, deuterium, a halogen, a (C1-C30)alkyl unsubstituted or substituted with deuterium or a halogen, a substituted or unsubstituted (C3-C30)cycloalkyl, a substituted or unsubstituted (C6-C30)aryl, a cyano, or a substituted or unsubstituted (C1-C30)alkoxy; adjacent substituents of $R_{106}$ to $R_{109}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl; and adjacent substituents of $R_{120}$ to $R_{123}$ may be linked to each other to form a substituted or unsubstituted fused ring, e.g., a quinoline unsubstituted or substituted with at least one of an alkyl, an aryl, an aralkyl, and an alkylaryl;

$R_{124}$ to $R_{133}$ and $R_{136}$ to $R_{139}$, each independently, represent hydrogen, deuterium, a halogen, a substituted or unsubstituted (C1-C30)alkyl, or a substituted or unsubstituted (C6-C30)aryl; and adjacent substituents of $R_{124}$ to $R_{127}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

X represents $CR_{51}R_{52}$, O, or S;

$R_{51}$ and $R_{52}$, each independently, represent a substituted or unsubstituted (C1-C10)alkyl, or a substituted or unsubstituted (C6-C30)aryl;

$R_{201}$ to $R_{211}$, each independently, represent hydrogen, deuterium, a halogen, a (C1-C30)alkyl unsubstituted or substituted with deuterium or a halogen, a substituted or unsubstituted (C3-C30)cycloalkyl, or a (C6-C30)aryl unsubstituted or substituted with an alkyl or deuterium; and adjacent substituents of $R_{208}$ to $R_{211}$ may be linked to each other to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

f and g, each independently, represent an integer of 1 to 3; where f or g is an integer of 2 or more, each $R_{100}$ may be the same or different; and s represents an integer of 1 to 3.

Specifically, the examples of the dopant compound are as follows, but not limited thereto.

D-1 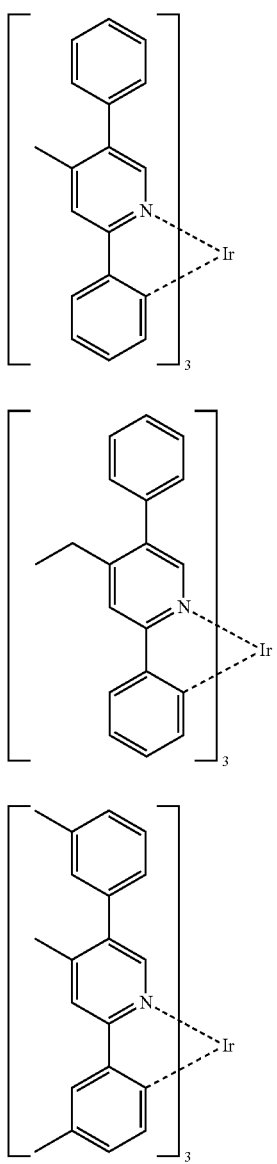 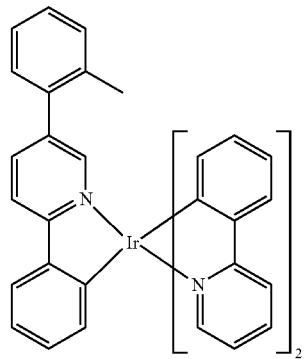
D-2
D-3
D-4 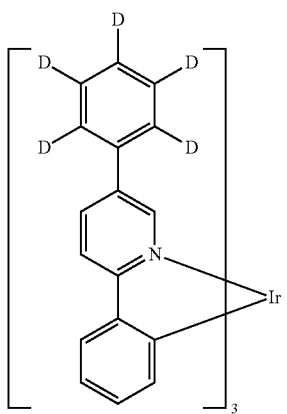
D-5
D-6 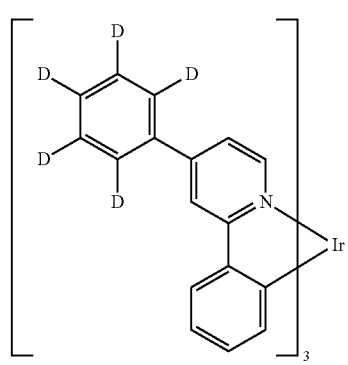
D-7 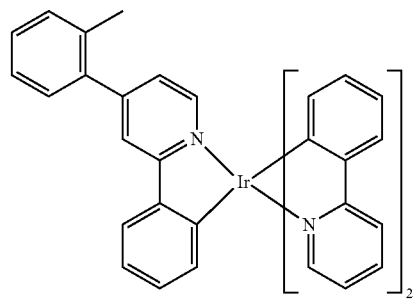
D-8 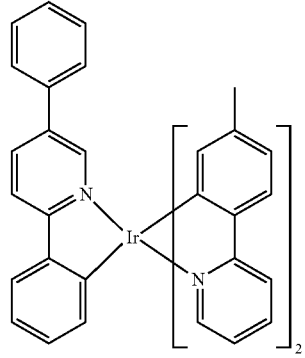

D-9
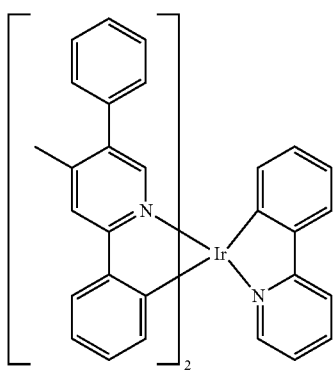
D-10
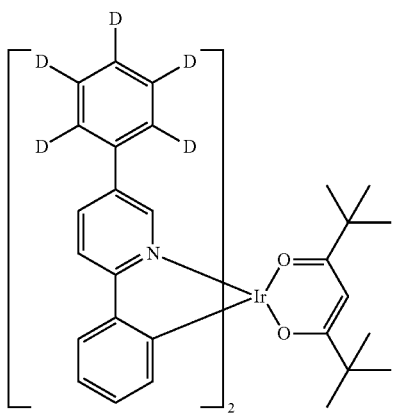
D-11
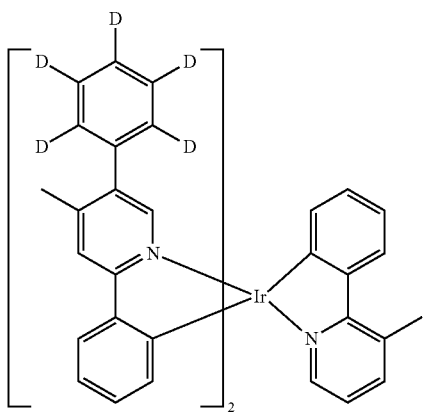
D-12
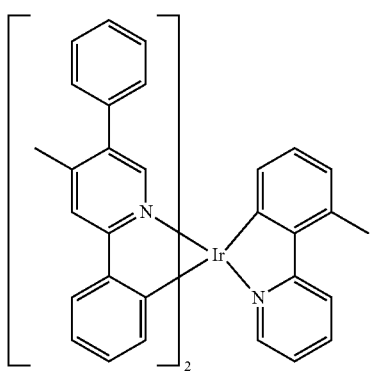
D-13
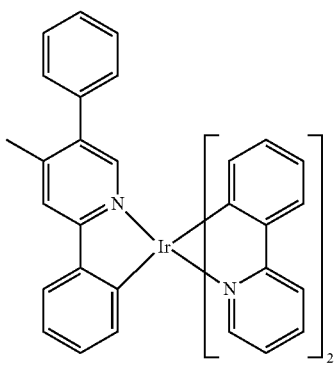
D-14
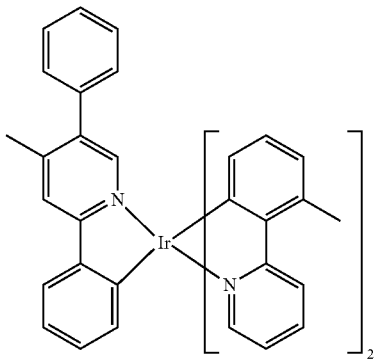
D-15
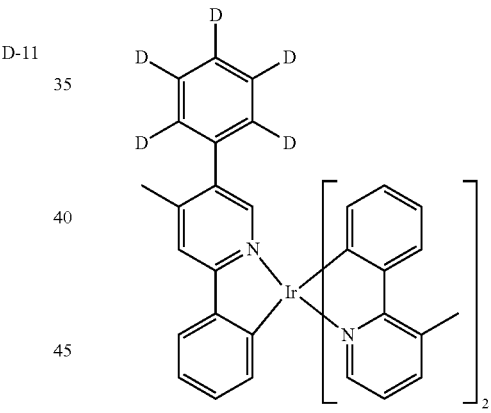
D-16
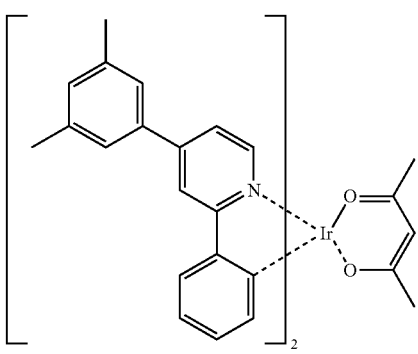

D-17
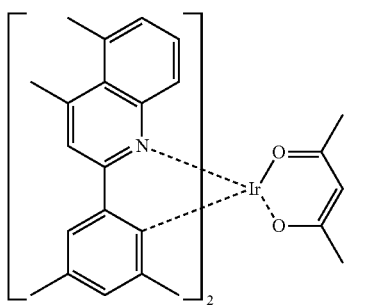
D-18
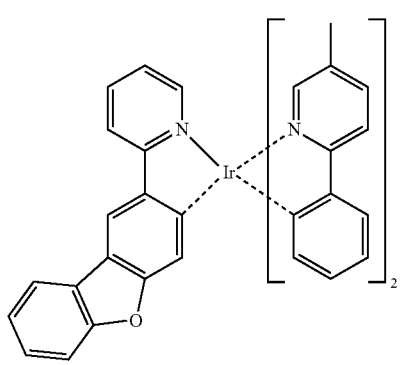
D-19
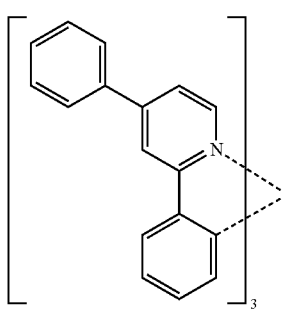
D-20
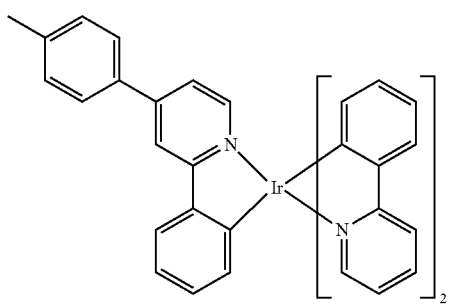
D-21
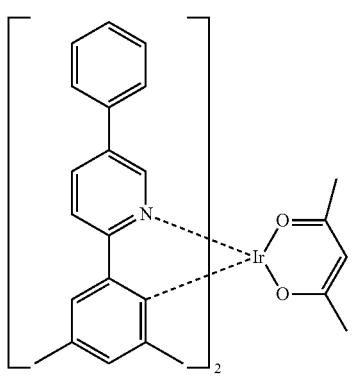
D-22
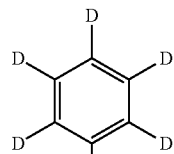
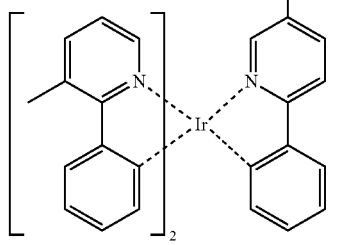
D-23
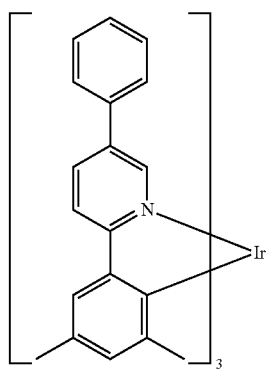
D-24
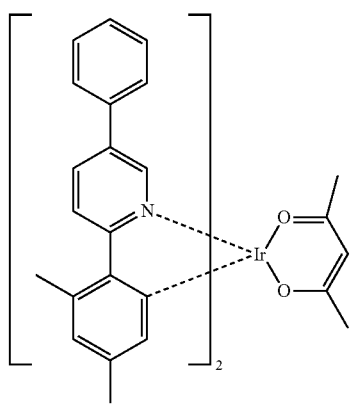
D-25
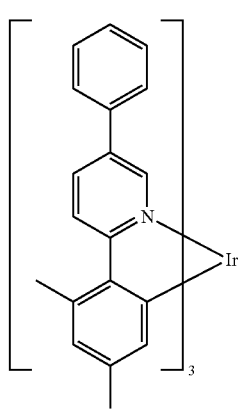

-continued
D-26
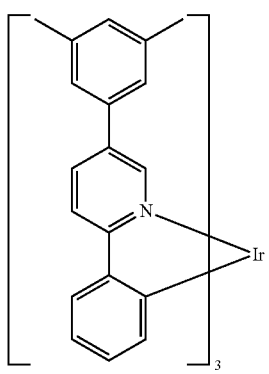
D-27
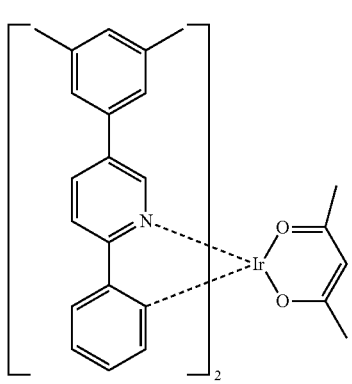
D-28
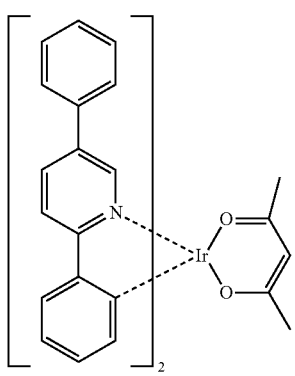
D-29
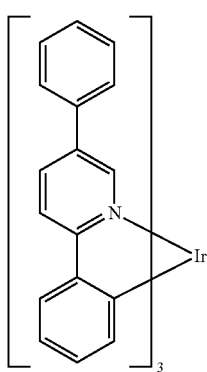
-continued
D-30
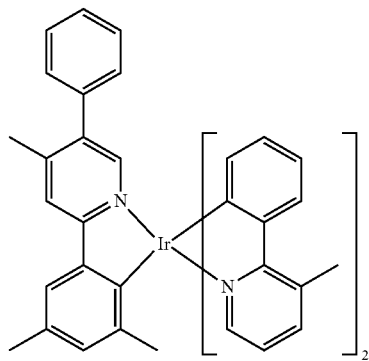
D-31
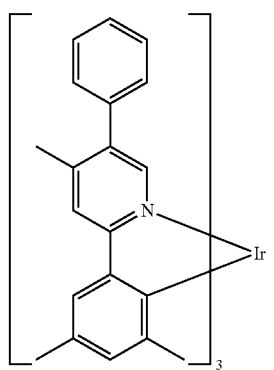
D-32
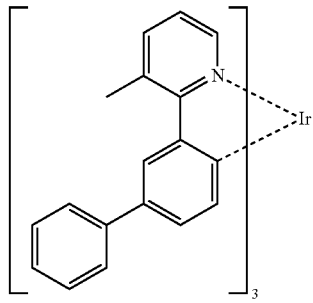
D-33
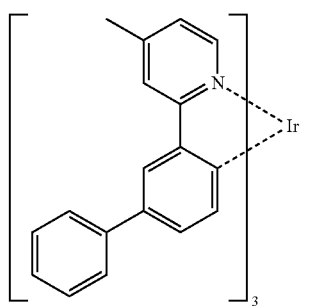
D-34

D-35
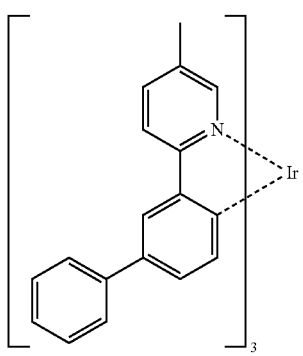
D-36
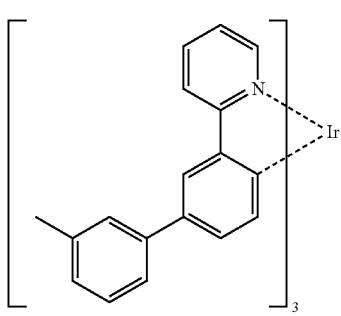
D-37
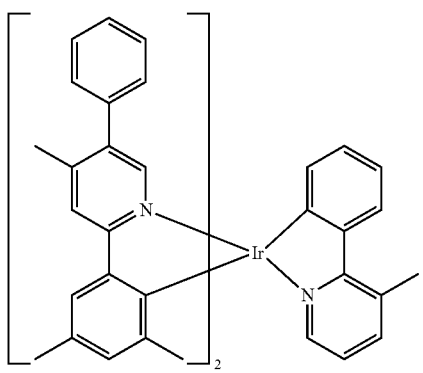
D-38
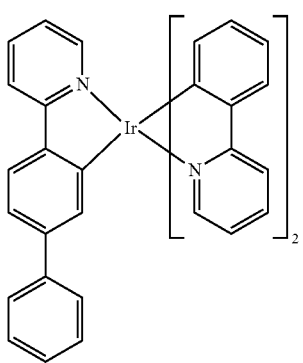
D-39
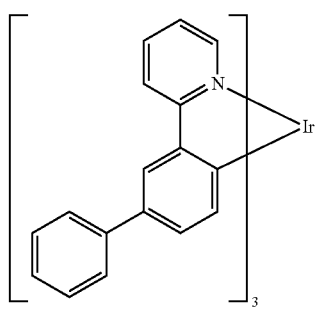
D-40
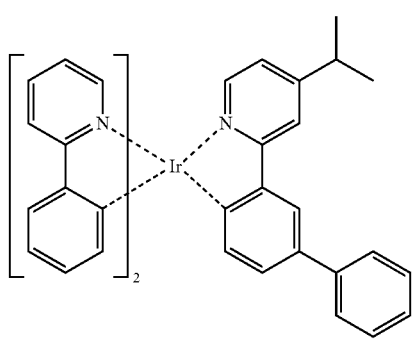
D-41
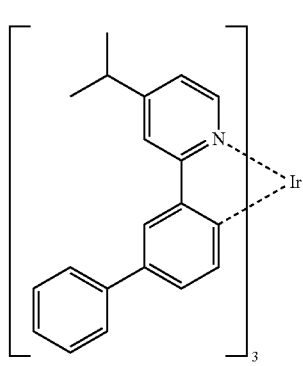
D-42
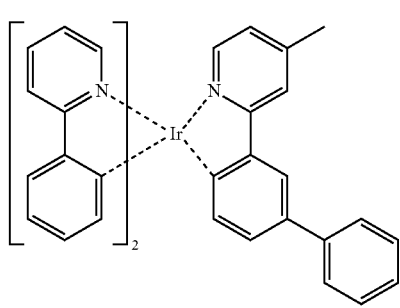

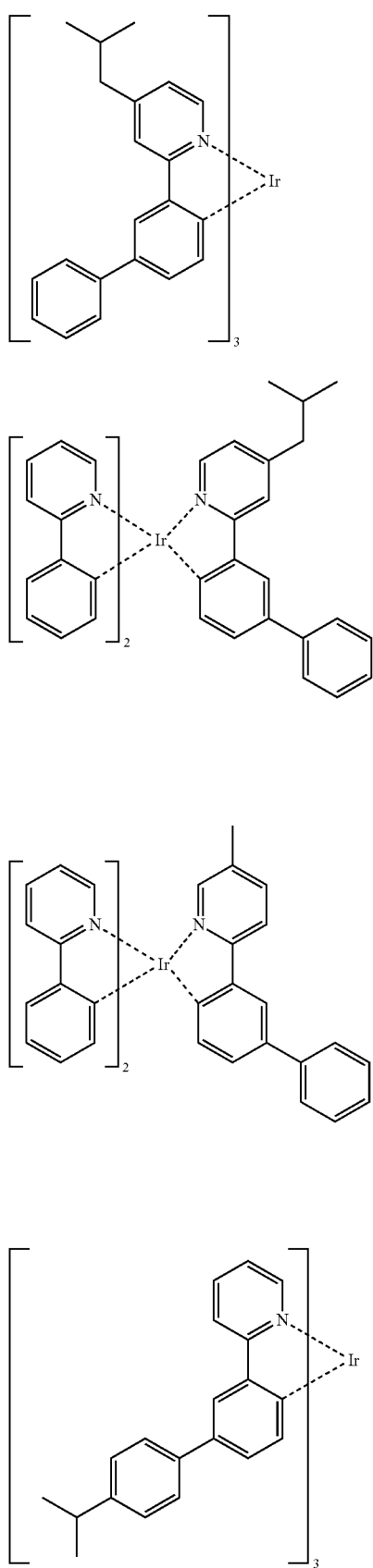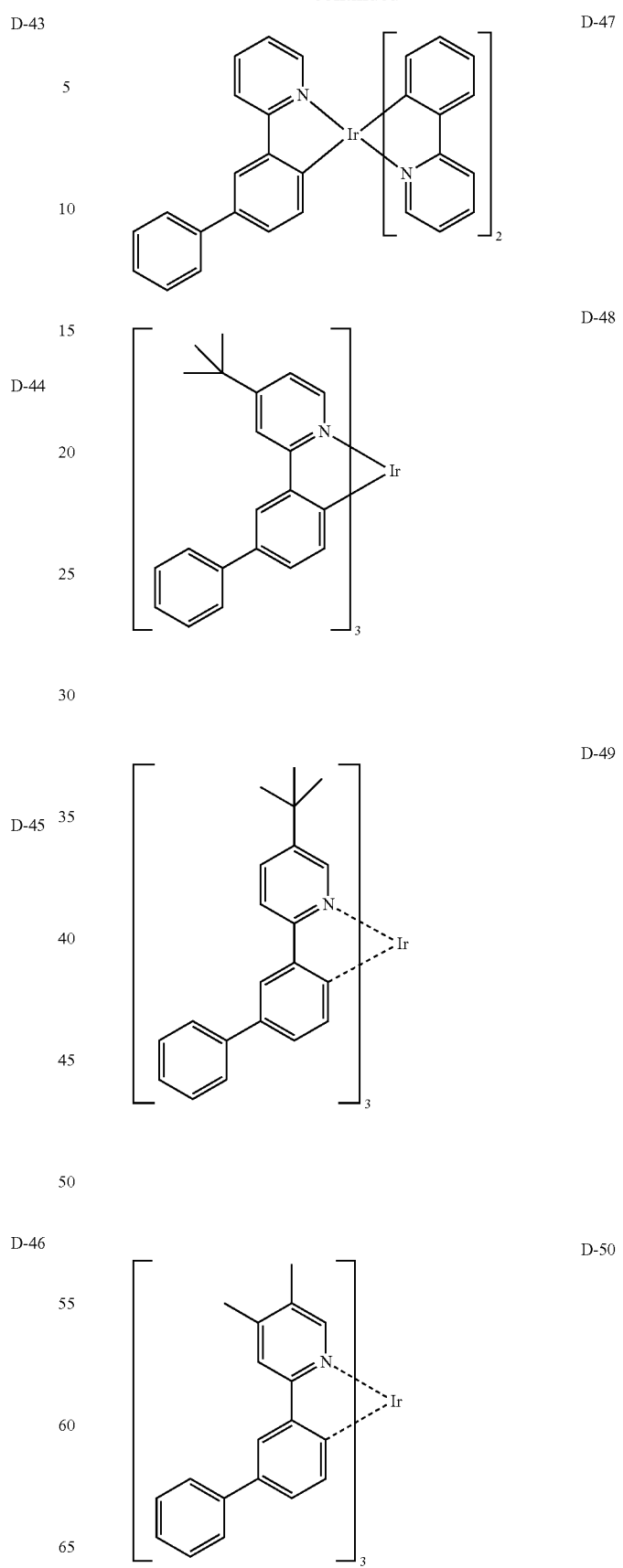

D-51 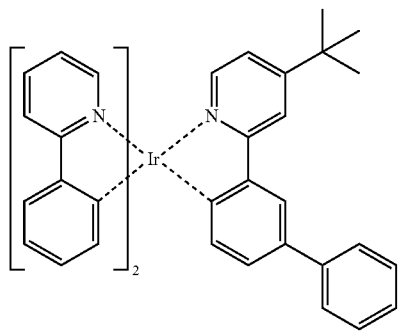
D-52 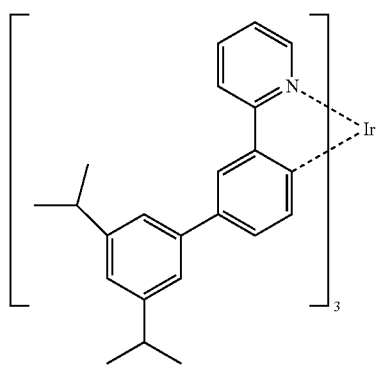
D-53 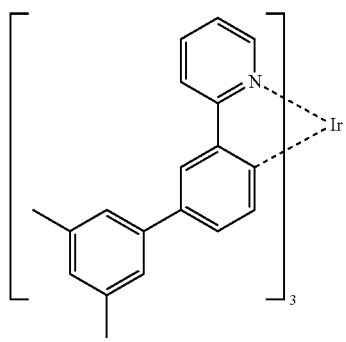
D-54 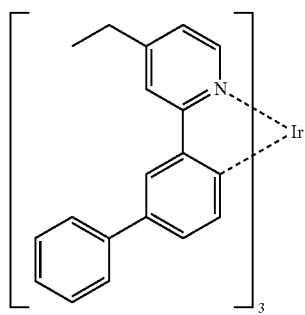
D-55 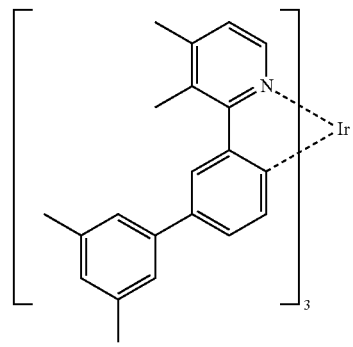
D-56 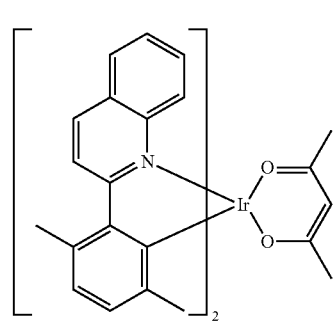
D-57 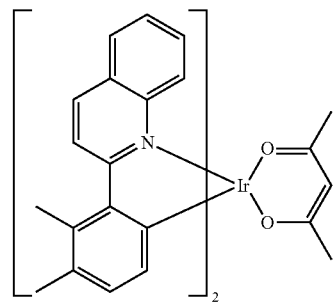
D-58 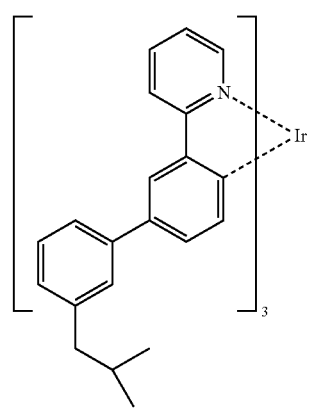

-continued
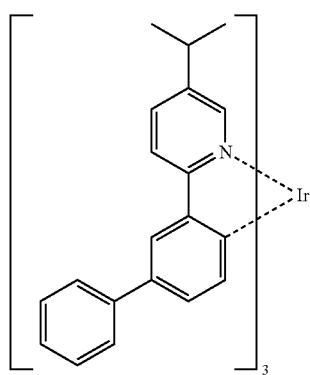
D-59
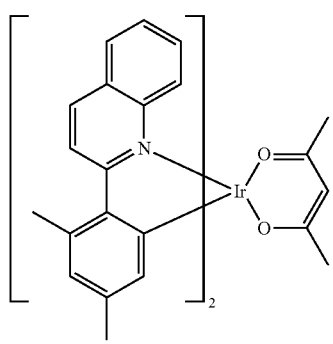
D-60
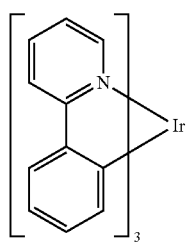
D-61
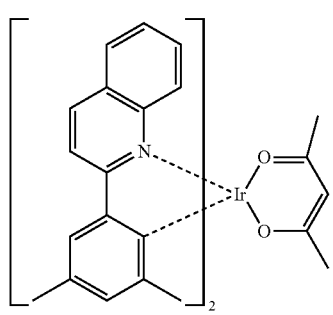
D-62
-continued
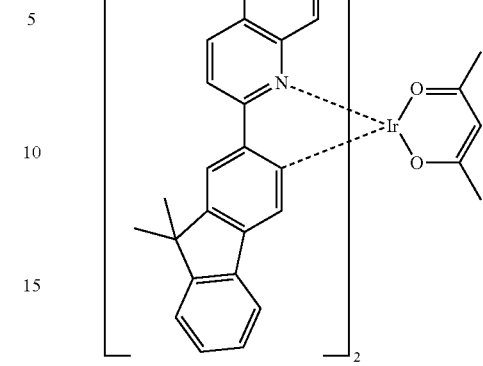
D-63
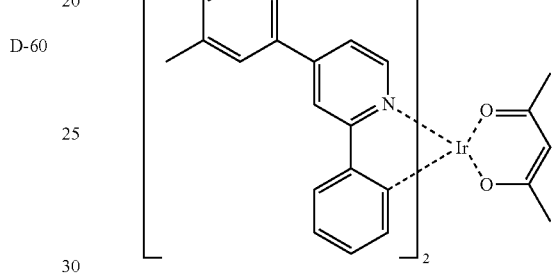
D-64
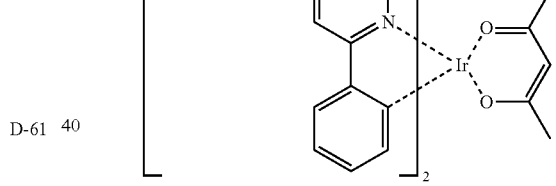
D-65
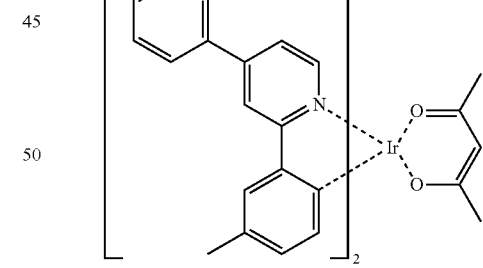
D-66
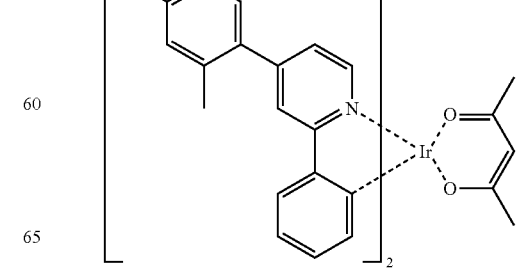
D-67

D-68 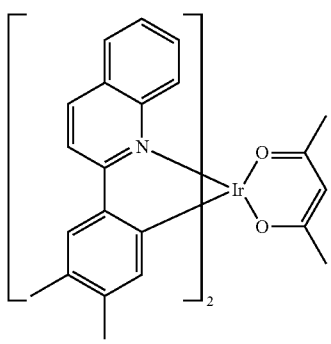
D-69 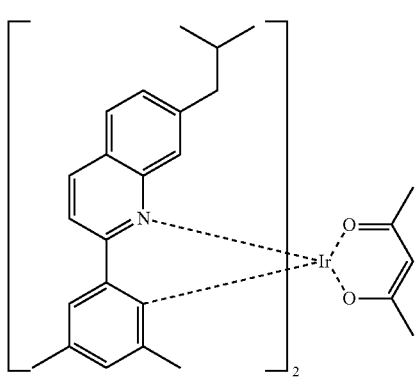
D-70 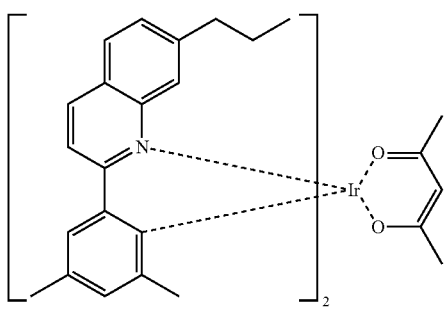
D-71 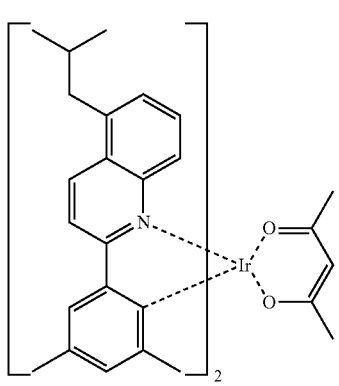
D-72 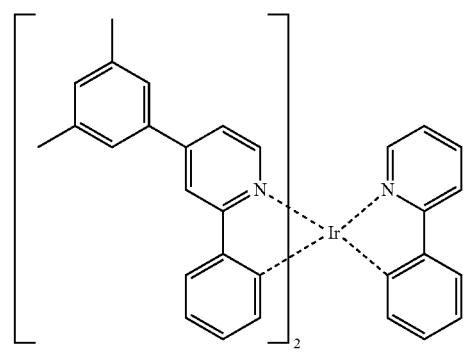
D-73 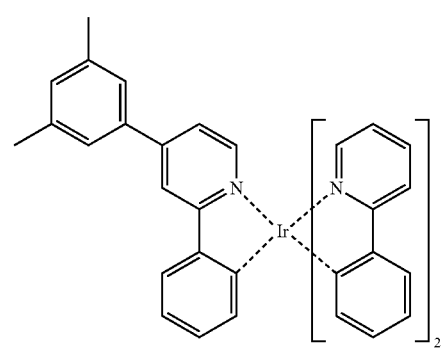
D-74 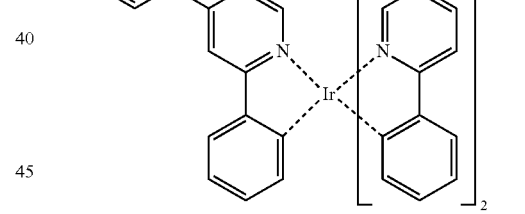
D-75 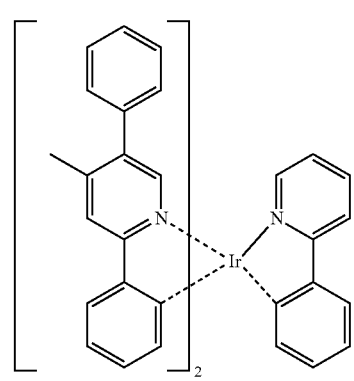

D-76
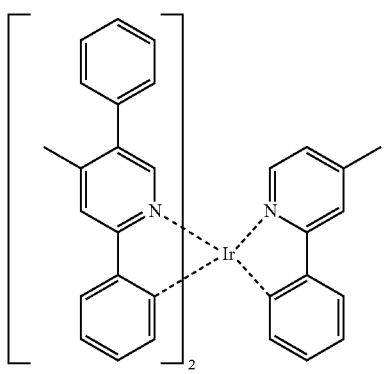
D-77
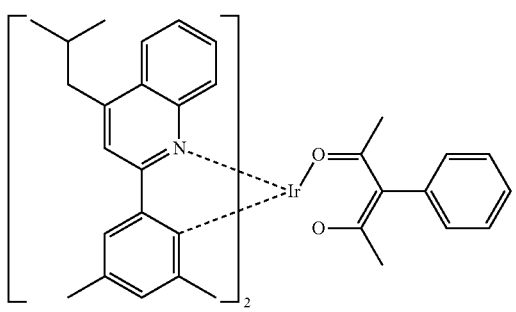
D-78
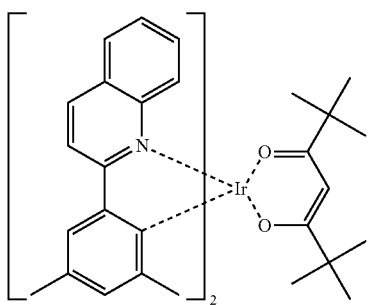
D-79
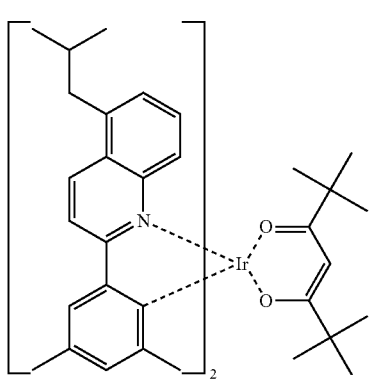
D-80
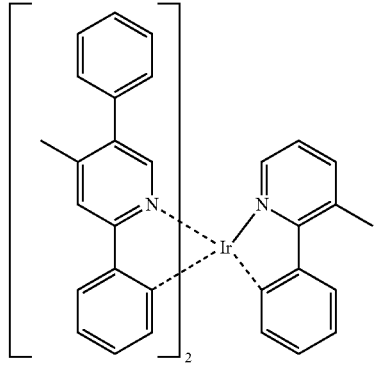
D-81
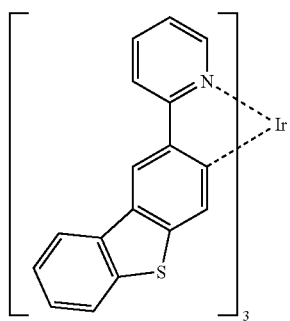
D-82
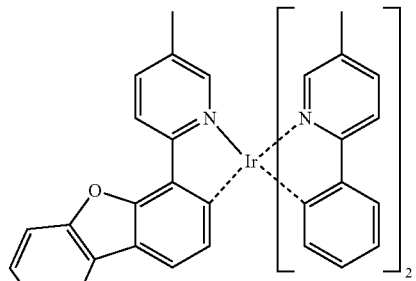
D-83
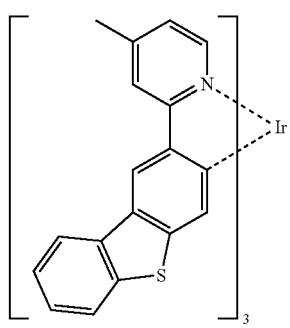
D-84
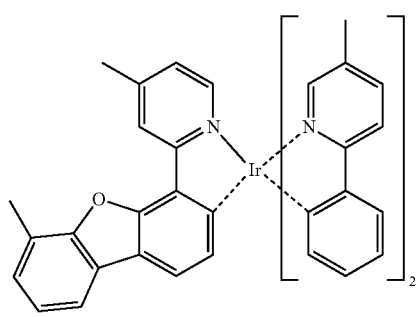

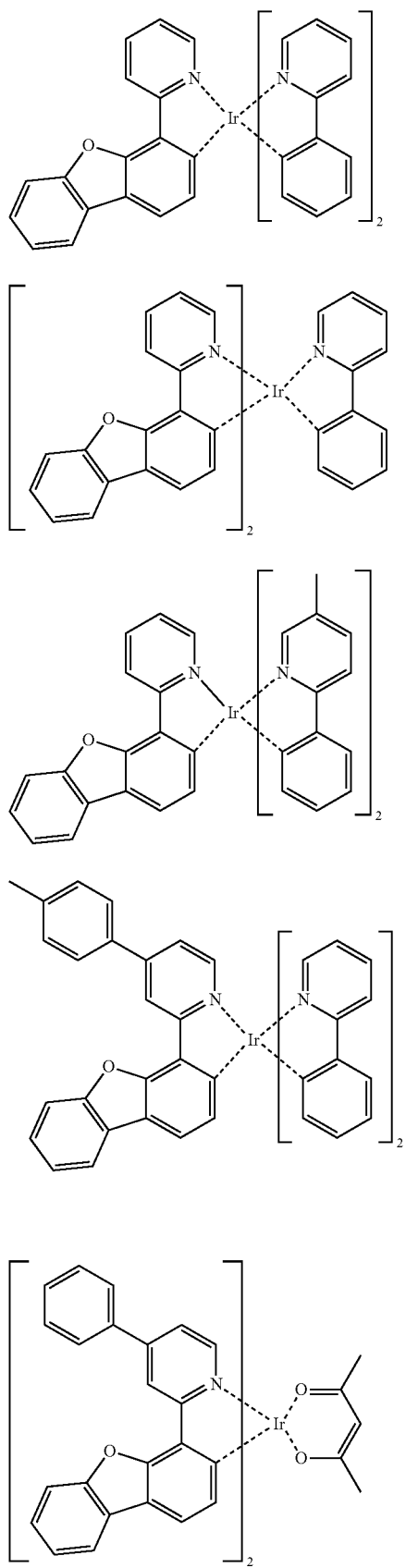

D-95
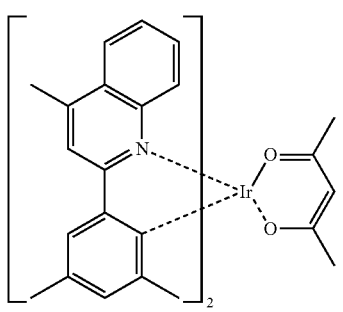
D-96
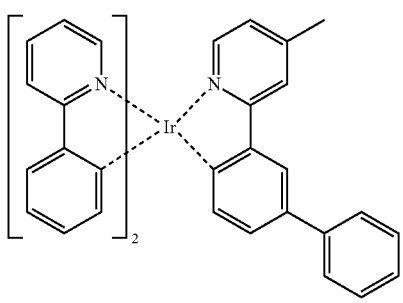
D-97
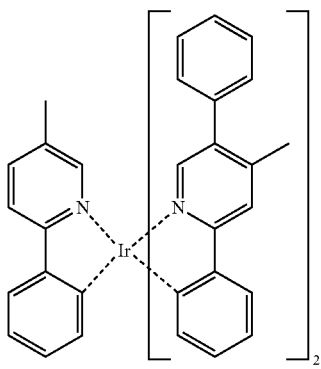
D-98
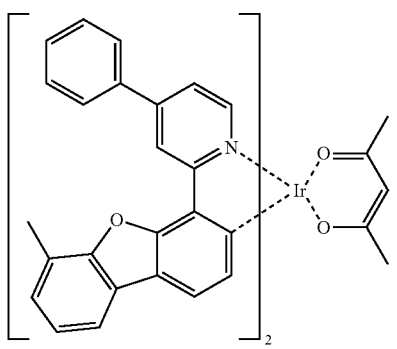
D-99
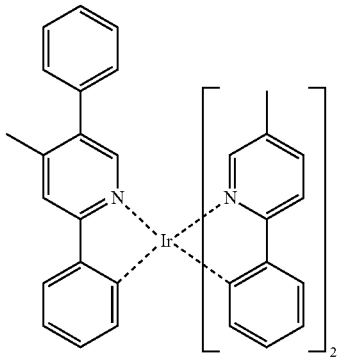
D-100
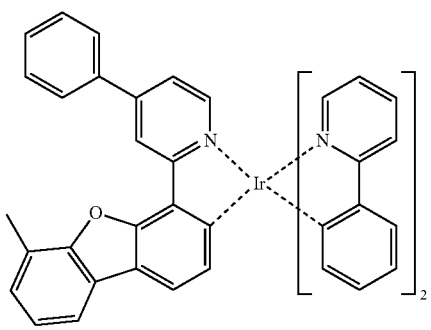
D-101
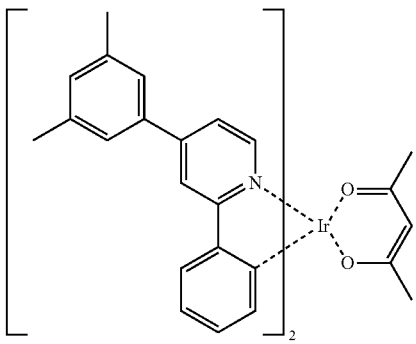
D-102
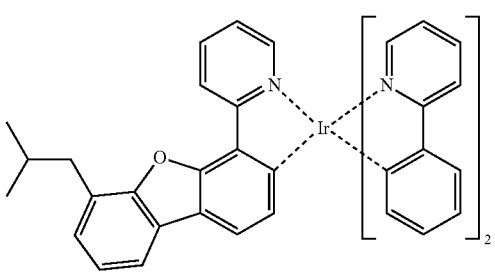

D-103
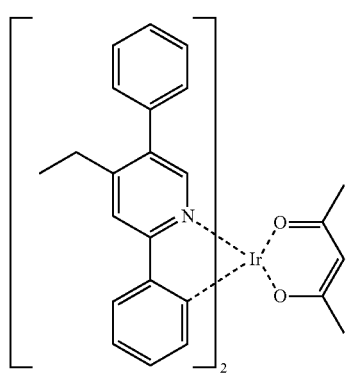
D-107
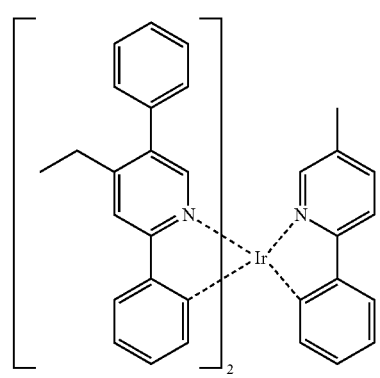
D-104
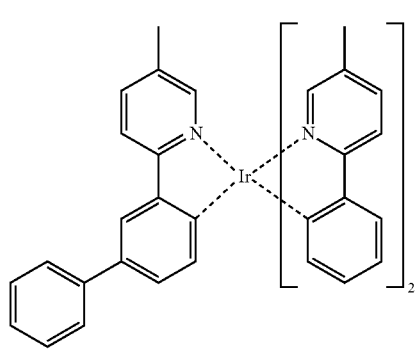
D-108
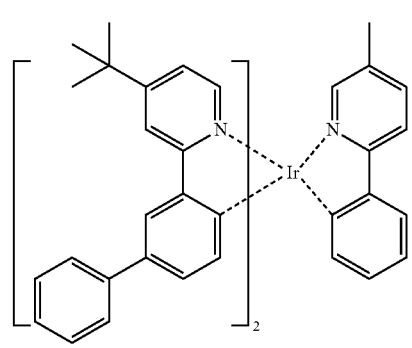
D-105
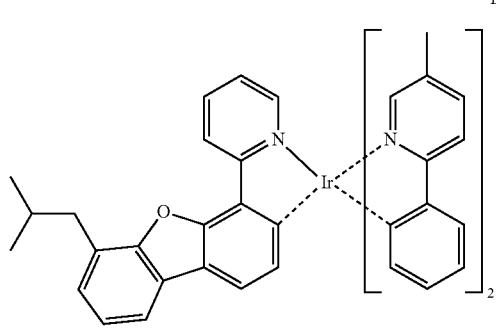
D-109
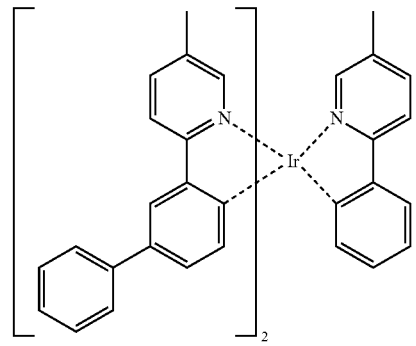
D-106
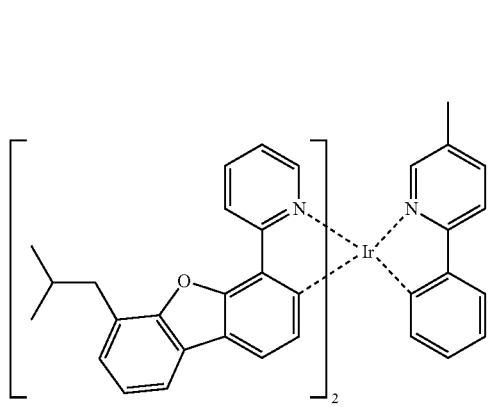
D-110
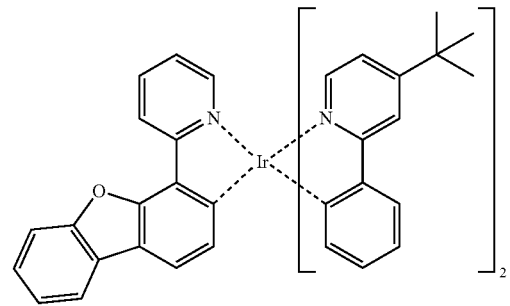

-continued
D-111
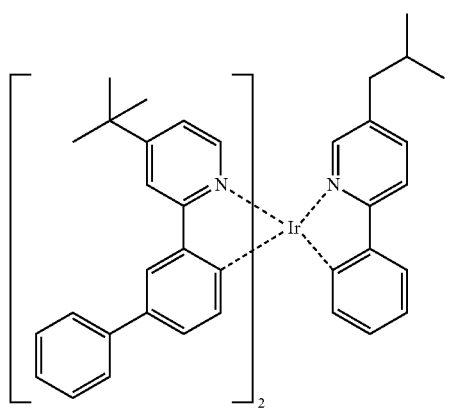
D-112
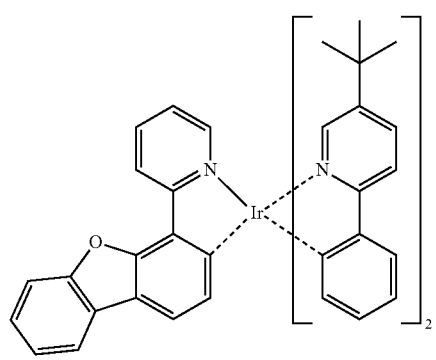
D-113
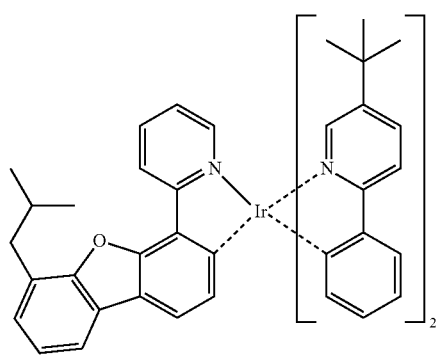
D-114
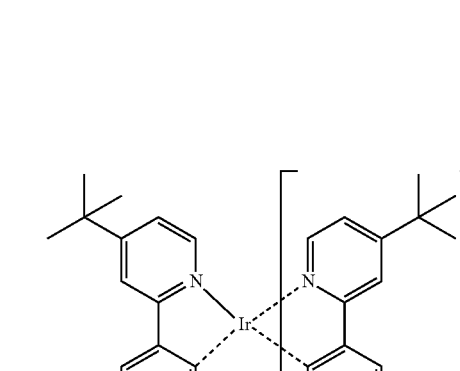
-continued
D-115
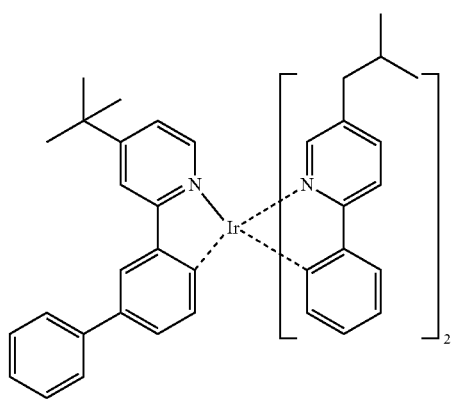
D-116
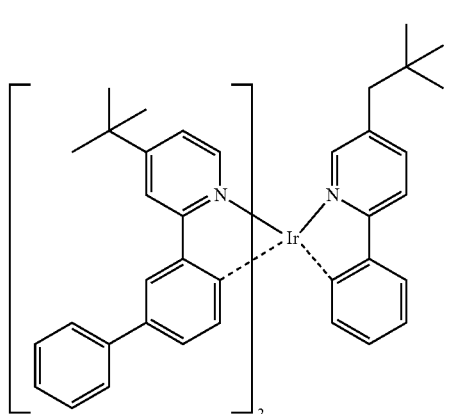
D-117
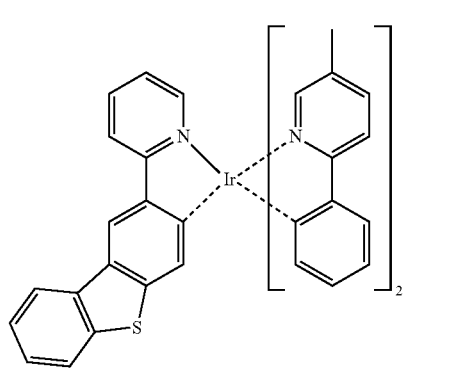
D-118
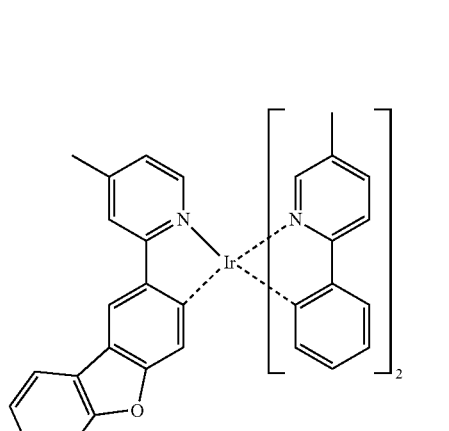

D-119
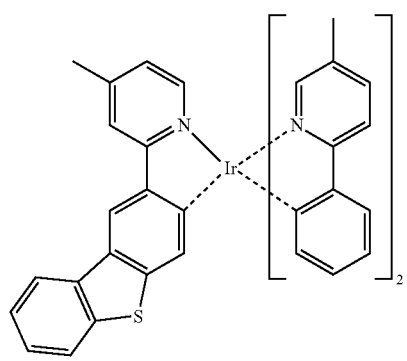
D-120
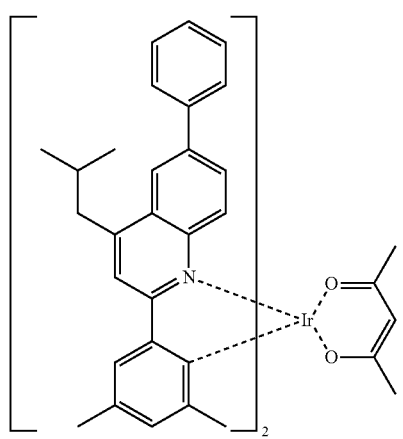
D-121
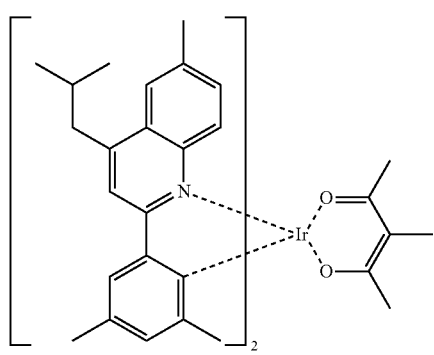
D-122
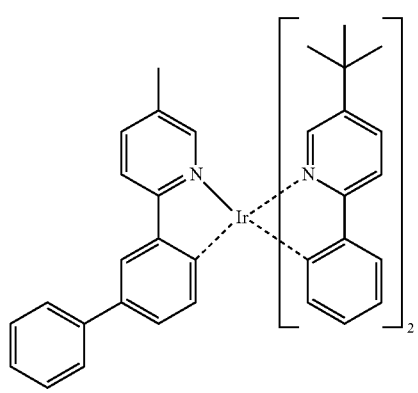
D-123
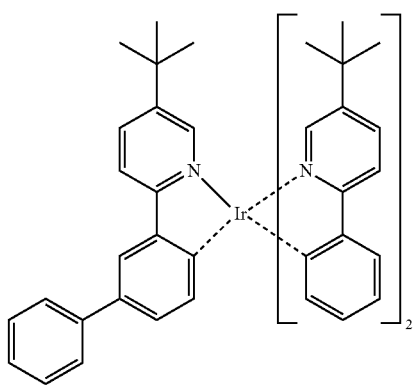
D-124
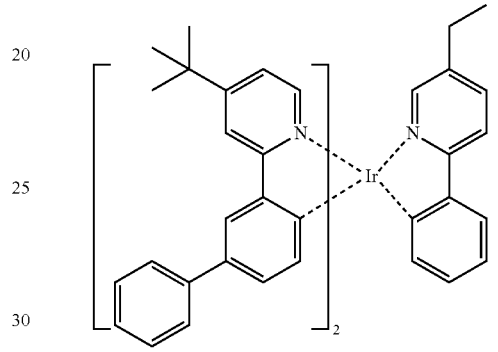
D-125
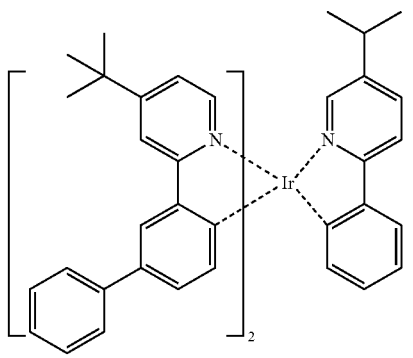
D-126
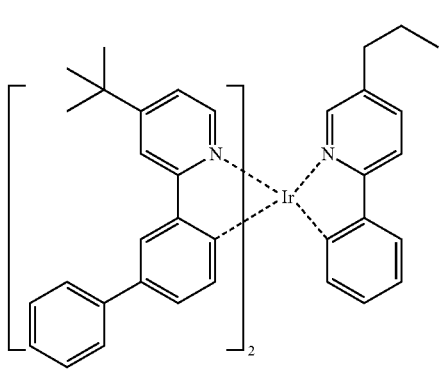

-continued
D-127
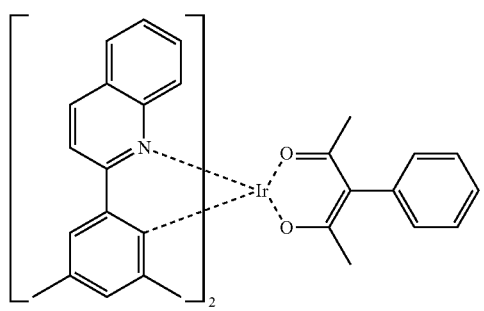
D-128
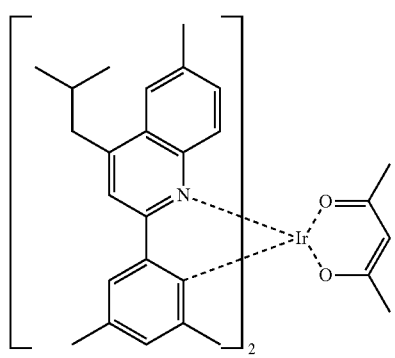
D-129
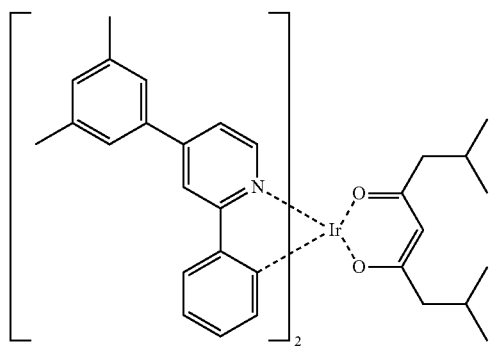
D-130
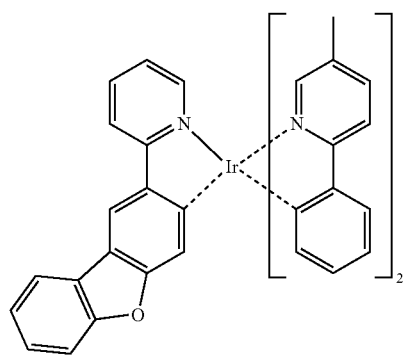
-continued
D-131
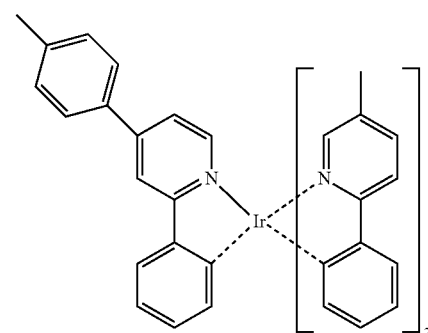
D-132
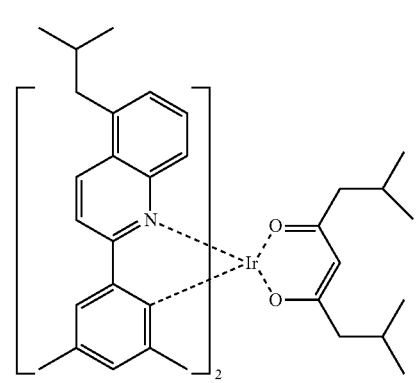
D-133
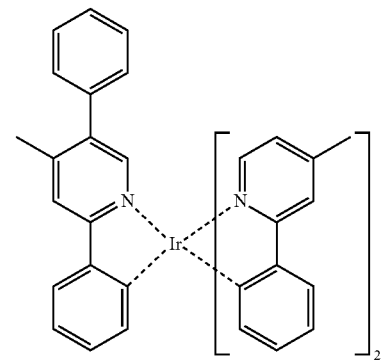
D-134
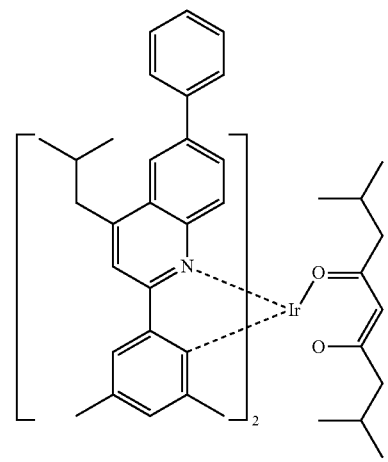

D-135
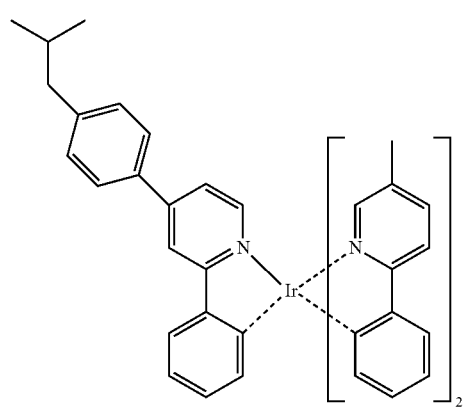
D-136
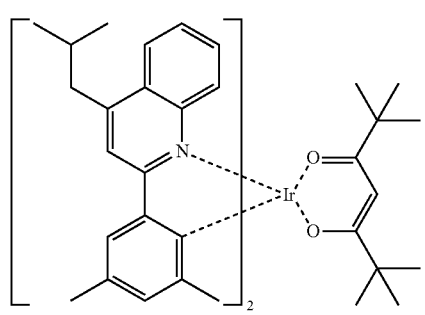
D-137
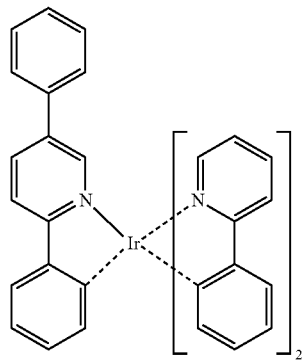
D-138
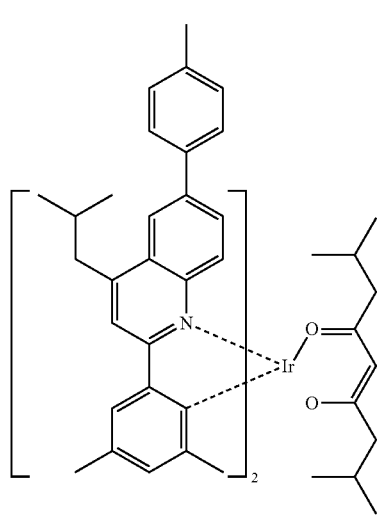
D-139
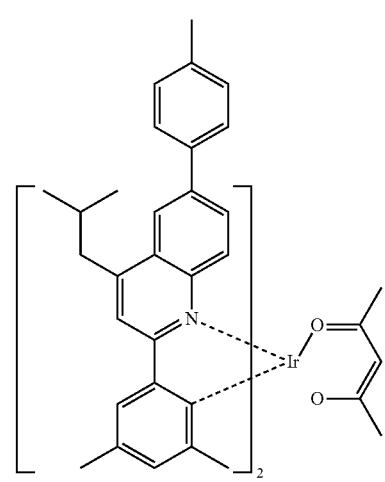
D-140
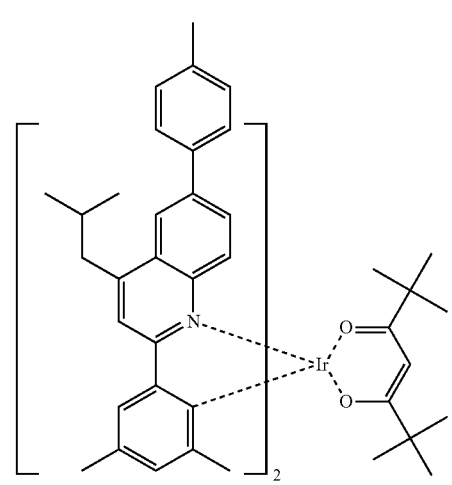
D-141
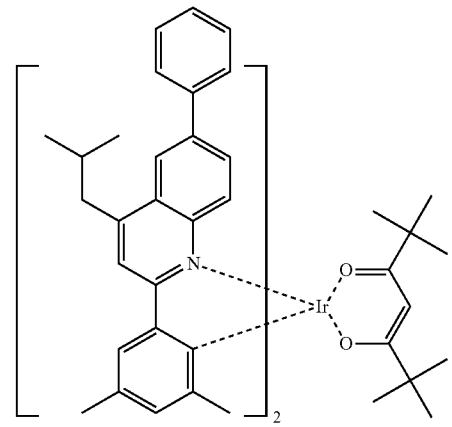

-continued
D-142
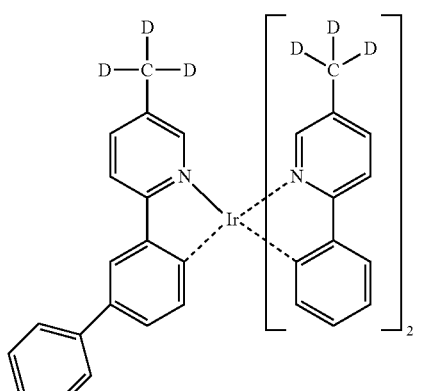
D-143
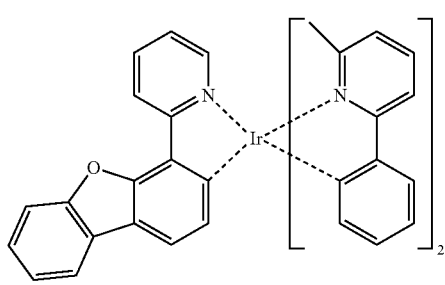
D-144
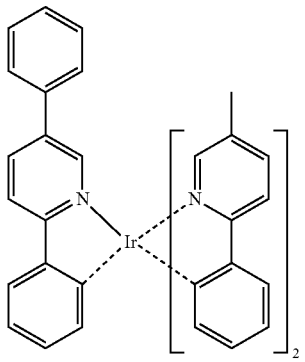
D-145
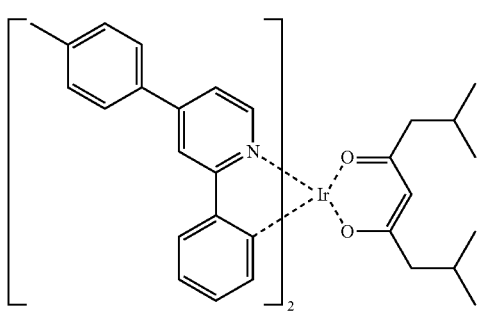
-continued
D-146
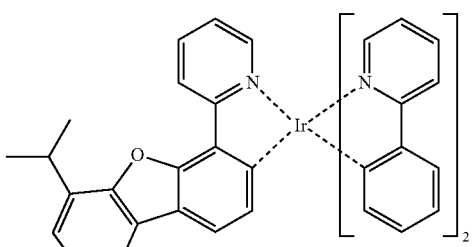
D-147
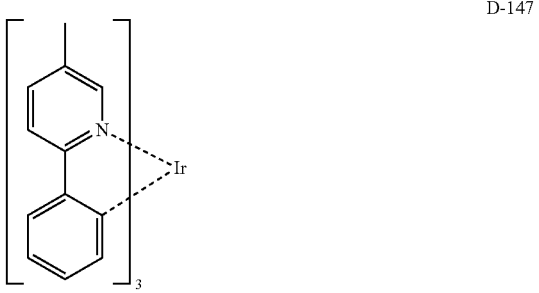
D-148
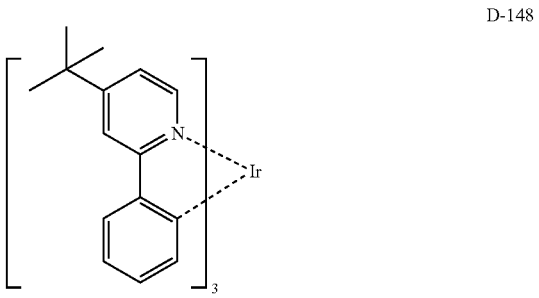
D-149
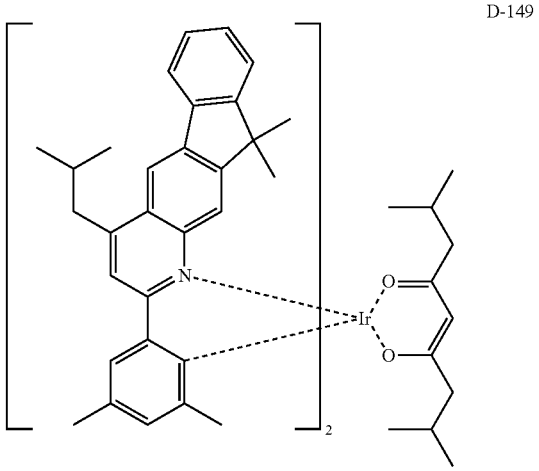

D-150
D-153
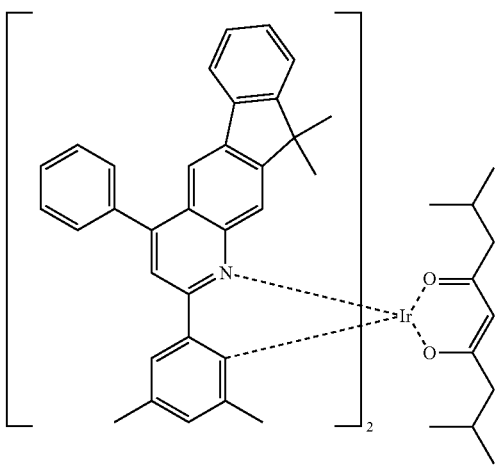
D-151
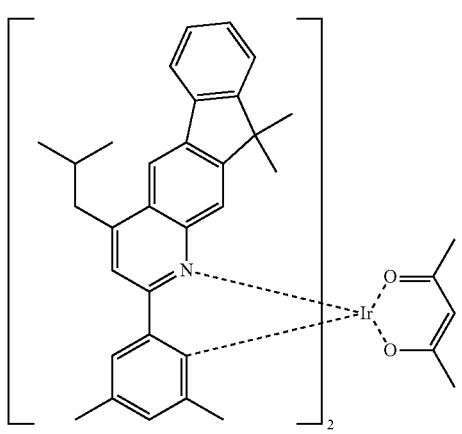
D-154
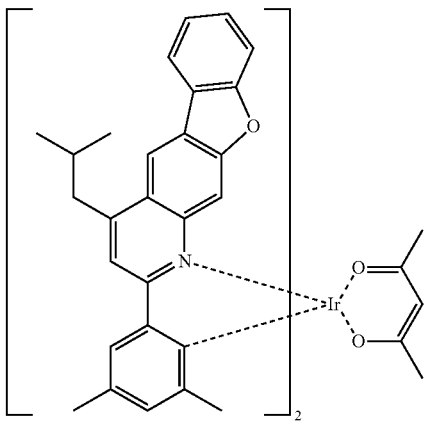
D-152
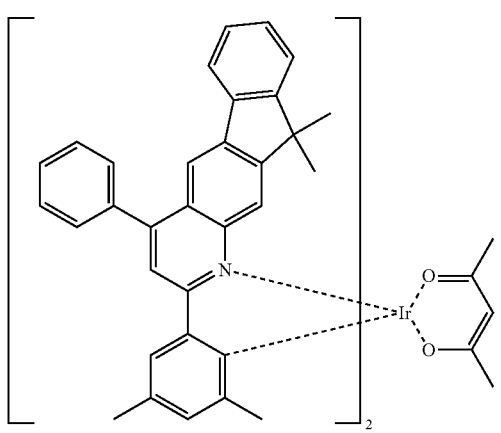
D-155
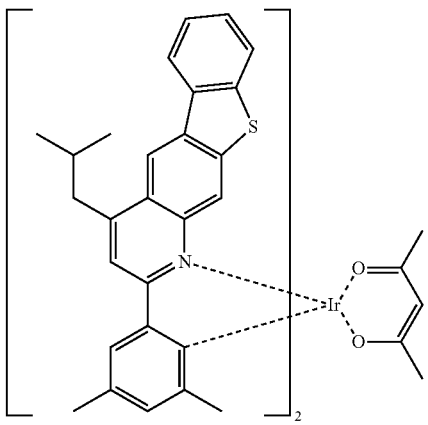

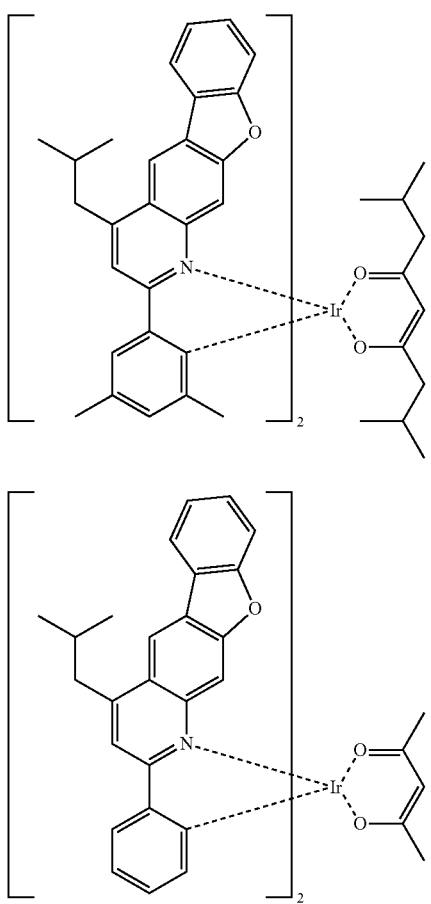

D-156

D-157

The organic electroluminescent device according to the present disclosure comprises a first electrode; a second electrode; and at least one organic layer between the first and second electrodes.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The organic layer may further comprise at least one compound selected from the group consisting of arylamine-based compounds and styrylarylamine-based compounds.

In addition, in the organic electroluminescent device according to the present disclosure, the organic layer may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal.

In addition, the organic electroluminescent device according to the present disclosure may emit white light by further comprising at least one light-emitting layer which comprises a blue electroluminescent compound, a red electroluminescent compound or a green electroluminescent compound known in the field, besides the compound according to the present disclosure. Also, if necessary, a yellow or orange light-emitting layer can be further comprised in the device.

In the organic electroluminescent device according to the present disclosure, at least one layer (hereinafter, "a surface layer") is preferably placed on an inner surface(s) of one or both electrode(s); selected from a chalcogenide layer, a metal halide layer, and a metal oxide layer. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, said chalcogenide includes $SiO_x$ ($1 \leq X \leq 2$), $AlO_x$ ($1 \leq X \leq 1.5$), SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The hole transport layer or the electron blocking layer may also be multilayers.

An electron buffer layer, a hole blocking layer, an electron transport layer, an electron injection layer, or a combination thereof can be used between the light-emitting layer and the cathode. The electron buffer layer may be multilayers in order to control the injection of the electron and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic EL device having two or more light-emitting layers which emits white light.

In order to form each layer constituting the organic electroluminescent device of the present disclosure, dry film-forming methods such as vacuum deposition, sputtering, plasma, ion plating methods, etc., or wet film-forming methods such as spin coating, dip coating, flow coating methods, etc., can be used. When forming the film of the first and second host compounds of the present disclosure, a co-evaporation or a mixed evaporation method is used.

When using a wet film-forming method, a thin film is formed by dissolving or dispersing the material constituting each layer in suitable solvents, such as ethanol, chloroform, tetrahydrofuran, dioxane, etc. The solvents are not specifically limited as long as the material constituting each layer is soluble or dispersible in the solvents, which do not cause any problems in forming a film.

By using the organic electroluminescent device of the present disclosure, a display device, for example, for smartphones, tablets, notebooks, PCs, TVs, or vehicles, or a lighting device, for example, an indoor or outdoor lighting device, can be produced.

Hereinafter, the preparation method of the compounds of the present disclosure, the physical properties of the compounds, and the luminous properties of the organic electroluminescent device comprising the compounds will be explained in detail with reference to the representative compounds of the present disclosure. However, the present disclosure is not limited to the Examples below.

Example 1: Preparation of Compound H-1

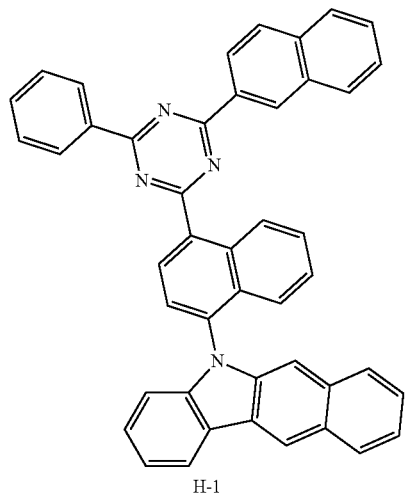

H-1

10 g of compound 1-1 (46 mmol), 27 g of 2-(4-bromonaphthalen-1-yl)-4-(naphthalen-2-yl)-6-phenyl-1,3,5-triazine (55 mmol), 1 g of palladium(II) acetate (5 mmol), 3.8 g of 2-dicyclohexylphosphino-2',6'-dimethoxybiphenyl (9 mmol), 6.6 g of sodium tert-butoxide (69 mmol), and 230 mL of o-xylene were introduced into a reaction vessel, and the mixture was stirred under reflux for 5 hours. After completion of the reaction, the mixture was washed with distilled water and extracted with ethyl acetate. The extracted organic layer was then dried with magnesium sulfate, and the solvent was removed with a rotary evaporator. Thereafter, the resulting product was purified by column chromatography to obtain 9.3 g of compound H-1 (yield: 32%).

|  | MW | UV | PL | M.P. |
|---|---|---|---|---|
| H-1 | 624.75 | 356 nm | 490 nm | 285° C. |

Example 2: Preparation of Compound H-2

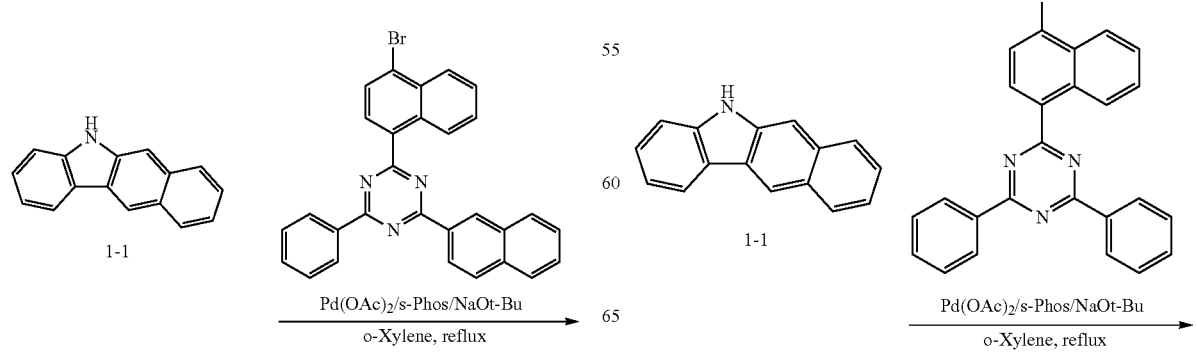

-continued

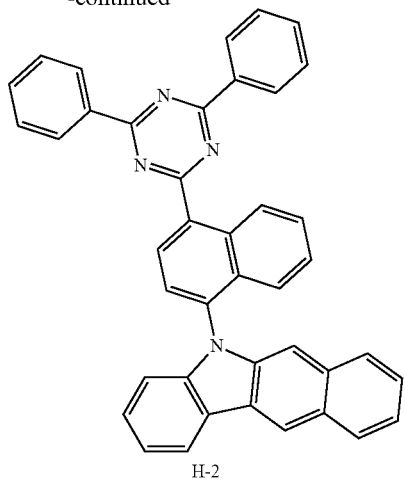

H-2

10 g of compound 1-1 (46 mmol), 24 g of 2-(4-bromonaphthalene)-4,6-diphenyl-1,3,5-triazine (55 mmol), 1 g of palladium(II) acetate (5 mmol), 3.8 g of 2-dicyclohexylphosphino-2',6'-dimethoxybiphenyl (9 mmol), 6.6 g of sodium tert-butoxide (69 mmol), and 230 mL of o-xylene were introduced into a reaction vessel, and the mixture was stirred under reflux for 5 hours. After completion of the reaction, the mixture was washed with distilled water and extracted with ethyl acetate. The extracted organic layer was then dried with magnesium sulfate, and the solvent was removed with a rotary evaporator. Thereafter, the resulting product was purified by column chromatography to obtain 8.2 g of compound H-2 (yield: 31%).

|     | MW     | UV     | PL     | M.P.    |
| --- | ------ | ------ | ------ | ------- |
| H-2 | 574.69 | 404 nm | 507 nm | 247° C. |

Device Examples 1 and 2: Production of an OLED Device Using the Organic Electroluminescent Compound According to the Present Disclosure in an Electron Transport Layer An organic light-emitting diode (OLED) device was produced comprising the compound of the present disclosure. A transparent electrode indium tin oxide (ITO) thin film (10 Ω/sq) on a glass substrate for an OLED device (Geomatec, Japan) was subjected to an ultrasonic washing with acetone and isopropyl alcohol, sequentially, and was then stored in isopropanol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-7}$ torr. Thereafter, an electric current was applied to the cell to evaporate the above-introduced material, thereby forming a first hole injection layer having a thickness of 60 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 20 nm on the second hole injection layer. Compound HT-2 was introduced into another cell of said vacuum vapor depositing apparatus, and was evaporated by applying an electric current to the cell, thereby forming a second hole transport layer having a thickness of 5 nm on the first hole transport layer. After forming the hole injection layers and the hole transport layers, a light-emitting layer was then deposited as follows. Compound BH-1 was introduced into one cell of the vacuum vapor depositing apparatus as a host, and compound BD-1 was introduced into another cell as a dopant. The two materials were evaporated at different rates and were deposited in a doping amount of 2 wt % based on the total amount of the host and dopant to form a light-emitting layer having a thickness of 20 nm on the second hole transport layer. Compound H-1 or H-2 and compound EI-1 were then introduced into other two cells, simultaneously evaporated at the rate of 1:1, and deposited to form an electron transport layer having a thickness of 35 nm on the light-emitting layer. Next, after depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced. All the materials used for producing the OLED device were purified by vacuum sublimation at $10^{-6}$ torr.

The driving voltage at 1 nit when the organic electroluminescent device begins to emit light and the time period for the luminance to decrease from 100% to 90% at a luminance of 2,000 nit of the produced OLED devices are provided in Table 1 below.

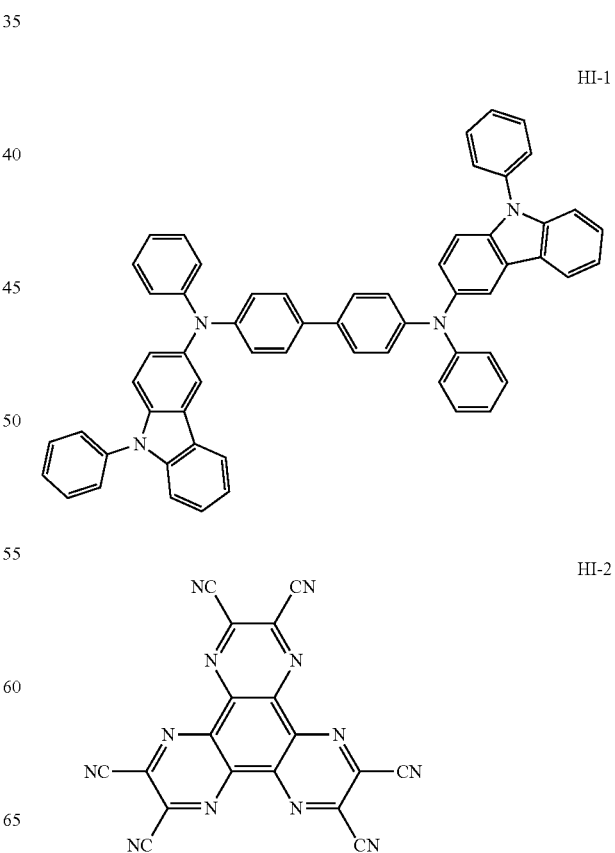

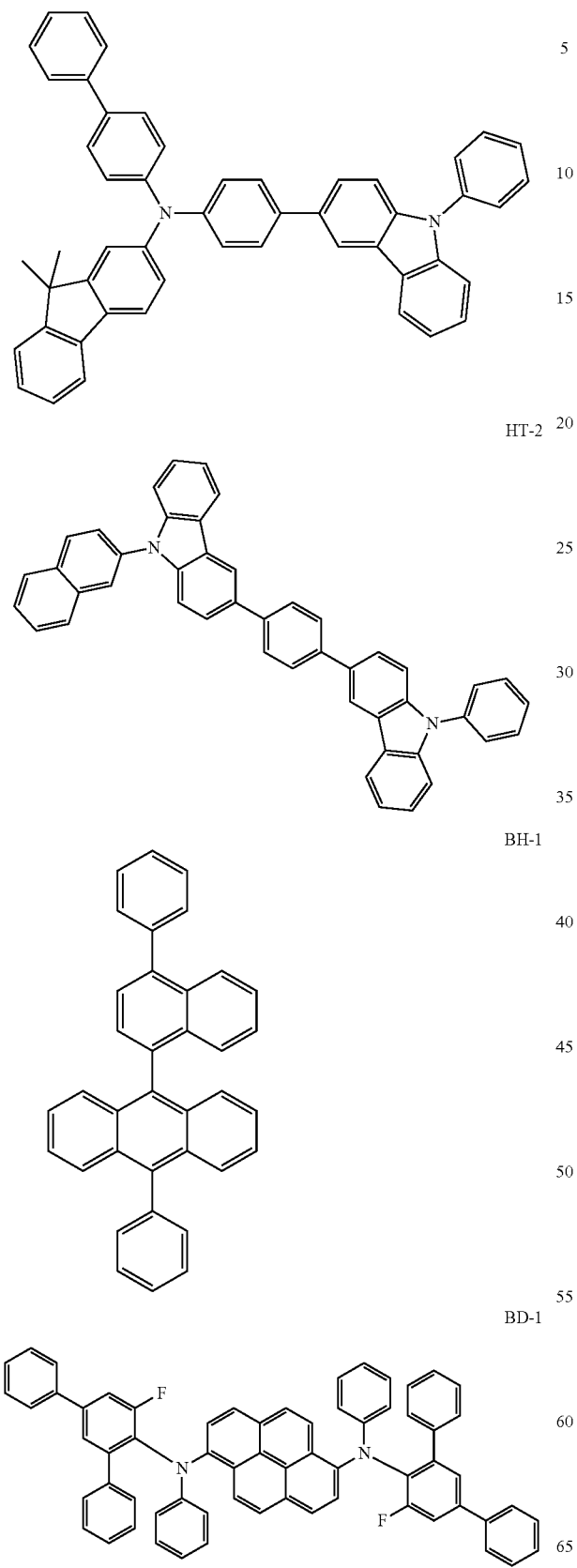
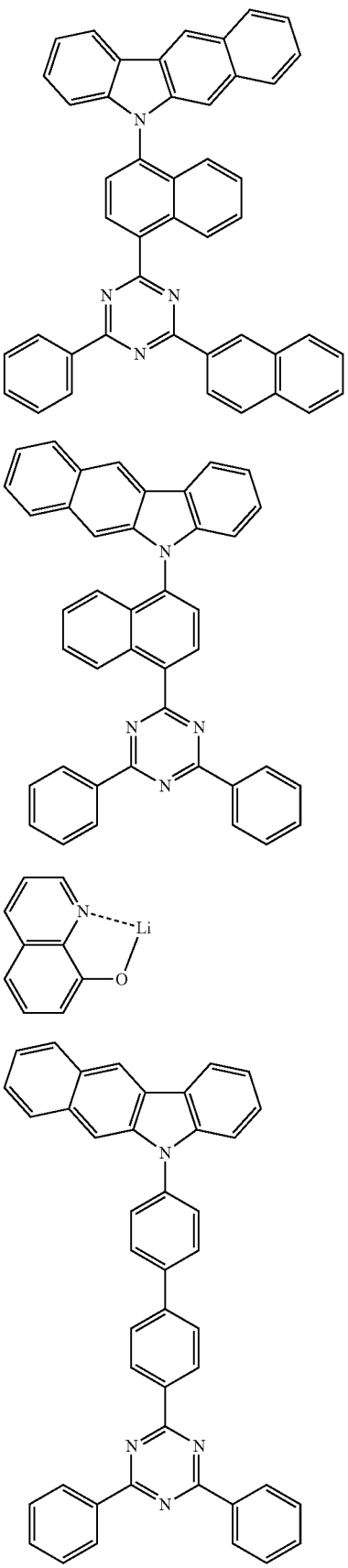

X-2

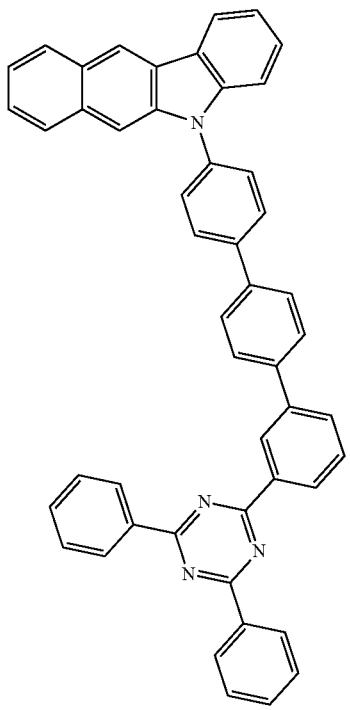

Comparative Examples 1 and 2: Production of an OLED Device Using a Conventional Organic Electroluminescent Compound in an Electron Transport Layer In Comparative Examples 1 and 2, an OLED device was produced in the same manner as in Device Examples 1 and 2, except that the electron transport material of Table 1 was used instead of H-1 or H-2. The evaluation results of the organic electroluminescent devices of Comparative Examples 1 and 2 are provided in Table 1 below.

TABLE 1

|  | Electron transport material | Driving voltage (V) | Color emitted | Lifespan (T90, hr) |
|---|---|---|---|---|
| Comparative Example 1 | X-1 | 3.0 | Blue | 21.5 |
| Comparative Example 2 | X-2 | 2.8 | Blue | 40.8 |
| Device Example 1 | H-1 | 3.3 | Blue | 55.4 |
| Device Example 2 | H-2 | 3.2 | Blue | 61.3 |

The organic electroluminescent device comprising the compound of the present disclosure retains good driving voltage characteristic similar to the organic electroluminescent device comprising the conventional compound, and exhibits significantly enhanced lifespan characteristic compared to the organic electroluminescent device comprising the conventional compound.

Device Example 3: Production of an OLED Device Using the Organic Electroluminescent Compound According to the Present Disclosure as a Host An OLED device was produced using the organic electroluminescent compound of the present disclosure. A transparent electrode indium tin oxide (ITO) thin film (10 Ω/sq) on a glass substrate for an OLED device (Geomatec, Japan) was subjected to an ultrasonic washing with trichloroethylene, acetone, ethanol, and distilled water, sequentially, and was then stored in isopropanol. Next, the ITO substrate was mounted on a substrate holder of a vacuum vapor depositing apparatus. Compound HI-1 as a first hole injection material was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 80 nm on the ITO substrate. Compound HI-2 as a second hole injection material was then introduced into another cell of said vacuum vapor depositing apparatus, and was evaporated by applying an electric current to the cell, thereby forming a second hole injection layer having a thickness of 5 nm on the first hole injection layer. Compound HT-1 as a first hole transport material was introduced into another cell of said vacuum vapor depositing apparatus, and was evaporated by applying an electric current to the cell, thereby forming a first hole transport layer having a thickness of 10 nm on the second hole injection layer. Compound HT-3 as a second hole transport material was introduced into another cell of said vacuum vapor depositing apparatus, and was evaporated by applying an electric current to the cell, thereby forming a second hole transport layer having a thickness of 60 nm on the first hole transport layer. After forming the hole injection layers and the hole transport layers, a light-emitting layer was then deposited as follows. Compound H-2 was introduced into one cell of the vacuum vapor depositing apparatus as a host, and compound D-71 was introduced into another cell as a dopant. The two materials were evaporated at different rates and were deposited in a doping amount of 3 wt % based on the total amount of the host and dopant to form a light-emitting layer having a thickness of 40 nm on the second hole transport layer. Compound ET-2 and compound EI-1 were then introduced into other two cells, simultaneously evaporated at the rate of 1:1, and deposited to form an electron transport layer having a thickness of 35 nm on the light-emitting layer. Next, after depositing compound EI-1 as an electron injection layer having a thickness of 2 nm, an Al cathode having a thickness of 80 nm was deposited by another vacuum vapor deposition apparatus. Thus, an OLED device was produced.

HI-1

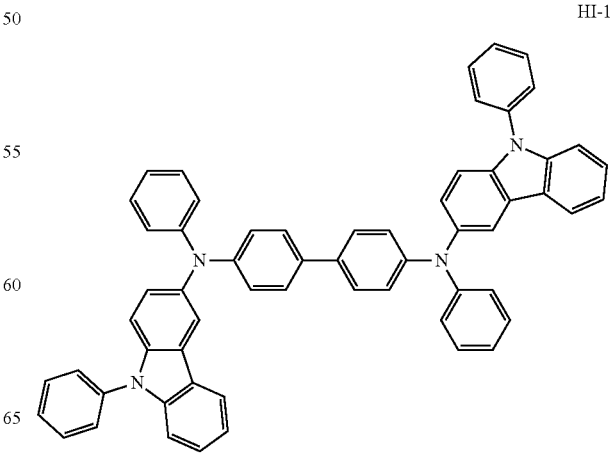

HI-2

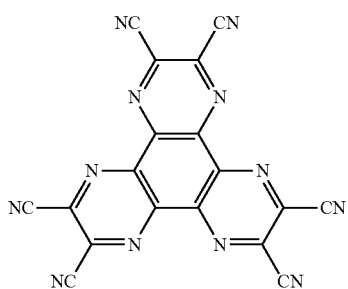

HT-1

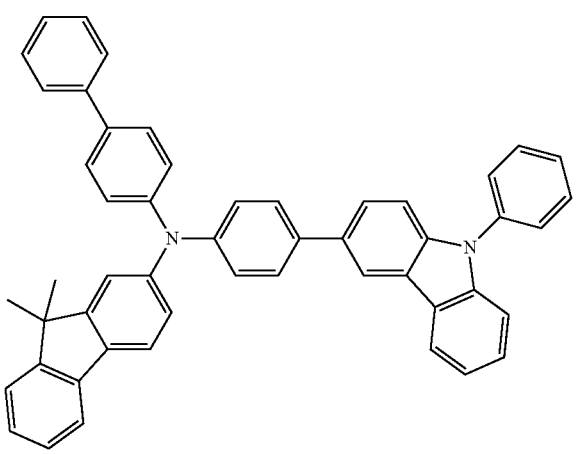

HT-3

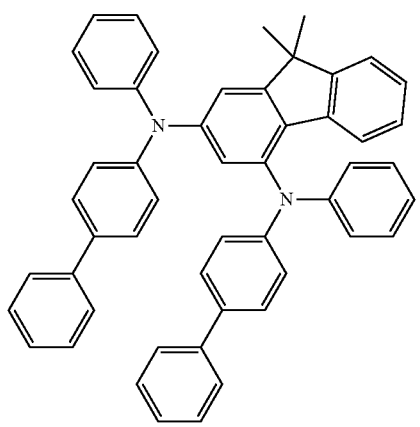

ET-2

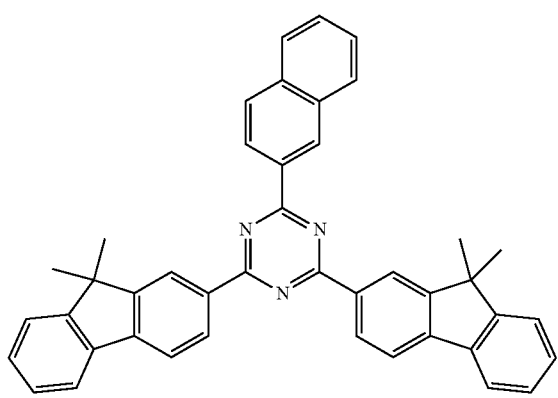

EI-1

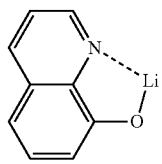

As a result, a power efficiency of 22.3 lm/W at 3.1 V was shown, red light of 1000 cd/m² was emitted, and the time taken to be reduced from 100% to 95% of the luminance at 5,000 nit and a constant current was 59 hours.

Comparative Example 3: Production of an OLED Device Using a Conventional Organic Electroluminescent Compound as a Host An OLED device was produced in the same manner as in Device Example 3, except that compound X-1 was used as a host instead of H-2.

As a result, a power efficiency of 18.7 lm/W at 3.6 V was shown, red light of 1000 cd/m² was emitted, and the time taken to be reduced from 100% to 95% of the luminance at 5,000 nit and a constant current was 31 hours.

X-1

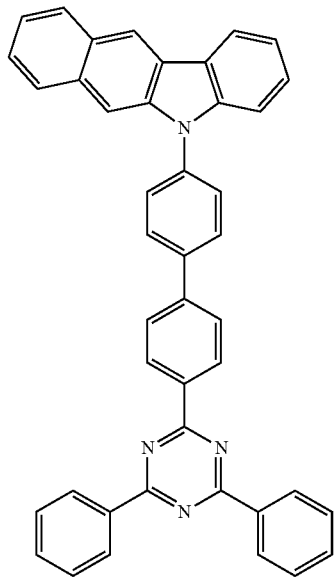

The organic electroluminescent device using the organic electroluminescent compound of the present disclosure as a host has a lower driving voltage, shows similar or better power efficiency, and particularly shows significantly better lifespan characteristic compared to the organic electroluminescent device comprising the conventional organic electroluminescent compound.

Device Examples 4 to 13: Production of an OLED Device Using the Organic Electroluminescent Compound According to the Present Disclosure as One of a Plurality of Hosts An OLED device was produced using the organic electroluminescent compound of the present disclosure. A transparent electrode indium tin oxide (ITO) thin film (10 Ω/sq)

on a glass substrate for an OLED device (Geomatec, Japan) was subjected to an ultrasonic washing with trichloroethylene, acetone, ethanol, and distilled water, sequentially, and was then stored in isopropanol. Next, the ITO substrate was mounted on a substrate holder of a vacuum vapor depositing apparatus. Compound HI-1 as a first hole injection material was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 80 nm on the ITO substrate. Compound HI-2 as a second hole injection material was then introduced into another cell of said vacuum vapor depositing apparatus, and was evaporated by applying an electric current to the cell, thereby forming a second hole injection layer having a thickness of 5 nm on the first hole injection layer. Compound HT-1 as a first hole transport material was introduced into another cell of said vacuum vapor depositing apparatus, and was evaporated by applying an electric current to the cell, thereby forming a first hole transport layer having a thickness of 10 nm on the second hole injection layer. Compound HT-2 as a second hole transport material was introduced into another cell of said vacuum vapor depositing apparatus, and was evaporated by applying an electric current to the cell, thereby forming a second hole transport layer having a thickness of 60 nm on the first hole transport layer. After forming the hole injection layers and the hole transport layers, a light-emitting layer was then deposited as follows. A first host of Table 2 was introduced into one cell of the vacuum vapor depositing apparatus, a second host was introduced into another cell, and compound D-71 was introduced into another cell as a dopant. The first and second hosts were evaporated at a rate of 1:1, and the dopant was deposited in a doping amount of 3 wt % based on the total amount of the host and dopant to form a light-emitting layer having a thickness of 40 nm on the second hole transport layer. Compound ET-2 and compound EI-1 were then introduced into other two cells, simultaneously evaporated at the rate of 1:1, and deposited to form an electron transport layer having a thickness of 35 nm on the light-emitting layer. Next, after depositing compound EI-1 as an electron injection layer having a thickness of 2 nm, an Al cathode having a thickness of 80 nm was deposited by another vacuum vapor deposition apparatus. Thus, an OLED device was produced.

The time period (T95) for the luminance to decrease from 100% to 95% at a luminance of 5,000 nit and a constant current of the produced OLED devices are provided in Table 2 below.

TABLE 2

|  | First host | Second host | Luminous efficiency (cd/A) | Lifespan (T95, hr) |
|---|---|---|---|---|
| Device Example 4 | H-2 | B-198 | 24.1 | 335 |
| Device Example 5 | H-2 | B-259 | 25.2 | 593 |
| Device Example 6 | H-2 | B-210 | 26.6 | 679 |
| Device Example 7 | H-2 | B-333 | 24.8 | 579 |
| Device Example 8 | H-2 | B-203 | 26.5 | 788 |
| Device Example 9 | H-2 | B-199 | 28.5 | 579 |
| Device Example 10 | H-2 | B-202 | 26.1 | 783 |
| Device Example 11 | H-2 | B-201 | 26.5 | 446 |
| Device Example 12 | H-2 | B-200 | 26.0 | 928 |
| Device Example 13 | H-1 | B-210 | 26.6 | 294 |

Table 2 shows that the organic electroluminescent device using the organic electroluminescent compound according to the present disclosure as one of a plurality of hosts exhibits excellent luminous efficiency and lifespan characteristics.

The invention claimed is:
1. An organic electroluminescent compound represented by the following formula 2:

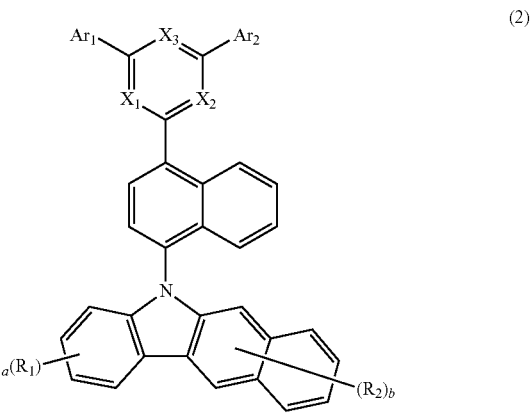

wherein
$X_1$ to $X_3$ each independently represent N or $CR_3$, with a proviso that at least one of them are N;
$R_1$ and $R_2$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;
$Ar_1$, $Ar_2$, and $R_3$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or are linked to an adjacent substituent to form a substituted or unsubstituted mono- or polycyclic (C3-C30) alicyclic, aromatic ring, or a combination thereof, whose carbon atom(s) may be replaced with at least one heteroatom selected from nitrogen, oxygen, and sulfur; the heteroaryl contains at least one heteroatom selected from B, N, O, S, Si, and P; a is an integer of 1 to 4, and b is an integer of 1 to 6; where a or b is an integer of 2 or more, each $R_1$ and each $R_2$ may be the same or different.

2. The organic electroluminescent compound according to claim 1, wherein the substituents of the substituted (C1-C30)alkyl, the substituted (C6-C30)aryl, the substituted (3- to 30-membered)heteroaryl, the substituted (C3-C30)cycloalkyl, the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C1-C30)alkyl(C6-C30)arylamino, and the substituted mono- or polycyclic, (C3-C30) alicyclic, aromatic ring, or a combination thereof in $Ar_1$, $Ar_2$, and $R_1$ to $R_3$ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3 C30)cycloalkyl; a (C3-C30)cycloalkenyl; a (3- to 7-membered)heterocycloalkyl; a (C6-C30)aryloxy; a (C6-C30)arylthio; a (5- to 30-membered)heteroaryl unsubstituted or substituted with a (C6-C30)aryl; a (C6-C30)aryl unsubstituted or substituted with a (5- to 30-membered)heteroaryl; a tri(C1-C30)alkylsilyl, a tri(C6-C30)arylsilyl; a di(C1-C30)alkyl(C6-C30)arylsilyl; a (C1-C30)alkyldi(C6-C30)arylsilyl; an amino; a mono- or di-(C1 C30)alkylamino; a mono- or di-(C6-C30)arylamino unsubstituted or substituted with a (C1-C30) alkyl; a (C1-C30)alkyl(C6-C30)arylamino; a (C1-C30)alkylcarbonyl; a (C1-C30)alkoxycarbonyl; a (C6-C30) arylcarbonyl; a di(C6-C30)arylboronyl; a di(C1-C30) alkylboronyl; a (C1-C30)alkyl(C6-C30)arylboronyl; a (C6-C30)aryl(C1-C30)alkyl; and a (C1-C30)alkyl(C6-C30)aryl.

3. The organic electroluminescent compound according to claim 1, wherein $X_1$ to $X_3$ each independently represent N or $CR_3$, with a proviso that at least two of them are N; $Ar_1$ and $Ar_2$ each independently represent a substituted or unsubstituted(C6-C25)aryl, or a substituted or unsubstituted (5- to 20-membered)heteroaryl; and $R_1$ to $R_3$ each independently represent hydrogen, a substituted or unsubstituted (C6-C20) aryl, or a substituted or unsubstituted (5- to 20-membered) heteroaryl.

4. The organic electroluminescent compound according to claim 3, wherein $X_1$ to $X_3$ each independently represent N or $CR_3$, with a proviso that at least two of them are N;

$Ar_1$ and $Ar_2$ each independently represent a (C6-C25) aryl unsubstituted or substituted with a (C1-C30) alkyl, or an unsubstituted (5- to 20-membered) heteroaryl; and
$R_1$ to $R_3$ each independently represent hydrogen, an unsubstituted(C6-C20)aryl, or an unsubstituted (5- to 20-membered)heteroaryl.

5. The organic electroluminescent compound according to claim 3, wherein the compound represented by formula 2 is selected from the group consisting of:

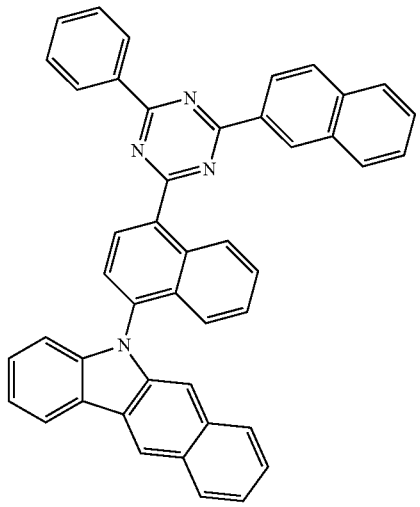

H-1

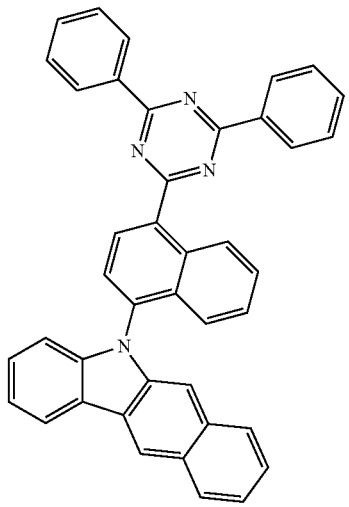

H-2

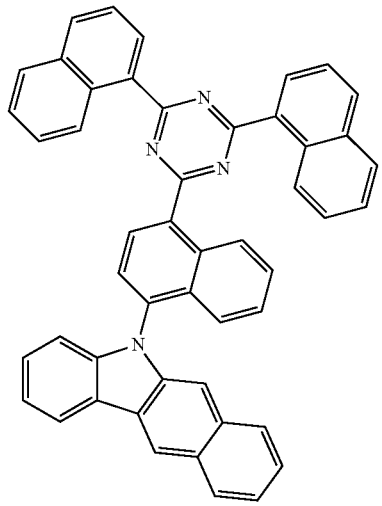

H-3

H-4
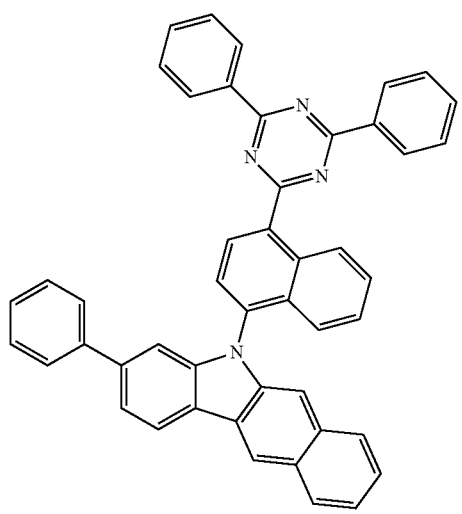
H-5
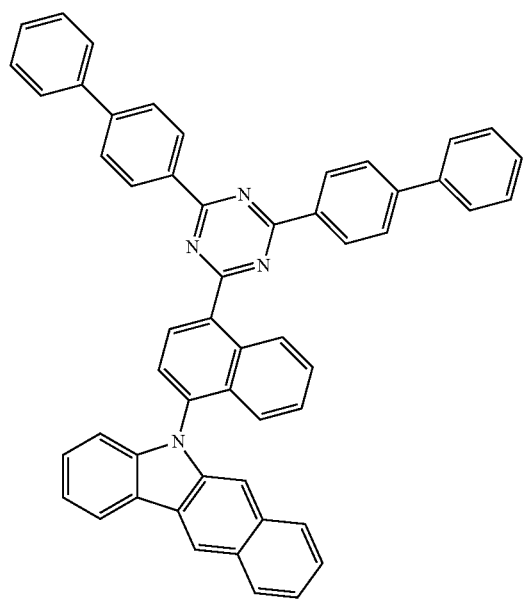
H-6
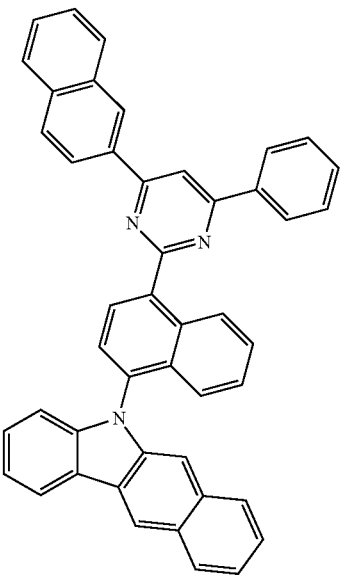
H-7
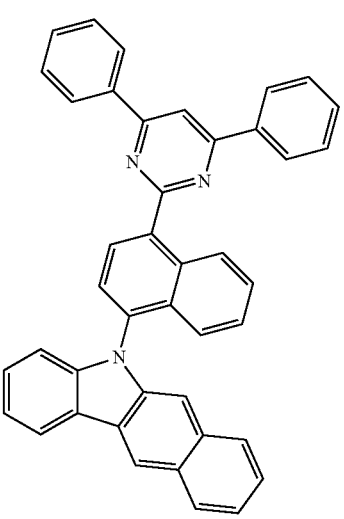
H-8
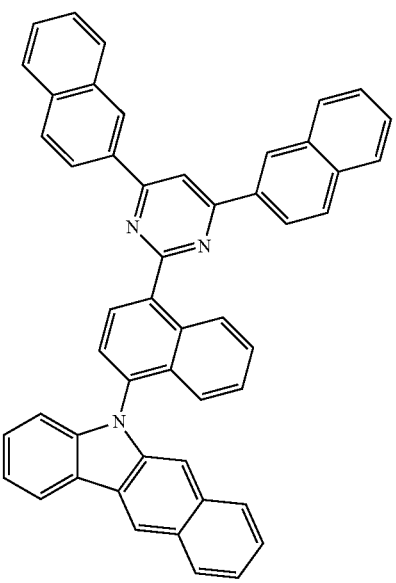

H-9
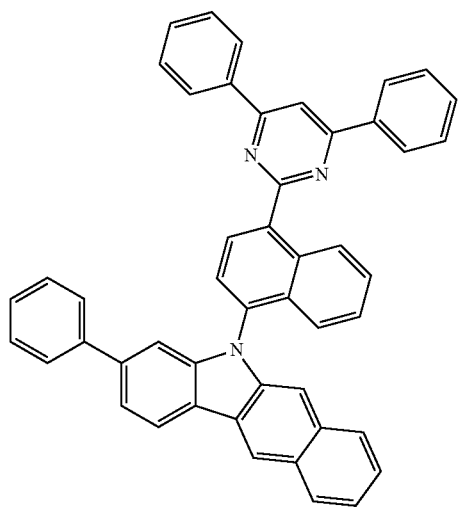
H-10
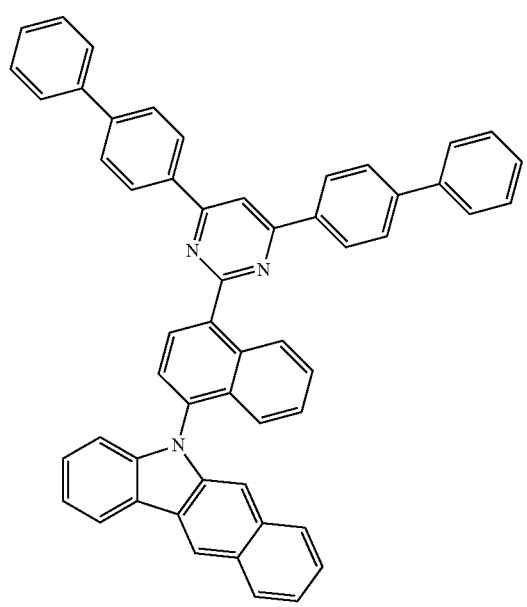
H-16
H-17
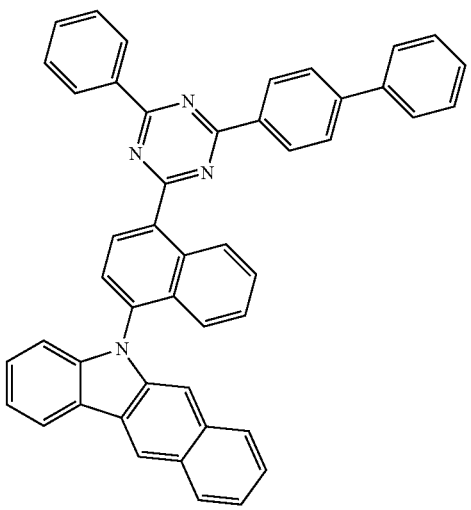
H-23
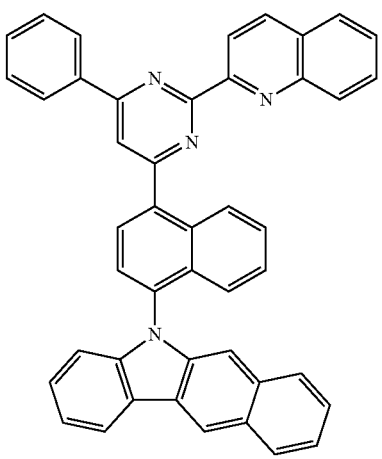
H-26
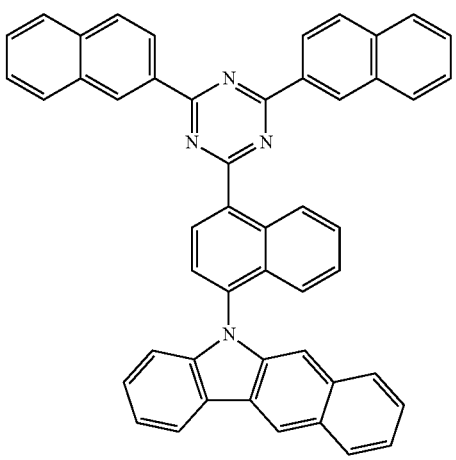

H-27
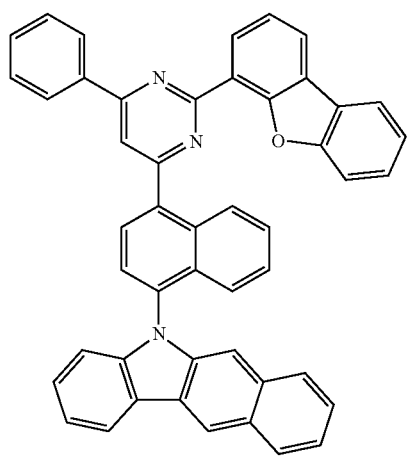
H-28
H-30
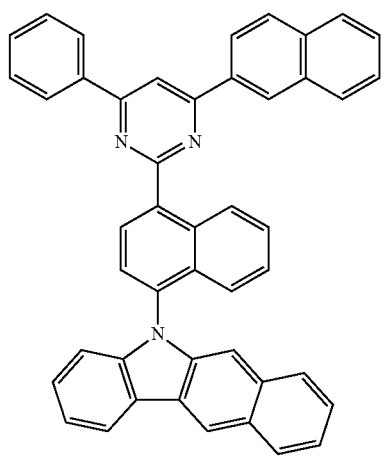
H-31
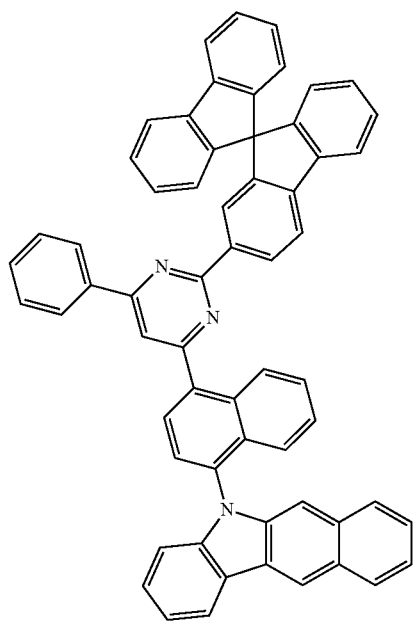
H-29
H-32
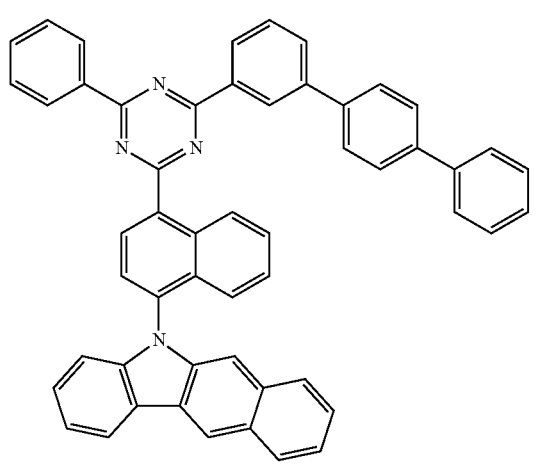

H-33
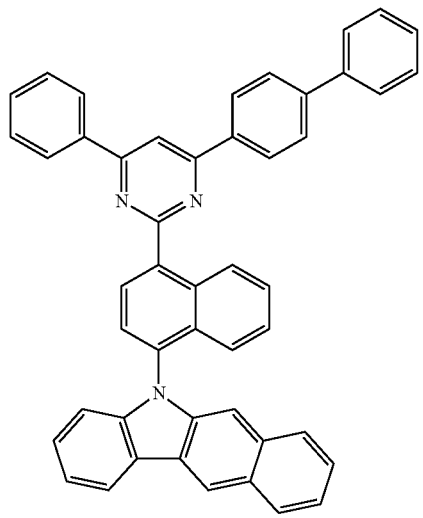
H-34
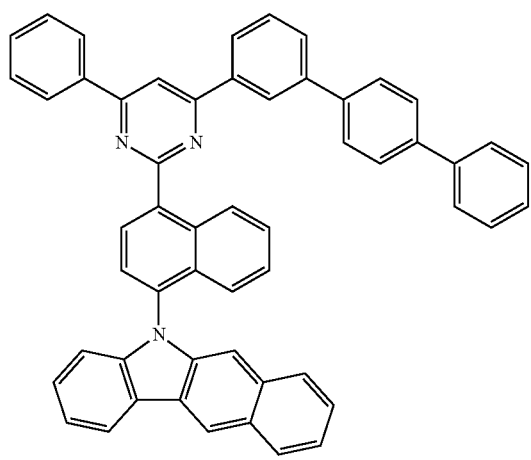
H-35
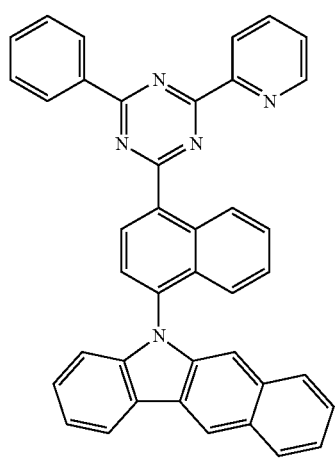
H-36
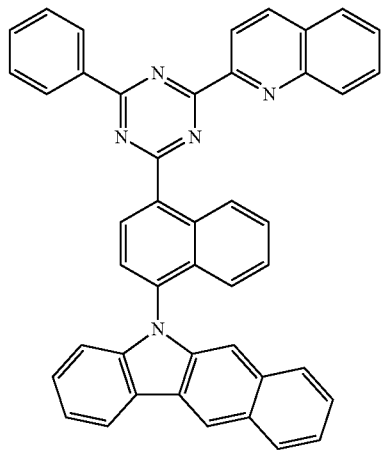
H-37
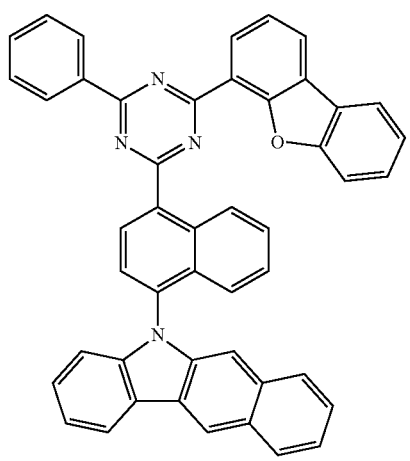
H-38
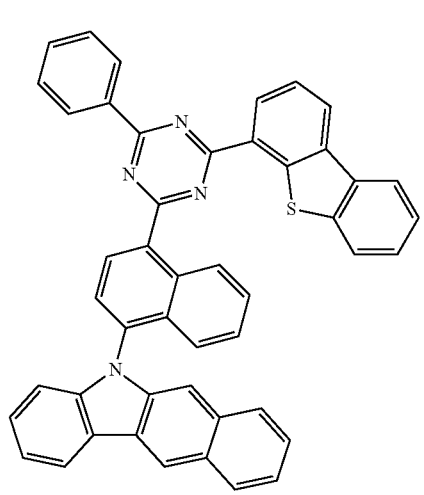

H-39
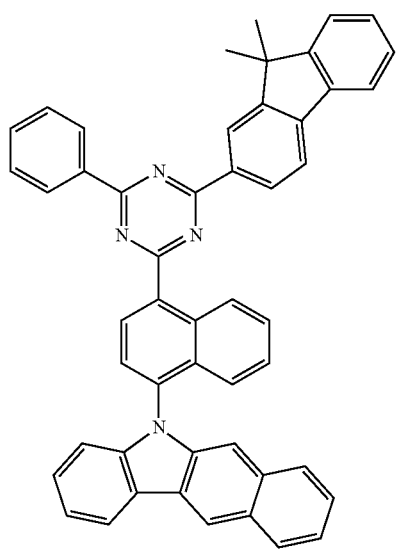
H-40
H-41
H-42
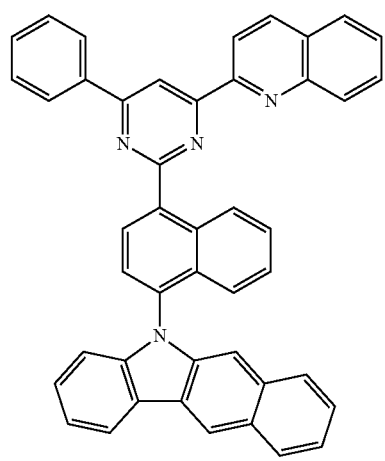
H-43
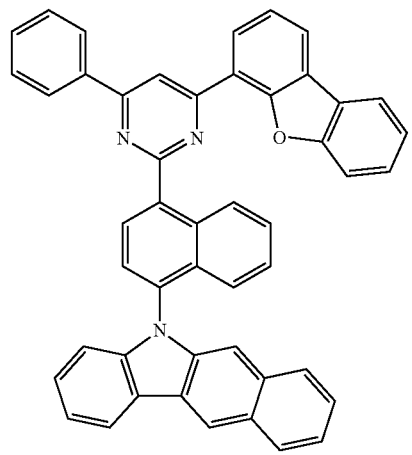
H-44
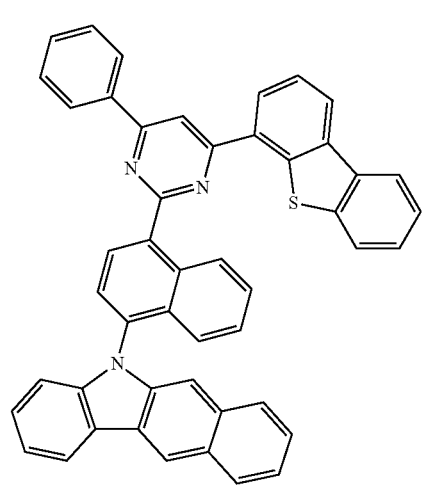

H-45
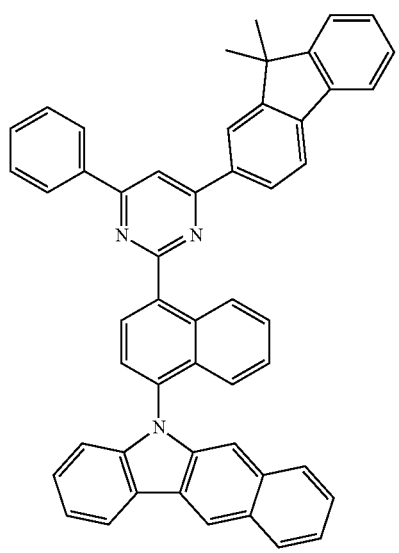
H-46
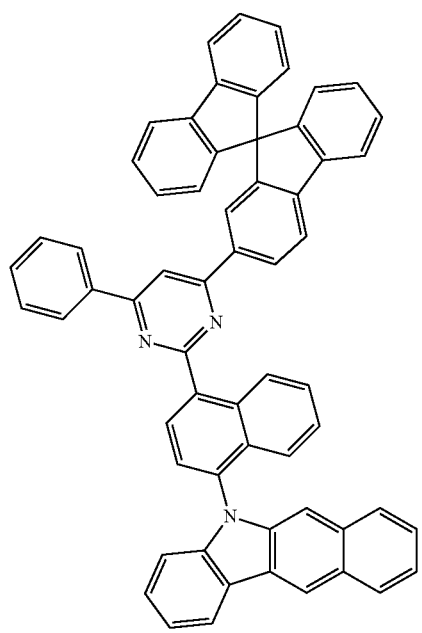
H-64
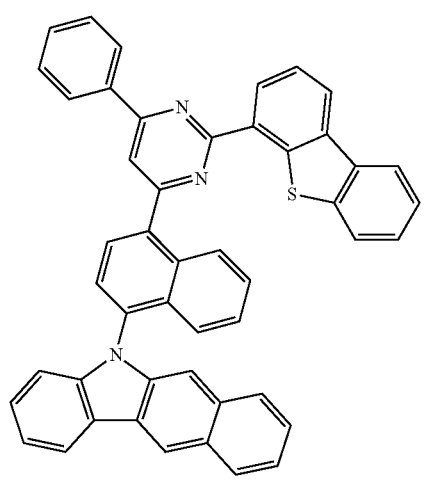
H-65
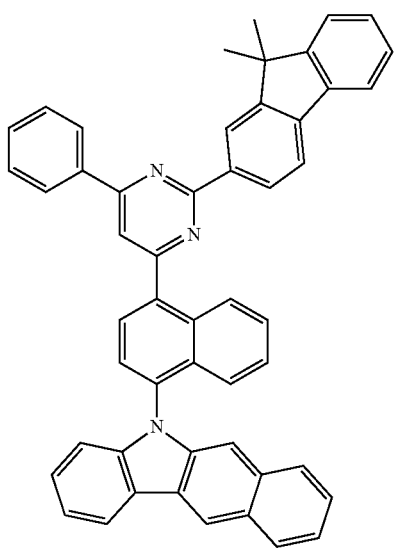
H-98
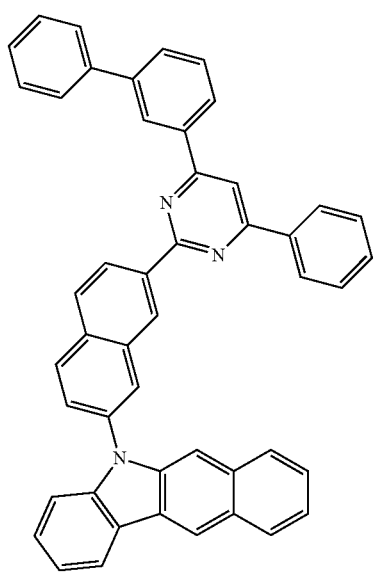
H-99
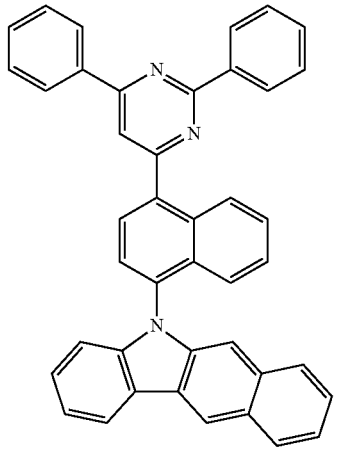

H-100

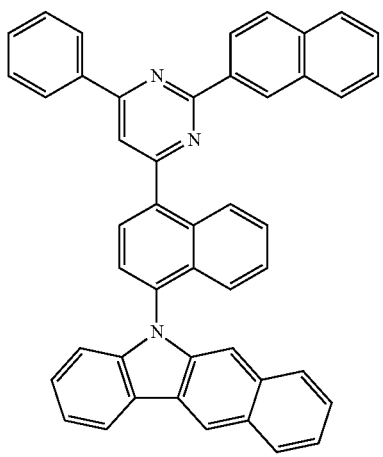

H-101

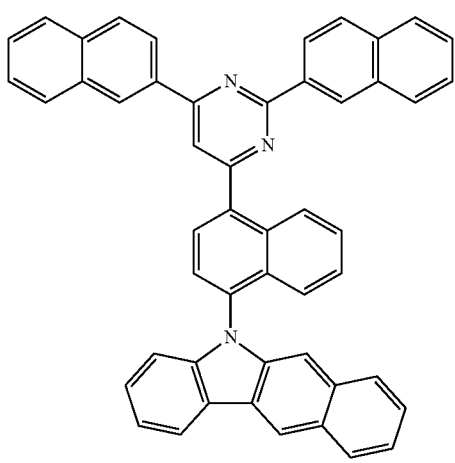

H-102

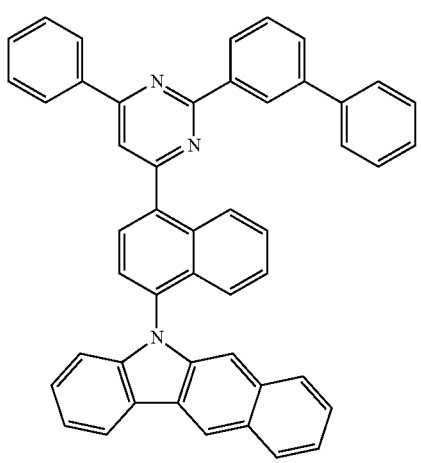

H-103

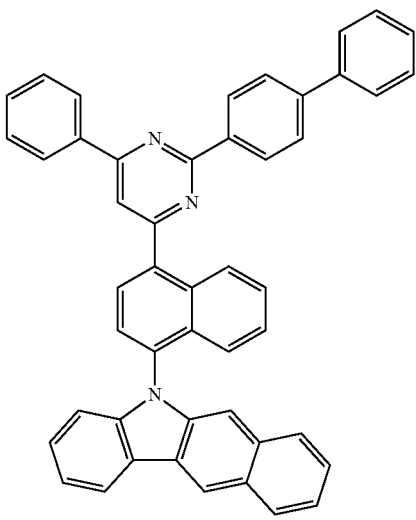

H-104

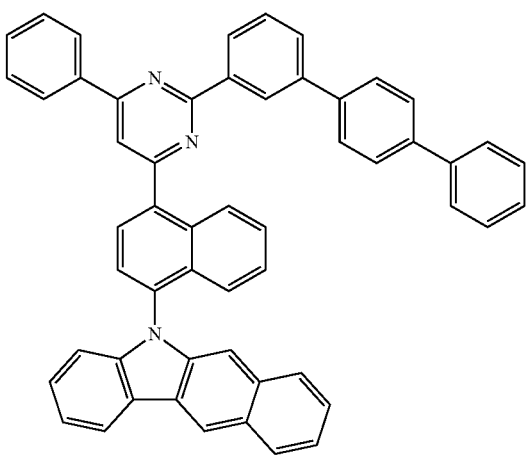

H-105

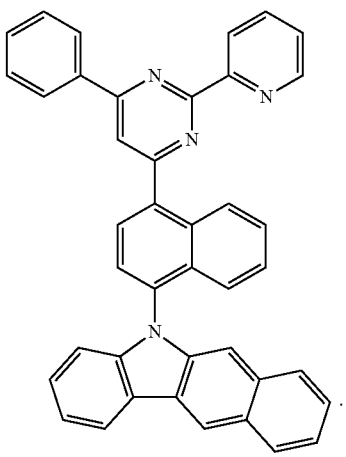

6. An organic electroluminescent material comprising the organic electroluminescent compound according to claim 3.

7. An organic electroluminescent device comprising the organic electroluminescent compound according to claim 3.

8. The organic electroluminescent device according to claim 7, wherein the organic electroluminescent compound is comprised in an electron transport layer, a light-emitting layer, or both of them.

9. The organic electroluminescent device according to claim 8, wherein the light-emitting layer further comprises an organic electroluminescent compound other than the organic electroluminescent compound of claim 8, and the further comprised organic electroluminescent compound is represented by any one of the following formulas 11 to 17:

H—(Cz—L$_4$)$_h$—M (11)

H—(Cz)$_i$—L$_4$—M (12)

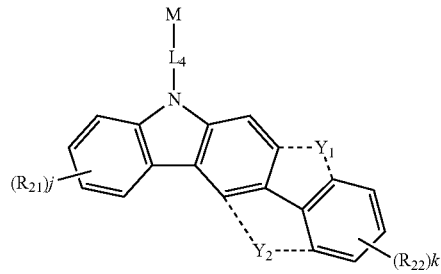 (13)

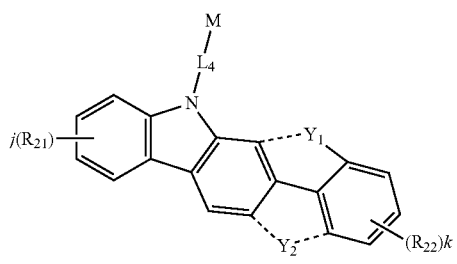 (14)

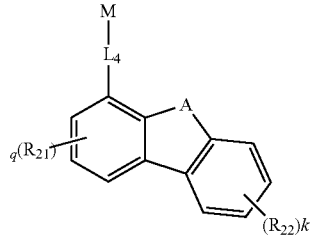 (15)

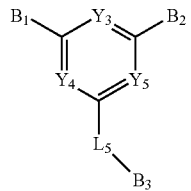 (16)

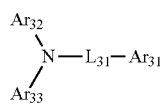 (17)

wherein
Cz represents the following structure:

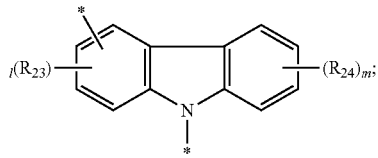

A represents —O— or —S—;

R$_{21}$ to R$_{24}$, each independently, represent hydrogen, deuterium, a halogen, a substituted or unsubstituted (C1-C30)alkyl, a substituted or unsubstituted (C6-C30)aryl, a substituted or unsubstituted (5- to 30-membered) heteroaryl, or —SiR$_{25}$R$_{26}$R$_{27}$; in which R$_{25}$ to R$_{27}$, each independently, represent a substituted or unsubstituted (C1-C30)alkyl, or a substituted or unsubstituted (C6-C30)aryl;

L$_4$ represents a single bond, a substituted or unsubstituted (C6-C30)arylene, or a substituted or unsubstituted (5- to 30-membered)heteroarylene; M represents a substituted or unsubstituted (C6-C30)aryl, or a substituted or unsubstituted (5- to 30-membered)heteroaryl; Y$_1$ and Y$_2$, each independently, represent —O—, —S—, —N(R$_{31}$)— or —C(R$_{32}$)(R$_{33}$)—, with the proviso that Y$_1$ and Y$_2$ are not present simultaneously; R$_{31}$ to R$_{33}$, each independently, represent a substituted or unsubstituted (C1-C30)alkyl, a substituted or unsubstituted (C6-C30)aryl, or a substituted or unsubstituted (5- to 30-membered)heteroaryl; R$_{32}$ and R$_{33}$ may be the same or different; h and i, each independently, represent an integer of 1 to 3; j, k, l, and m, each independently, represent an integer of 1 to 4; q represents an integer of 1 to 3; if h, i, j, k, l, m, or q represents an integer of 2 or more, each (Cz-L$_4$), each (Cz), each R$_{21}$, each R$_{22}$, each R$_{23}$, or each R$_{24}$ may be the same or different;

Y$_3$ to Y$_5$, each independently, represent CR$_{34}$ or N;

R$_{34}$ represents hydrogen, a substituted or unsubstituted (C1-C30)alkyl, a substituted or unsubstituted (C6-C30) aryl, or a substituted or unsubstituted (5- to 30-membered)heteroaryl;

B$_1$ and B$_2$, each independently, represent hydrogen, a substituted or unsubstituted (C6-C30)aryl, or a substituted or unsubstituted (5- to 30-membered)heteroaryl;

B$_3$ represents a substituted or unsubstituted (C6-C30)aryl, or a substituted or unsubstituted (5- to 30-membered) heteroaryl;

L$_5$ represents a single bond, a substituted or unsubstituted (C6-C30)arylene, or a substituted or unsubstituted (5- to 30-membered)heteroarylene;

Ar$_{31}$ to Ar$_{33}$, each independently, represent a substituted or unsubstituted (C6-C30)aryl, or a substituted or unsubstituted (3- to 30-membered)heteroaryl; or are linked to an adjacent substituent to form a substituted or unsubstituted, mono- or polycyclic, (3- to 30-membered) alicyclic, aromatic ring, or a combination thereof; and L$_{31}$ represents a single bond, a substituted or unsubstituted (C6-C30)arylene, or a substituted or unsubstituted (3- to 30-membered)heteroarylene.

* * * * *